(12) United States Patent
Reichert et al.

(10) Patent No.: US 8,679,472 B1
(45) Date of Patent: Mar. 25, 2014

(54) CRYSTAL OF HUMAN INTERFERON ALPHA 2B IN COMPLEX WITH ZINC

(75) Inventors: Paul Reichert, Montville, NJ (US); Marianna Marshall Long, Birmingham, AL (US); Alan W. Hruza, Hackettstown, NJ (US); Peter Orth, New York, NY (US); Tattanahalli L. Nagabhushan, Parsippany, NJ (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 210 days.

(21) Appl. No.: 11/973,362

(22) Filed: Oct. 5, 2007

Related U.S. Application Data

(60) Provisional application No. 60/849,520, filed on Oct. 5, 2006.

(51) Int. Cl.
*A61K 38/21* (2006.01)
*A61M 5/00* (2006.01)

(52) U.S. Cl.
USPC ............ 424/85.7; 514/1.1; 514/4.3; 604/187

(58) Field of Classification Search
None
See application file for complete search history.

(56) References Cited

U.S. PATENT DOCUMENTS

| | | | |
|---|---|---|---|
| 5,441,734 A | 8/1995 | Reichert et al. | |
| 5,460,956 A | 10/1995 | Reichert et al. | |
| 5,908,621 A | 6/1999 | Glue et al. | |
| 5,935,566 A | 8/1999 | Yuen et al. | |
| 5,951,974 A | 9/1999 | Gilbert et al. | |
| 5,972,331 A | 10/1999 | Reichert et al. | |
| 6,004,549 A * | 12/1999 | Reichert et al. | 424/85.7 |
| 6,027,565 A | 2/2000 | Bugg | |
| 6,042,822 A | 3/2000 | Gilbert et al. | |
| 6,177,074 B1 | 1/2001 | Glue et al. | |
| 6,180,096 B1 | 1/2001 | Kline | |
| 6,250,469 B1 | 6/2001 | Kline | |
| 6,482,613 B1 | 11/2002 | Goeddel et al. | |
| 6,524,570 B1 | 2/2003 | Glue et al. | |
| 6,610,830 B1 | 8/2003 | Goeddel et al. | |
| 2008/0201123 A1 * | 8/2008 | Cosgrove | 703/11 |

OTHER PUBLICATIONS

Ramagopal et al., Acta Crystallographica Section D, Biological Crystallography D59:868-875, 2003.*
Kitago et al., Acta Crystallographica Section D, Biological Crystallography D61:1013-1021, 2005.*
Radhakrishnan et al., Zinc mediated dimer of human interferon-α2b revealed by X-ray crystallography. Structure (1996) 4(12): 1453-1463.
Physicians Desk Reference® Electronic Library-Rebetron®, Rebetol®, Intron®A (last accessed Oct. 2007).
Physicians Desk Reference® Electronic Library-Pegasys® (last accessed Oct. 2007).
Physicians Desk Reference® Electronic Library-Actimmune® (last accessed Oct. 2007).
Physicians Desk Reference® Electronic Library-Betaseron® (last accessed Oct. 2007).
Physicians Desk Reference® Electronic Library-Pegintron® (last accessed Oct. 2007).
Physicians Desk Reference® Electronic Library-Infergen® (last accessed Oct. 2007).
Physicians Desk Reference® Electronic Library-Alferon N injection® (last accessed Oct. 2007).
Physicians Desk Reference® Electronic Library-Rebif® (last accessed Oct. 2007).
Intron® A Product Information; www.IntronA.com (last accessed Oct. 2007).
In "Preparation and analysis of protein crystals" By Alexander McPherson, Robert E. Krieger Publishing Co. Krieger Drive, Malabar, Florida 1989, p. 174-180.

* cited by examiner

*Primary Examiner* — David J Steadman

(57) ABSTRACT

This application covers a novel PEGylated interferon and a novel crystalline form of interferon which are useful, inter alia, for detailed structural analysis of interferon as well as treatment and prevention of viral infections and hyperproliferative diseases such as leukemia.

12 Claims, 2 Drawing Sheets

SEQUENCE LISTING

```
<160> NUMBER OF SEQ ID NOS: 1

<210> SEQ ID NO 1
<211> LENGTH: 165
<212> TYPE: PRT
<213> ORGANISM: Artificial Sequence
<220> FEATURE:
<223> OTHER INFORMATION: Interferon alpha 2b
<220> FEATURE:
<221> NAME/KEY: MISC_FEATURE
<222> LOCATION: (1)..(165)
<223> OTHER INFORMATION: optional methionine at N-terminus

<400> SEQUENCE: 1

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
```

-continued

```
               50                  55                  60
Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
                165
```

CRYSTAL OF HUMAN INTERFERON ALPHA 2B IN COMPLEX WITH ZINC

This application claims the benefit of U.S. provisional patent application No. 60/849,520, filed Oct. 5, 2006; which is herein incorporated by reference in its entirety.

FIELD OF THE INVENTION

The present application relates to interferon polypeptide compositions

BACKGROUND OF THE INVENTION

The human interferon alphas are a family of proteins comprising at least 24 subspecies, Zoon K. C, Interferon 9:1-12 (1987), Gresser I., ed. Academic Press, New York. They were originally described as agents capable of inducing an antiviral state in cells but are known as pleitropic lymphokines affecting many functions of the immune system, Opdenakker, et al., Expermentia 45: 513-520 (1989). Apart from their in vitro biological activities, the human interferon alphas are currently used for several indications, e.g., hairy cell leukemia, Kaposi Sarcoma, venereal warts, hepatitis B and hepatitis C.

Presently, interferon is administered to patients by injection. Injection suffers from several drawbacks including pain and poor patient compliance. An alternative mode of administration of interferon or PEG-interferon would be beneficial.

Macromolecules have limited modes of administration. Transdermal or oral delivery is difficult because of their sheer size which usually has a molecular weight greater than 7,000 KDa, and instability in the gastrointestinal environment. In general, protein drugs are administered either by subcutaneous or intravenous injection usually in hospital or clinical settings. Proteins having a molecular weight less than 30,000 have serum half-lives duration of hours when injected subcutaneously or intravenously and characteristically show a "burst" (rapid blood serum clearance rate) profile when blood levels are measured over time. There is increasing awareness that drug release patterns (continuous versus pulsatile) significantly affect therapeutic responses.

Pulmonary delivery of a crystalline interferon alpha has been described previously (U.S. Pat. No. 5,972,331). The patent describes a method for preparing a crystalline interferon alpha suitable for aerosol formulation either for systemic or topical (inhaled) drug delivery.

There remains a need in the art for high quality, highly ordered interferon crystals that are particularly useful for pulmonary delivery or delivery in a sustained release formulation. A $Zn^{2+}$ mediated interferon alpha 2b dimeric crystal was produced previously (see Radhakrishnan et al., Structure. 4(12):1453-63 (1996); see also U.S. Pat. No. 5,441,734 to Reichert et al.); however, interferon structural data gained from the prior art crystals, was only to a 2.7 Å or 2.9 Å resolution.

Due to the ongoing strong scientific interest in understanding interferon and its properties, there is also an interest in obtaining crystals which are of superior quality and particularly useful for interferon structural determination.

SUMMARY OF THE INVENTION

The present invention provides a complex comprising an interferon alpha 2 dimer complexed with a divalent cation wherein said interferon is chemically modified with a half-life extending moiety wherein less than 50% of said moieties are on His 34. In an embodiment of the invention, about 0% of said moieties are on His 34. In an embodiment of the invention, more than 50% of said moieties are on Lys 49, Lys 121, Lys 31, His 7 and Cys 1. In an embodiment of the invention about 100% of said moieties are on Lys 49, Lys 121, Lys 31, His 7 and Cys 1. In an embodiment of the invention, said interferon is interferon alpha 2b (e.g., SEQ ID NO:1). In an embodiment of the invention, the complex is crystalline (e.g., which belongs to space group C2 or space group $P2_1$). In an embodiment of the invention, the crystal diffracts X-rays to about 2 Å resolution.

In an embodiment of the invention, the crystal belongs to space group $P2_1$ and diffracts X-rays to about 1.95 Å resolution.

The present invention provides a crystalline composition comprising comprising a complex of interferon-a2b-$Zn^{2+}$-interferon-a2b or a structural homologue thereof, wherein the complex three dimensional structure is characterized by structural coordinates comprising a root mean square deviation of common residue backbone atoms or alpha carbon atoms of less than about 1.5 Å when superimposed on backbone atoms or alpha carbon atoms described by structural coordinates of Table 3 or 4. In an embodiment of the invention, the composition comprises an interferon alpha 2b dimer complexed with $Zn^{2+}$ wherein said crystal belongs to C2 space group. In an embodiment of the invention, the crystal diffracts X-rays to a 2 Å resolution.

The present invention provides, a crystalline composition comprising an interferon alpha 2b dimer complexed with $Zn^{2+}$ wherein said crystal belongs to $P2_1$ space group and diffracts X-rays to about 1.95 Å resolution. In an embodiment of the invention, the crystal belongs to space group $P2_1$ comprising unit cell parameters a=62.2 Å, b=75.3 Å, c=149.2 Å and β=91.4°. In an embodiment of the invention, the crystal belongs to space group C2 comprising unit cell parameters a=114.7 Å, b=98.4 Å, c=62.4 Å and β=93.9°. In an embodiment of the invention, said crystal comprises a particle diameter of from about 1 μm to about 70 μm or from about 0.5 μm to about 7 μm.

The present invention also provides a pharmaceutical composition (e.g., sustained release formulation or a composition suitable for pulmonary delivery such as a dry powder) comprising any of the foregoing compositions and a pharmaceutically acceptable carrier. Also provided is an injectable device comprising the pharmaceutical composition. The present invention also provides a pharmaceutical composition of the invention in an inhaler.

The present invention also provides a method for producing a complex comprising an interferon alpha 2 dimer bound to a divalent cation wherein said interferon is chemically modified with a half-life extending moiety wherein less than 50% of said moieties are on His 34 comprising (1) expressing the interferon polypeptide in a bacterial cell;
(2) isolating a soluble fraction comprising the polypeptide from said cell;
(3) chromatographically purifying said polypeptide from said soluble fraction by cation exchange chromatography, weak anion exchange chromatography and cibacron Blue 3G chromatography;
(4) dialyzing said polypeptide against distilled water; and
(5) PEGylating said polypeptide.

Any complex produced by such a method is also part of the present invention along with any pharmaceutical composition thereof.

The present invention also provides a method for treating a host infected with a virus which is a member of the Flaviviridae family of viruses (e.g., hepatitis C virus) or preventing the infection by such a virus or for treating or preventing a hyperproliferative disease (e.g., leukemia), comprising administering (e.g., a sustained-release formuation or by inhalation) to said host a therapeutically effective amount of any of the interferon compositions set forth herein (e.g., crystalline compositions).

The present invention also provides a method for producing a complex comprising an interferon alpha 2 dimer bound to a divalent cation such as $Zn^{2+}$ comprising the steps of expressing the interferon polypeptide in a bacterial cell (e.g., *E. coli*, e.g., HB101); and isolating a soluble fraction comprising the interferon polypeptide from said cell (e.g., by the acidification and neutralization procedure of Liebowitz et al., U.S. Pat. No. 4,315,852 (discussed below)); optionally chromatographically purifying said polypeptide from said soluble fraction by standard chromatography steps such as cation exchange chromatography, weak anion exchange chromatography and cibacron Blue 3G chromatography (e.g., in that order), optionally dialyzing said polypeptide against distilled water and optionally dessicating or lyophilizing to a powder. In an embodiment of the invention, the Liebowitz extraction process mentioned above comprises the steps of acidifying the suspension of interferon-containing bacterial cells (e.g., with sulfuric acid or phosphoric acid, e.g., to pH of about 1.3-4.0 or 2.0-2.5), removing substantially all of the suspension liquid from the cells, preparing a second suspension of the acidified cells, neutralizing said second suspension (e.g., with potassium hydroxide or sodium hydroxide, e.g., to a pH of about 7.0-8.0 or 7.2-7.6), separating the interferon containing liquid from the suspended cells, and extracting the interferon from said liquid. Any product of such a method is with the scope of the present invention.

DETAILED DESCRIPTION OF THE INVENTION

Figure 1:
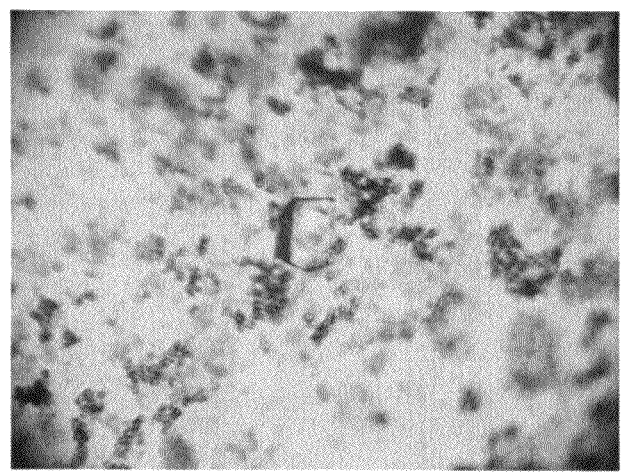
FIG. 1. Photomicrograph of crystals derived from flight based experiment at 70× magnification; Flight bottle #285.

The present invention comprises a novel crystal form of a zinc-interferon complex and a method for preparation of a crystalline interferon suspension. The interferon crystals of the present invention are highly ordered and of superior quality for therapeutic uses as well as for structural determination. The highly ordered structure is evidenced by the ability of the crystals of the invention to provide interferon structural data at a high resolution. The highly ordered structure of the crystals of the present invention make them particularly suitable for formulation in a sustained release formulation or for pulmonary delivery. X-ray crystallographic structures derived from these crystals have produced structures of interferon far better than any previous published reports. The work set forth herein produced crystals which belong to space group $P2_1$ which is the same space group as previously published in Radhardisrishnan, et al. Structure 4(12): 1453-1463 (1996). However, the crystal of the present invention led to the generation of a surprisingly high resolution structure (1.95 Å)—the previously developed crystal led to generation of only a 2.95 Å resolution structure.

Moreover, the work set forth herein produced an additional new crystal form-space group C2-which also diffracted beyond 2 Å resolution.

As stated above, the high quality structures obtained with the crystals of the present invention are also particularly useful because they allowed for determination of structural features of interferon not visible by the available, published lower quality structures. The availability of exceptionally high quality structural data relating to interferon aids in the understanding of the intermolecular interactions between interferon and other molecules and to the development of inhibitors and enhancers thereof as well as the development of modified interferon molecules possessing superior activity (e.g., anti-viral activity).

The present invention also provides $Zn^{2+}$ complexed interferon dimers and methods of production thereof. The dimers of the invention are useful, for example, in the treatment or prevention of viral infection as well as for the production of chemically modified (e.g., PEGylated) interferon which is modified preferentially on exposed amino acid residues. The dimerized, $Zn^{2+}$ complexed interferon of the invention is particularly suitable for the generation of a PEGylated version of the molecule since its natural state is a dimer. In an embodiment of the invention, the origin of $Zn^{2+}$ in the complex is the microbial cell (e.g., the cytoplasmic fluid) in which it is expressed. Naturally occurring interferon in the body of a human similarly encounters $Zn^{2+}$ and thereby forms a complex. The similarity of $Zn^{2+}$ complexed interferon to its natural state makes it particularly advantageous in the treatment or prevention of viral infections and hyperproliferative disorders.

The term "interferon" or "IFN" includes any form or type of interferon from any species (e.g., human). The term includes for example, interferon alpha 2a, interferon alpha 2b, interferon beta (e.g., beta 1A or beta 1B), consensus interferon, interferon gamma (e.g., gamma 1B) or interferon alpha N3. In an embodiment of the invention, the amino acid sequence of human interferon alfa-2b (IFNa2b or IFNa2b or interferon alpha 2b or interferon a2b) is as follows:

```
(SEQ ID NO: 1; optionally comprising an N-terminal
methionine)
Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn Leu Gln Glu Ser Leu Arg Ser Lys Glu.
```

Interferon alpha 2a (IFNa2a) is identical to IFNa2b but for the presence of a lysine at position 23 instead of an arginine (see e.g., Genbank accession no. 1ITF).

"Interferon alpha 2" includes interferon alpha 2a and interferon alpha 2b.

Crystals

The present invention comprises dimeric, metal complexed, interferon alpha 2a or 2b crystals (e.g., interferon alpha 2b crystals) exhibiting superior qualities (IFNa2-M-IFNa2; wherein M is a metal, e.g., a divalent cation such as $Zn^{2+}$, $Mg^{2+}$, $Mn^{2+}$, $Cd^{2+}$, $Ni^{2+}$, $Ca^{2+}$ or $Co^{2+}$). For example, the dimeric, metal complexed interferon alpha 2b crystals of the invention are of a high quality allowing for structural determination to a high resolution (e.g., about 1.95 or 2 Å).

Several crystallization methods are known in the art (Giegé, et al., (1994) Acta Crystallogr. D50: 339-350; McPherson, (1990) Eur. J. Biochem. 189: 1-23). Such methods include microbatch, hanging drop, seeding and dialysis. Preferably, hanging-drop vapor diffusion (McPherson, (1976) J. Biol. Chem. 251: 6300-6303) or microbatch methods (Chayen (1997) Structure 5: 1269-1274) are used. In each of these methods, it is important to promote continued crystal growth after nucleation by maintaining a supersaturated solution. In the microbatch method, polypeptide is mixed with precipitants to achieve supersaturation, the vessel is sealed and set aside until crystals appear. In the dialysis method, polypeptide is retained in a sealed dialysis membrane which is placed into a solution containing precipitant. Equilibration across the membrane increases the precipitant concentration thereby causing the polypeptide to reach supersaturation levels. It is desirable to use an IFNa2-M-IFNa2 (e.g., IFNa2b-$Zn^{2+}$-IFNa2b) protein preparation having a concentration of at least about 1 mg/mL, for example, from about 3 to about 10 mg/mL. It may also be desirable to include a protein stabilizing agent.

Crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing high-quality crystals which are preferred for diffraction analysis.

Once a crystal of the present invention is grown, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of IFNa2-M-IFNa2 (e.g., IFNa2b-$Zn^{2+}$-IFNa2b) or a fragment or fusion thereof. The present invention includes crystals which effectively diffract X-rays for the determination of the atomic coordinates of IFNa2-M-IFNa2 (e.g., IFNa2b-$Zn^{2+}$-IFNa2b) or a fragment or fusion thereof to a resolution of greater than about 5.0 Angstroms (e.g., about 4.5 Å, about 4.0 Å, about 3 Å, about 2.5 Å, about 2 Å, about 1.95 Å, about 1 Å), preferably greater than about 4.0 Angstroms (e.g., about 3 Å, about 2.5 Å, about 2 Å, about 1.95 Å, about 1 Å), more preferably greater than about 2.8 Angstroms (e.g., about 2.5 Å, about 2 Å, about 1.95 Å, about 1 Å) and most preferably greater than about 2.0 Angstroms (e.g., about 1.95 Å, about 1.5 Å, about 1.0 Å).

The present invention includes IFNa2-M-IFNa2 (e.g., IFNa2b-$Zn^{2+}$-IFNa2b) crystals whose three-dimensional structure is described by the structure coordinates set forth in Tables 3 and 4. The scope of the present invention also includes crystals that possess structural coordinates which are similar to those set forth in Tables 3 and 4. In an embodiment, the crystals include a polypeptide which includes the amino acid sequence of SEQ ID NO: 1. Structural similarity between crystals is discussed in detail below.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The present invention includes crystals exhibiting structural coordinates which are similar to those set forth in Table 3 or 4 but for crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the coordinates of Tables 3 or 4, the resulting three-dimensional shape is considered to be the same and, accordingly, the modified crystal is considered to be within the scope of the present invention.

Various computational analyses may be used to determine whether a crystal is sufficiently similar to the crystals whose structural coordinates are set forth in Tables 3 or 4 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation; and 4) analyze the results. Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as alpha carbon atoms (Ca) or all protein backbone atoms (N, Cα, C and O) for all conserved residues between the two structures being compared. When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Angstroms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

The term "least squares" relates to a method based on the principle that the best estimate of a value is that in which the sum of the squares of the deviations of observed values is a minimum.

For the purpose of this invention, any crystalline molecule characterized by a set of structure coordinates that has a RMSD of conserved residue backbone atoms (N, Cα, C, O) or of alpha carbon atoms (Cα) only of less than about 1.5 Å when superimposed—using backbone atoms or alpha carbon atoms—on the relevant structure coordinates of Table 3 or 4 are considered identical and are within the scope of the present invention. In an embodiment of the invention, the crystal comprises a polypeptide comprising the amino acid sequence of SEQ ID NO: 1. In an embodiment, the root mean square deviation is about 1.0 Å or about 0.75 Å or about 0.5 Å or about 0.25 Å or about 0.10 Å.

Computers

In accordance with the present invention, the structure coordinates of IFNa2-M-IFNa2 (e.g., IFNa2b-$Zn^{2+}$-IFNa2b) may be stored in a machine-readable storage medium. Such data may be used for a variety of purposes, such as X-ray crystallographic analysis of a protein crystal (e.g., for producing a three-dimensional representation of IFNa2b-$Zn^{2+}$-IFNa2b). Accordingly, one aspect of this invention provides a machine-readable data storage medium comprising a data storage material encoded with the structure coordinates set forth in Tables 3 or 4. The machine-readable data storage medium may also include any set of structure coordinates of a molecule that has a root mean square deviation of alpha carbon atoms (Cα) or of conserved residue backbone atoms (N, Cα, C, O) of less than about 1.5 Å, preferably, less than about 1.0 Å, more preferably less than about 0.5 Å and even more preferably less than about 0.1 Å when superimposed—using backbone atoms or only alpha carbon atoms (Ca)—on the relevant structure coordinates of Table 3 or 4.

A computer system, useful in reading the machine readable data storage medium, includes a computer comprising a central processing unit ("CPU") and a memory storage device and is also within the scope of the present invention. In general, the computer system may be any computer with an operating system such as MS-DOS, PC-DOS, Windows, OS/2, Unix, Unix variant or MacOS. Particularly preferred computer systems are the Silicon Graphics Octane workstation or Compaq AlphaServer DS20. Other hardware systems and software packages will be known to those skilled in the art.

Input hardware coupled to the computer system by input line, may be implemented in a variety of ways. Machine-readable data of this invention may be input via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal (e.g., a cathode ray tube (CRT)) for displaying a graphical representation of the three dimensional structure of IFN2b or a portion thereof using a program such as INSIGHT (Molecular Simulations Inc., San Diego, Calif.) or QUANTA as described herein. Output hardware might also include a printer, so that hard copy output may be produced, or a disk drive, to store system output for later use. In preferred embodiments, the computer possesses a display which is displaying a three dimensional representation of IFN2b or a fragment or homologue thereof.

In operation, the central processing unit (CPU) coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a manner which may be conventional, machine readable data, such as that described herein, for execution by a system as described herein. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In general, in the case of CD-ROM, as is well known, disk coating is reflective and is impressed with a plurality of pits to encode the machine-readable data. The arrangement of the pits is read by reflecting laser light off the surface of the coating. A protective coating, which preferably is substantially transparent, is provided on top of the coating.

In general, in the case of a magneto-optical disk, as is well known, disk coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Modified Interferon

The present invention comprises a chemically-modified interferon (e.g., interferon alpha 2, such as interferon-alpha 2b) composition along with methods for making the composition. The composition comprises a dimeric cationic metal such as $Zn^{2+}$ complexed with dimerized IFNa2 (e.g., IFNa2b such as SEQ ID NO: 1) which is preferentially chemically modified (e.g., PEGylated) on amino acid residues that are exposed and not buried in the IFNa2 interface. The chemically-modified interferon compositions of the present invention comprise a high proportion of dimerized interferon, the natural biological form of the protein (see e.g., Nagabhushan et al., Can. J. Chem. 80:1166-1173 (2002)). The presence of a high proportion of the naturally occurring interferon dimer is an advantage of the present invention since the dimers will exhibit high levels of biological activity (e.g., anti-viral activity when administered to a patient). Chemical modification on sites other than those that are buried in an interferon alpha 2 dimer, for example, other than on residues that are buried in the intermolecular IFNa2 dimer interface, allows a greater proportion of the interferon alpha 2 in a composition to assume the natural dimerized state.

The scope of the present invention includes embodiments wherein the chemically modified, $Zn^{2+}$ complexed and dimerized IFNa is a crystalline composition. For example, the complexed, dimerized interferon alpha, that is PEGylated, can be any such crystal as described herein (e.g., IFNa2b-$Zn^{2+}$-IFNa2b belonging to the P21 or C2 space group and/or characterized by structural coordinates set forth in table 3 or 4).

Moreover, individual monomers of such a chemically modified dimer of the invention are within the scope of the invention.

The interferon can be modified with any chemical moiety, for example, a polymer such as succinimidyl carbonyl methoxypolyethylene glycol 5000 (SC PEG5000), a polyalkylene oxide comprising an alkyl terminal, polypropylene glycol, dextran, polyvinyl pyrrolidones, polyacryl amides, polyvinyl alcohols or any carbohydrate-based polymer.

In an embodiment of the invention, the chemical modification is PEGylation (attachment of polyethylene glycol (PEG) molecules to amino acid residues in the interferon). PEGylation can occur on any of several exposed residues in the $Zn^{2+}$ complexed and dimerized IFNa2 (e.g., IFNa2b).

In an embodiment of the invention, His 34 is blocked from chemical modification (e.g., PEGylation) in the dimerized interferon alpha. In an embodiment, Lys 49, Lys 121, Lys 31, His 7 and Cys 1 are exposed in a dimerized interferon alpha and are preferentially modified (e.g., PEGylated in a PEG-interferon alpha 2 molecule (e.g., IFNa2b)).

In an embodiment of the invention, in a composition comprising dimerized interferon alpha (e.g., IFNa2b), modification, such as PEGylation, at His 34 constitutes less than 50% of the overall modification (e.g., PEGylation (e.g., essentially 0%)). In an embodiment of the invention, essentially 100% of modification (e.g., PEGylation) in a composition comprising dimerized modified interferon (e.g., PEG-interferon (e.g., PEG-IFNa2b)) is on residues Lys 49, Lys 121, Lys 31, His 7 and Cys 1. In an embodiment of the invention, essentially 100% of modification (e.g., PEGylation) in a composition comprising dimerized modified interferon (e.g., PEG-interferon (e.g., PEG-interferon alpha 2a)) is on residues Lys 49, Lys 121, Lys 31. As used in this context, % of overall modification refers to the percentage of a given interferon residue in a composition that are modified, e.g., by PEGylation. For example, an embodiment of the invention, comprise interferon wherein less than 50% of the His 34 interferon residues in a given composition are modified.

Methods for PEGylating interferon alpha 2 (e.g., IFNa2b) are well known in the art (see e.g., U.S. Pat. No. 5,711,944). In an embodiment of the invention, a $Zn^{2+}$ complexed and dimerized PEG-IFNa2 (e.g., PEG-IFNa2b) is generated by a method comprising the steps of first forming the dimer, then contacting the dimer with from about a 1 to about an 8-fold molar excess of an activated PEG in the presence of a surfactant (e.g., ionic surfactant such as sodium dodecyl syulfate or lithium dodecyl sulfate, quaternary ammonium compounds, taurocholic acid, caprylic acid, decane sulfonic acid or mixtures thereof) under conditions sufficient to form conjugates of said dimer and said PEG and thereafter fractionating the conjugates to isolate the conjugates containing about 1-4 PEG strands per IFNa2 (e.g., IFNa2b) dimer.

The PEG can be of any size. For example, in an embodiment of the invention, the PEG is from about 200 to about 35,000 or 40,000 or from about 1,000 to about 15,000 or from about 2,000 to about 12,500. PEG can be straight chain or branched (e.g., PEG 40,000 branched chain). Branched chain PEG-interferon a2b is e.g., described in Ramon et al., Pharm Res. 22(8):1374-86 (2005).

The present invention provides a method for producing purified $Zn^{2+}$ complexed INFa2 (e.g., IFNa2b) dimer comprising expressing the protein in *E. coli*, for example as disclosed by Weissmann, et al. Science, 209: 1342 (1980). The *E. coli* cells expressing the protein are lysed and a soluble fraction is obtained. The soluble fraction is then purified chromatographically using S-sepharose, blue sepharose and DEAE sepharose. The chromatographically purified material is then dialyzed versus water (e.g., double glass distilled water) and lyophilized to an amorphous solid. In an embodiment of the invention, the purified $Zn^{2+}$ complexed IFNa2 (e.g., IFNa2b) dimer is chemically modified (e.g., PEGylated). The protein can be PEGylated by any of several methods known in the art. For example, Zalipsky et al., reported use of a succinimidyl carbonate form of PEG (SC-PEG) as a reagent for protein PEGylation (Biotechnol Appi Biochem. 15(1):100-114 (1992)). Any IFNa2 polypeptide produced by such a procedure along with any use of such a polypeptide, for example, as set forth herein, forms part of the present invention. In an embodiment of the invention, the $Zn^{2+}$ in the complex is not specifically added to the inferferon; rather, it becomes complexed with interferon due to its presence in the cells in which the interferon polypeptide is expressed. The present invention also comprises methods and compositions wherein the $Zn^{2+}$ is specifically added.

Therapeutic Methods

Compositions of the invention, for example, any crystalline IFNa2 set forth herein (e.g., IFNa2b-$Zn^{2+}$-IFNa2b comprising the structural coordinates set forth in Table 3 or 4) or a chemically modified IFNa2 (e.g., PEG-IFNa2b) of the invention can be used therapeutically for the treatment or prevention of a cell proliferation disorder or a viral infection (e.g., Flaviviridae virus such as hepatitis C virus). The crystalline complex is particularly suitable for pulmonary delivery to a patient. For example, an embodiment of the present invention comprises treating or preventing viral infection or a cell proliferation disorder, in a subject, by pulmonary administration (e.g., by inhalation), to the subject, of crystalline metal-complexed and dimerized IFNa2 by inhalation (e.g., IFNa2b-$Zn^{2+}$-IFNa2b). Another embodiment of the present invention comprises treating or preventing viral infection or a cell proliferation disorder, in a subject, by administering an interferon of the present invention, for example, crystalline metal-complexed and dimerized IFNa2 (e.g., IFNa2b-$Zn^{2+}$-IFNa2b) or a PEG-IFNa2 of the invention (e.g., PEG-IFNa2b), in a sustained release pharmaceutical formulation, to the subject.

In an embodiment of the invention, an interferon of the present invention (e.g., crystalline IFNa2b-$Zn^{2+}$-IFNa2b or PEG-IFNa2b) is administered to the subject in association with any further chemotherapeutic agent (e.g., an anti-viral agent such as ribavirin or an anti-proliferative agent).

In an embodiment of the invention, the metal-complexed and dimerized IFNa2 (e.g., IFNa2b-$Zn^{2+}$-IFNa2b) or a PEG-IFNa2 (e.g., PEG-IFNa2b-$Zn^{2+}$-PEG-IFNa2b) of the invention is administered in a "therapeutically effective" amount or dosage. A therapeutically effective amount or dosage is any amount or dosage that is sufficient to prevent a cell proliferation disorder or a viral infection or to treat any symptom or effect of the cell proliferation disorder or viral infection including, for example, eradication of the infection or disorder. In an embodiment of the invention, a therapeutically effective amount or dosage is about 1.0 µg/kg/week. The present invention also includes embodiments wherein the interferon or PEGylated interferon is administered at 0.1 µg/kg/week, 0.25 µg/kg/week, 0.5 µg/kg/week, 0.75 µg/kg/week, 2 µg/kg/week, 3 µg/kg/week, 4 µg/kg/week, 5 µg/kg/week, 6 µg/kg/week, 7 µg/kg/week, 8 µg/kg/week, 9 µg/kg/week, 10 µg/kg/week, 50 µg/kg/week, 75 µg/kg/week, 100 µg/kg/week, 125 µg/kg/week, 150 µg/kg/week or 200 µg/kg/week. The dosage can be given for any period of time including, for example, 1 month, 3 months, 6 months, 1 year or more.

Dosage regimens can be adjusted to provide the optimum desired response (e.g., a therapeutic response). For example, the dose can be reduced or increased as indicated by exigencies of the therapeutic situation. For example, dosage can be adjusted, by a practitioner of ordinary skill in the art (e.g., physician or veterinarian) according to the drug's efficacy, progression or persistence of the disease or any of its symptoms or the patient's age, weight, height, past medical history, present medications and the potential for cross-reaction, allergies, sensitivities and adverse side-effects.

A physician or veterinarian having ordinary skill in the art can readily determine and prescribe the effective amount of the pharmaceutical composition required. For example, the physician or veterinarian could start doses of an interferon of the invention or a pharmaceutical composition thereof at levels lower than that required in order to achieve the desired therapeutic effect and gradually increase the dosage until the desired effect is achieved.

For example, the progress and severity of a viral infection, for example an HCV infection, can be monitored by periodic determination of the following profiles in the subject being treated:
(a) elevated ALT and/or AST,
(b) positive test for anti-HCV antibodies,
(c) presence of HCV as demonstrated by a positive test for HCV-RNA,
(d) clinical stigmata of chronic liver disease,
(e) hepatocelluar damage.

Elevated serum alanine aminotransferase (ALT) and aspartate aminotransferase (AST) are known to occur in uncontrolled hepatitis C, and a complete response to treatment is generally defined as the normalization of these serum enzymes, particularly ALT (Davis et al., New Eng. J. Med. 321:1501-1506 (1989)). ALT is an enzyme released when liver cells are destroyed and is symptomatic of HCV infection. Interferon causes synthesis of the enzyme 2',5'-oligoadenylate synthetase (2'5'OAS), which, in turn, results in the degradation of the viral mRNA. (Houglum, Clinical Pharmacology 2:20-28 (1983)). Increases in serum levels of the 2'5'OAS coincide with decrease in ALT levels.

In order to follow the course of HCV replication in subjects in response to drug treatment, HCV RNA may be measured in serum samples by, for example, a nested polymerase chain reaction assay that uses two sets of primers derived from the N53 and N54 non-structural gene regions of the HCV genome. (Farci et al., New Eng. J. Med. 325:98-104 (1991); Ulrich et al., J. Clin. Invest., 86:1609-1614 (1990)).

Histological examination of liver biopsy samples may be used as a second criteria for evaluation. See, e.g., Knodell et al., Hepatology 1:431-435 (1981), whose Histological Activity Index (portal inflammation, piecemeal or bridging necrosis, lobular injury and fibrosis) provides a scoring method for disease activity.

Any clinician or veterinarian of ordinary skill in the art could interpret the results of such tests and alter the dosage regimen accordingly so as to obtain the desired therapeutic effect.

An embodiment of the invention comprises treating HCV infection for a period of time sufficient to eradicate detectable HCV RNA and to maintain no detectable HCV RNA for at least twelve weeks after the end of the treatment time period (e.g., 24 weeks, 48 weeks or 1 year).

The term Flaviviridae virus includes for example, viruses of the *Hepacivirus* genus which includes the Hepatitis C virus (HCV). HCV includes several types, subtypes and isolates:
Hepatitis C virus (isolate 1)
Hepatitis C virus (isolate BK)
Hepatitis C virus (isolate EC1)
Hepatitis C virus (isolate EC10)
Hepatitis C virus (isolate HC-J2)
Hepatitis C virus (isolate HC-J5)
Hepatitis C virus (isolate HC-J6)
Hepatitis C virus (isolate HC-J7)
Hepatitis C virus (isolate HC-J8)
Hepatitis C virus (isolate HC-JT)
Hepatitis C virus (isolate HCT18)
Hepatitis C virus (isolate HCT27)
Hepatitis C virus (isolate HCV-476)
Hepatitis C virus (isolate HCV-KF)
Hepatitis C virus (isolate Hunan)
Hepatitis C virus (isolate Japanese)
Hepatitis C virus (isolate Taiwan)
Hepatitis C virus (isolate TH)
Hepatitis C virus isolate H
Hepatitis C virus type 1
Hepatitis C virus type 1a
Hepatitis C virus strain H77
Hepatitis C virus type 1b
Hepatitis C virus type 1c
Hepatitis C virus type 1d
Hepatitis C virus type 1e
Hepatitis C virus type 1f
Hepatitis C virus type 10
Hepatitis C virus type 2
Hepatitis C virus type 2a
Hepatitis C virus type 2b
Hepatitis C virus type 2c
Hepatitis C virus type 2d
Hepatitis C virus type 2f
Hepatitis C virus type 3
Hepatitis C virus type 3a
Hepatitis C virus type 3b
Hepatitis C virus type 3g
Hepatitis C virus type 4
Hepatitis C virus type 4a
Hepatitis C virus type 4c
Hepatitis C virus type 4d
Hepatitis C virus type 4f
Hepatitis C virus type 4h
Hepatitis C virus type 4k
Hepatitis C virus type 5
Hepatitis C virus type 5a
Hepatitis C virus type 6
Hepatitis C virus type 6a
Hepatitis C virus type 7
Hepatitis C virus type 7a
Hepatitis C virus type 7b
Hepatitis C virus type 8
Hepatitis C virus type 8a The present invention also includes methods for treating or preventing infection caused by members of the *Flavivirus* genus. The *Flavivirus* genus includes Yellow fever virus; Tick-borne viruses such as the Gadgets Gully virus, Kadam virus, Kyasanur Forest disease virus, Langat virus, Omsk hemorrhagic fever virus, Powassan virus, Royal Farm virus, Karshi virus, Tick-borne encephalitis virus, Neudoerfl virus, Neudoerfl virus, Sofjin virus, Louping ill virus and the Negishi virus; seabird tick-borne viruses such as the Meaban virus, Saumarez Reef virus, and the Tyuleniy virus; mosquito-borne viruses such as the Aroa virus, Bussuquara virus, Iguape virus and the Naranjal virus; Dengue viruses such as the Dengue virus and the Kedougou virus; Japanese encephalitis viruses such as the Cacipacore virus, Koutango virus, Japanese encephalitis virus, Murray Valley encephalitis virus, Alfuy virus, St. Louis encephalitis virus, Usutu virus, West Nile virus, Kunjin virus and the Yaounde virus; Kokobera viruses such as the Kokobera virus and the Stratford virus; Ntaya viruses such as the Bagaza virus, Ilheus virus, Rocio virus, Israel turkey meningoencephalomyelitis virus, Ntaya virus and the Tembusu virus; Spondweni viruses such as the Zika virus and the Spondweni virus; Yellow fever viruses such as the Banzi virus, Bouboui virus, Edge Hill virus, Jugra virus, Saboya virus, Potiskum virus, Sepik virus, Uganda S virus, Wesselsbron virus and the Yellow fever virus; Entebbe viruses such as the Entebbe bat virus, Sokoluk virus, and the Yokose virus; Modoc viruses such as the Apoi virus, Cowbone Ridge virus, Jutiapa virus, Modoc virus, Sal Vieja virus and the San Perlita virus; Rio Bravo viruses such as the Bukalasa bat virus, Carey Island virus, Dakar bat virus, Montana myotis leukoencephalitis virus, Phnom Penh bat virus, Batu Cave virus, Rio Bravo virus, Tamana bat virus, and the Cell fusing agent virus. The present invention includes methods for treating or preventing infection caused by members of the *Pestivirus* genus. The *Pestivirus* genus includes Bovine viral diarrhea virus 1, Border disease virus (sheep), Bovine viral diarrhea virus 1, Bovine viral diarrhea virus 2, Classical swine fever virus and Hog cholera virus.

Moreover, the present invention includes methods for treating or preventing infections caused by Hepatitis G virus or Hepatitis GB virus-A, B or C.

The term "cell proliferation disorder" includes, but is not limited to, for example, any type of cancer such as, for example, any type of leukemia including hairy cell leukemia, Kaposi's sarcoma, chronic myelogenous leukemia, multiple myeloma, basal cell carcinoma and malignant melanoma, ovarian cancer, cutaneous T cell lymphoma or for chronic phase, Philadelphia chromosome (Ph) positive chronic myelogenous leukemia (CML).

Pharmaceutical Compositions

The scope of the present invention comprises any of the crystals of the present invention formulated in a pharmaceutically acceptable carrier. Examples of pharmaceutically acceptable carriers and methods of manufacture for various compositions may be found in A. Gennaro (ed.), *Remington's Pharmaceutical Sciences*, 18th edition, (1990), Mack Publishing Co., Easton, Pa. or in Howard C. Ansel, Pharmaceutical Dosage Forms and Drug Delivery Systems, $6^{th}$ edition, (1995), Williams & Wilkins, Media, Pa.

Pharmaceutical compositions of an interferon of the invention suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g., human plasma albumin), toxicity agents (e.g., NaCl), preservatives (e.g. thimerosol, cresol or benzyl alcohol), and surfactants (e.g., tween or polysorbates) in sterile water for injection. For example, an embodiment of the invention includes a pharmaceutical composition comprising a soluble polypeptide IFNa2-$Zn^{2+}$-IFNa2 complex or a complex between chemically modified interferon alpha 2 and $Zn^{2+}$ (e.g., PEGylated IFNa2 and $Zn^{2+}$), for example (PEG-IFNa2b)-$Zn^{2+}$-(PEG-IFNa2b), in association with a pharmaceutically acceptable carrier. In an embodiment, as discussed herein, the (PEG-IFNa2b)-$Zn^{2+}$-(PEG-IFNa2b) is preferentially PEGylated on exposed residues. The interferon may be stored as a lyophilized powder under refrigeration at 2°-8° C. The reconstituted aqueous solutions are stable when stored between 2°-8° C. and used within 24 hours of reconstitution. See, for example, U.S. Pat. Nos. 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alpha powder in a separate compartment.

The present invention comprises a sustained-release, controlled-release, prolonged-release, timed-release, slow-release, sustained-action, prolonged action, extended action or rate-controlled pharmaceutical formulation comprising an interferon crystal of the invention (e.g., a crystal comprising an IFNa2b-$Zn^{2+}$-IFNa2b complex). The present invention also comprises a pharmaceutical formulation comprising a crystal of the invention suitable for pulmonary administration, e.g., by inhalation. The crystals of the present invention are particularly suitable for pulmonary or sustained release pharmaceutical formulations and administration, for example, because the crystals diffract to a higher resolution than other interferon crystals. For example, in an embodiment of the invention, a crystal of the invention diffracts to a resolution of about 1 Å. The ability to diffract and yield a high resolution structure indicates that the molecules in the crystals are highly ordered. Highly ordered crystals will exhibit a highly predictable dissolution rate when placed in an aqueous environment, such as the subcutaneous tissue or the lungs. A highly predictable dissolution rate allows the pharmacokinetic parameters of a crystal, that has been administered to a subject, to be predicted relatively easily and for dosage to be predicted and controlled relatively easily.

In an embodiment of the invention, a crystal of the invention, suitable for a sustained release formulation comprises a size of from about 1 µm to about 70 µm (diameter). Methods for making sustained-release formulations are well known in the art.

In an embodiment of the invention, a sustained-release of an interferon of the invention is a sustained and/or modulated release of the IFN from a biocompatible polymeric matrix. For example, an embodiment of the invention includes a composition for the controlled release of an interferon of the invention from a polymeric matrix, comprising a biocompatible polymer; and crystalline particles of the interferon, wherein said particles are dispersed within the biocompatible polymer. For example, in an embodiment of the invention, a sustained release is a release of an interferon of the invention over a period of up to about one week to about six months. A sustained release of an interferon of the invention from a polymeric matrix can be continuous or non-continuous release with relatively constant or varying rates of release. The continuity of interferon release and level of interferon release can be affected by use of one or more types of polymer compositions, interferon loadings, and/or selection of excipients to produce the desired effect.

In an embodiment of the invention, a sustained release formulation comprises an interferon crystal of the invention in a GRAS (generally recognized as safe) formulation suitable for subcutaneous injection. For example, in an embodiment of the invention, the formulation comprises a sterile IFNa2-$Zn^{2+}$-IFNa2 (e.g., IFNa2b-$Zn^{2+}$-IFNa2b; e.g., SEQ ID NO: 1) crystalline suspension ($34\times10^6$ IU/dose) in 10 mM sodium acetate, 10 mM zinc acetate and 0.4 mM protamine sulfate, pH 5.5 buffer. Accordingly, the present invention comprises methods for treating or preventing a viral infection (e.g., HCV) or treating or preventing a hyperproliferative disease (e.g., leukemia) by administering such a formulation to a subject (e.g., a mammal such as a human), for example, by subcutaneous injection. Moreover, the scope of the present invention comprises an injectable device comprising such a formulation.

In an embodiment of the invention, a biocompatible, biodegradable polymer for use in a sustained-release of an interferon of the invention includes, for example, poly(lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetals, polycyanoacrylates, polyetheresters, poly(dioxanone)s, poly(alkylene alkylate)s, copolymers of polyethylene glycol and polyorthoester, biodegradable polyurethanes, blends and copolymers thereof.

In an embodiment of the invention, a biocompatible, non-biodegradable polymer suitable for the modulated release composition of this invention includes non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

A polymer, or polymeric matrix, is biocompatible if the polymer, and any degradation products of the polymer, are non-toxic to the recipient and also present no significant deleterious or untoward effects on the recipient's body, such as an immunological reaction at the injection site.

In an embodiment of the invention, an interferon crystal of the invention is formulated into a liposome for sustained release. In this embodiment of the invention, the crystal is formulated into a single- or multi-layer vesicle which comprises an aqueous vesicle comprising the crystal surrounded by either a single lipid layer or a concentric lipid layer. Generally, the lipid layer is a phospholipid. In an embodiment of the invention, the formulation is suitable for parenteral administration.

In an embodiment of the invention, a sustained release pharmaceutical formulation of the invention comprises an interferon crystal of the invention in a highly viscous carrier. In an embodiment of the invention, the formulation is suitable for parenteral administration. In an embodiment of the invention, the medium is thickened with an agent such as methylcellulose, sodium carboxymethylcellulose or polyvinylpyrrolidone.

In an embodiment of the invention, a sustained release pharmaceutical formulation of the invention comprises an interferon crystal of the invention in an oil solution, suspension or emulsion. In an embodiment of the invention, the formulation is suitable for parenteral administration. In an embodiment of the invention, the oil is sesame oil, olive oil, arachnis, maize, almond oil, cottonseed oil, or castor oil.

In an embodiment of the invention, a sustained release pharmaceutical formulation of the invention comprises an interferon crystal of the invention in an implantable device/formulation. For example, in an embodiment of the invention, the crystal is encapsulated in a compartment that is enclosed by a rate-limiting polymeric membrane.

In an embodiment of the invention, a sustained release pharmaceutical formulation of the invention is administered by injection under the skin of a subject, subcutaneously.

The present invention comprises a pharmaceutical formulation for inhaled/pulmonary delivery comprising an interferon crystal of the invention (e.g., a crystal comprising an interferon-a2b-$Zn2^+$-interferon-a2b complex). There are numerous formulations known in the art for pulmonary delivery of polypeptides and crystals thereof which can be used to formulate and deliver an interferon of the invention. In an embodiment of the invention, the particle size of the interferon crystal is from about 0.5 µm to about 7 µm (diameter). In an embodiment of the invention, the particle size is less than about 1 µm. The present invention comprises a dry powder inhaler, metered-dose inhaler or a nebulizer comprising an interferon of the invention. A metered-dose inhaler product typically contains an interferon of the invention dissolved or suspended in a propellant, a mixture of propellants, or a mixture of solvents, propellants, and/or other excipients in compact pressurized aerosol dispensers.

An embodiment of the invention comprises a pulmonary delivery formulation of the invention comprising a crystalline suspension of an interferon of the invention (e.g., $10\text{–}50\times10^6$ international units) suspended in sterile filtered 5 mM sodium acetate, pH 6.1 and 0.1% Tween 80 (pharmaceutical grade).

For example, an embodiment of the invention includes a concentrated stable, aqueous formulation of an interferon of the invention for pulmonary/aerosol delivery comprising the interferon of the invention; a buffer system (e.g., acetic acid, arginine, ascorbic acid, asparagines, benzoic acid, boric acid, citrate, cysteine, fumaric acid, glutamic acid, glycyl-glycine, histidine, homocysteine, hydroxylysine, lysine, malic acid, phosphate, succinate, tris or tartaric acid buffer system); a stabilizer (e.g., poly(oxy-1,2-ethanediyl) derivative, such as polyoxyyethlene 20 sorbitan monolaurate or sorbitan, monododecanoate, also called Polysorbate 20 or Tween 20, or high purity Polysorbate 20 or Tween 20 derived from non-animal sources with low peroxide and low carbonyl content); and water.

A dry powder inhaler can be, for example, a pre-metered inhaler or a device-metered dry powder inhalers, both of which can be driven by patient inspiration alone or with power-assistance of some type. Pre-metered dry powder inhalers typically contain previously measured doses or dose fractions in some type of units (e.g., single or multiple presentations in blisters, capsules, or other cavities) that are subsequently inserted into the device during manufacture or by the patient before use. Thereafter, the dose may be inhaled directly from the pre-metered unit or it may be transferred to a chamber before being inhaled by the patient. Device-metered dry powder inhalers typically have an internal reservoir containing sufficient formulation for multiple doses that are metered by the device itself during actuation by the patient.

Compositions comprising any interferon of the present invention (e.g., crystalline IFNa2b (e.g., comprising structural coordinates set forth in Table 3 or 4) or a chemically modified PEG-IFN (e.g., PEG-IFNa2b)) in association with a further chemotherapeutic agent are within the scope of the present invention.

In an embodiment of the invention, the interferon is provided in association with an anti-viral or anti-cancer chemotherapeutic agent. For example, in an embodiment of the present invention, the further chemotherapeutic agent is one or more members selected from the group consisting of: gemcitabine

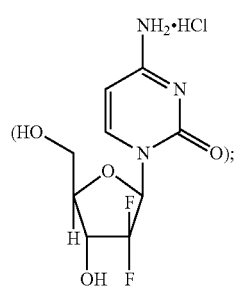

VX497

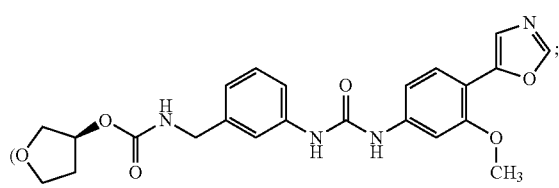

mycophenolate mofetil (MMF; 2-morpholinoethyl (E)-6-(1, 3-dihydro-4-hydroxy-6-methoxy-7-methyl-3-oxo-5-isobenzofuranyl)-4-methyl-4-hexenoate); administering EICAR

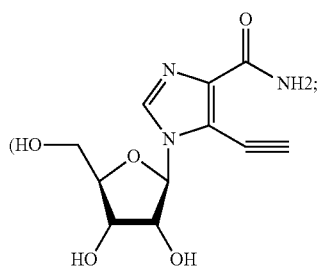

5-ethynyl-1-beta-D-ribofuranosylimidazole-4-carboxamide; Balzarini et al., J. Biol. Chem. 268(33): 24591-24598 (1993)); isatoribine

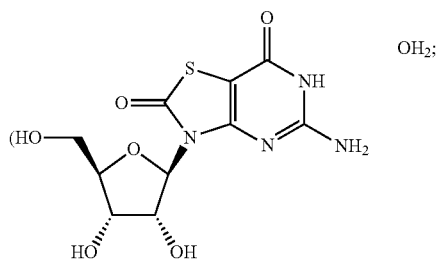

ANA245; 5-Amino-3-beta-D-ribofuranosylthiazolo(4,5-d) pyrimidine-2,7(3H,6H)-dione monohydrate; Thiazolo(4,5-d)pyrimidine-2,7(3H,4H)-dione, 5-amino-3-beta-D-ribofuranosyl-, monohydrate); VX-950

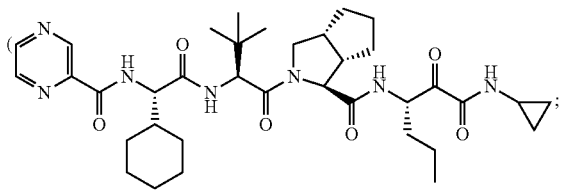 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]

Lin et al., J. Biol. Chem. 279(17): 17508-17514 (2004)); viramidine

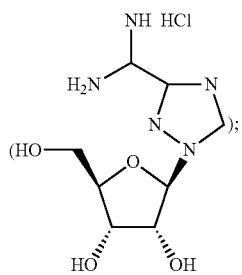

levovirin

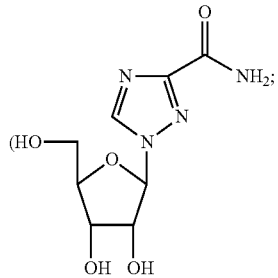

and ribavirin

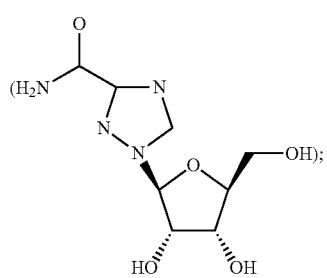

1-β-D-ribofuranosyl-1H-1,2,4-triazole-3-carboxamide).

The term "in association" indicates that the components of the combinations of the invention can be formulated into a single composition for simultaneous delivery or formulated separately into two or more compositions (e.g., a kit). Furthermore, each component of a combination of the invention can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., orally, intravenously, subcutaneously).

The scope of the present invention also comprises administering any interferon composition of the invention in association with a further chemotherapeutic agent to treat or prevent a medical disorder such as viral infection or a cell proliferation disorder (e.g., as discussed above).

EXAMPLES

The following Examples are intended for exemplification of the present invention only and should not be construed to limit the scope of the invention. Any composition or method disclosed in the Examples section forms part of the present invention.

Ground and flight based crystals were generated using a protein crystallization facility (PCF) apparatus (see U.S. Pat. No. 6,027,565).

Example 1

Preparation and Purification of Interferon Alpha-2b Dimers Coordinated with Zinc The interferon alfa-2 employed was recombinant human interferon alfa-2b expressed in *E. coli* as described in Weissmann, et al. Science, 209, 1342 (1980). The cells were cultured, harvested and extracted as previously reported in Leibowitz, P. et al (1982) U.S. Pat. No. 4,315,852. Briefly, the extraction involved acidifying the suspension of interferon-containing bacterial cells, removing the suspension liquid from the cells, preparing a second suspension of the acidified cells and neutralizing the second suspension, then separating the interferon containing liquid from the suspended cells, and extracting the interferon from the liquid. This extraction method efficiently released the interferon from the cells, upon neutralization of the suspension of acidified cells, without the need for mechanical or enzymatic disruption of the cell surface. The resulting extracts were purified by a combination of conventional purification steps (cation exchange, weak anion exchange and cibacron Blue 3G chromatography). The resulting purified interferon alpha-2b (4 liters; 5.4 mg/ml) preparation was dialyzed versus 20 l of double glass distilled water (Corning Mega Pure water purification unit; Corning, N.Y.) (2×20 li) and lyophilized to amorphous solid. In the examples set forth below, two sets of interferon crystallization experiments were performed in parallel. One set was performed on the Space Shuttle Columbia (STS-107). The other set was performed on the ground.

Example 2

Crystallization Conditions for Flight Experiments

Pre-Crystallization Processing (Flight).

All operations were performed under clean room conditions at 4° C. 109 mg of lyophilized interferon alpha 2b amorphous solid as described in example 1, was dissolved in 11 ml of 30 mM sodium acetate (Fluka BioChemika Buchs, AG; sodium acetate anhydrous cat #71183), pH 6.03 (1M Sodium chloride (Fluka BioChemika Buchs, AG; sodium chloride anhydrous cat #71376) stock solution was added drop wise to a conductivity reading of 5 milli-siemens) at 4° C. The resulting solution was dialyzed in a Spectrum (Rancho Dominguez, Ca, USA; Spectra/por RC float-a-lyzer cat #23510; 10 thousand molecular weight cutoff) versus a dialyzate 200 mL of 30 mM sodium acetate, pH 6.03(1 M Sodium chloride stock solution was added drop wise to a conductivity reading of 5 milli-siemens). The dialysis was continued with a fresh dialyzate (200 ml) for 18 hours at 4° C. The resulting solution was filtered using a 0.22 micron 50 ml tube top filter (Corning Inc. Corning N.Y., USA cat #430320). Prior to loading into 70% ethanol/sterile water washed 1 ml PCF (protein crystallization facility) polysulfone sample bottles, the pH was adjusted drop-wise with either 0.1 M acetic acid or 0.1 M sodium hydroxide to final pH 5.95-6.0. The PCF polysulfone sample bottles were stacked and placed in the containment hardware before being placed in a pre-cooled commercial refrigerator module (C-RIM).

Crystallization Processing (Flight).

The fully loaded C-RIM was integrated onto the Space Shuttle Columbia 48 hours prior to launch in a Spacehab modular locker. After launch of STS-107, and once in orbit, the crew initiated the linear temperature ramp program 4-22° C. over 48 hours. Once the terminal temperature was reached, the temperature was maintained at 22° C. for the duration of the remaining 14 days of the flight. The shuttle disintegrated on re-entry, however, some crystal samples were recovered.

Post Flight Processing (Flight).

Sampling for photo microscopy and X-ray crystallographic analysis.

Using a Pasteur glass pipette, aliquots of crystalline suspension from the recovered bottles was harvested for microscopic inspection. These aliquots were examined using photo microscopy using a Nikon SMZ-U microscope/Kodak DSC 402 camera system. In Example 4 is shown a photomicrograph of an observed crystal from flight bottle #285 (70× magnification).

Bio-Physical and Bioactivity Analysis:

Bottle contents were sampled by taking aliquots (100 ul) of crystalline suspension using centrifugation at 5K RPM/5 minutes using an Eppindorf microfuge to separate suspended solids from centrifugate. The supernatant was decanted from the pellet. The pellet was washed with 30 mM sodium acetate, pH 6.05 (2× at 22° C.). Subsequently, the pellet was dissolved in 25 mM sodium phosphate, pH 7.5, 150 mM sodium chloride (2° C.) by vortexing for 30 seconds (5×). The resulting solution was clarified by centrifugation using a 5K RPM/5 minutes using an Eppindorf microfuge to separate suspended solids from centrifugate. The resulting supernatant was characterized by biochemical and bioactivity methods described in example 6.

Example 3

Ground Crystallization Experiments

Pre-Crystallization Processing (Ground).

All operations were performed under clean room conditions at 4° C. 109 mg of lyophilized interferon alpha 2b amorphous solid as described in example 1 was dissolved in 11 ml of 30 mM sodium acetate, pH 6.03 (Fluka BioChemika, Buchs, AG; sodium acetate anhydrous, cat #71183), 1M Sodium chloride (Fluka BioChemika Buchs, AG; sodium chloride anhydrous cat #71376) stock solution was added drop wise to a conductivity reading of 5 milli-siemens) at 4° C. The resulting solution was dialyzed in a Spectrum (Rancho Dominguez, Ca, USA; Spectra/por RC float-a-lyzer cat #235105; 10 thousand molecular weight cutoff) versus a dialyzate 200 ml of 30 mM sodium acetate, pH 6.03 (1 M Sodium chloride stock solution was added drop wise to a conductivity reading of 5 milli-siemens). The dialysis was continued with a fresh dialyzate (200 ml) for 18 hours at 4° C.

The resulting solution was filtered using a 0.22 micron 50 ml tube top filter (Corning Inc.; Corning, N.Y.). Prior to loading into 70% ethanol/sterile water washed 1 ml PCF bottles, the pH was adjusted drop wise with either 0.1M acetic acid or 0.1 M sodium hydroxide to final pH 5.95-6.0. The PCF bottles were stacked and placed in the containment hardware before being placed in a pre-cooled commercial refrigerator module (C-RIM).

Crystallization Processing (Ground).

The fully loaded C-RIM was maintained at 4° C. until the linear temperature ramp program 4-22° C. over 48 hours was initiated corresponding to the same time as the flight experiment described in example 2. Once the terminal temperature was reached the temperature was maintained at 22° C. for 8 months (post crystallization processing).

Post Crystallization Processing (Ground).

Sampling for photo microscopy and X-ray crystallographic analysis:

Using a Pasteur glass pipette, aliquots of crystalline suspension from the recovered bottles was harvested for microscopic inspection. These aliquots were examined using photo microscopy using a Nikon SMZ-U microscope/Kodak DSC 402 camera system. In Example 5 is shown a photomicrograph of an observed crystal from a ground bottle #G-III-7 (70× magnification).

Bio-Physical and Bioactivity Analysis:

Bottle contents were sampled by taking aliquots (100 ul) of crystalline suspension using centrifugation at 5K RPM/5 minutes using an Eppindorf microfuge to separate suspended solids from centrifugate. The supernatant was decanted from the pellet. The pellet was washed with 30 mM sodium acetate, pH 6.05 (2×@22° C.). Subsequently, the pellet was dissolved in 25 mM sodium phosphate, pH 7.5, 150 mM sodium chloride (2° C.) by vortexing for 30 seconds (5×). The resulting solution was clarified by centrifugation using a 5K RPM/5 minutes using an Eppindorf microfuge to separate suspended solids from centrifugate. The resulting supernatant was characterized by biochemical and bioactivity methods described in example 6.

Example 4

Photomicrograph of Crystal from Flight Experiment

See FIG. 1.

Example 5

Photomicrograph of Crystal from Ground Based Experiments

Figure 2:
FIG. 2. Photomicrograph of crystals derived from ground based experiment at 70× magnification; Ground bottle # G-III-7.

See FIG. 2. This photomicrograph was taken with a Nikon SMZ-U microscope/Kodak DSC 402 digital camera. The crystalline suspension was placed on a glass ringed slide, covered and visualized/photographed with polarized light.

Example 6

Crystal Biophysical Characterization Studies

Studies were initiated to characterize the zinc interferon alfa-2b crystals using physical biochemical methods to determine molecular integrity, protein zinc content and retention of biological activity after dissolution.

Protein Assay.

An aliquot (100 ul) of interferon alfa-2b crystals from flight bottle #285 was dialyzed against 2 liters of 35 mM sodium acetate, pH 5.5 at 22° C. for 4 days. The suspension was centrifuged and the wash solution was removed with a Pasteur pipette. The washed crystals were redissolved in a normal saline sodium phosphate solution at 4° C. Protein concentration was determined by a modified Bradford assay using pure human interferon alfa-2b as a reference standard. Bradford assay: A modification of the standard Coomassie blue dye binding assay was used so that the absorbance is directly proportional to protein concentration. Details are in Braford, M. (1976) Anal. Biochem. 72, 248-254.

Mass Spectral Analysis.

An aliquot (100 ul) of interferon alfa-2b crystals from flight bottle #285, 297 and 311 were dialyzed against 2 liters of 35 mM sodium acetate, pH 5.5 at 22° C. for 4 days. The suspension was centrifuged and the wash solution was removed with a Pasteur pipette. The washed crystals were redissolved in a normal saline sodium phosphate solution at 4° C. The supernatants and redissolved pellets were analyzed by MALDI-TOF MS. The derived molecular ions from the redissolved crystal samples were consistent with intact interferon alpha-2b [predicted vs. observed (19,265 vs. 19,261)]. The supernatant samples derived molecular ions were consistent with intact chicken lysozyme [predicted vs. observed (14,300 vs. 14,318)].

Cytopathic Inhibition Assay.

An aliquot of crystalline suspension was centrifuged and washed to remove soluble interferon alfa-2b, dissolved using phosphate buffer and analyzed for specific activity in a standard biological assay for interferon; the cytopathic inhibition assay (CPE). The CPE antiviral activity was determined by a CPE assay using human foreskin diploid fibroblasts and encephalomyocarditis virus (ATCC-VR-129). A detailed description of the assay is provided in S. Rubinstein, P.C. Familetti and S. Petska, J. Virol. 37 (1981)755-758. The redissolved solution yielded a specific activity of $2.0 \times 10^8$ IU/mg. This value is the same as that predicted for the original interferon alfa-2b preparation prior to crystallization, within the limits of the assay (typically within the range $1 \times 10^8$ to $3 \times 10^8$ IU/mg).

N-terminal Analysis.

An aliquot (100 ul) of interferon alfa-2b crystals from flight bottle #285, 297 and 311 were dialyzed against 2 liters of 35 mM sodium acetate, pH 5.5 at 22° C. for 4 days. The suspension was centrifuged and the wash solution was removed with a Pasteur pipette. The washed crystals were redissolved in a normal saline sodium phosphate solution at 4° C. The supernatants and redsissolved pellets were analyzed by N-terminal analysis. The results are shown in table 1 below.

TABLE 1

| Sample | N-terminal Analysis observed sequence residues |
|---|---|
| Supernatant | KVFGRC (chicken egg white lysozyme only) |
| Wash | not detected |
| "Redissolved crystals" | CDLPQT (interferon only) |

From the experimental results described herein, there is clearly no reason to suppose that any chemical changes or any denaturing of the protein took place during the crystallization or reconstitution.

Molar Ratio of Complexed Zinc vs. Interferon Content.

An experiment was designed to determine the molar ratio of complexed zinc vs. interferon molar content. Six crystals from bottle #G-II-7 were transferred into 250 ul of normal saline phosphate buffer GibcoBRL phosphate buffered saline, pH 7.2 Cat #20012-027 Lot #1062284.

Bio-Rad Bradford assay: 3.2 mg/ml samples were subjected to inductively coupled plasma analysis (ICP). Elemental concentrations can be measured to ppb (parts per billion) levels using the inductively coupled plasma emission spectrophotometer (ICP). The ICP spectrophotometer utilizes plasma to excite elemental electrons which produce photons unique to each element. Results are shown in table 2 below:

TABLE 2

| Sample | Protein Concentration (mM) | ICP Analysis | IFN:Zinc ratio (mM) |
|---|---|---|---|
| Ground six crystals dissolve in PBS | 3.2 mg/ml (0.17 mM) | 12 ppm-Zn<br>4 ppm-Si<br>2 ppm-Al<br>3 ppm-Ca | 0.94-1.0 (0.17-0.18) |
| 10 mM zinc acetate positive control | — | 827 ppm-Zn | 12.3 mM Zn |
| pre-crystallization interferon control | 5.4 mg/ml (0.28 mM) | 18 ppm-Zn | 1:1 (0.28-0.28) |
| PBS negative control | — | <1 ppm-Zn | — |

Example 8

Crystallographic Analysis of Ground Based Experiments (Form 1)

Prior to data collection, crystals were washed with the reservoir solution of the crystallization setup and transferred into the same solution with 20% glycerol added. The crystals were then flash-cooled in liquid nitrogen. X-ray diffraction was collected using a synchrotron radiation at the IMCA-CAT beam line ID17 equipped with an ADCS detector. Data were integrated and scaled using the HKL package.

| Data collection statistics: | |
|---|---|
| Resolution | 20.0 – 1.95 Å |
| No. of collected reflections | 279123 |
| No. of unique reflections (F >= 0) | 93817 |
| R-sym | 6.0% |
| Percent of theoretical (I/s >= 1) | 92.7% |
| Unit Cell | a = 62.2 Å, b = 75.3 Å, c = 149.2 Å, $\alpha = 90°$, $\beta = 91.4°$, $\gamma = 90°$ |
| Space Group | $P2_1$ |
| Asymmetric unit | 6 molecules |

Example 9

Structure Determination of Ground-Based Derived Crystals (Form 1)

The crystal structure was solved using molecular replacement using the search models 1 RH2 from the PDB. Refinement was done using the program Refmac.

TABLE 3

Atomic Coordinates of $Zn^{2+}$ Complexed Interferon Alpha 2b Dimer-Crystal Form $P2_1$

| Resolution Limits | 20.0 – 1.95 Å |
|---|---|
| Number of reflections in working set | 92416 (92.7%) |
| Number of reflections in test set | 1401 (1.5%) |
| Number of protein residues | 859 |
| Number of solvent atoms | 375 |
| Number of ions | 6 zinc ions |
| R-factor | 0.197 |
| R-free | 0.219 |
| RMSD bond length | 0.024 Å |
| RMSD bond angles | 1.77° |

The following table contains one line for each atom of the six alpha-interferon monomers, seven zinc atoms and 375 water molecules in the asymmetric unit of the $P2_1$-primitiv monoclinic space group. The six monomers are listed sequentially with the first monomer containing residues from 6 to 160 of SEQ ID NO:1, the second monomer from 8 to 156 of SEQ ID NO:1, the third monomer from 6 to 156 of SEQ ID NO:1, the fourth monomer from 9 to 157 of SEQ ID NO:1, the fifth monomer from 3 to 156 of SEQ ID NO:1, and the sixth monomer from 6 to 160 of SEQ ID NO:1. The following 7 atom are the zinc atoms and at the end 375 water molecules are listed. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| 6 | T | N | 456 | 746 | 792 | 70 |
|---|---|---|---|---|---|---|
| 6 | T | CA | 452 | 733 | 786 | 70 |
| 6 | T | CB | 465 | 726 | 782 | 70 |
| 6 | T | OG1 | 472 | 733 | 771 | 73 |
| 6 | T | CG2 | 462 | 712 | 775 | 69 |
| 6 | T | C | 444 | 725 | 796 | 69 |
| 6 | T | O | 433 | 729 | 800 | 69 |
| 7 | H | N | 450 | 714 | 801 | 66 |
| 7 | H | CA | 445 | 705 | 811 | 63 |
| 7 | H | CB | 456 | 701 | 821 | 63 |
| 7 | H | CG | 455 | 688 | 826 | 62 |
| 7 | H | ND1 | 462 | 677 | 821 | 60 |
| 7 | H | CE1 | 459 | 666 | 828 | 63 |
| 7 | H | NE2 | 450 | 669 | 837 | 64 |
| 7 | H | CD2 | 447 | 683 | 836 | 62 |
| 7 | H | C | 433 | 709 | 820 | 61 |
| 7 | H | O | 433 | 719 | 826 | 61 |
| 8 | S | N | 422 | 700 | 820 | 58 |
| 8 | S | CA | 410 | 704 | 828 | 55 |
| 8 | S | CB | 398 | 696 | 822 | 56 |
| 8 | S | OG | 392 | 687 | 831 | 53 |
| 8 | S | C | 413 | 701 | 843 | 54 |
| 8 | S | O | 419 | 690 | 846 | 53 |
| 9 | L | N | 409 | 710 | 851 | 52 |
| 9 | L | CA | 411 | 710 | 866 | 50 |
| 9 | L | CB | 407 | 723 | 873 | 51 |
| 9 | L | CG | 403 | 722 | 888 | 53 |
| 9 | L | CD1 | 415 | 722 | 898 | 58 |
| 9 | L | CD2 | 392 | 731 | 893 | 55 |
| 9 | L | C | 402 | 698 | 871 | 47 |
| 9 | L | O | 406 | 692 | 881 | 46 |
| 10 | G | N | 391 | 696 | 865 | 43 |
| 10 | G | CA | 382 | 686 | 869 | 40 |
| 10 | G | C | 389 | 673 | 867 | 37 |
| 10 | G | O | 387 | 664 | 874 | 35 |
| 11 | S | N | 396 | 672 | 856 | 37 |
| 11 | S | CA | 404 | 660 | 853 | 36 |
| 11 | S | CB | 411 | 662 | 840 | 38 |
| 11 | S | OG | 418 | 651 | 837 | 43 |
| 11 | S | C | 414 | 656 | 864 | 35 |
| 11 | S | O | 416 | 644 | 868 | 34 |
| 12 | R | N | 421 | 666 | 869 | 33 |
| 12 | R | CA | 431 | 664 | 880 | 32 |
| 12 | R | CB | 438 | 677 | 883 | 33 |

| | | | | | | | | | | | | |
|---|---|---|---|---|---|---|---|---|---|---|---|---|
| 12 | R | CG | 446 | 683 | 871 | 40 | 22 | R | N | 410 | 554 | 981 | 38 |
| 12 | R | CD | 458 | 692 | 876 | 43 | 22 | R | CA | 417 | 541 | 983 | 41 |
| 12 | R | NE | 465 | 699 | 865 | 47 | 22 | R | CB | 431 | 542 | 979 | 41 |
| 12 | R | CZ | 474 | 694 | 857 | 46 | 22 | R | CG | 438 | 528 | 979 | 42 |
| 12 | R | NH1 | 478 | 681 | 858 | 44 | 22 | R | CD | 453 | 530 | 978 | 48 |
| 12 | R | NH2 | 479 | 702 | 847 | 50 | 22 | R | NE | 460 | 519 | 974 | 52 |
| 12 | R | C | 424 | 661 | 893 | 30 | 22 | R | CZ | 474 | 517 | 975 | 56 |
| 12 | R | O | 428 | 653 | 900 | 30 | 22 | R | NH1 | 480 | 507 | 970 | 54 |
| 13 | R | N | 413 | 667 | 895 | 29 | 22 | R | NH2 | 481 | 527 | 981 | 58 |
| 13 | R | CA | 406 | 665 | 908 | 32 | 22 | R | C | 416 | 537 | 998 | 42 |
| 13 | R | CB | 395 | 675 | 910 | 33 | 22 | R | O | 418 | 545 | 1007 | 41 |
| 13 | R | CG | 401 | 689 | 914 | 41 | 23 | R | N | 412 | 524 | 1000 | 43 |
| 13 | R | CD | 390 | 700 | 916 | 50 | 23 | R | CA | 410 | 520 | 1014 | 46 |
| 13 | R | NE | 386 | 700 | 930 | 61 | 23 | R | CB | 396 | 514 | 1016 | 45 |
| 13 | R | CZ | 380 | 690 | 937 | 63 | 23 | R | CG | 385 | 525 | 1013 | 48 |
| 13 | R | NH1 | 378 | 679 | 931 | 69 | 23 | R | CD | 372 | 525 | 1022 | 52 |
| 13 | R | NH2 | 377 | 691 | 950 | 64 | 23 | R | NE | 368 | 511 | 1025 | 62 |
| 13 | R | C | 399 | 651 | 908 | 31 | 23 | R | CZ | 355 | 508 | 1028 | 65 |
| 13 | R | O | 399 | 645 | 918 | 31 | 23 | R | NH1 | 352 | 495 | 1030 | 67 |
| 14 | T | N | 395 | 647 | 896 | 28 | 23 | R | NH2 | 345 | 517 | 1029 | 66 |
| 14 | T | CA | 390 | 633 | 895 | 28 | 23 | R | C | 420 | 509 | 1017 | 47 |
| 14 | T | CB | 386 | 630 | 880 | 28 | 23 | R | O | 425 | 509 | 1029 | 48 |
| 14 | T | OG1 | 376 | 640 | 877 | 30 | 24 | I | N | 424 | 501 | 1008 | 49 |
| 14 | T | CG2 | 379 | 617 | 878 | 29 | 24 | I | CA | 433 | 490 | 1010 | 52 |
| 14 | T | C | 400 | 623 | 899 | 28 | 24 | I | CB | 426 | 477 | 1011 | 52 |
| 14 | T | O | 397 | 613 | 907 | 27 | 24 | I | CG1 | 418 | 473 | 999 | 50 |
| 15 | L | N | 412 | 624 | 894 | 25 | 24 | I | CD1 | 415 | 458 | 997 | 51 |
| 15 | L | CA | 423 | 615 | 898 | 28 | 24 | I | CG2 | 416 | 478 | 1023 | 52 |
| 15 | L | CB | 435 | 618 | 889 | 30 | 24 | I | C | 444 | 490 | 999 | 54 |
| 15 | L | CG | 432 | 613 | 875 | 32 | 24 | I | O | 442 | 497 | 989 | 55 |
| 15 | L | CD1 | 444 | 617 | 865 | 32 | 25 | S | N | 454 | 481 | 1000 | 57 |
| 15 | L | CD2 | 432 | 597 | 875 | 30 | 25 | S | CA | 465 | 481 | 991 | 61 |
| 15 | L | C | 427 | 616 | 913 | 29 | 25 | S | CB | 479 | 480 | 999 | 61 |
| 15 | L | O | 430 | 606 | 920 | 29 | 25 | S | OG | 479 | 469 | 1007 | 61 |
| 16 | M | N | 427 | 629 | 918 | 30 | 25 | S | C | 465 | 469 | 982 | 63 |
| 16 | M | CA | 430 | 631 | 932 | 31 | 25 | S | O | 458 | 459 | 985 | 63 |
| 16 | M | CB | 430 | 646 | 935 | 31 | 26 | A | N | 472 | 470 | 971 | 67 |
| 16 | M | CG | 434 | 651 | 949 | 36 | 26 | A | CA | 472 | 460 | 960 | 70 |
| 16 | M | SD | 419 | 656 | 957 | 56 | 26 | A | CB | 479 | 466 | 948 | 70 |
| 16 | M | CE | 419 | 673 | 953 | 47 | 26 | A | C | 478 | 446 | 964 | 72 |
| 16 | M | C | 419 | 624 | 942 | 31 | 26 | A | O | 480 | 438 | 956 | 73 |
| 16 | M | O | 422 | 617 | 952 | 31 | 27 | A | N | 481 | 444 | 977 | 75 |
| 17 | L | N | 406 | 625 | 938 | 31 | 27 | A | CA | 486 | 431 | 982 | 76 |
| 17 | L | CA | 396 | 619 | 946 | 30 | 27 | A | CB | 500 | 433 | 988 | 77 |
| 17 | L | CB | 382 | 625 | 941 | 30 | 27 | A | C | 476 | 425 | 993 | 77 |
| 17 | L | CG | 380 | 640 | 945 | 35 | 27 | A | O | 470 | 433 | 1001 | 78 |
| 17 | L | CD1 | 368 | 646 | 936 | 35 | 28 | S | N | 475 | 412 | 992 | 77 |
| 17 | L | CD2 | 378 | 642 | 960 | 34 | 28 | S | CA | 464 | 404 | 997 | 77 |
| 17 | L | C | 396 | 604 | 945 | 31 | 28 | S | CB | 457 | 411 | 1009 | 77 |
| 17 | L | O | 394 | 598 | 956 | 32 | 28 | S | OG | 445 | 405 | 1012 | 77 |
| 18 | L | N | 399 | 599 | 933 | 31 | 28 | S | C | 455 | 401 | 985 | 76 |
| 18 | L | CA | 401 | 585 | 932 | 31 | 28 | S | O | 448 | 390 | 984 | 76 |
| 18 | L | CB | 405 | 580 | 918 | 32 | 29 | C | N | 455 | 411 | 976 | 75 |
| 18 | L | CG | 392 | 578 | 910 | 29 | 29 | C | CA | 449 | 410 | 963 | 74 |
| 18 | L | CD1 | 395 | 578 | 895 | 33 | 29 | C | CB | 442 | 424 | 961 | 73 |
| 18 | L | CD2 | 384 | 566 | 915 | 32 | 29 | C | SG | 435 | 431 | 976 | 68 |
| 18 | L | C | 413 | 580 | 941 | 34 | 29 | C | C | 460 | 407 | 953 | 74 |
| 18 | L | O | 412 | 570 | 948 | 35 | 29 | C | O | 467 | 416 | 949 | 74 |
| 19 | A | N | 424 | 587 | 941 | 35 | 30 | A | N | 461 | 394 | 949 | 73 |
| 19 | A | CA | 435 | 584 | 950 | 35 | 30 | A | CA | 470 | 390 | 938 | 72 |
| 19 | A | CB | 447 | 593 | 948 | 35 | 30 | A | CB | 483 | 385 | 944 | 72 |
| 19 | A | C | 431 | 585 | 965 | 35 | 30 | A | C | 464 | 380 | 929 | 71 |
| 19 | A | O | 434 | 576 | 973 | 36 | 30 | A | O | 467 | 381 | 916 | 71 |
| 20 | Q | N | 423 | 595 | 969 | 37 | 31 | A | N | 456 | 372 | 934 | 69 |
| 20 | Q | CA | 419 | 596 | 983 | 37 | 31 | A | CA | 447 | 363 | 926 | 68 |
| 20 | Q | CB | 413 | 610 | 986 | 38 | 31 | A | CB | 442 | 352 | 935 | 68 |
| 20 | Q | CG | 422 | 621 | 982 | 42 | 31 | A | C | 436 | 370 | 919 | 67 |
| 20 | Q | CD | 416 | 634 | 984 | 54 | 31 | A | O | 429 | 364 | 910 | 67 |
| 20 | Q | OE1 | 422 | 644 | 988 | 60 | 32 | D | N | 435 | 383 | 922 | 66 |
| 20 | Q | NE2 | 403 | 635 | 982 | 57 | 32 | D | CA | 424 | 392 | 917 | 64 |
| 20 | Q | C | 408 | 585 | 987 | 38 | 32 | D | CB | 417 | 400 | 928 | 64 |
| 20 | Q | O | 407 | 583 | 999 | 34 | 32 | D | CG | 412 | 391 | 939 | 66 |
| 21 | M | N | 401 | 580 | 977 | 36 | 32 | D | OD1 | 404 | 382 | 936 | 66 |
| 21 | M | CA | 391 | 569 | 980 | 37 | 32 | D | OD2 | 415 | 393 | 951 | 69 |
| 21 | M | CB | 383 | 566 | 968 | 37 | 32 | D | C | 429 | 401 | 905 | 62 |
| 21 | M | CG | 374 | 576 | 966 | 37 | 32 | D | O | 420 | 406 | 897 | 61 |
| 21 | M | SD | 364 | 572 | 950 | 42 | 33 | R | N | 442 | 404 | 905 | 59 |
| 21 | M | CE | 361 | 587 | 948 | 32 | 33 | R | CA | 448 | 412 | 893 | 58 |
| 21 | M | C | 398 | 556 | 985 | 38 | 33 | R | CB | 463 | 410 | 893 | 59 |
| 21 | M | O | 391 | 548 | 991 | 38 | 33 | R | CG | 468 | 396 | 888 | 63 |

| | | | | | | | | | | | | |
|---|---|---|---|---|---|---|---|---|---|---|---|---|
| 33 | R | CD | 476 | 396 | 875 | 71 | 42 | E | CD | 388 | 530 | 701 | 43 |
| 33 | R | NE | 468 | 397 | 863 | 76 | 42 | E | OE1 | 383 | 534 | 691 | 47 |
| 33 | R | CZ | 472 | 397 | 850 | 78 | 42 | E | OE2 | 395 | 519 | 701 | 56 |
| 33 | R | NH1 | 485 | 395 | 848 | 79 | 42 | E | C | 411 | 566 | 710 | 34 |
| 33 | R | NH2 | 464 | 398 | 840 | 76 | 42 | E | O | 403 | 575 | 706 | 33 |
| 33 | R | C | 441 | 407 | 880 | 55 | 43 | F | N | 420 | 568 | 719 | 35 |
| 33 | R | O | 438 | 395 | 878 | 54 | 43 | F | CA | 424 | 581 | 724 | 41 |
| 34 | H | N | 439 | 416 | 871 | 51 | 43 | F | CB | 425 | 582 | 740 | 37 |
| 34 | H | CA | 431 | 413 | 859 | 48 | 43 | F | CG | 412 | 577 | 746 | 38 |
| 34 | H | CB | 416 | 413 | 863 | 48 | 43 | F | CD1 | 409 | 564 | 748 | 36 |
| 34 | H | CG | 407 | 407 | 852 | 51 | 43 | F | CE1 | 398 | 560 | 754 | 38 |
| 34 | H | ND1 | 401 | 415 | 843 | 54 | 43 | F | CZ | 389 | 570 | 758 | 40 |
| 34 | H | CE1 | 394 | 407 | 835 | 55 | 43 | F | CE2 | 392 | 583 | 756 | 33 |
| 34 | H | NE2 | 395 | 394 | 840 | 57 | 43 | F | CD2 | 403 | 587 | 750 | 42 |
| 34 | H | CD2 | 403 | 394 | 851 | 55 | 43 | F | C | 437 | 587 | 718 | 44 |
| 34 | H | C | 434 | 424 | 847 | 45 | 43 | F | O | 440 | 598 | 721 | 47 |
| 34 | H | O | 435 | 436 | 850 | 45 | 44 | G | N | 444 | 579 | 710 | 46 |
| 35 | D | N | 435 | 419 | 835 | 40 | 44 | G | CA | 457 | 583 | 706 | 51 |
| 35 | D | CA | 436 | 429 | 824 | 36 | 44 | G | C | 459 | 590 | 693 | 53 |
| 35 | D | CB | 448 | 425 | 814 | 36 | 44 | G | O | 450 | 595 | 686 | 54 |
| 35 | D | CG | 451 | 435 | 804 | 37 | 45 | N | N | 472 | 591 | 689 | 55 |
| 35 | D | OD1 | 462 | 434 | 798 | 38 | 45 | N | CA | 477 | 600 | 678 | 55 |
| 35 | D | OD2 | 443 | 444 | 800 | 32 | 45 | N | CB | 492 | 599 | 677 | 57 |
| 35 | D | C | 423 | 430 | 816 | 35 | 45 | N | CG | 499 | 610 | 685 | 61 |
| 35 | D | O | 418 | 421 | 810 | 33 | 45 | N | OD1 | 493 | 617 | 693 | 66 |
| 36 | F | N | 417 | 442 | 818 | 31 | 45 | N | ND2 | 512 | 611 | 683 | 65 |
| 36 | F | CA | 404 | 445 | 812 | 29 | 45 | N | C | 471 | 597 | 664 | 54 |
| 36 | F | CB | 397 | 456 | 821 | 29 | 45 | N | O | 472 | 605 | 655 | 54 |
| 36 | F | CG | 394 | 451 | 835 | 29 | 46 | Q | N | 465 | 585 | 663 | 52 |
| 36 | F | CD1 | 404 | 455 | 845 | 28 | 46 | Q | CA | 459 | 582 | 650 | 52 |
| 36 | F | CE1 | 401 | 451 | 858 | 30 | 46 | Q | CB | 459 | 567 | 647 | 52 |
| 36 | F | CZ | 389 | 443 | 861 | 29 | 46 | Q | CG | 447 | 560 | 653 | 55 |
| 36 | F | CE2 | 380 | 440 | 851 | 25 | 46 | Q | CD | 447 | 545 | 648 | 57 |
| 36 | F | CD2 | 383 | 444 | 838 | 26 | 46 | Q | OE1 | 457 | 539 | 649 | 53 |
| 36 | F | C | 405 | 450 | 798 | 28 | 46 | Q | NE2 | 437 | 541 | 641 | 60 |
| 36 | F | O | 394 | 452 | 792 | 27 | 46 | Q | C | 446 | 590 | 647 | 51 |
| 37 | G | N | 417 | 451 | 792 | 27 | 46 | Q | O | 442 | 591 | 636 | 49 |
| 37 | G | CA | 417 | 454 | 778 | 27 | 47 | F | N | 441 | 597 | 658 | 50 |
| 37 | G | C | 411 | 467 | 774 | 27 | 47 | F | CA | 429 | 605 | 657 | 51 |
| 37 | G | O | 403 | 469 | 765 | 29 | 47 | F | CB | 418 | 599 | 666 | 50 |
| 38 | F | N | 416 | 478 | 781 | 27 | 47 | F | CG | 415 | 585 | 663 | 49 |
| 38 | F | CA | 411 | 491 | 778 | 27 | 47 | F | CD1 | 409 | 582 | 651 | 50 |
| 38 | F | CB | 417 | 501 | 789 | 26 | 47 | F | CE1 | 405 | 569 | 647 | 50 |
| 38 | F | CG | 414 | 515 | 787 | 29 | 47 | F | CZ | 408 | 559 | 656 | 49 |
| 38 | F | CD1 | 400 | 520 | 788 | 26 | 47 | F | CE2 | 414 | 562 | 669 | 47 |
| 38 | F | CE1 | 397 | 533 | 786 | 30 | 47 | F | CD2 | 418 | 575 | 672 | 45 |
| 38 | F | CZ | 406 | 542 | 783 | 28 | 47 | F | C | 432 | 620 | 660 | 52 |
| 38 | F | CE2 | 420 | 538 | 781 | 31 | 47 | F | O | 440 | 623 | 669 | 53 |
| 38 | F | CD2 | 423 | 525 | 783 | 29 | 48 | A | N | 424 | 629 | 654 | 52 |
| 38 | F | C | 416 | 496 | 764 | 27 | 48 | A | CA | 424 | 643 | 658 | 53 |
| 38 | F | O | 427 | 495 | 761 | 29 | 48 | A | CB | 416 | 651 | 647 | 53 |
| 39 | P | N | 406 | 500 | 756 | 28 | 48 | A | C | 417 | 644 | 671 | 53 |
| 39 | P | CA | 410 | 504 | 742 | 28 | 48 | A | O | 409 | 636 | 676 | 53 |
| 39 | P | CB | 396 | 505 | 735 | 28 | 49 | A | N | 422 | 654 | 679 | 53 |
| 39 | P | CG | 386 | 509 | 747 | 27 | 49 | A | CA | 417 | 657 | 692 | 53 |
| 39 | P | CD | 392 | 502 | 759 | 25 | 49 | A | CB | 423 | 671 | 698 | 53 |
| 39 | P | C | 417 | 518 | 741 | 28 | 49 | A | C | 402 | 657 | 693 | 52 |
| 39 | P | O | 411 | 528 | 736 | 30 | 49 | A | O | 396 | 649 | 701 | 52 |
| 40 | Q | N | 429 | 518 | 747 | 29 | 50 | A | N | 396 | 664 | 684 | 50 |
| 40 | Q | CA | 436 | 531 | 747 | 30 | 50 | A | CA | 381 | 665 | 683 | 49 |
| 40 | Q | CB | 449 | 529 | 755 | 30 | 50 | A | CB | 377 | 675 | 672 | 50 |
| 40 | Q | CG | 459 | 521 | 747 | 31 | 50 | A | C | 375 | 652 | 680 | 47 |
| 40 | Q | CD | 472 | 520 | 755 | 38 | 50 | A | O | 363 | 650 | 684 | 47 |
| 40 | Q | OE1 | 472 | 515 | 766 | 35 | 51 | E | N | 382 | 642 | 674 | 45 |
| 40 | Q | NE2 | 483 | 526 | 749 | 40 | 51 | E | CA | 377 | 629 | 671 | 43 |
| 40 | Q | C | 439 | 537 | 733 | 29 | 51 | E | CB | 386 | 622 | 661 | 44 |
| 40 | Q | O | 441 | 549 | 732 | 31 | 51 | E | CG | 384 | 624 | 646 | 51 |
| 41 | E | N | 438 | 528 | 723 | 29 | 51 | E | CD | 395 | 617 | 638 | 58 |
| 41 | E | CA | 440 | 533 | 709 | 30 | 51 | E | OE1 | 406 | 623 | 636 | 57 |
| 41 | E | CB | 441 | 521 | 699 | 29 | 51 | E | OE2 | 393 | 605 | 635 | 58 |
| 41 | E | CG | 427 | 514 | 696 | 31 | 51 | E | C | 376 | 620 | 684 | 40 |
| 41 | E | CD | 423 | 504 | 707 | 28 | 51 | E | O | 369 | 610 | 684 | 41 |
| 41 | E | OE1 | 431 | 503 | 717 | 32 | 52 | T | N | 384 | 624 | 694 | 36 |
| 41 | E | OE2 | 413 | 498 | 706 | 29 | 52 | T | CA | 384 | 616 | 706 | 35 |
| 41 | E | C | 430 | 543 | 705 | 31 | 52 | T | CB | 398 | 616 | 712 | 34 |
| 41 | E | O | 432 | 551 | 696 | 32 | 52 | T | OG1 | 401 | 629 | 716 | 36 |
| 42 | E | N | 418 | 542 | 711 | 31 | 52 | T | CG2 | 408 | 611 | 701 | 35 |
| 42 | E | CA | 408 | 552 | 707 | 32 | 52 | T | C | 374 | 621 | 717 | 34 |
| 42 | E | CB | 394 | 550 | 713 | 30 | 52 | T | O | 372 | 614 | 726 | 32 |
| 42 | E | CG | 388 | 537 | 713 | 39 | 53 | I | N | 368 | 633 | 715 | 32 |

| | | | | | | | | | | | | | |
|---|---|---|---|---|---|---|---|---|---|---|---|---|---|
| 53 | I | CA | 359 | 638 | 725 | 32 | 62 | Q | C | 313 | 554 | 838 | 23 |
| 53 | I | CB | 353 | 652 | 721 | 33 | 62 | Q | O | 309 | 546 | 847 | 23 |
| 53 | I | CG1 | 365 | 662 | 721 | 35 | 63 | I | N | 323 | 562 | 840 | 24 |
| 53 | I | CD1 | 373 | 660 | 733 | 40 | 63 | I | CA | 328 | 563 | 854 | 23 |
| 53 | I | CG2 | 343 | 656 | 731 | 32 | 63 | I | CB | 340 | 573 | 854 | 22 |
| 53 | I | C | 347 | 628 | 727 | 29 | 63 | I | CG1 | 352 | 566 | 847 | 24 |
| 53 | I | O | 344 | 626 | 739 | 30 | 63 | I | CD1 | 363 | 577 | 843 | 27 |
| 54 | P | N | 341 | 622 | 717 | 28 | 63 | I | CG2 | 345 | 576 | 869 | 23 |
| 54 | P | CA | 330 | 613 | 719 | 29 | 63 | I | C | 318 | 567 | 864 | 24 |
| 54 | P | CB | 327 | 607 | 705 | 28 | 63 | I | O | 316 | 562 | 875 | 24 |
| 54 | P | CG | 332 | 620 | 696 | 28 | 64 | F | N | 309 | 577 | 860 | 25 |
| 54 | P | CD | 344 | 624 | 703 | 30 | 64 | F | CA | 298 | 581 | 869 | 24 |
| 54 | P | C | 334 | 602 | 729 | 27 | 64 | F | CB | 290 | 592 | 863 | 25 |
| 54 | P | O | 326 | 598 | 738 | 25 | 64 | F | CG | 277 | 595 | 870 | 28 |
| 55 | V | N | 346 | 596 | 727 | 26 | 64 | F | CD1 | 277 | 602 | 883 | 26 |
| 55 | V | CA | 351 | 586 | 736 | 28 | 64 | F | CE1 | 265 | 603 | 890 | 30 |
| 55 | V | CB | 363 | 578 | 729 | 30 | 64 | F | CZ | 253 | 598 | 885 | 26 |
| 55 | V | CG1 | 368 | 568 | 738 | 31 | 64 | F | CE2 | 253 | 590 | 873 | 26 |
| 55 | V | CG2 | 357 | 570 | 718 | 35 | 64 | F | CD2 | 265 | 589 | 865 | 26 |
| 55 | V | C | 355 | 590 | 750 | 26 | 64 | F | C | 289 | 569 | 871 | 26 |
| 55 | V | O | 352 | 583 | 760 | 24 | 64 | F | O | 284 | 566 | 883 | 29 |
| 56 | L | N | 361 | 602 | 752 | 25 | 65 | N | N | 285 | 562 | 860 | 25 |
| 56 | L | CA | 363 | 607 | 765 | 24 | 65 | N | CA | 276 | 550 | 862 | 27 |
| 56 | L | CB | 372 | 619 | 764 | 24 | 65 | N | CB | 273 | 543 | 849 | 26 |
| 56 | L | CG | 374 | 626 | 778 | 29 | 65 | N | CG | 266 | 551 | 838 | 26 |
| 56 | L | CD1 | 382 | 617 | 787 | 27 | 65 | N | OD1 | 266 | 547 | 826 | 30 |
| 56 | L | CD2 | 382 | 639 | 775 | 35 | 65 | N | ND2 | 259 | 562 | 843 | 21 |
| 56 | L | C | 350 | 610 | 772 | 22 | 65 | N | C | 281 | 540 | 872 | 28 |
| 56 | L | O | 349 | 607 | 784 | 23 | 65 | N | O | 273 | 535 | 880 | 28 |
| 57 | H | N | 341 | 615 | 765 | 22 | 66 | L | N | 294 | 538 | 870 | 27 |
| 57 | H | CA | 328 | 618 | 771 | 23 | 66 | L | CA | 301 | 528 | 879 | 27 |
| 57 | H | CB | 319 | 625 | 760 | 23 | 66 | L | CB | 315 | 525 | 873 | 27 |
| 57 | H | CG | 305 | 629 | 765 | 25 | 66 | L | CG | 325 | 516 | 882 | 31 |
| 57 | H | ND1 | 294 | 621 | 763 | 26 | 66 | L | CD1 | 319 | 501 | 882 | 32 |
| 57 | H | CE1 | 284 | 627 | 768 | 29 | 66 | L | CD2 | 340 | 516 | 876 | 27 |
| 57 | H | NE2 | 287 | 638 | 773 | 29 | 66 | L | C | 301 | 531 | 893 | 28 |
| 57 | H | CD2 | 301 | 640 | 771 | 27 | 66 | L | O | 300 | 523 | 902 | 28 |
| 57 | H | C | 321 | 606 | 776 | 24 | 67 | F | N | 304 | 544 | 896 | 27 |
| 57 | H | O | 316 | 605 | 788 | 22 | 67 | F | CA | 306 | 548 | 910 | 28 |
| 58 | E | N | 320 | 595 | 768 | 24 | 67 | F | CB | 318 | 558 | 911 | 27 |
| 58 | E | CA | 315 | 582 | 772 | 25 | 67 | F | CG | 331 | 551 | 910 | 28 |
| 58 | E | CB | 315 | 572 | 760 | 24 | 67 | F | CD1 | 338 | 549 | 898 | 26 |
| 58 | E | CG | 307 | 559 | 764 | 24 | 67 | F | CE1 | 351 | 543 | 897 | 29 |
| 58 | E | CD | 292 | 561 | 765 | 27 | 67 | F | CZ | 357 | 538 | 908 | 32 |
| 58 | E | OE1 | 285 | 554 | 773 | 29 | 67 | F | CE2 | 350 | 540 | 921 | 34 |
| 58 | E | OE2 | 286 | 570 | 758 | 28 | 67 | F | CD2 | 337 | 546 | 922 | 32 |
| 58 | E | C | 322 | 577 | 784 | 25 | 67 | F | C | 294 | 553 | 917 | 28 |
| 58 | E | O | 316 | 571 | 793 | 25 | 67 | F | O | 295 | 557 | 928 | 30 |
| 59 | M | N | 336 | 577 | 784 | 25 | 68 | S | N | 283 | 553 | 910 | 29 |
| 59 | M | CA | 343 | 572 | 795 | 25 | 68 | S | CA | 270 | 559 | 915 | 29 |
| 59 | M | CB | 358 | 576 | 792 | 28 | 68 | S | CB | 264 | 569 | 906 | 27 |
| 59 | M | CG | 368 | 571 | 802 | 39 | 68 | S | OG | 260 | 564 | 894 | 27 |
| 59 | M | SD | 371 | 554 | 799 | 48 | 68 | S | C | 260 | 549 | 919 | 32 |
| 59 | M | CE | 387 | 556 | 810 | 44 | 68 | S | O | 248 | 552 | 922 | 34 |
| 59 | M | C | 339 | 580 | 809 | 25 | 69 | T | N | 264 | 536 | 919 | 31 |
| 59 | M | O | 337 | 573 | 819 | 24 | 69 | T | CA | 254 | 526 | 923 | 33 |
| 60 | I | N | 337 | 593 | 808 | 23 | 69 | T | CB | 258 | 512 | 917 | 30 |
| 60 | I | CA | 333 | 600 | 820 | 24 | 69 | T | OG1 | 271 | 508 | 923 | 35 |
| 60 | I | CB | 334 | 615 | 818 | 23 | 69 | T | CG2 | 261 | 512 | 901 | 31 |
| 60 | I | CG1 | 349 | 619 | 816 | 26 | 69 | T | C | 253 | 524 | 938 | 34 |
| 60 | I | CD1 | 351 | 631 | 808 | 32 | 69 | T | O | 262 | 529 | 945 | 32 |
| 60 | I | CG2 | 327 | 624 | 829 | 23 | 70 | A | N | 244 | 516 | 942 | 35 |
| 60 | I | C | 319 | 596 | 824 | 23 | 70 | A | CA | 243 | 513 | 957 | 36 |
| 60 | I | O | 317 | 594 | 836 | 26 | 70 | A | CB | 230 | 505 | 960 | 37 |
| 61 | Q | N | 310 | 595 | 815 | 23 | 70 | A | C | 255 | 505 | 961 | 35 |
| 61 | Q | CA | 297 | 591 | 819 | 22 | 70 | A | O | 260 | 507 | 972 | 35 |
| 61 | Q | CB | 287 | 591 | 807 | 23 | 71 | D | N | 260 | 496 | 952 | 35 |
| 61 | Q | CG | 274 | 584 | 810 | 25 | 71 | D | CA | 273 | 489 | 955 | 35 |
| 61 | Q | CD | 264 | 593 | 818 | 29 | 71 | D | CB | 276 | 479 | 945 | 35 |
| 61 | Q | OE1 | 257 | 588 | 828 | 30 | 71 | D | CG | 264 | 470 | 942 | 38 |
| 61 | Q | NE2 | 264 | 606 | 815 | 24 | 71 | D | OD1 | 263 | 460 | 950 | 43 |
| 61 | Q | C | 297 | 577 | 825 | 22 | 71 | D | OD2 | 256 | 472 | 933 | 42 |
| 61 | Q | O | 291 | 574 | 835 | 25 | 71 | D | C | 285 | 498 | 957 | 35 |
| 62 | Q | N | 305 | 568 | 819 | 22 | 71 | D | O | 293 | 495 | 966 | 36 |
| 62 | Q | CA | 306 | 554 | 825 | 22 | 72 | S | N | 286 | 509 | 949 | 35 |
| 62 | Q | CB | 314 | 545 | 815 | 23 | 72 | S | CA | 297 | 518 | 951 | 34 |
| 62 | Q | CG | 307 | 542 | 801 | 26 | 72 | S | CB | 297 | 528 | 939 | 33 |
| 62 | Q | CD | 293 | 535 | 804 | 31 | 72 | S | OG | 308 | 537 | 942 | 36 |
| 62 | Q | OE1 | 292 | 527 | 813 | 33 | 72 | S | C | 295 | 526 | 964 | 33 |
| 62 | Q | NE2 | 283 | 538 | 796 | 30 | 72 | S | O | 305 | 528 | 971 | 32 |

| | | | | | | | | | | | | |
|---|---|---|---|---|---|---|---|---|---|---|---|---|
| 73 | S | N | 283 | 530 | 967 | 35 | 83 | K | CB | 339 | 658 | 961 | 33 |
| 73 | S | CA | 280 | 537 | 980 | 38 | 83 | K | CG | 337 | 666 | 974 | 36 |
| 73 | S | CB | 266 | 541 | 981 | 39 | 83 | K | CD | 350 | 667 | 982 | 43 |
| 73 | S | OG | 263 | 551 | 971 | 45 | 83 | K | CE | 348 | 675 | 995 | 51 |
| 73 | S | C | 284 | 529 | 992 | 39 | 83 | K | NZ | 357 | 671 | 1006 | 54 |
| 73 | S | O | 288 | 534 | 1003 | 39 | 83 | K | C | 331 | 649 | 939 | 30 |
| 74 | A | N | 285 | 515 | 991 | 39 | 83 | K | O | 333 | 657 | 930 | 30 |
| 74 | A | CA | 289 | 507 | 1002 | 39 | 84 | F | N | 333 | 636 | 939 | 28 |
| 74 | A | CB | 281 | 493 | 1000 | 39 | 84 | F | CA | 337 | 629 | 926 | 29 |
| 74 | A | C | 304 | 504 | 1003 | 40 | 84 | F | CB | 339 | 614 | 929 | 28 |
| 74 | A | O | 309 | 500 | 1014 | 40 | 84 | F | CG | 345 | 605 | 918 | 30 |
| 75 | A | N | 311 | 507 | 992 | 36 | 84 | F | CD1 | 357 | 607 | 913 | 29 |
| 75 | A | CA | 325 | 504 | 991 | 36 | 84 | F | CE1 | 363 | 598 | 904 | 31 |
| 75 | A | CB | 329 | 498 | 977 | 36 | 84 | F | CZ | 356 | 587 | 899 | 27 |
| 75 | A | C | 334 | 517 | 994 | 35 | 84 | F | CE2 | 343 | 585 | 905 | 31 |
| 75 | A | O | 345 | 515 | 998 | 36 | 84 | F | CD2 | 338 | 594 | 914 | 28 |
| 76 | W | N | 328 | 529 | 992 | 34 | 84 | F | C | 326 | 631 | 915 | 29 |
| 76 | W | CA | 337 | 541 | 992 | 34 | 84 | F | O | 329 | 636 | 904 | 29 |
| 76 | W | CB | 338 | 547 | 978 | 33 | 85 | Y | N | 313 | 629 | 919 | 30 |
| 76 | W | CG | 343 | 537 | 968 | 31 | 85 | Y | CA | 303 | 631 | 909 | 28 |
| 76 | W | CD1 | 336 | 532 | 957 | 27 | 85 | Y | CB | 289 | 629 | 915 | 27 |
| 76 | W | NE1 | 344 | 522 | 950 | 29 | 85 | Y | CG | 287 | 615 | 922 | 29 |
| 76 | W | CE2 | 356 | 521 | 957 | 29 | 85 | Y | CD1 | 294 | 604 | 918 | 24 |
| 76 | W | CD2 | 356 | 530 | 968 | 33 | 85 | Y | CE1 | 292 | 592 | 924 | 30 |
| 76 | W | CE3 | 367 | 531 | 976 | 32 | 85 | Y | CZ | 283 | 591 | 935 | 31 |
| 76 | W | CZ3 | 378 | 523 | 973 | 33 | 85 | Y | OH | 282 | 579 | 942 | 27 |
| 76 | W | CH2 | 378 | 514 | 962 | 35 | 85 | Y | CE2 | 277 | 602 | 940 | 34 |
| 76 | W | CZ2 | 367 | 513 | 954 | 30 | 85 | Y | CD2 | 278 | 614 | 933 | 28 |
| 76 | W | C | 331 | 552 | 1001 | 35 | 85 | Y | C | 303 | 645 | 904 | 29 |
| 76 | W | O | 319 | 552 | 1004 | 32 | 85 | Y | O | 300 | 648 | 892 | 27 |
| 77 | D | N | 340 | 561 | 1005 | 36 | 86 | T | N | 305 | 655 | 913 | 29 |
| 77 | D | CA | 335 | 573 | 1013 | 38 | 86 | T | CA | 305 | 669 | 909 | 31 |
| 77 | D | CB | 347 | 581 | 1017 | 37 | 86 | T | CB | 307 | 678 | 922 | 32 |
| 77 | D | CG | 343 | 592 | 1027 | 43 | 86 | T | OG1 | 294 | 679 | 928 | 36 |
| 77 | D | OD1 | 340 | 604 | 1023 | 41 | 86 | T | CG2 | 309 | 693 | 917 | 35 |
| 77 | D | OD2 | 341 | 589 | 1039 | 46 | 86 | T | C | 315 | 671 | 898 | 29 |
| 77 | D | C | 324 | 581 | 1007 | 39 | 86 | T | O | 313 | 679 | 887 | 29 |
| 77 | D | O | 326 | 587 | 996 | 38 | 87 | E | N | 327 | 666 | 900 | 27 |
| 78 | E | N | 313 | 583 | 1014 | 38 | 87 | E | CA | 337 | 668 | 889 | 27 |
| 78 | E | CA | 302 | 591 | 1009 | 40 | 87 | E | CB | 350 | 662 | 894 | 28 |
| 78 | E | CB | 291 | 592 | 1020 | 42 | 87 | E | CG | 356 | 668 | 907 | 31 |
| 78 | E | CG | 279 | 599 | 1015 | 44 | 87 | E | CD | 358 | 684 | 906 | 39 |
| 78 | E | CD | 267 | 599 | 1026 | 54 | 87 | E | OE1 | 361 | 689 | 895 | 35 |
| 78 | E | OE1 | 256 | 602 | 1022 | 58 | 87 | E | OE2 | 356 | 691 | 916 | 42 |
| 78 | E | OE2 | 270 | 596 | 1038 | 53 | 87 | E | C | 334 | 661 | 876 | 26 |
| 78 | E | C | 306 | 605 | 1005 | 39 | 87 | E | O | 336 | 666 | 865 | 26 |
| 78 | E | O | 301 | 610 | 995 | 38 | 88 | L | N | 328 | 649 | 877 | 26 |
| 79 | T | N | 314 | 612 | 1013 | 38 | 88 | L | CA | 323 | 642 | 865 | 26 |
| 79 | T | CA | 317 | 625 | 1010 | 39 | 88 | L | CB | 318 | 628 | 869 | 26 |
| 79 | T | CB | 325 | 631 | 1022 | 40 | 88 | L | CG | 329 | 620 | 875 | 23 |
| 79 | T | OG1 | 316 | 631 | 1033 | 45 | 88 | L | CD1 | 322 | 607 | 881 | 26 |
| 79 | T | CG2 | 328 | 646 | 1021 | 41 | 88 | L | CD2 | 340 | 616 | 865 | 27 |
| 79 | T | C | 326 | 626 | 997 | 35 | 88 | L | C | 312 | 650 | 857 | 27 |
| 79 | T | O | 324 | 635 | 990 | 35 | 88 | L | O | 314 | 652 | 846 | 27 |
| 80 | L | N | 336 | 617 | 996 | 35 | 89 | Y | N | 302 | 656 | 864 | 26 |
| 80 | L | CA | 345 | 617 | 985 | 35 | 89 | Y | CA | 292 | 664 | 857 | 28 |
| 80 | L | CB | 356 | 607 | 987 | 35 | 89 | Y | CB | 281 | 670 | 867 | 26 |
| 80 | L | CG | 366 | 611 | 998 | 36 | 89 | Y | CG | 275 | 661 | 876 | 31 |
| 80 | L | CD1 | 377 | 600 | 997 | 34 | 89 | Y | CD1 | 272 | 647 | 872 | 30 |
| 80 | L | CD2 | 373 | 625 | 995 | 35 | 89 | Y | CE1 | 266 | 639 | 881 | 30 |
| 80 | L | C | 337 | 614 | 972 | 33 | 89 | Y | CZ | 262 | 643 | 894 | 32 |
| 80 | L | O | 338 | 621 | 961 | 33 | 89 | Y | OH | 256 | 634 | 902 | 31 |
| 81 | L | N | 327 | 605 | 973 | 34 | 89 | Y | CE2 | 265 | 656 | 898 | 30 |
| 81 | L | CA | 318 | 602 | 962 | 33 | 89 | Y | CD2 | 271 | 665 | 889 | 29 |
| 81 | L | CB | 308 | 590 | 965 | 33 | 89 | Y | C | 298 | 675 | 850 | 29 |
| 81 | L | CG | 315 | 576 | 965 | 31 | 89 | Y | O | 294 | 679 | 839 | 28 |
| 81 | L | CD1 | 305 | 564 | 970 | 35 | 90 | Q | N | 308 | 682 | 856 | 31 |
| 81 | L | CD2 | 322 | 572 | 951 | 31 | 90 | Q | CA | 314 | 694 | 850 | 32 |
| 81 | L | C | 311 | 614 | 957 | 33 | 90 | Q | CB | 322 | 701 | 860 | 33 |
| 81 | L | O | 310 | 616 | 945 | 32 | 90 | Q | CG | 327 | 716 | 856 | 42 |
| 82 | D | N | 305 | 621 | 967 | 34 | 90 | Q | CD | 315 | 725 | 851 | 49 |
| 82 | D | CA | 297 | 633 | 962 | 34 | 90 | Q | OE1 | 316 | 732 | 841 | 51 |
| 82 | D | CB | 289 | 638 | 974 | 37 | 90 | Q | NE2 | 303 | 725 | 858 | 51 |
| 82 | D | CG | 284 | 652 | 972 | 40 | 90 | Q | C | 322 | 691 | 838 | 30 |
| 82 | D | OD1 | 274 | 654 | 965 | 45 | 90 | Q | O | 322 | 698 | 828 | 29 |
| 82 | D | OD2 | 290 | 662 | 977 | 44 | 91 | Q | N | 330 | 680 | 838 | 29 |
| 82 | D | C | 305 | 643 | 955 | 33 | 91 | Q | CA | 337 | 676 | 826 | 27 |
| 82 | D | O | 301 | 649 | 945 | 33 | 91 | Q | CB | 346 | 664 | 829 | 27 |
| 83 | K | N | 318 | 645 | 960 | 32 | 91 | Q | CG | 357 | 668 | 838 | 28 |
| 83 | K | CA | 326 | 655 | 953 | 31 | 91 | Q | CD | 365 | 656 | 843 | 29 |

| | | | | | | |
|---|---|---|---|---|---|---|
| 91 | Q | OE1 | 374 | 652 | 837 | 30 |
| 91 | Q | NE2 | 361 | 651 | 855 | 29 |
| 91 | Q | C | 327 | 672 | 814 | 26 |
| 91 | Q | O | 330 | 675 | 803 | 27 |
| 92 | L | N | 316 | 666 | 817 | 24 |
| 92 | L | CA | 306 | 662 | 807 | 27 |
| 92 | L | CB | 294 | 654 | 814 | 26 |
| 92 | L | CG | 297 | 640 | 818 | 26 |
| 92 | L | CD1 | 286 | 634 | 826 | 27 |
| 92 | L | CD2 | 300 | 631 | 805 | 27 |
| 92 | L | C | 301 | 676 | 801 | 27 |
| 92 | L | O | 300 | 677 | 789 | 28 |
| 93 | N | N | 298 | 685 | 810 | 29 |
| 93 | N | CA | 292 | 698 | 807 | 31 |
| 93 | N | CB | 290 | 707 | 819 | 33 |
| 93 | N | CG | 286 | 721 | 816 | 36 |
| 93 | N | OD1 | 276 | 726 | 821 | 50 |
| 93 | N | ND2 | 294 | 728 | 809 | 44 |
| 93 | N | C | 302 | 705 | 797 | 31 |
| 93 | N | O | 298 | 710 | 787 | 32 |
| 94 | D | N | 315 | 706 | 801 | 32 |
| 94 | D | CA | 325 | 712 | 792 | 33 |
| 94 | D | CB | 338 | 713 | 799 | 33 |
| 94 | D | CG | 338 | 722 | 812 | 38 |
| 94 | D | OD1 | 329 | 729 | 814 | 46 |
| 94 | D | OD2 | 347 | 721 | 821 | 45 |
| 94 | D | C | 327 | 706 | 779 | 32 |
| 94 | D | O | 327 | 714 | 769 | 34 |
| 95 | L | N | 327 | 693 | 778 | 31 |
| 95 | L | CA | 328 | 686 | 765 | 31 |
| 95 | L | CB | 330 | 671 | 767 | 30 |
| 95 | L | CG | 343 | 668 | 775 | 34 |
| 95 | L | CD1 | 343 | 653 | 778 | 31 |
| 95 | L | CD2 | 356 | 672 | 767 | 34 |
| 95 | L | C | 316 | 688 | 756 | 31 |
| 95 | L | O | 318 | 691 | 744 | 32 |
| 96 | E | N | 304 | 688 | 762 | 31 |
| 96 | E | CA | 292 | 690 | 754 | 32 |
| 96 | E | CB | 280 | 687 | 763 | 30 |
| 96 | E | CG | 279 | 672 | 766 | 30 |
| 96 | E | CD | 269 | 669 | 778 | 32 |
| 96 | E | OE1 | 262 | 678 | 782 | 30 |
| 96 | E | OE2 | 269 | 657 | 782 | 32 |
| 96 | E | C | 291 | 704 | 750 | 34 |
| 96 | E | O | 286 | 707 | 738 | 33 |
| 97 | A | N | 294 | 714 | 759 | 36 |
| 97 | A | CA | 291 | 728 | 756 | 38 |
| 97 | A | CB | 295 | 737 | 769 | 38 |
| 97 | A | C | 300 | 732 | 744 | 40 |
| 97 | A | O | 296 | 739 | 735 | 41 |
| 98 | C | N | 312 | 726 | 744 | 42 |
| 98 | C | CA | 322 | 729 | 733 | 45 |
| 98 | C | CB | 335 | 722 | 735 | 44 |
| 98 | C | SG | 345 | 734 | 746 | 56 |
| 98 | C | C | 316 | 725 | 719 | 45 |
| 98 | C | O | 317 | 732 | 709 | 46 |
| 99 | V | N | 310 | 713 | 719 | 43 |
| 99 | V | CA | 304 | 708 | 706 | 43 |
| 99 | V | CB | 303 | 692 | 705 | 43 |
| 99 | V | CG1 | 290 | 687 | 711 | 45 |
| 99 | V | CG2 | 303 | 688 | 690 | 44 |
| 99 | V | C | 291 | 716 | 702 | 44 |
| 99 | V | O | 290 | 718 | 690 | 42 |
| 100 | I | N | 283 | 719 | 711 | 43 |
| 100 | I | CA | 271 | 727 | 708 | 44 |
| 100 | I | CB | 262 | 729 | 721 | 45 |
| 100 | I | CG1 | 256 | 715 | 726 | 44 |
| 100 | I | CD1 | 247 | 708 | 715 | 50 |
| 100 | I | CG2 | 250 | 739 | 719 | 44 |
| 100 | I | C | 275 | 741 | 703 | 45 |
| 100 | I | O | 267 | 747 | 695 | 45 |
| 101 | Q | N | 286 | 746 | 707 | 46 |
| 101 | Q | CA | 292 | 759 | 701 | 48 |
| 101 | Q | CB | 299 | 766 | 712 | 48 |
| 101 | Q | CG | 289 | 774 | 721 | 54 |
| 101 | Q | CD | 295 | 781 | 733 | 60 |
| 101 | Q | OE1 | 289 | 791 | 738 | 63 |
| 101 | Q | NE2 | 306 | 775 | 738 | 59 |
| 101 | Q | C | 301 | 757 | 689 | 49 |
| 101 | Q | O | 307 | 766 | 685 | 48 |
| 102 | G | N | 300 | 745 | 683 | 50 |
| 102 | G | CA | 306 | 742 | 670 | 55 |
| 102 | G | C | 321 | 740 | 670 | 58 |
| 102 | G | O | 327 | 737 | 660 | 58 |
| 103 | V | N | 327 | 740 | 682 | 62 |
| 103 | V | CA | 342 | 737 | 684 | 65 |
| 103 | V | CB | 347 | 741 | 698 | 65 |
| 103 | V | CG1 | 362 | 737 | 700 | 66 |
| 103 | V | CG2 | 345 | 755 | 701 | 67 |
| 103 | V | C | 344 | 723 | 679 | 68 |
| 103 | V | O | 339 | 714 | 685 | 68 |
| 104 | G | N | 352 | 721 | 669 | 71 |
| 104 | G | CA | 356 | 708 | 663 | 75 |
| 104 | G | C | 346 | 701 | 655 | 77 |
| 104 | G | O | 346 | 689 | 654 | 78 |
| 105 | V | N | 337 | 708 | 648 | 79 |
| 105 | V | CA | 326 | 701 | 641 | 82 |
| 105 | V | CB | 311 | 705 | 646 | 82 |
| 105 | V | CG1 | 310 | 704 | 661 | 81 |
| 105 | V | CG2 | 308 | 720 | 642 | 83 |
| 105 | V | C | 327 | 701 | 625 | 83 |
| 105 | V | O | 321 | 709 | 618 | 84 |
| 106 | A | N | 336 | 692 | 621 | 84 |
| 106 | A | CA | 339 | 691 | 606 | 85 |
| 106 | A | CB | 352 | 682 | 604 | 85 |
| 106 | A | C | 327 | 685 | 598 | 85 |
| 106 | A | O | 323 | 691 | 588 | 85 |
| 110 | A | N | 321 | 618 | 609 | 62 |
| 110 | A | CA | 321 | 620 | 623 | 62 |
| 110 | A | CB | 314 | 633 | 626 | 62 |
| 110 | A | C | 313 | 608 | 631 | 61 |
| 110 | A | O | 304 | 611 | 639 | 63 |
| 111 | N | N | 316 | 596 | 627 | 61 |
| 111 | N | CA | 310 | 584 | 633 | 58 |
| 111 | N | CB | 303 | 575 | 621 | 59 |
| 111 | N | CG | 294 | 564 | 627 | 63 |
| 111 | N | OD1 | 298 | 555 | 634 | 62 |
| 111 | N | ND2 | 281 | 565 | 623 | 66 |
| 111 | N | C | 319 | 576 | 642 | 55 |
| 111 | N | O | 330 | 571 | 637 | 55 |
| 112 | K | N | 315 | 575 | 654 | 50 |
| 112 | K | CA | 323 | 569 | 664 | 44 |
| 112 | K | CB | 329 | 580 | 674 | 44 |
| 112 | K | CG | 339 | 590 | 667 | 48 |
| 112 | K | CD | 350 | 583 | 659 | 51 |
| 112 | K | CE | 362 | 580 | 669 | 53 |
| 112 | K | NZ | 375 | 577 | 662 | 56 |
| 112 | K | C | 315 | 560 | 672 | 38 |
| 112 | K | O | 318 | 557 | 683 | 35 |
| 113 | E | N | 304 | 555 | 665 | 36 |
| 113 | E | CA | 295 | 547 | 673 | 35 |
| 113 | E | CB | 283 | 543 | 665 | 36 |
| 113 | E | CG | 273 | 554 | 662 | 44 |
| 113 | E | CD | 268 | 560 | 676 | 49 |
| 113 | E | OE1 | 262 | 553 | 684 | 53 |
| 113 | E | OE2 | 272 | 572 | 678 | 54 |
| 113 | E | C | 301 | 534 | 679 | 33 |
| 113 | E | O | 298 | 530 | 690 | 33 |
| 114 | D | N | 310 | 527 | 671 | 29 |
| 114 | D | CA | 317 | 515 | 676 | 30 |
| 114 | D | CB | 324 | 508 | 664 | 30 |
| 114 | D | CG | 314 | 502 | 654 | 38 |
| 114 | D | OD1 | 317 | 502 | 642 | 43 |
| 114 | D | OD2 | 303 | 497 | 658 | 43 |
| 114 | D | C | 327 | 518 | 686 | 27 |
| 114 | D | O | 329 | 510 | 696 | 28 |
| 115 | S | N | 334 | 529 | 686 | 27 |
| 115 | S | CA | 343 | 533 | 696 | 29 |
| 115 | S | CB | 351 | 545 | 692 | 29 |
| 115 | S | OG | 360 | 542 | 681 | 33 |
| 115 | S | C | 336 | 536 | 709 | 28 |
| 115 | S | O | 341 | 533 | 720 | 29 |
| 116 | I | N | 325 | 543 | 708 | 27 |
| 116 | I | CA | 317 | 546 | 720 | 27 |
| 116 | I | CB | 304 | 554 | 716 | 27 |
| 116 | I | CG1 | 308 | 569 | 715 | 29 |
| 116 | I | CD1 | 297 | 577 | 707 | 31 |
| 116 | I | CG2 | 293 | 554 | 728 | 27 |
| 116 | I | C | 313 | 533 | 726 | 27 |
| 116 | I | O | 314 | 531 | 738 | 27 |

| | | | | | | |
|---|---|---|---|---|---|---|
| 117 | L | N | 308 | 523 | 717 | 28 |
| 117 | L | CA | 305 | 510 | 723 | 27 |
| 117 | L | CB | 298 | 501 | 711 | 28 |
| 117 | L | CG | 295 | 487 | 715 | 35 |
| 117 | L | CD1 | 283 | 486 | 725 | 41 |
| 117 | L | CD2 | 291 | 478 | 703 | 45 |
| 117 | L | C | 317 | 503 | 728 | 27 |
| 117 | L | O | 315 | 495 | 738 | 27 |
| 118 | A | N | 329 | 504 | 723 | 26 |
| 118 | A | CA | 341 | 498 | 729 | 26 |
| 118 | A | CB | 354 | 501 | 720 | 26 |
| 118 | A | C | 343 | 503 | 743 | 26 |
| 118 | A | O | 347 | 495 | 752 | 27 |
| 119 | V | N | 341 | 516 | 746 | 26 |
| 119 | V | CA | 342 | 521 | 760 | 25 |
| 119 | V | CB | 341 | 536 | 760 | 26 |
| 119 | V | CG1 | 341 | 542 | 775 | 26 |
| 119 | V | CG2 | 352 | 543 | 752 | 29 |
| 119 | V | C | 331 | 514 | 768 | 26 |
| 119 | V | O | 334 | 510 | 779 | 24 |
| 120 | R | N | 319 | 513 | 763 | 25 |
| 120 | R | CA | 309 | 506 | 771 | 27 |
| 120 | R | CB | 296 | 506 | 764 | 28 |
| 120 | R | CG | 290 | 520 | 762 | 31 |
| 120 | R | CD | 275 | 521 | 759 | 33 |
| 120 | R | NE | 273 | 535 | 757 | 31 |
| 120 | R | CZ | 265 | 540 | 747 | 35 |
| 120 | R | NH1 | 257 | 532 | 740 | 32 |
| 120 | R | NH2 | 264 | 553 | 746 | 28 |
| 120 | R | C | 312 | 492 | 774 | 25 |
| 120 | R | O | 309 | 487 | 785 | 25 |
| 121 | K | N | 318 | 485 | 765 | 26 |
| 121 | K | CA | 321 | 471 | 767 | 27 |
| 121 | K | CB | 325 | 464 | 753 | 26 |
| 121 | K | CG | 313 | 461 | 745 | 29 |
| 121 | K | CD | 317 | 457 | 730 | 36 |
| 121 | K | CE | 305 | 452 | 721 | 40 |
| 121 | K | NZ | 299 | 440 | 727 | 44 |
| 121 | K | C | 332 | 469 | 777 | 26 |
| 121 | K | O | 333 | 460 | 785 | 26 |
| 122 | Y | N | 342 | 479 | 777 | 25 |
| 122 | Y | CA | 352 | 479 | 787 | 25 |
| 122 | Y | CB | 362 | 491 | 785 | 24 |
| 122 | Y | CG | 370 | 495 | 796 | 25 |
| 122 | Y | CD1 | 369 | 507 | 802 | 26 |
| 122 | Y | CE1 | 377 | 511 | 813 | 26 |
| 122 | Y | CZ | 388 | 503 | 817 | 27 |
| 122 | Y | OH | 396 | 507 | 827 | 28 |
| 122 | Y | CE2 | 390 | 491 | 810 | 25 |
| 122 | Y | CD2 | 382 | 487 | 800 | 24 |
| 122 | Y | C | 346 | 480 | 801 | 25 |
| 122 | Y | O | 349 | 472 | 811 | 25 |
| 123 | F | N | 336 | 489 | 803 | 25 |
| 123 | F | CA | 330 | 490 | 816 | 25 |
| 123 | F | CB | 322 | 504 | 817 | 23 |
| 123 | F | CG | 331 | 515 | 820 | 25 |
| 123 | F | CD1 | 333 | 518 | 834 | 25 |
| 123 | F | CE1 | 343 | 529 | 837 | 27 |
| 123 | F | CZ | 349 | 536 | 826 | 25 |
| 123 | F | CE2 | 346 | 532 | 812 | 27 |
| 123 | F | CD2 | 337 | 522 | 810 | 24 |
| 123 | F | C | 320 | 478 | 820 | 25 |
| 123 | F | O | 319 | 474 | 831 | 26 |
| 124 | Q | N | 315 | 472 | 809 | 25 |
| 124 | Q | CA | 308 | 460 | 812 | 26 |
| 124 | Q | CB | 301 | 455 | 799 | 27 |
| 124 | Q | CG | 289 | 464 | 795 | 28 |
| 124 | Q | CD | 283 | 461 | 780 | 39 |
| 124 | Q | OE1 | 289 | 453 | 773 | 37 |
| 124 | Q | NE2 | 272 | 468 | 777 | 43 |
| 124 | Q | C | 317 | 449 | 817 | 28 |
| 124 | Q | O | 313 | 442 | 827 | 28 |
| 125 | R | N | 329 | 447 | 812 | 28 |
| 125 | R | CA | 338 | 438 | 817 | 28 |
| 125 | R | CB | 351 | 438 | 809 | 30 |
| 125 | R | CG | 349 | 433 | 794 | 28 |
| 125 | R | CD | 362 | 430 | 787 | 28 |
| 125 | R | NE | 370 | 442 | 783 | 27 |
| 125 | R | CZ | 367 | 449 | 772 | 27 |
| 125 | R | NH1 | 357 | 446 | 764 | 28 |
| 125 | R | NH2 | 376 | 459 | 769 | 25 |
| 125 | R | C | 342 | 442 | 831 | 29 |
| 125 | R | O | 343 | 433 | 840 | 28 |
| 126 | I | N | 344 | 454 | 834 | 27 |
| 126 | I | CA | 346 | 458 | 848 | 27 |
| 126 | I | CB | 349 | 474 | 849 | 27 |
| 126 | I | CG1 | 363 | 477 | 843 | 31 |
| 126 | I | CD1 | 366 | 491 | 841 | 33 |
| 126 | I | CG2 | 349 | 478 | 864 | 29 |
| 126 | I | C | 334 | 455 | 857 | 29 |
| 126 | I | O | 336 | 450 | 869 | 30 |
| 127 | T | N | 322 | 457 | 853 | 29 |
| 127 | T | CA | 310 | 455 | 861 | 32 |
| 127 | T | CB | 298 | 461 | 853 | 32 |
| 127 | T | OG1 | 298 | 475 | 855 | 38 |
| 127 | T | CG2 | 285 | 456 | 860 | 40 |
| 127 | T | C | 308 | 440 | 863 | 32 |
| 127 | T | O | 305 | 436 | 874 | 34 |
| 128 | L | N | 310 | 432 | 853 | 30 |
| 128 | L | CA | 309 | 417 | 854 | 32 |
| 128 | L | CB | 311 | 410 | 841 | 30 |
| 128 | L | CG | 309 | 395 | 840 | 36 |
| 128 | L | CD1 | 296 | 390 | 847 | 40 |
| 128 | L | CD2 | 310 | 389 | 826 | 38 |
| 128 | L | C | 320 | 412 | 864 | 32 |
| 128 | L | O | 317 | 403 | 873 | 32 |
| 129 | Y | N | 332 | 418 | 863 | 32 |
| 129 | Y | CA | 342 | 415 | 873 | 32 |
| 129 | Y | CB | 356 | 422 | 869 | 33 |
| 129 | Y | CG | 367 | 421 | 879 | 31 |
| 129 | Y | CD1 | 376 | 411 | 879 | 34 |
| 129 | Y | CE1 | 386 | 410 | 888 | 37 |
| 129 | Y | CZ | 387 | 420 | 898 | 37 |
| 129 | Y | OH | 397 | 419 | 907 | 36 |
| 129 | Y | CE2 | 378 | 430 | 898 | 35 |
| 129 | Y | CD2 | 368 | 430 | 889 | 33 |
| 129 | Y | C | 338 | 417 | 887 | 33 |
| 129 | Y | O | 341 | 408 | 896 | 35 |
| 130 | L | N | 332 | 429 | 890 | 32 |
| 130 | L | CA | 328 | 432 | 904 | 33 |
| 130 | L | CB | 323 | 446 | 906 | 32 |
| 130 | L | CG | 334 | 457 | 906 | 34 |
| 130 | L | CD1 | 327 | 470 | 904 | 33 |
| 130 | L | CD2 | 342 | 456 | 919 | 32 |
| 130 | L | C | 317 | 422 | 909 | 35 |
| 130 | L | O | 317 | 417 | 921 | 34 |
| 131 | K | N | 308 | 419 | 900 | 36 |
| 131 | K | CA | 296 | 410 | 903 | 39 |
| 131 | K | CB | 287 | 410 | 892 | 40 |
| 131 | K | CG | 275 | 400 | 893 | 45 |
| 131 | K | CD | 268 | 400 | 879 | 55 |
| 131 | K | CE | 253 | 395 | 881 | 60 |
| 131 | K | NZ | 254 | 381 | 887 | 64 |
| 131 | K | C | 302 | 396 | 906 | 41 |
| 131 | K | O | 299 | 390 | 917 | 42 |
| 132 | E | N | 311 | 391 | 898 | 40 |
| 132 | E | CA | 317 | 378 | 900 | 42 |
| 132 | E | CB | 324 | 373 | 887 | 43 |
| 132 | E | CG | 314 | 370 | 876 | 47 |
| 132 | E | CD | 319 | 364 | 863 | 55 |
| 132 | E | OE1 | 331 | 365 | 859 | 55 |
| 132 | E | OE2 | 310 | 359 | 855 | 59 |
| 132 | E | C | 325 | 376 | 913 | 42 |
| 132 | E | O | 326 | 365 | 919 | 41 |
| 133 | K | N | 331 | 387 | 917 | 40 |
| 133 | K | CA | 339 | 387 | 930 | 40 |
| 133 | K | CB | 351 | 396 | 928 | 39 |
| 133 | K | CG | 360 | 393 | 917 | 44 |
| 133 | K | CD | 370 | 382 | 919 | 49 |
| 133 | K | CE | 382 | 383 | 911 | 52 |
| 133 | K | NZ | 391 | 371 | 911 | 56 |
| 133 | K | C | 331 | 391 | 941 | 38 |
| 133 | K | O | 336 | 394 | 952 | 39 |
| 134 | K | N | 318 | 392 | 939 | 38 |
| 134 | K | CA | 308 | 397 | 948 | 39 |
| 134 | K | CB | 303 | 386 | 958 | 41 |
| 134 | K | CG | 303 | 372 | 951 | 46 |
| 134 | K | CD | 300 | 361 | 962 | 55 |
| 134 | K | CE | 313 | 356 | 969 | 58 |
| 134 | K | NZ | 311 | 343 | 977 | 62 |

| 134 | K | C   | 313 | 410 | 956  | 39 |
|-----|---|-----|-----|-----|------|----|
| 134 | K | O   | 311 | 412 | 968  | 36 |
| 135 | Y | N   | 318 | 419 | 948  | 39 |
| 135 | Y | CA  | 321 | 433 | 953  | 38 |
| 135 | Y | CB  | 308 | 440 | 956  | 38 |
| 135 | Y | CG  | 300 | 442 | 944  | 42 |
| 135 | Y | CD1 | 290 | 432 | 941  | 45 |
| 135 | Y | CE1 | 282 | 433 | 930  | 45 |
| 135 | Y | CZ  | 284 | 444 | 922  | 43 |
| 135 | Y | OH  | 276 | 444 | 911  | 41 |
| 135 | Y | CE2 | 293 | 454 | 924  | 41 |
| 135 | Y | CD2 | 302 | 452 | 935  | 40 |
| 135 | Y | C   | 330 | 433 | 964  | 38 |
| 135 | Y | O   | 328 | 441 | 973  | 39 |
| 136 | S | N   | 340 | 424 | 964  | 39 |
| 136 | S | CA  | 348 | 424 | 976  | 42 |
| 136 | S | CB  | 357 | 412 | 976  | 42 |
| 136 | S | OG  | 366 | 412 | 964  | 43 |
| 136 | S | C   | 357 | 436 | 977  | 43 |
| 136 | S | O   | 360 | 442 | 966  | 43 |
| 137 | P | N   | 362 | 440 | 989  | 44 |
| 137 | P | CA  | 372 | 451 | 990  | 44 |
| 137 | P | CB  | 377 | 449 | 1005 | 44 |
| 137 | P | CG  | 365 | 444 | 1013 | 45 |
| 137 | P | CD  | 357 | 435 | 1002 | 44 |
| 137 | P | C   | 384 | 450 | 980  | 44 |
| 137 | P | O   | 388 | 460 | 974  | 45 |
| 138 | C | N   | 389 | 438 | 978  | 43 |
| 138 | C | CA  | 400 | 436 | 969  | 43 |
| 138 | C | CB  | 405 | 422 | 970  | 44 |
| 138 | C | SG  | 418 | 420 | 983  | 58 |
| 138 | C | C   | 396 | 438 | 954  | 41 |
| 138 | C | O   | 405 | 443 | 947  | 38 |
| 139 | A | N   | 384 | 434 | 950  | 38 |
| 139 | A | CA  | 380 | 435 | 937  | 36 |
| 139 | A | CB  | 368 | 427 | 934  | 36 |
| 139 | A | C   | 377 | 450 | 934  | 35 |
| 139 | A | O   | 380 | 455 | 924  | 34 |
| 140 | W | N   | 371 | 456 | 944  | 33 |
| 140 | W | CA  | 369 | 471 | 943  | 34 |
| 140 | W | CB  | 361 | 476 | 955  | 32 |
| 140 | W | CG  | 346 | 478 | 952  | 35 |
| 140 | W | CD1 | 336 | 471 | 959  | 34 |
| 140 | W | NE1 | 324 | 476 | 953  | 34 |
| 140 | W | CE2 | 326 | 485 | 943  | 35 |
| 140 | W | CD2 | 340 | 486 | 942  | 35 |
| 140 | W | CE3 | 345 | 495 | 932  | 32 |
| 140 | W | CZ3 | 336 | 502 | 924  | 34 |
| 140 | W | CH2 | 322 | 500 | 926  | 36 |
| 140 | W | CZ2 | 317 | 492 | 935  | 35 |
| 140 | W | C   | 383 | 479 | 942  | 34 |
| 140 | W | O   | 383 | 490 | 935  | 32 |
| 141 | E | N   | 393 | 475 | 950  | 35 |
| 141 | E | CA  | 406 | 481 | 948  | 35 |
| 141 | E | CB  | 415 | 477 | 960  | 36 |
| 141 | E | CG  | 430 | 481 | 958  | 35 |
| 141 | E | CD  | 431 | 497 | 956  | 36 |
| 141 | E | OE1 | 422 | 504 | 961  | 35 |
| 141 | E | OE2 | 442 | 501 | 951  | 41 |
| 141 | E | C   | 412 | 479 | 935  | 34 |
| 141 | E | O   | 419 | 488 | 929  | 34 |
| 142 | V | N   | 412 | 466 | 929  | 32 |
| 142 | V | CA  | 416 | 464 | 915  | 33 |
| 142 | V | CB  | 413 | 449 | 911  | 32 |
| 142 | V | CG1 | 413 | 447 | 896  | 34 |
| 142 | V | CG2 | 422 | 439 | 918  | 34 |
| 142 | V | C   | 408 | 474 | 905  | 33 |
| 142 | V | O   | 415 | 480 | 897  | 32 |
| 143 | V | N   | 395 | 475 | 907  | 31 |
| 143 | V | CA  | 388 | 484 | 898  | 31 |
| 143 | V | CB  | 373 | 482 | 901  | 29 |
| 143 | V | CG1 | 364 | 492 | 894  | 30 |
| 143 | V | CG2 | 370 | 467 | 895  | 29 |
| 143 | V | C   | 391 | 499 | 900  | 30 |
| 143 | V | O   | 394 | 506 | 891  | 31 |
| 144 | R | N   | 392 | 503 | 913  | 30 |
| 144 | R | CA  | 396 | 517 | 915  | 30 |
| 144 | R | CB  | 398 | 520 | 930  | 31 |
| 144 | R | CG  | 399 | 535 | 934  | 30 |
| 144 | R | CD  | 406 | 537 | 948  | 31 |
| 144 | R | NE  | 418 | 529 | 948  | 32 |
| 144 | R | CZ  | 430 | 534 | 943  | 38 |
| 144 | R | NH1 | 430 | 547 | 939  | 37 |
| 144 | R | NH2 | 441 | 527 | 942  | 42 |
| 144 | R | C   | 410 | 520 | 909  | 30 |
| 144 | R | O   | 411 | 531 | 902  | 29 |
| 145 | A | N   | 419 | 511 | 911  | 29 |
| 145 | A | CA  | 433 | 513 | 905  | 31 |
| 145 | A | CB  | 443 | 502 | 909  | 30 |
| 145 | A | C   | 432 | 513 | 890  | 30 |
| 145 | A | O   | 440 | 520 | 883  | 33 |
| 146 | E | N   | 424 | 504 | 884  | 28 |
| 146 | E | CA  | 423 | 503 | 870  | 28 |
| 146 | E | CB  | 413 | 491 | 867  | 30 |
| 146 | E | CG  | 408 | 491 | 852  | 29 |
| 146 | E | CD  | 419 | 489 | 842  | 33 |
| 146 | E | OE1 | 417 | 493 | 830  | 32 |
| 146 | E | OE2 | 430 | 484 | 845  | 35 |
| 146 | E | C   | 417 | 516 | 863  | 26 |
| 146 | E | O   | 422 | 520 | 853  | 27 |
| 147 | I | N   | 407 | 522 | 870  | 24 |
| 147 | I | CA  | 401 | 534 | 865  | 26 |
| 147 | I | CB  | 387 | 537 | 872  | 28 |
| 147 | I | CG1 | 378 | 526 | 868  | 26 |
| 147 | I | CD1 | 374 | 524 | 852  | 28 |
| 147 | I | CG2 | 382 | 552 | 868  | 26 |
| 147 | I | C   | 411 | 546 | 866  | 27 |
| 147 | I | O   | 411 | 555 | 857  | 27 |
| 148 | M | N   | 418 | 546 | 877  | 28 |
| 148 | M | CA  | 429 | 557 | 878  | 30 |
| 148 | M | CB  | 438 | 556 | 890  | 31 |
| 148 | M | CG  | 432 | 564 | 900  | 39 |
| 148 | M | SD  | 442 | 567 | 914  | 50 |
| 148 | M | CE  | 453 | 582 | 908  | 43 |
| 148 | M | C   | 438 | 556 | 866  | 29 |
| 148 | M | O   | 441 | 566 | 860  | 27 |
| 149 | R | N   | 442 | 544 | 863  | 30 |
| 149 | R | CA  | 451 | 541 | 852  | 29 |
| 149 | R | CB  | 456 | 526 | 852  | 31 |
| 149 | R | CG  | 466 | 521 | 842  | 34 |
| 149 | R | CD  | 466 | 505 | 840  | 40 |
| 149 | R | NE  | 454 | 500 | 834  | 42 |
| 149 | R | CZ  | 452 | 501 | 821  | 47 |
| 149 | R | NH1 | 461 | 505 | 812  | 46 |
| 149 | R | NH2 | 440 | 497 | 816  | 44 |
| 149 | R | C   | 445 | 545 | 838  | 30 |
| 149 | R | O   | 451 | 552 | 830  | 28 |
| 150 | S | N   | 433 | 540 | 835  | 28 |
| 150 | S | CA  | 427 | 542 | 822  | 28 |
| 150 | S | CB  | 417 | 532 | 819  | 27 |
| 150 | S | OG  | 405 | 534 | 828  | 25 |
| 150 | S | C   | 423 | 557 | 821  | 29 |
| 150 | S | O   | 423 | 562 | 810  | 29 |
| 151 | F | N   | 418 | 563 | 831  | 28 |
| 151 | F | CA  | 413 | 577 | 830  | 28 |
| 151 | F | CB  | 406 | 581 | 843  | 27 |
| 151 | F | CG  | 400 | 595 | 841  | 26 |
| 151 | F | CD1 | 390 | 597 | 832  | 33 |
| 151 | F | CE1 | 384 | 611 | 830  | 36 |
| 151 | F | CZ  | 390 | 621 | 838  | 31 |
| 151 | F | CE2 | 400 | 619 | 847  | 33 |
| 151 | F | CD2 | 405 | 606 | 848  | 30 |
| 151 | F | C   | 425 | 586 | 828  | 31 |
| 151 | F | O   | 425 | 595 | 819  | 28 |
| 152 | S | N   | 436 | 584 | 835  | 33 |
| 152 | S | CA  | 448 | 591 | 834  | 39 |
| 152 | S | CB  | 458 | 587 | 844  | 36 |
| 152 | S | OG  | 470 | 593 | 840  | 47 |
| 152 | S | C   | 453 | 590 | 819  | 40 |
| 152 | S | O   | 456 | 600 | 813  | 41 |
| 153 | L | N   | 454 | 578 | 815  | 43 |
| 153 | L | CA  | 459 | 574 | 801  | 45 |
| 153 | L | CB  | 458 | 559 | 799  | 46 |
| 153 | L | CG  | 465 | 551 | 789  | 50 |
| 153 | L | CD1 | 480 | 554 | 787  | 50 |
| 153 | L | CD2 | 463 | 536 | 793  | 49 |
| 153 | L | C   | 451 | 581 | 791  | 46 |
| 153 | L | O   | 457 | 588 | 782  | 47 |
| 154 | S | N   | 438 | 580 | 791  | 44 |
| 154 | S | CA  | 428 | 586 | 782  | 45 |

-continued

| | | | | | | |
|---|---|---|---|---|---|---|
| 154 | S | CB | 414 | 579 | 784 | 44 |
| 154 | S | OG | 406 | 586 | 793 | 46 |
| 154 | S | C | 428 | 602 | 783 | 44 |
| 154 | S | O | 426 | 609 | 774 | 45 |
| 155 | T | N | 431 | 608 | 795 | 41 |
| 155 | T | CA | 432 | 622 | 794 | 42 |
| 155 | T | CB | 429 | 628 | 808 | 42 |
| 155 | T | OG1 | 436 | 620 | 817 | 41 |
| 155 | T | CG2 | 415 | 626 | 812 | 39 |
| 155 | T | C | 445 | 626 | 789 | 45 |
| 155 | T | O | 446 | 636 | 782 | 44 |
| 156 | N | N | 456 | 619 | 792 | 47 |
| 156 | N | CA | 470 | 623 | 788 | 51 |
| 156 | N | CB | 481 | 616 | 795 | 51 |
| 156 | N | CG | 482 | 620 | 810 | 55 |
| 156 | N | OD1 | 490 | 614 | 817 | 61 |
| 156 | N | ND2 | 475 | 631 | 813 | 57 |
| 156 | N | C | 471 | 622 | 773 | 53 |
| 156 | N | O | 475 | 632 | 766 | 54 |
| 157 | L | N | 467 | 611 | 767 | 54 |
| 157 | L | CA | 467 | 609 | 753 | 56 |
| 157 | L | CB | 463 | 595 | 749 | 56 |
| 157 | L | CG | 474 | 584 | 750 | 57 |
| 157 | L | CD1 | 468 | 571 | 754 | 56 |
| 157 | L | CD2 | 482 | 584 | 737 | 60 |
| 157 | L | C | 458 | 619 | 746 | 57 |
| 157 | L | O | 462 | 626 | 737 | 56 |
| 158 | Q | N | 445 | 620 | 751 | 59 |
| 158 | Q | CA | 435 | 629 | 745 | 63 |
| 158 | Q | CB | 422 | 629 | 753 | 63 |
| 158 | Q | CG | 409 | 634 | 746 | 66 |
| 158 | Q | CD | 409 | 649 | 745 | 68 |
| 158 | Q | OE1 | 414 | 657 | 754 | 70 |
| 158 | Q | NE2 | 403 | 654 | 734 | 71 |
| 158 | Q | C | 440 | 643 | 742 | 64 |
| 158 | Q | O | 436 | 649 | 732 | 64 |
| 159 | E | N | 448 | 649 | 751 | 66 |
| 159 | E | CA | 452 | 663 | 750 | 68 |
| 159 | E | CB | 453 | 669 | 764 | 68 |
| 159 | E | CG | 467 | 667 | 771 | 69 |
| 159 | E | CD | 467 | 675 | 784 | 71 |
| 159 | E | OE1 | 478 | 675 | 790 | 70 |
| 159 | E | OE2 | 457 | 681 | 788 | 75 |
| 159 | E | C | 465 | 666 | 742 | 69 |
| 159 | E | O | 467 | 677 | 737 | 69 |
| 160 | S | N | 474 | 656 | 741 | 70 |
| 160 | S | CA | 487 | 658 | 733 | 71 |
| 160 | S | CB | 498 | 648 | 738 | 72 |
| 160 | S | OG | 495 | 635 | 733 | 72 |
| 160 | S | C | 484 | 657 | 718 | 72 |
| 160 | S | O | 493 | 659 | 710 | 73 |
| 160 | S | OXT | 474 | 654 | 713 | 72 |
| 8 | A | N | 371 | 355 | 511 | 54 |
| 8 | A | CA | 358 | 350 | 515 | 53 |
| 8 | A | CB | 348 | 353 | 504 | 54 |
| 8 | A | C | 359 | 335 | 517 | 52 |
| 8 | A | O | 356 | 330 | 528 | 52 |
| 9 | L | N | 362 | 328 | 506 | 51 |
| 9 | L | CA | 363 | 314 | 506 | 50 |
| 9 | L | CB | 364 | 308 | 492 | 51 |
| 9 | L | CG | 366 | 292 | 490 | 56 |
| 9 | L | CD1 | 355 | 283 | 497 | 58 |
| 9 | L | CD2 | 366 | 289 | 475 | 61 |
| 9 | L | C | 374 | 309 | 516 | 48 |
| 9 | L | O | 373 | 299 | 523 | 47 |
| 10 | G | N | 385 | 317 | 516 | 45 |
| 10 | G | CA | 397 | 315 | 525 | 42 |
| 10 | G | C | 392 | 316 | 539 | 41 |
| 10 | G | O | 396 | 308 | 548 | 39 |
| 11 | S | N | 384 | 326 | 542 | 39 |
| 11 | S | CA | 381 | 328 | 556 | 40 |
| 11 | S | CB | 376 | 342 | 558 | 40 |
| 11 | S | OG | 364 | 344 | 552 | 45 |
| 11 | S | C | 371 | 317 | 560 | 38 |
| 11 | S | O | 371 | 312 | 572 | 37 |
| 12 | R | N | 362 | 312 | 551 | 38 |
| 12 | R | CA | 354 | 301 | 554 | 38 |
| 12 | R | CB | 343 | 298 | 544 | 38 |
| 12 | R | CG | 332 | 309 | 544 | 45 |
| 12 | R | CD | 321 | 306 | 533 | 49 |
| 12 | R | NE | 321 | 317 | 524 | 59 |
| 12 | R | CZ | 322 | 316 | 511 | 60 |
| 12 | R | NH1 | 322 | 327 | 503 | 66 |
| 12 | R | NH2 | 323 | 304 | 505 | 61 |
| 12 | R | C | 361 | 288 | 557 | 37 |
| 12 | R | O | 357 | 280 | 566 | 35 |
| 13 | R | N | 372 | 285 | 550 | 36 |
| 13 | R | CA | 380 | 274 | 552 | 36 |
| 13 | R | CB | 391 | 272 | 541 | 37 |
| 13 | R | CG | 385 | 267 | 528 | 45 |
| 13 | R | CD | 395 | 260 | 519 | 57 |
| 13 | R | NE | 392 | 262 | 504 | 67 |
| 13 | R | CZ | 397 | 272 | 497 | 71 |
| 13 | R | NH1 | 394 | 273 | 484 | 74 |
| 13 | R | NH2 | 406 | 281 | 503 | 71 |
| 13 | R | C | 387 | 275 | 565 | 34 |
| 13 | R | O | 389 | 265 | 573 | 33 |
| 14 | T | N | 392 | 287 | 569 | 32 |
| 14 | T | CA | 398 | 289 | 581 | 31 |
| 14 | T | CB | 403 | 303 | 582 | 32 |
| 14 | T | OG1 | 413 | 305 | 572 | 35 |
| 14 | T | CG2 | 410 | 307 | 595 | 28 |
| 14 | T | C | 389 | 285 | 593 | 31 |
| 14 | T | O | 393 | 279 | 603 | 30 |
| 15 | L | N | 377 | 290 | 593 | 30 |
| 15 | L | CA | 367 | 288 | 603 | 31 |
| 15 | L | CB | 354 | 296 | 600 | 30 |
| 15 | L | CG | 354 | 311 | 603 | 31 |
| 15 | L | CD1 | 341 | 318 | 598 | 33 |
| 15 | L | CD2 | 357 | 313 | 618 | 30 |
| 15 | L | C | 363 | 273 | 604 | 29 |
| 15 | L | O | 362 | 267 | 615 | 31 |
| 16 | M | N | 362 | 267 | 592 | 30 |
| 16 | M | CA | 360 | 252 | 592 | 29 |
| 16 | M | CB | 359 | 247 | 578 | 29 |
| 16 | M | CG | 352 | 234 | 577 | 36 |
| 16 | M | SD | 353 | 227 | 560 | 44 |
| 16 | M | CE | 340 | 215 | 562 | 48 |
| 16 | M | C | 371 | 244 | 599 | 30 |
| 16 | M | O | 368 | 235 | 608 | 30 |
| 17 | L | N | 384 | 248 | 597 | 28 |
| 17 | L | CA | 395 | 241 | 604 | 29 |
| 17 | L | CB | 408 | 246 | 597 | 29 |
| 17 | L | CG | 410 | 240 | 583 | 31 |
| 17 | L | CD1 | 422 | 248 | 575 | 28 |
| 17 | L | CD2 | 414 | 224 | 584 | 30 |
| 17 | L | C | 394 | 244 | 619 | 27 |
| 17 | L | O | 397 | 234 | 626 | 27 |
| 18 | L | N | 392 | 256 | 623 | 27 |
| 18 | L | CA | 391 | 259 | 637 | 27 |
| 18 | L | CB | 388 | 274 | 639 | 28 |
| 18 | L | CG | 400 | 283 | 639 | 30 |
| 18 | L | CD1 | 396 | 298 | 637 | 32 |
| 18 | L | CD2 | 409 | 280 | 652 | 28 |
| 18 | L | C | 380 | 250 | 644 | 27 |
| 18 | L | O | 382 | 245 | 655 | 28 |
| 19 | A | N | 369 | 249 | 637 | 26 |
| 19 | A | CA | 357 | 241 | 642 | 28 |
| 19 | A | CB | 345 | 244 | 633 | 27 |
| 19 | A | C | 360 | 226 | 643 | 28 |
| 19 | A | O | 356 | 219 | 652 | 29 |
| 20 | Q | N | 369 | 221 | 633 | 27 |
| 20 | Q | CA | 373 | 207 | 633 | 27 |
| 20 | Q | CB | 377 | 203 | 619 | 28 |
| 20 | Q | CG | 366 | 203 | 609 | 31 |
| 20 | Q | CD | 371 | 200 | 595 | 38 |
| 20 | Q | OE1 | 382 | 206 | 591 | 37 |
| 20 | Q | NE2 | 365 | 191 | 587 | 41 |
| 20 | Q | C | 384 | 205 | 643 | 28 |
| 20 | Q | O | 386 | 193 | 648 | 29 |
| 21 | M | N | 391 | 216 | 647 | 27 |
| 21 | M | CA | 401 | 214 | 658 | 28 |
| 21 | M | CB | 410 | 226 | 658 | 29 |
| 21 | M | CG | 420 | 225 | 646 | 29 |
| 21 | M | SD | 428 | 242 | 643 | 35 |
| 21 | M | CE | 434 | 244 | 656 | 26 |
| 21 | M | C | 395 | 212 | 671 | 29 |
| 21 | M | O | 402 | 206 | 680 | 29 |
| 22 | R | N | 383 | 216 | 674 | 29 |
| 22 | R | CA | 376 | 215 | 687 | 29 |

| | | | | | | | | | | | | |
|---|---|---|---|---|---|---|---|---|---|---|---|---|
| 22 | R | CB | 361 | 218 | 686 | 30 | 31 | K | C | 370 | 287 | 847 | 33 |
| 22 | R | CG | 356 | 222 | 700 | 32 | 31 | K | O | 375 | 296 | 854 | 32 |
| 22 | R | CD | 342 | 220 | 705 | 41 | 32 | D | N | 373 | 285 | 835 | 31 |
| 22 | R | NE | 337 | 207 | 707 | 39 | 32 | D | CA | 384 | 292 | 828 | 33 |
| 22 | R | CZ | 326 | 203 | 713 | 32 | 32 | D | CB | 392 | 282 | 821 | 33 |
| 22 | R | NH1 | 324 | 190 | 713 | 30 | 32 | D | CG | 399 | 272 | 830 | 38 |
| 22 | R | NH2 | 317 | 211 | 720 | 31 | 32 | D | OD1 | 406 | 277 | 840 | 39 |
| 22 | R | C | 378 | 201 | 693 | 30 | 32 | D | OD2 | 397 | 259 | 829 | 41 |
| 22 | R | O | 375 | 191 | 686 | 30 | 32 | D | C | 380 | 303 | 818 | 33 |
| 23 | R | N | 382 | 200 | 705 | 29 | 32 | D | O | 388 | 308 | 810 | 32 |
| 23 | R | CA | 384 | 187 | 712 | 32 | 33 | R | N | 367 | 305 | 818 | 33 |
| 23 | R | CB | 398 | 185 | 717 | 32 | 33 | R | CA | 361 | 315 | 809 | 36 |
| 23 | R | CG | 408 | 183 | 706 | 34 | 33 | R | CB | 345 | 316 | 810 | 36 |
| 23 | R | CD | 423 | 181 | 709 | 42 | 33 | R | CG | 341 | 323 | 823 | 39 |
| 23 | R | NE | 425 | 169 | 717 | 51 | 33 | R | CD | 325 | 321 | 825 | 46 |
| 23 | R | CZ | 435 | 166 | 725 | 56 | 33 | R | NE | 320 | 327 | 837 | 48 |
| 23 | R | NH1 | 435 | 155 | 732 | 58 | 33 | R | CZ | 322 | 322 | 850 | 54 |
| 23 | R | NH2 | 446 | 174 | 725 | 53 | 33 | R | NH1 | 330 | 312 | 853 | 51 |
| 23 | R | C | 373 | 186 | 723 | 33 | 33 | R | NH2 | 316 | 329 | 860 | 55 |
| 23 | R | O | 367 | 175 | 725 | 35 | 33 | R | C | 367 | 328 | 811 | 35 |
| 24 | I | N | 373 | 196 | 732 | 31 | 33 | R | O | 371 | 332 | 822 | 35 |
| 24 | I | CA | 363 | 195 | 743 | 32 | 34 | H | N | 369 | 336 | 800 | 35 |
| 24 | I | CB | 371 | 195 | 757 | 32 | 34 | H | CA | 377 | 349 | 801 | 33 |
| 24 | I | CG1 | 379 | 208 | 759 | 31 | 34 | H | CB | 391 | 345 | 800 | 35 |
| 24 | I | CD1 | 387 | 208 | 773 | 36 | 34 | H | CG | 400 | 356 | 804 | 39 |
| 24 | I | CG2 | 379 | 182 | 758 | 34 | 34 | H | ND1 | 405 | 366 | 795 | 43 |
| 24 | I | C | 354 | 207 | 742 | 31 | 34 | H | CE1 | 413 | 374 | 802 | 44 |
| 24 | I | O | 357 | 217 | 735 | 30 | 34 | H | NE2 | 413 | 371 | 814 | 49 |
| 25 | S | N | 343 | 207 | 750 | 30 | 34 | H | CD2 | 405 | 360 | 816 | 43 |
| 25 | S | CA | 333 | 218 | 750 | 30 | 34 | H | C | 372 | 358 | 789 | 33 |
| 25 | S | CB | 320 | 213 | 756 | 29 | 34 | H | O | 370 | 352 | 778 | 34 |
| 25 | S | OG | 311 | 224 | 756 | 31 | 35 | D | N | 372 | 371 | 791 | 30 |
| 25 | S | C | 338 | 230 | 758 | 29 | 35 | D | CA | 368 | 380 | 781 | 31 |
| 25 | S | O | 342 | 228 | 770 | 30 | 35 | D | CB | 357 | 390 | 785 | 31 |
| 26 | L | N | 335 | 242 | 754 | 28 | 35 | D | CG | 352 | 398 | 774 | 34 |
| 26 | L | CA | 338 | 254 | 762 | 29 | 35 | D | OD1 | 340 | 403 | 774 | 32 |
| 26 | L | CB | 333 | 266 | 753 | 29 | 35 | D | OD2 | 360 | 401 | 764 | 33 |
| 26 | L | CG | 334 | 279 | 760 | 32 | 35 | D | C | 381 | 388 | 778 | 29 |
| 26 | L | CD1 | 349 | 282 | 764 | 40 | 35 | D | O | 386 | 394 | 787 | 28 |
| 26 | L | CD2 | 331 | 290 | 749 | 36 | 36 | F | N | 386 | 386 | 765 | 28 |
| 26 | L | C | 330 | 253 | 775 | 29 | 36 | F | CA | 399 | 392 | 762 | 27 |
| 26 | L | O | 334 | 258 | 785 | 30 | 36 | F | CB | 407 | 383 | 752 | 27 |
| 27 | F | N | 318 | 247 | 773 | 30 | 36 | F | CG | 410 | 370 | 757 | 28 |
| 27 | F | CA | 309 | 245 | 785 | 31 | 36 | F | CD1 | 400 | 359 | 755 | 26 |
| 27 | F | CB | 295 | 243 | 780 | 29 | 36 | F | CE1 | 403 | 346 | 761 | 25 |
| 27 | F | CG | 289 | 255 | 775 | 31 | 36 | F | CZ | 415 | 344 | 768 | 25 |
| 27 | F | CD1 | 283 | 264 | 784 | 30 | 36 | F | CE2 | 424 | 354 | 770 | 29 |
| 27 | F | CE1 | 277 | 276 | 779 | 34 | 36 | F | CD2 | 421 | 367 | 765 | 26 |
| 27 | F | CZ | 278 | 279 | 765 | 33 | 36 | F | C | 398 | 406 | 756 | 28 |
| 27 | F | CE2 | 284 | 270 | 756 | 29 | 36 | F | O | 408 | 412 | 752 | 26 |
| 27 | F | CD2 | 290 | 258 | 762 | 29 | 37 | G | N | 386 | 412 | 757 | 27 |
| 27 | F | C | 314 | 235 | 795 | 32 | 37 | G | CA | 384 | 425 | 751 | 28 |
| 27 | F | O | 308 | 234 | 806 | 35 | 37 | G | C | 389 | 427 | 737 | 28 |
| 28 | S | N | 324 | 227 | 792 | 33 | 37 | G | O | 397 | 436 | 735 | 28 |
| 28 | S | CA | 331 | 219 | 803 | 35 | 38 | F | N | 385 | 419 | 727 | 26 |
| 28 | S | CB | 337 | 207 | 797 | 35 | 38 | F | CA | 388 | 419 | 713 | 27 |
| 28 | S | OG | 328 | 200 | 789 | 37 | 38 | F | CB | 381 | 409 | 705 | 27 |
| 28 | S | C | 342 | 227 | 809 | 36 | 38 | F | CG | 384 | 409 | 691 | 27 |
| 28 | S | O | 350 | 222 | 817 | 36 | 38 | F | CD1 | 397 | 408 | 686 | 25 |
| 29 | C | N | 344 | 240 | 804 | 35 | 38 | F | CE1 | 399 | 408 | 672 | 27 |
| 29 | C | CA | 355 | 248 | 809 | 34 | 38 | F | CZ | 389 | 411 | 663 | 29 |
| 29 | C | CB | 364 | 251 | 797 | 34 | 38 | F | CE2 | 376 | 412 | 668 | 32 |
| 29 | C | SG | 370 | 235 | 789 | 39 | 38 | F | CD2 | 373 | 412 | 681 | 27 |
| 29 | C | C | 351 | 261 | 815 | 34 | 38 | F | C | 383 | 433 | 708 | 28 |
| 29 | C | O | 360 | 270 | 814 | 33 | 38 | F | O | 372 | 436 | 709 | 27 |
| 30 | L | N | 339 | 262 | 821 | 33 | 39 | P | N | 393 | 441 | 702 | 27 |
| 30 | L | CA | 334 | 276 | 825 | 34 | 39 | P | CA | 389 | 455 | 697 | 27 |
| 30 | L | CB | 320 | 275 | 829 | 35 | 39 | P | CB | 402 | 462 | 695 | 27 |
| 30 | L | CG | 311 | 272 | 817 | 36 | 39 | P | CG | 412 | 450 | 692 | 29 |
| 30 | L | CD1 | 296 | 272 | 821 | 40 | 39 | P | CD | 407 | 439 | 701 | 26 |
| 30 | L | CD2 | 312 | 282 | 805 | 39 | 39 | P | C | 382 | 454 | 684 | 29 |
| 30 | L | C | 343 | 282 | 835 | 33 | 39 | P | O | 387 | 458 | 673 | 28 |
| 30 | L | O | 343 | 294 | 837 | 33 | 40 | Q | N | 369 | 449 | 684 | 30 |
| 31 | K | N | 349 | 273 | 843 | 33 | 40 | Q | CA | 362 | 447 | 671 | 30 |
| 31 | K | CA | 358 | 279 | 854 | 34 | 40 | Q | CB | 349 | 439 | 674 | 33 |
| 31 | K | CB | 364 | 268 | 863 | 37 | 40 | Q | CG | 339 | 448 | 681 | 37 |
| 31 | K | CG | 375 | 260 | 856 | 39 | 40 | Q | CD | 326 | 440 | 685 | 44 |
| 31 | K | CD | 382 | 250 | 866 | 49 | 40 | Q | OE1 | 326 | 432 | 693 | 44 |
| 31 | K | CE | 394 | 243 | 860 | 48 | 40 | Q | NE2 | 315 | 443 | 678 | 49 |
| 31 | K | NZ | 391 | 239 | 845 | 48 | 40 | Q | C | 359 | 460 | 664 | 30 |

| | | | | | | | | | | | | | |
|---|---|---|---|---|---|---|---|---|---|---|---|---|---|
| 40 | Q | O | 357 | 460 | 652 | 31 | 50 | A | O | 430 | 496 | 538 | 56 |
| 41 | E | N | 359 | 471 | 671 | 29 | 51 | E | N | 412 | 507 | 545 | 52 |
| 41 | E | CA | 357 | 485 | 665 | 30 | 51 | E | CA | 419 | 511 | 557 | 50 |
| 41 | E | CB | 357 | 496 | 676 | 30 | 51 | E | CB | 415 | 525 | 563 | 51 |
| 41 | E | CG | 370 | 499 | 682 | 28 | 51 | E | CG | 400 | 526 | 566 | 56 |
| 41 | E | CD | 373 | 490 | 694 | 29 | 51 | E | CD | 395 | 541 | 568 | 62 |
| 41 | E | OE1 | 365 | 480 | 696 | 34 | 51 | E | OE1 | 384 | 543 | 564 | 64 |
| 41 | E | OE2 | 383 | 492 | 700 | 32 | 51 | E | OE2 | 403 | 550 | 572 | 61 |
| 41 | E | C | 368 | 487 | 654 | 31 | 51 | E | C | 420 | 501 | 568 | 47 |
| 41 | E | O | 365 | 495 | 644 | 32 | 51 | E | O | 427 | 502 | 577 | 46 |
| 42 | E | N | 379 | 482 | 656 | 31 | 52 | T | N | 412 | 490 | 567 | 44 |
| 42 | E | CA | 390 | 484 | 645 | 33 | 52 | T | CA | 412 | 480 | 577 | 42 |
| 42 | E | CB | 403 | 478 | 648 | 34 | 52 | T | CB | 399 | 474 | 581 | 42 |
| 42 | E | CG | 411 | 481 | 660 | 39 | 52 | T | OG1 | 393 | 469 | 569 | 47 |
| 42 | E | CD | 408 | 494 | 667 | 42 | 52 | T | CG2 | 389 | 486 | 583 | 42 |
| 42 | E | OE1 | 411 | 505 | 663 | 42 | 52 | T | C | 422 | 468 | 574 | 40 |
| 42 | E | OE2 | 402 | 493 | 678 | 45 | 52 | T | O | 426 | 460 | 582 | 38 |
| 42 | E | C | 386 | 478 | 632 | 35 | 53 | I | N | 427 | 469 | 561 | 37 |
| 42 | E | O | 393 | 482 | 622 | 35 | 53 | I | CA | 437 | 459 | 556 | 36 |
| 43 | F | N | 376 | 470 | 631 | 35 | 53 | I | CB | 442 | 462 | 542 | 37 |
| 43 | F | CA | 374 | 463 | 619 | 39 | 53 | I | CG1 | 431 | 461 | 532 | 40 |
| 43 | F | CB | 373 | 448 | 621 | 37 | 53 | I | CD1 | 421 | 449 | 533 | 48 |
| 43 | F | CG | 386 | 442 | 626 | 35 | 53 | I | CG2 | 453 | 452 | 537 | 37 |
| 43 | F | CD1 | 389 | 442 | 639 | 29 | 53 | I | C | 448 | 457 | 566 | 34 |
| 43 | F | CE1 | 401 | 437 | 644 | 36 | 53 | I | O | 452 | 445 | 569 | 33 |
| 43 | F | CZ | 411 | 432 | 635 | 33 | 54 | P | N | 455 | 467 | 570 | 35 |
| 43 | F | CE2 | 408 | 432 | 622 | 35 | 54 | P | CA | 466 | 465 | 580 | 34 |
| 43 | F | CD2 | 396 | 438 | 617 | 35 | 54 | P | CB | 471 | 479 | 583 | 33 |
| 43 | F | C | 361 | 468 | 612 | 43 | 54 | P | CG | 466 | 487 | 572 | 35 |
| 43 | F | O | 358 | 463 | 601 | 46 | 54 | P | CD | 454 | 481 | 566 | 33 |
| 44 | G | N | 353 | 476 | 619 | 46 | 54 | P | C | 462 | 458 | 593 | 34 |
| 44 | G | CA | 339 | 477 | 615 | 49 | 54 | P | O | 471 | 451 | 599 | 32 |
| 44 | G | C | 337 | 489 | 606 | 52 | 55 | V | N | 450 | 461 | 598 | 33 |
| 44 | G | O | 346 | 494 | 599 | 52 | 55 | V | CA | 447 | 454 | 611 | 32 |
| 45 | N | N | 324 | 494 | 605 | 55 | 55 | V | CB | 436 | 462 | 620 | 34 |
| 45 | N | CA | 320 | 505 | 596 | 57 | 55 | V | CG1 | 442 | 475 | 624 | 41 |
| 45 | N | CB | 305 | 505 | 594 | 59 | 55 | V | CG2 | 424 | 464 | 611 | 35 |
| 45 | N | CG | 302 | 493 | 584 | 62 | 55 | V | C | 443 | 440 | 609 | 30 |
| 45 | N | OD1 | 293 | 485 | 587 | 67 | 55 | V | O | 445 | 431 | 617 | 31 |
| 45 | N | ND2 | 309 | 492 | 573 | 62 | 56 | L | N | 436 | 437 | 597 | 30 |
| 45 | N | C | 326 | 519 | 598 | 58 | 56 | L | CA | 432 | 424 | 594 | 31 |
| 45 | N | O | 324 | 527 | 589 | 58 | 56 | L | CB | 424 | 423 | 581 | 32 |
| 46 | Q | N | 332 | 522 | 609 | 57 | 56 | L | CG | 420 | 409 | 577 | 38 |
| 46 | Q | CA | 339 | 535 | 611 | 58 | 56 | L | CD1 | 414 | 401 | 590 | 43 |
| 46 | Q | CB | 345 | 536 | 625 | 58 | 56 | L | CD2 | 410 | 409 | 566 | 40 |
| 46 | Q | CG | 334 | 537 | 636 | 56 | 56 | L | C | 446 | 416 | 592 | 31 |
| 46 | Q | CD | 340 | 539 | 650 | 51 | 56 | L | O | 447 | 404 | 596 | 30 |
| 46 | Q | OE1 | 332 | 541 | 659 | 46 | 57 | H | N | 455 | 422 | 585 | 29 |
| 46 | Q | NE2 | 353 | 537 | 652 | 49 | 57 | H | CA | 468 | 415 | 583 | 29 |
| 46 | Q | C | 350 | 536 | 601 | 60 | 57 | H | CB | 477 | 424 | 574 | 29 |
| 46 | Q | O | 356 | 547 | 600 | 60 | 57 | H | CG | 491 | 418 | 571 | 28 |
| 47 | F | N | 354 | 525 | 594 | 60 | 57 | H | ND1 | 501 | 421 | 579 | 28 |
| 47 | F | CA | 365 | 524 | 586 | 62 | 57 | H | CE1 | 512 | 415 | 574 | 28 |
| 47 | F | CB | 376 | 516 | 593 | 61 | 57 | H | NE2 | 509 | 408 | 563 | 29 |
| 47 | F | CG | 381 | 522 | 606 | 62 | 57 | H | CD2 | 495 | 410 | 561 | 29 |
| 47 | F | CD1 | 377 | 516 | 618 | 59 | 57 | H | C | 475 | 412 | 597 | 29 |
| 47 | F | CE1 | 381 | 521 | 630 | 61 | 57 | H | O | 480 | 401 | 598 | 28 |
| 47 | F | CZ | 389 | 533 | 631 | 63 | 58 | E | N | 475 | 422 | 606 | 28 |
| 47 | F | CE2 | 394 | 539 | 619 | 65 | 58 | E | CA | 481 | 419 | 619 | 29 |
| 47 | F | CD2 | 389 | 533 | 606 | 63 | 58 | E | CB | 481 | 432 | 628 | 28 |
| 47 | F | C | 362 | 518 | 572 | 62 | 58 | E | CG | 487 | 430 | 642 | 27 |
| 47 | F | O | 354 | 509 | 571 | 62 | 58 | E | CD | 503 | 429 | 641 | 31 |
| 48 | A | N | 368 | 525 | 562 | 63 | 58 | E | OE1 | 510 | 422 | 648 | 32 |
| 48 | A | CA | 367 | 519 | 548 | 65 | 58 | E | OE2 | 508 | 436 | 632 | 29 |
| 48 | A | CB | 372 | 530 | 538 | 65 | 58 | E | C | 474 | 408 | 626 | 29 |
| 48 | A | C | 376 | 506 | 547 | 65 | 58 | E | O | 480 | 399 | 632 | 27 |
| 48 | A | O | 386 | 505 | 553 | 65 | 59 | M | N | 461 | 407 | 625 | 29 |
| 49 | K | N | 370 | 497 | 539 | 66 | 59 | M | CA | 452 | 397 | 631 | 30 |
| 49 | K | CA | 377 | 484 | 536 | 65 | 59 | M | CB | 438 | 400 | 628 | 30 |
| 49 | K | CB | 371 | 478 | 523 | 66 | 59 | M | CG | 428 | 390 | 632 | 36 |
| 49 | K | CG | 358 | 469 | 525 | 69 | 59 | M | SD | 425 | 392 | 650 | 43 |
| 49 | K | CD | 349 | 469 | 513 | 73 | 59 | M | CE | 410 | 380 | 652 | 43 |
| 49 | K | CE | 348 | 455 | 506 | 75 | 59 | M | C | 456 | 383 | 626 | 29 |
| 49 | K | N2 | 344 | 455 | 492 | 77 | 59 | M | O | 459 | 374 | 633 | 29 |
| 49 | K | C | 392 | 485 | 534 | 63 | 60 | I | N | 457 | 381 | 613 | 30 |
| 49 | K | O | 399 | 477 | 541 | 64 | 60 | I | CA | 461 | 369 | 607 | 31 |
| 50 | A | N | 396 | 494 | 526 | 61 | 60 | I | CB | 458 | 369 | 592 | 32 |
| 50 | A | CA | 411 | 495 | 524 | 58 | 60 | I | CG1 | 442 | 370 | 590 | 33 |
| 50 | A | CB | 413 | 505 | 512 | 59 | 60 | I | CD1 | 437 | 370 | 577 | 37 |
| 50 | A | C | 418 | 500 | 536 | 56 | 60 | I | CG2 | 463 | 357 | 584 | 31 |

| | | | | | | | | | | | | |
|---|---|---|---|---|---|---|---|---|---|---|---|---|
| 60 | I | C | 475 | 364 | 610 | 32 | 70 | A | CA | 553 | 240 | 702 | 37 |
| 60 | I | O | 478 | 353 | 614 | 31 | 70 | A | CB | 566 | 239 | 710 | 38 |
| 61 | Q | N | 484 | 374 | 610 | 31 | 70 | A | C | 541 | 236 | 711 | 36 |
| 61 | Q | CA | 498 | 370 | 614 | 31 | 70 | A | O | 536 | 225 | 712 | 35 |
| 61 | Q | CB | 507 | 382 | 612 | 32 | 71 | D | N | 537 | 246 | 719 | 35 |
| 61 | Q | CG | 521 | 380 | 619 | 33 | 71 | D | CA | 525 | 245 | 728 | 36 |
| 61 | Q | CD | 530 | 372 | 610 | 36 | 71 | D | CB | 524 | 257 | 736 | 37 |
| 61 | Q | OE1 | 531 | 374 | 598 | 33 | 71 | D | CG | 536 | 260 | 744 | 43 |
| 61 | Q | NE2 | 537 | 363 | 617 | 34 | 71 | D | OD1 | 539 | 252 | 754 | 45 |
| 61 | Q | C | 498 | 366 | 629 | 31 | 71 | D | OD2 | 544 | 269 | 742 | 46 |
| 61 | Q | O | 506 | 357 | 632 | 31 | 71 | D | C | 513 | 241 | 720 | 36 |
| 62 | Q | N | 491 | 373 | 638 | 28 | 71 | D | O | 505 | 233 | 724 | 35 |
| 62 | Q | CA | 491 | 369 | 652 | 26 | 72 | S | N | 511 | 248 | 708 | 35 |
| 62 | Q | CB | 483 | 379 | 661 | 27 | 72 | S | CA | 499 | 246 | 700 | 34 |
| 62 | Q | CG | 491 | 392 | 662 | 28 | 72 | S | CB | 498 | 257 | 689 | 33 |
| 62 | Q | CD | 504 | 391 | 668 | 33 | 72 | S | OG | 488 | 254 | 680 | 32 |
| 62 | Q | OE1 | 507 | 383 | 678 | 37 | 72 | S | C | 500 | 233 | 693 | 35 |
| 62 | Q | NE2 | 513 | 401 | 665 | 30 | 72 | S | O | 490 | 225 | 692 | 31 |
| 62 | Q | C | 484 | 355 | 653 | 25 | 73 | S | N | 512 | 229 | 688 | 36 |
| 62 | Q | O | 488 | 348 | 663 | 28 | 73 | S | CA | 515 | 216 | 683 | 37 |
| 63 | I | N | 474 | 351 | 646 | 27 | 73 | S | CB | 529 | 215 | 678 | 38 |
| 63 | I | CA | 467 | 338 | 647 | 27 | 73 | S | OG | 531 | 223 | 667 | 42 |
| 63 | I | CB | 455 | 337 | 638 | 27 | 73 | S | C | 511 | 204 | 692 | 37 |
| 63 | I | CG1 | 444 | 346 | 644 | 25 | 73 | S | O | 506 | 194 | 687 | 39 |
| 63 | I | CD1 | 432 | 349 | 635 | 27 | 74 | A | N | 513 | 206 | 705 | 37 |
| 63 | I | CG2 | 450 | 323 | 637 | 26 | 74 | A | CA | 509 | 196 | 715 | 36 |
| 63 | I | C | 478 | 327 | 643 | 28 | 74 | A | CB | 516 | 200 | 728 | 37 |
| 63 | I | O | 480 | 317 | 649 | 27 | 74 | A | C | 494 | 196 | 718 | 37 |
| 64 | F | N | 485 | 330 | 632 | 30 | 74 | A | O | 489 | 187 | 724 | 35 |
| 64 | F | CA | 497 | 322 | 628 | 30 | 75 | A | N | 487 | 207 | 715 | 35 |
| 64 | F | CB | 503 | 326 | 615 | 33 | 75 | A | CA | 473 | 209 | 718 | 34 |
| 64 | F | CG | 514 | 317 | 610 | 29 | 75 | A | CB | 470 | 225 | 721 | 32 |
| 64 | F | CD1 | 511 | 307 | 601 | 38 | 75 | A | C | 463 | 204 | 707 | 33 |
| 64 | F | CE1 | 522 | 298 | 598 | 41 | 75 | A | O | 452 | 200 | 710 | 35 |
| 64 | F | CZ | 534 | 300 | 604 | 38 | 76 | W | N | 467 | 205 | 695 | 33 |
| 64 | F | CE2 | 537 | 310 | 613 | 41 | 76 | W | CA | 458 | 203 | 684 | 32 |
| 64 | F | CD2 | 526 | 318 | 616 | 34 | 76 | W | CB | 456 | 216 | 676 | 30 |
| 64 | F | C | 507 | 321 | 640 | 30 | 76 | W | CG | 452 | 228 | 685 | 29 |
| 64 | F | O | 510 | 309 | 644 | 31 | 76 | W | CD1 | 459 | 239 | 688 | 29 |
| 65 | N | N | 511 | 332 | 647 | 30 | 76 | W | NE1 | 453 | 247 | 698 | 31 |
| 65 | N | CA | 521 | 331 | 657 | 30 | 76 | W | CE2 | 440 | 241 | 700 | 29 |
| 65 | N | CB | 525 | 344 | 663 | 32 | 76 | W | CD2 | 440 | 229 | 693 | 29 |
| 65 | N | CG | 531 | 354 | 653 | 36 | 76 | W | CE3 | 428 | 221 | 694 | 28 |
| 65 | N | OD1 | 535 | 350 | 642 | 33 | 76 | W | CZ3 | 418 | 225 | 703 | 27 |
| 65 | N | ND2 | 532 | 367 | 658 | 35 | 76 | W | CH2 | 419 | 237 | 710 | 26 |
| 65 | N | C | 516 | 322 | 668 | 32 | 76 | W | CZ2 | 430 | 245 | 709 | 27 |
| 65 | N | O | 524 | 315 | 675 | 29 | 76 | W | C | 463 | 193 | 674 | 34 |
| 66 | L | N | 503 | 324 | 671 | 29 | 76 | W | O | 475 | 191 | 673 | 36 |
| 66 | L | CA | 497 | 317 | 682 | 29 | 77 | D | N | 454 | 188 | 666 | 34 |
| 66 | L | CB | 483 | 323 | 685 | 28 | 77 | D | CA | 457 | 178 | 655 | 36 |
| 66 | L | CG | 474 | 317 | 695 | 30 | 77 | D | CB | 445 | 174 | 648 | 34 |
| 66 | L | CD1 | 480 | 317 | 709 | 28 | 77 | D | CG | 448 | 163 | 637 | 37 |
| 66 | L | CD2 | 460 | 324 | 696 | 29 | 77 | D | OD1 | 448 | 166 | 625 | 37 |
| 66 | L | C | 496 | 302 | 680 | 28 | 77 | D | OD2 | 449 | 152 | 641 | 46 |
| 66 | L | O | 499 | 295 | 689 | 30 | 77 | D | C | 467 | 184 | 645 | 37 |
| 67 | F | N | 492 | 298 | 668 | 28 | 77 | D | O | 465 | 194 | 639 | 34 |
| 67 | F | CA | 490 | 284 | 665 | 28 | 78 | E | N | 478 | 176 | 643 | 38 |
| 67 | F | CB | 477 | 282 | 656 | 28 | 78 | E | CA | 489 | 180 | 634 | 39 |
| 67 | F | CG | 464 | 284 | 664 | 29 | 78 | E | CB | 500 | 169 | 634 | 41 |
| 67 | F | CD1 | 459 | 296 | 664 | 30 | 78 | E | CG | 511 | 172 | 624 | 47 |
| 67 | F | CE1 | 446 | 299 | 671 | 30 | 78 | E | CD | 521 | 160 | 624 | 57 |
| 67 | F | CZ | 441 | 288 | 679 | 29 | 78 | E | OE1 | 517 | 148 | 628 | 56 |
| 67 | F | CE2 | 447 | 275 | 678 | 32 | 78 | E | OE2 | 533 | 162 | 621 | 58 |
| 67 | F | CD2 | 459 | 273 | 671 | 29 | 78 | E | C | 484 | 183 | 619 | 37 |
| 67 | F | C | 502 | 276 | 660 | 31 | 78 | E | O | 488 | 193 | 613 | 39 |
| 67 | F | O | 501 | 264 | 658 | 30 | 79 | T | N | 475 | 175 | 614 | 36 |
| 68 | S | N | 513 | 283 | 658 | 31 | 79 | T | CA | 470 | 175 | 600 | 36 |
| 68 | S | CA | 525 | 276 | 652 | 32 | 79 | T | CB | 463 | 163 | 597 | 38 |
| 68 | S | CB | 531 | 286 | 641 | 32 | 79 | T | OG1 | 472 | 151 | 595 | 42 |
| 68 | S | OG | 536 | 298 | 647 | 34 | 79 | T | CG2 | 457 | 163 | 583 | 36 |
| 68 | S | C | 535 | 273 | 663 | 34 | 79 | T | C | 461 | 188 | 598 | 34 |
| 68 | S | O | 546 | 268 | 660 | 34 | 79 | T | O | 461 | 194 | 587 | 33 |
| 69 | T | N | 532 | 276 | 675 | 33 | 80 | L | N | 453 | 190 | 608 | 34 |
| 69 | T | CA | 541 | 273 | 686 | 35 | 80 | L | CA | 445 | 202 | 608 | 33 |
| 69 | T | CB | 539 | 280 | 699 | 35 | 80 | L | CB | 434 | 202 | 619 | 32 |
| 69 | T | OG1 | 526 | 275 | 705 | 33 | 80 | L | CG | 424 | 191 | 617 | 32 |
| 69 | T | CG2 | 538 | 295 | 698 | 38 | 80 | L | CD1 | 415 | 190 | 630 | 34 |
| 69 | T | C | 541 | 257 | 689 | 36 | 80 | L | CD2 | 416 | 192 | 604 | 31 |
| 69 | T | O | 534 | 250 | 684 | 36 | 80 | L | C | 454 | 215 | 609 | 31 |
| 70 | A | N | 551 | 254 | 697 | 38 | 80 | L | O | 451 | 224 | 602 | 31 |

| | | | | | | |
|---|---|---|---|---|---|---|
| 81 | L | N | 463 | 215 | 618 | 30 |
| 81 | L | CA | 472 | 227 | 619 | 32 |
| 81 | L | CB | 482 | 225 | 631 | 30 |
| 81 | L | CG | 477 | 228 | 645 | 32 |
| 81 | L | CD1 | 488 | 224 | 655 | 32 |
| 81 | L | CD2 | 473 | 243 | 647 | 29 |
| 81 | L | C | 479 | 230 | 607 | 33 |
| 81 | L | O | 481 | 241 | 603 | 32 |
| 82 | D | N | 484 | 219 | 600 | 35 |
| 82 | D | CA | 491 | 221 | 587 | 37 |
| 82 | D | CB | 500 | 209 | 584 | 41 |
| 82 | D | CG | 513 | 209 | 594 | 47 |
| 82 | D | OD1 | 512 | 206 | 606 | 55 |
| 82 | D | OD2 | 524 | 213 | 589 | 56 |
| 82 | D | C | 482 | 227 | 576 | 36 |
| 82 | D | O | 486 | 236 | 569 | 35 |
| 83 | K | N | 469 | 223 | 576 | 35 |
| 83 | K | CA | 460 | 229 | 566 | 35 |
| 83 | K | CB | 447 | 221 | 565 | 36 |
| 83 | K | CG | 450 | 207 | 560 | 42 |
| 83 | K | CD | 437 | 199 | 557 | 50 |
| 83 | K | CE | 440 | 186 | 549 | 55 |
| 83 | K | NZ | 429 | 177 | 549 | 60 |
| 83 | K | C | 457 | 244 | 571 | 34 |
| 83 | K | O | 455 | 252 | 562 | 35 |
| 84 | F | N | 456 | 246 | 584 | 32 |
| 84 | F | CA | 454 | 259 | 590 | 30 |
| 84 | F | CB | 453 | 258 | 605 | 31 |
| 84 | F | CG | 448 | 270 | 613 | 29 |
| 84 | F | CD1 | 435 | 275 | 609 | 34 |
| 84 | F | CE1 | 430 | 286 | 617 | 34 |
| 84 | F | CZ | 437 | 291 | 628 | 31 |
| 84 | F | CE2 | 450 | 285 | 632 | 33 |
| 84 | F | CD2 | 454 | 274 | 624 | 29 |
| 84 | F | C | 466 | 269 | 586 | 32 |
| 84 | F | O | 463 | 280 | 581 | 31 |
| 85 | Y | N | 478 | 265 | 587 | 32 |
| 85 | Y | CA | 490 | 273 | 583 | 33 |
| 85 | Y | CB | 503 | 266 | 585 | 33 |
| 85 | Y | CG | 505 | 262 | 599 | 33 |
| 85 | Y | CD1 | 500 | 269 | 609 | 32 |
| 85 | Y | CE1 | 502 | 265 | 622 | 31 |
| 85 | Y | CZ | 509 | 254 | 625 | 35 |
| 85 | Y | OH | 511 | 249 | 638 | 34 |
| 85 | Y | CE2 | 514 | 246 | 615 | 36 |
| 85 | Y | CD2 | 512 | 250 | 602 | 32 |
| 85 | Y | C | 489 | 277 | 568 | 34 |
| 85 | Y | O | 490 | 289 | 565 | 34 |
| 86 | T | N | 485 | 268 | 560 | 34 |
| 86 | T | CA | 483 | 270 | 546 | 35 |
| 86 | T | CB | 480 | 257 | 539 | 36 |
| 86 | T | OG1 | 491 | 248 | 539 | 39 |
| 86 | T | CG2 | 477 | 260 | 523 | 34 |
| 86 | T | C | 473 | 281 | 543 | 36 |
| 86 | T | O | 475 | 289 | 534 | 34 |
| 87 | E | N | 461 | 280 | 549 | 32 |
| 87 | E | CA | 451 | 290 | 547 | 33 |
| 87 | E | CB | 438 | 287 | 555 | 33 |
| 87 | E | CG | 431 | 274 | 550 | 34 |
| 87 | E | CD | 428 | 275 | 535 | 44 |
| 87 | E | OE1 | 424 | 286 | 530 | 40 |
| 87 | E | OE2 | 430 | 265 | 528 | 46 |
| 87 | E | C | 456 | 304 | 552 | 32 |
| 87 | E | O | 453 | 314 | 545 | 32 |
| 88 | L | N | 462 | 304 | 564 | 31 |
| 88 | L | CA | 468 | 316 | 569 | 33 |
| 88 | L | CB | 473 | 314 | 583 | 31 |
| 88 | L | CG | 463 | 310 | 594 | 30 |
| 88 | L | CD1 | 470 | 307 | 607 | 27 |
| 88 | L | CD2 | 452 | 320 | 596 | 32 |
| 88 | L | C | 478 | 323 | 560 | 34 |
| 88 | L | O | 478 | 335 | 558 | 34 |
| 89 | Y | N | 488 | 316 | 555 | 34 |
| 89 | Y | CA | 498 | 321 | 545 | 36 |
| 89 | Y | CB | 507 | 310 | 540 | 37 |
| 89 | Y | CG | 517 | 304 | 550 | 41 |
| 89 | Y | CD1 | 525 | 312 | 557 | 44 |
| 89 | Y | CE1 | 534 | 306 | 566 | 46 |
| 89 | Y | CZ | 536 | 292 | 567 | 47 |
| 89 | Y | OH | 545 | 287 | 576 | 50 |
| 89 | Y | CE2 | 528 | 284 | 560 | 42 |
| 89 | Y | CD2 | 518 | 290 | 551 | 44 |
| 89 | Y | C | 491 | 327 | 533 | 36 |
| 89 | Y | O | 495 | 338 | 529 | 36 |
| 90 | Q | N | 481 | 321 | 528 | 35 |
| 90 | Q | CA | 474 | 325 | 516 | 37 |
| 90 | Q | CB | 465 | 315 | 510 | 38 |
| 90 | Q | CG | 458 | 319 | 497 | 45 |
| 90 | Q | CD | 467 | 321 | 485 | 54 |
| 90 | Q | OE1 | 472 | 312 | 479 | 57 |
| 90 | Q | NE2 | 469 | 334 | 481 | 54 |
| 90 | Q | C | 467 | 339 | 519 | 38 |
| 90 | Q | O | 467 | 348 | 510 | 36 |
| 91 | Q | N | 461 | 340 | 530 | 36 |
| 91 | Q | CA | 454 | 352 | 534 | 34 |
| 91 | Q | CB | 445 | 351 | 547 | 33 |
| 91 | Q | CG | 433 | 343 | 543 | 33 |
| 91 | Q | CD | 425 | 338 | 555 | 43 |
| 91 | Q | OE1 | 415 | 345 | 559 | 44 |
| 91 | Q | NE2 | 428 | 327 | 561 | 39 |
| 91 | Q | C | 465 | 363 | 536 | 33 |
| 91 | Q | O | 463 | 375 | 532 | 34 |
| 92 | L | N | 476 | 360 | 543 | 32 |
| 92 | L | CA | 486 | 370 | 545 | 34 |
| 92 | L | CB | 498 | 364 | 553 | 34 |
| 92 | L | CG | 495 | 363 | 568 | 36 |
| 92 | L | CD1 | 507 | 354 | 574 | 38 |
| 92 | L | CD2 | 494 | 377 | 575 | 35 |
| 92 | L | C | 491 | 376 | 531 | 37 |
| 92 | L | O | 493 | 388 | 529 | 35 |
| 93 | N | N | 492 | 367 | 522 | 36 |
| 93 | N | CA | 497 | 370 | 509 | 40 |
| 93 | N | CB | 498 | 357 | 502 | 41 |
| 93 | N | CG | 511 | 355 | 495 | 50 |
| 93 | N | OD1 | 512 | 357 | 483 | 57 |
| 93 | N | ND2 | 520 | 351 | 504 | 53 |
| 93 | N | C | 488 | 379 | 501 | 39 |
| 93 | N | O | 493 | 388 | 495 | 38 |
| 94 | D | N | 475 | 375 | 501 | 38 |
| 94 | D | CA | 464 | 383 | 495 | 41 |
| 94 | D | CB | 451 | 376 | 497 | 42 |
| 94 | D | CG | 448 | 364 | 489 | 50 |
| 94 | D | OD1 | 457 | 359 | 482 | 55 |
| 94 | D | OD2 | 437 | 358 | 489 | 59 |
| 94 | D | C | 464 | 397 | 501 | 40 |
| 94 | D | O | 462 | 407 | 493 | 40 |
| 95 | L | N | 466 | 398 | 514 | 38 |
| 95 | L | CA | 466 | 411 | 520 | 37 |
| 95 | L | CB | 464 | 410 | 536 | 36 |
| 95 | L | CG | 450 | 404 | 540 | 35 |
| 95 | L | CD1 | 450 | 399 | 554 | 31 |
| 95 | L | CD2 | 439 | 415 | 538 | 38 |
| 95 | L | C | 478 | 420 | 517 | 38 |
| 95 | L | O | 477 | 432 | 515 | 38 |
| 96 | E | N | 490 | 413 | 516 | 38 |
| 96 | E | CA | 502 | 420 | 513 | 40 |
| 96 | E | CB | 514 | 411 | 517 | 39 |
| 96 | E | CG | 517 | 410 | 532 | 42 |
| 96 | E | CD | 527 | 399 | 535 | 43 |
| 96 | E | OE1 | 535 | 396 | 526 | 41 |
| 96 | E | OE2 | 527 | 395 | 547 | 40 |
| 96 | E | C | 503 | 425 | 498 | 41 |
| 96 | E | O | 510 | 435 | 495 | 41 |
| 97 | A | N | 495 | 418 | 490 | 43 |
| 97 | A | CA | 493 | 422 | 476 | 48 |
| 97 | A | CB | 485 | 412 | 468 | 47 |
| 97 | A | C | 487 | 436 | 474 | 51 |
| 97 | A | O | 489 | 443 | 464 | 52 |
| 98 | C | N | 480 | 441 | 484 | 55 |
| 98 | C | CA | 474 | 454 | 485 | 59 |
| 98 | C | CB | 464 | 455 | 496 | 58 |
| 98 | C | SG | 450 | 443 | 494 | 60 |
| 98 | C | C | 484 | 466 | 485 | 61 |
| 98 | C | O | 481 | 477 | 481 | 62 |
| 99 | V | N | 496 | 464 | 490 | 64 |
| 99 | V | CA | 506 | 475 | 491 | 67 |
| 99 | V | CB | 518 | 473 | 501 | 68 |
| 99 | V | CG1 | 514 | 463 | 512 | 67 |
| 99 | V | CG2 | 531 | 470 | 494 | 68 |
| 99 | V | C | 510 | 480 | 477 | 70 |

| | | | | | | |
|---|---|---|---|---|---|---|
| 99 | V | O | 512 | 492 | 475 | 70 |
| 100 | I | N | 512 | 471 | 467 | 72 |
| 100 | I | CA | 516 | 474 | 453 | 75 |
| 100 | I | CB | 521 | 462 | 445 | 75 |
| 100 | I | CG1 | 512 | 449 | 446 | 77 |
| 100 | I | CD1 | 502 | 447 | 434 | 78 |
| 100 | I | CG2 | 536 | 459 | 448 | 76 |
| 100 | I | C | 504 | 481 | 446 | 76 |
| 100 | I | O | 506 | 491 | 439 | 76 |
| 101 | A | N | 492 | 476 | 448 | 77 |
| 101 | A | CA | 479 | 481 | 443 | 78 |
| 101 | A | CB | 467 | 473 | 447 | 77 |
| 101 | A | C | 477 | 496 | 447 | 78 |
| 101 | A | O | 474 | 504 | 439 | 78 |
| 102 | G | N | 480 | 499 | 460 | 78 |
| 102 | G | CA | 479 | 512 | 465 | 78 |
| 102 | G | C | 492 | 520 | 465 | 79 |
| 102 | G | O | 492 | 533 | 465 | 79 |
| 110 | A | N | 472 | 571 | 553 | 72 |
| 110 | A | CA | 464 | 573 | 566 | 72 |
| 110 | A | CB | 449 | 573 | 562 | 72 |
| 110 | A | C | 467 | 562 | 576 | 71 |
| 110 | A | O | 459 | 552 | 578 | 72 |
| 111 | A | N | 479 | 563 | 583 | 69 |
| 111 | A | CA | 485 | 552 | 591 | 66 |
| 111 | A | CB | 500 | 554 | 593 | 67 |
| 111 | A | C | 479 | 549 | 605 | 63 |
| 111 | A | O | 475 | 558 | 612 | 65 |
| 112 | K | N | 478 | 536 | 607 | 59 |
| 112 | K | CA | 470 | 530 | 618 | 53 |
| 112 | K | CB | 462 | 518 | 612 | 56 |
| 112 | K | CG | 455 | 520 | 598 | 58 |
| 112 | K | CD | 441 | 527 | 600 | 65 |
| 112 | K | CE | 433 | 523 | 612 | 68 |
| 112 | K | NZ | 421 | 531 | 614 | 71 |
| 112 | K | C | 478 | 523 | 629 | 49 |
| 112 | K | O | 474 | 512 | 633 | 47 |
| 113 | E | N | 489 | 529 | 633 | 44 |
| 113 | E | CA | 498 | 522 | 642 | 40 |
| 113 | E | CB | 510 | 531 | 644 | 40 |
| 113 | E | CG | 516 | 535 | 631 | 46 |
| 113 | E | CD | 519 | 524 | 622 | 53 |
| 113 | E | OE1 | 517 | 525 | 609 | 59 |
| 113 | E | OE2 | 524 | 513 | 627 | 53 |
| 113 | E | C | 492 | 518 | 655 | 38 |
| 113 | E | O | 495 | 507 | 661 | 34 |
| 114 | D | N | 483 | 526 | 661 | 34 |
| 114 | D | CA | 477 | 522 | 674 | 35 |
| 114 | D | CB | 471 | 534 | 681 | 35 |
| 114 | D | CG | 482 | 545 | 684 | 40 |
| 114 | D | OD1 | 480 | 556 | 679 | 45 |
| 114 | D | OD2 | 491 | 543 | 691 | 44 |
| 114 | D | C | 467 | 512 | 672 | 32 |
| 114 | D | O | 465 | 504 | 682 | 34 |
| 115 | S | N | 460 | 511 | 661 | 32 |
| 115 | S | CA | 451 | 500 | 659 | 33 |
| 115 | S | CB | 443 | 502 | 647 | 33 |
| 115 | S | OG | 433 | 513 | 649 | 39 |
| 115 | S | C | 458 | 486 | 657 | 32 |
| 115 | S | O | 453 | 476 | 662 | 30 |
| 116 | I | N | 469 | 486 | 649 | 30 |
| 116 | I | CA | 477 | 474 | 648 | 29 |
| 116 | I | CB | 490 | 478 | 639 | 29 |
| 116 | I | CG1 | 485 | 477 | 625 | 31 |
| 116 | I | CD1 | 495 | 484 | 614 | 39 |
| 116 | I | CG2 | 501 | 467 | 642 | 29 |
| 116 | I | C | 482 | 470 | 661 | 30 |
| 116 | I | O | 481 | 458 | 665 | 32 |
| 117 | L | N | 486 | 480 | 669 | 29 |
| 117 | L | CA | 490 | 476 | 682 | 30 |
| 117 | L | CB | 495 | 489 | 688 | 33 |
| 117 | L | CG | 507 | 488 | 696 | 42 |
| 117 | L | CD1 | 519 | 485 | 686 | 44 |
| 117 | L | CD2 | 510 | 501 | 704 | 50 |
| 117 | L | C | 479 | 471 | 691 | 30 |
| 117 | L | O | 482 | 463 | 700 | 28 |
| 118 | A | N | 467 | 476 | 690 | 29 |
| 118 | A | CA | 456 | 471 | 698 | 29 |
| 118 | A | CB | 444 | 478 | 695 | 27 |
| 118 | A | C | 454 | 456 | 695 | 29 |
| 118 | A | O | 452 | 448 | 704 | 29 |
| 119 | V | N | 455 | 452 | 682 | 30 |
| 119 | V | CA | 454 | 438 | 678 | 32 |
| 119 | V | CB | 454 | 436 | 663 | 32 |
| 119 | V | CG1 | 454 | 421 | 659 | 31 |
| 119 | V | CG2 | 442 | 443 | 657 | 33 |
| 119 | V | C | 466 | 430 | 685 | 32 |
| 119 | V | O | 463 | 420 | 691 | 28 |
| 120 | R | N | 478 | 435 | 684 | 33 |
| 120 | R | CA | 489 | 428 | 692 | 32 |
| 120 | R | CB | 503 | 435 | 691 | 34 |
| 120 | R | CG | 507 | 436 | 678 | 34 |
| 120 | R | CD | 523 | 438 | 677 | 36 |
| 120 | R | NE | 524 | 440 | 663 | 33 |
| 120 | R | CZ | 531 | 450 | 657 | 34 |
| 120 | R | NH1 | 538 | 458 | 664 | 32 |
| 120 | R | NH2 | 531 | 451 | 644 | 33 |
| 120 | R | C | 487 | 427 | 706 | 34 |
| 120 | R | O | 490 | 416 | 712 | 34 |
| 121 | K | N | 482 | 437 | 713 | 31 |
| 121 | K | CA | 479 | 436 | 727 | 31 |
| 121 | K | CB | 476 | 449 | 734 | 30 |
| 121 | K | CG | 488 | 459 | 736 | 35 |
| 121 | K | CD | 482 | 473 | 739 | 37 |
| 121 | K | CE | 493 | 484 | 737 | 41 |
| 121 | K | NZ | 502 | 484 | 749 | 42 |
| 121 | K | C | 469 | 426 | 731 | 29 |
| 121 | K | O | 470 | 419 | 741 | 29 |
| 122 | Y | N | 458 | 425 | 723 | 29 |
| 122 | Y | CA | 448 | 414 | 724 | 28 |
| 122 | Y | CB | 439 | 416 | 712 | 26 |
| 122 | Y | CG | 429 | 404 | 710 | 25 |
| 122 | Y | CD1 | 430 | 396 | 699 | 23 |
| 122 | Y | CE1 | 422 | 385 | 696 | 26 |
| 122 | Y | CZ | 411 | 382 | 705 | 25 |
| 122 | Y | OH | 403 | 372 | 702 | 26 |
| 122 | Y | CE2 | 410 | 390 | 716 | 26 |
| 122 | Y | CD2 | 419 | 401 | 719 | 26 |
| 122 | Y | C | 455 | 400 | 723 | 27 |
| 122 | Y | O | 453 | 392 | 732 | 27 |
| 123 | F | N | 463 | 398 | 714 | 28 |
| 123 | F | CA | 471 | 385 | 713 | 28 |
| 123 | F | CB | 477 | 383 | 700 | 27 |
| 123 | F | CG | 467 | 378 | 689 | 29 |
| 123 | F | CD1 | 464 | 365 | 688 | 28 |
| 123 | F | CE1 | 454 | 361 | 678 | 26 |
| 123 | F | CZ | 448 | 371 | 670 | 31 |
| 123 | F | CE2 | 451 | 384 | 672 | 29 |
| 123 | F | CD2 | 460 | 388 | 682 | 27 |
| 123 | F | C | 480 | 382 | 726 | 31 |
| 123 | F | O | 482 | 371 | 730 | 28 |
| 124 | Q | N | 486 | 393 | 731 | 29 |
| 124 | Q | CA | 494 | 393 | 743 | 31 |
| 124 | Q | CB | 501 | 406 | 746 | 29 |
| 124 | Q | CG | 513 | 409 | 737 | 34 |
| 124 | Q | CD | 517 | 424 | 737 | 43 |
| 124 | Q | OE1 | 512 | 432 | 745 | 37 |
| 124 | Q | NE2 | 524 | 429 | 727 | 46 |
| 124 | Q | C | 486 | 388 | 755 | 31 |
| 124 | Q | O | 490 | 381 | 764 | 32 |
| 125 | R | N | 473 | 393 | 755 | 30 |
| 125 | R | CA | 465 | 389 | 767 | 28 |
| 125 | R | CB | 452 | 397 | 767 | 30 |
| 125 | R | CG | 454 | 413 | 770 | 31 |
| 125 | R | CD | 442 | 420 | 774 | 32 |
| 125 | R | NE | 433 | 422 | 762 | 27 |
| 125 | R | CZ | 435 | 432 | 753 | 28 |
| 125 | R | NH1 | 445 | 441 | 755 | 29 |
| 125 | R | NH2 | 426 | 434 | 744 | 28 |
| 125 | R | C | 462 | 374 | 765 | 29 |
| 125 | R | O | 461 | 367 | 775 | 28 |
| 126 | I | N | 459 | 370 | 753 | 26 |
| 126 | I | CA | 456 | 356 | 750 | 28 |
| 126 | I | CB | 453 | 353 | 736 | 29 |
| 126 | I | CG1 | 438 | 358 | 734 | 27 |
| 126 | I | CD1 | 434 | 358 | 718 | 26 |
| 126 | I | CG2 | 454 | 338 | 732 | 29 |
| 126 | I | C | 468 | 347 | 755 | 30 |
| 126 | I | O | 467 | 336 | 761 | 28 |
| 127 | T | N | 480 | 351 | 749 | 30 |

-continued

| | | | | | |
|---|---|---|---|---|---|
| 127 | T | CA | 493 | 344 | 752 | 34 |
| 127 | T | CB | 504 | 352 | 744 | 33 |
| 127 | T | OG1 | 502 | 347 | 731 | 39 |
| 127 | T | CG2 | 517 | 348 | 748 | 42 |
| 127 | T | C | 496 | 343 | 767 | 34 |
| 127 | T | O | 500 | 333 | 772 | 35 |
| 128 | L | N | 494 | 355 | 775 | 34 |
| 128 | L | CA | 496 | 354 | 789 | 34 |
| 128 | L | CB | 496 | 369 | 794 | 34 |
| 128 | L | CG | 497 | 371 | 809 | 37 |
| 128 | L | CD1 | 511 | 365 | 814 | 38 |
| 128 | L | CD2 | 496 | 386 | 814 | 36 |
| 128 | L | C | 486 | 346 | 796 | 35 |
| 128 | L | O | 490 | 338 | 806 | 34 |
| 129 | Y | N | 474 | 346 | 792 | 31 |
| 129 | Y | CA | 464 | 337 | 798 | 32 |
| 129 | Y | CB | 450 | 340 | 790 | 30 |
| 129 | Y | CG | 439 | 329 | 792 | 30 |
| 129 | Y | CD1 | 430 | 331 | 802 | 28 |
| 129 | Y | CE1 | 420 | 322 | 804 | 29 |
| 129 | Y | CZ | 419 | 311 | 795 | 26 |
| 129 | Y | OH | 408 | 302 | 799 | 29 |
| 129 | Y | CE2 | 427 | 309 | 785 | 28 |
| 129 | Y | CD2 | 438 | 319 | 783 | 27 |
| 129 | Y | C | 468 | 323 | 796 | 31 |
| 129 | Y | O | 467 | 315 | 805 | 32 |
| 130 | L | N | 472 | 319 | 784 | 32 |
| 130 | L | CA | 476 | 305 | 782 | 34 |
| 130 | L | CB | 480 | 302 | 768 | 31 |
| 130 | L | CG | 468 | 300 | 759 | 32 |
| 130 | L | CD1 | 473 | 302 | 745 | 27 |
| 130 | L | CD2 | 461 | 286 | 761 | 28 |
| 130 | L | C | 488 | 301 | 791 | 36 |
| 130 | L | O | 488 | 289 | 797 | 36 |
| 131 | K | N | 498 | 310 | 793 | 37 |
| 131 | K | CA | 509 | 307 | 802 | 39 |
| 131 | K | CB | 520 | 319 | 800 | 41 |
| 131 | K | CG | 534 | 315 | 805 | 46 |
| 131 | K | CD | 543 | 327 | 804 | 55 |
| 131 | K | CE | 557 | 324 | 810 | 57 |
| 131 | K | NZ | 567 | 334 | 805 | 62 |
| 131 | K | C | 505 | 305 | 816 | 39 |
| 131 | K | O | 508 | 296 | 823 | 40 |
| 132 | E | N | 496 | 314 | 821 | 39 |
| 132 | E | CA | 492 | 313 | 835 | 40 |
| 132 | E | CB | 484 | 325 | 839 | 41 |
| 132 | E | CG | 492 | 338 | 836 | 48 |
| 132 | E | CD | 488 | 350 | 843 | 57 |
| 132 | E | OE1 | 475 | 353 | 842 | 58 |
| 132 | E | OE2 | 496 | 357 | 849 | 63 |
| 132 | E | C | 484 | 301 | 838 | 40 |
| 132 | E | O | 485 | 295 | 849 | 38 |
| 133 | K | N | 476 | 296 | 828 | 38 |
| 133 | K | CA | 468 | 284 | 830 | 38 |
| 133 | K | CB | 456 | 285 | 820 | 38 |
| 133 | K | CG | 447 | 296 | 823 | 35 |
| 133 | K | CD | 438 | 293 | 834 | 39 |
| 133 | K | CE | 426 | 303 | 834 | 39 |
| 133 | K | NZ | 418 | 299 | 846 | 43 |
| 133 | K | C | 476 | 271 | 826 | 38 |
| 133 | K | O | 470 | 261 | 825 | 39 |
| 134 | K | N | 489 | 273 | 823 | 37 |
| 134 | K | CA | 498 | 262 | 819 | 37 |
| 134 | K | CB | 502 | 253 | 831 | 39 |
| 134 | K | CG | 508 | 261 | 843 | 43 |
| 134 | K | CD | 510 | 253 | 855 | 52 |
| 134 | K | CE | 510 | 262 | 868 | 57 |
| 134 | K | NZ | 524 | 265 | 871 | 59 |
| 134 | K | C | 493 | 254 | 808 | 37 |
| 134 | K | O | 493 | 241 | 808 | 35 |
| 135 | Y | N | 487 | 261 | 798 | 34 |
| 135 | Y | CA | 483 | 254 | 785 | 34 |
| 135 | Y | CB | 495 | 250 | 777 | 35 |
| 135 | Y | CG | 504 | 262 | 774 | 38 |
| 135 | Y | CD1 | 515 | 265 | 783 | 44 |
| 135 | Y | CE1 | 523 | 276 | 780 | 46 |
| 135 | Y | CZ | 521 | 283 | 769 | 44 |
| 135 | Y | OH | 529 | 294 | 766 | 46 |
| 135 | Y | CE2 | 510 | 281 | 760 | 41 |
| 135 | Y | CD2 | 502 | 270 | 763 | 39 |
| 135 | Y | C | 474 | 243 | 788 | 32 |
| 135 | Y | O | 474 | 233 | 781 | 34 |
| 136 | S | N | 465 | 244 | 797 | 33 |
| 136 | S | CA | 456 | 233 | 800 | 34 |
| 136 | S | CB | 448 | 236 | 813 | 34 |
| 136 | S | OG | 439 | 246 | 811 | 37 |
| 136 | S | C | 446 | 231 | 788 | 35 |
| 136 | S | O | 445 | 240 | 779 | 34 |
| 137 | P | N | 441 | 219 | 786 | 35 |
| 137 | P | CA | 431 | 216 | 776 | 34 |
| 137 | P | CB | 426 | 202 | 779 | 35 |
| 137 | P | CG | 439 | 195 | 786 | 36 |
| 137 | P | CD | 445 | 206 | 794 | 37 |
| 137 | P | C | 419 | 226 | 777 | 33 |
| 137 | P | O | 415 | 230 | 766 | 32 |
| 138 | C | N | 415 | 230 | 788 | 31 |
| 138 | C | CA | 404 | 240 | 790 | 32 |
| 138 | C | CB | 398 | 241 | 803 | 32 |
| 138 | C | SG | 386 | 227 | 807 | 39 |
| 138 | C | C | 408 | 254 | 785 | 32 |
| 138 | C | O | 400 | 261 | 779 | 30 |
| 139 | A | N | 420 | 258 | 790 | 30 |
| 139 | A | CA | 425 | 272 | 785 | 29 |
| 139 | A | CB | 438 | 275 | 792 | 28 |
| 139 | A | C | 426 | 272 | 770 | 28 |
| 139 | A | O | 423 | 283 | 764 | 28 |
| 140 | W | N | 431 | 261 | 764 | 26 |
| 140 | W | CA | 432 | 261 | 750 | 27 |
| 140 | W | CB | 440 | 248 | 745 | 27 |
| 140 | W | CG | 455 | 251 | 742 | 29 |
| 140 | W | CD1 | 466 | 245 | 749 | 28 |
| 140 | W | NE1 | 478 | 250 | 743 | 32 |
| 140 | W | CE2 | 475 | 259 | 733 | 33 |
| 140 | W | CD2 | 461 | 260 | 732 | 30 |
| 140 | W | CE3 | 455 | 269 | 723 | 29 |
| 140 | W | CZ3 | 464 | 277 | 715 | 29 |
| 140 | W | CH2 | 478 | 275 | 716 | 29 |
| 140 | W | CZ2 | 484 | 267 | 725 | 33 |
| 140 | W | C | 418 | 261 | 743 | 27 |
| 140 | W | O | 417 | 266 | 732 | 24 |
| 141 | E | N | 408 | 254 | 748 | 26 |
| 141 | E | CA | 395 | 255 | 742 | 27 |
| 141 | E | CB | 386 | 245 | 749 | 28 |
| 141 | E | CG | 371 | 247 | 745 | 27 |
| 141 | E | CD | 369 | 246 | 729 | 26 |
| 141 | E | OE1 | 378 | 241 | 721 | 29 |
| 141 | E | OE2 | 358 | 251 | 725 | 27 |
| 141 | E | C | 389 | 269 | 743 | 27 |
| 141 | E | O | 383 | 273 | 733 | 26 |
| 142 | V | N | 391 | 275 | 754 | 25 |
| 142 | V | CA | 386 | 289 | 756 | 27 |
| 142 | V | CB | 390 | 295 | 770 | 28 |
| 142 | V | CG1 | 388 | 310 | 770 | 26 |
| 142 | V | CG2 | 381 | 288 | 781 | 28 |
| 142 | V | C | 393 | 298 | 745 | 27 |
| 142 | V | O | 386 | 306 | 738 | 25 |
| 143 | V | N | 405 | 296 | 742 | 27 |
| 143 | V | CA | 413 | 304 | 732 | 26 |
| 143 | V | CB | 428 | 302 | 734 | 25 |
| 143 | V | CG1 | 436 | 307 | 721 | 24 |
| 143 | V | CG2 | 432 | 309 | 747 | 23 |
| 143 | V | C | 408 | 300 | 718 | 25 |
| 143 | V | O | 406 | 309 | 710 | 23 |
| 144 | R | N | 407 | 287 | 715 | 24 |
| 144 | R | CA | 402 | 283 | 702 | 25 |
| 144 | R | CB | 402 | 268 | 700 | 24 |
| 144 | R | CG | 398 | 263 | 687 | 26 |
| 144 | R | CD | 391 | 249 | 688 | 25 |
| 144 | R | NE | 379 | 250 | 695 | 29 |
| 144 | R | CZ | 367 | 254 | 690 | 29 |
| 144 | R | NH1 | 366 | 257 | 677 | 29 |
| 144 | R | NH2 | 356 | 256 | 698 | 25 |
| 144 | R | C | 388 | 290 | 699 | 25 |
| 144 | R | O | 386 | 295 | 687 | 24 |
| 145 | A | N | 379 | 288 | 708 | 26 |
| 145 | A | CA | 365 | 293 | 707 | 25 |
| 145 | A | CB | 356 | 290 | 719 | 25 |
| 145 | A | C | 366 | 309 | 704 | 25 |
| 145 | A | O | 359 | 314 | 696 | 25 |
| 146 | E | N | 374 | 315 | 713 | 25 |

| | | | | | | |
|---|---|---|---|---|---|---|
| 146 | E | CA | 376 | 329 | 712 | 25 |
| 146 | E | CB | 386 | 334 | 723 | 26 |
| 146 | E | CG | 392 | 348 | 721 | 26 |
| 146 | E | CD | 382 | 359 | 723 | 31 |
| 146 | E | OE1 | 383 | 370 | 716 | 28 |
| 146 | E | OE2 | 372 | 357 | 730 | 29 |
| 146 | E | C | 381 | 334 | 698 | 27 |
| 146 | E | O | 375 | 343 | 692 | 26 |
| 147 | I | N | 391 | 327 | 692 | 26 |
| 147 | I | CA | 396 | 331 | 679 | 25 |
| 147 | I | CB | 410 | 323 | 676 | 27 |
| 147 | I | CG1 | 420 | 327 | 686 | 28 |
| 147 | I | CD1 | 425 | 342 | 685 | 32 |
| 147 | I | CG2 | 414 | 325 | 661 | 27 |
| 147 | I | C | 386 | 329 | 669 | 27 |
| 147 | I | O | 384 | 337 | 659 | 26 |
| 148 | M | N | 379 | 317 | 670 | 25 |
| 148 | M | CA | 368 | 315 | 660 | 27 |
| 148 | M | CB | 362 | 301 | 663 | 28 |
| 148 | M | CG | 357 | 294 | 651 | 35 |
| 148 | M | SD | 349 | 279 | 656 | 35 |
| 148 | M | CE | 337 | 279 | 642 | 35 |
| 148 | M | C | 358 | 327 | 660 | 27 |
| 148 | M | O | 354 | 331 | 649 | 27 |
| 149 | R | N | 354 | 332 | 671 | 26 |
| 149 | R | CA | 345 | 343 | 672 | 27 |
| 149 | R | CB | 340 | 345 | 686 | 28 |
| 149 | R | CG | 331 | 334 | 691 | 29 |
| 149 | R | CD | 323 | 336 | 705 | 28 |
| 149 | R | NE | 332 | 342 | 715 | 30 |
| 149 | R | CZ | 339 | 335 | 724 | 30 |
| 149 | R | NH1 | 347 | 342 | 732 | 30 |
| 149 | R | NH2 | 340 | 322 | 724 | 30 |
| 149 | R | C | 351 | 356 | 667 | 26 |
| 149 | R | O | 346 | 362 | 658 | 25 |
| 150 | S | N | 364 | 359 | 671 | 26 |
| 150 | S | CA | 370 | 372 | 667 | 28 |
| 150 | S | CB | 381 | 376 | 676 | 29 |
| 150 | S | OG | 392 | 366 | 675 | 29 |
| 150 | S | C | 374 | 372 | 653 | 29 |
| 150 | S | O | 372 | 382 | 645 | 28 |
| 151 | F | N | 379 | 360 | 648 | 27 |
| 151 | F | CA | 382 | 359 | 634 | 29 |
| 151 | F | CB | 390 | 346 | 630 | 29 |
| 151 | F | CG | 393 | 344 | 615 | 32 |
| 151 | F | CD1 | 404 | 350 | 610 | 34 |
| 151 | F | CE1 | 407 | 349 | 596 | 37 |
| 151 | F | CZ | 399 | 342 | 588 | 36 |
| 151 | F | CE2 | 387 | 335 | 594 | 36 |
| 151 | F | CD2 | 385 | 337 | 607 | 34 |
| 151 | F | C | 370 | 361 | 625 | 30 |
| 151 | F | O | 370 | 367 | 614 | 27 |
| 152 | S | N | 358 | 354 | 628 | 32 |
| 152 | S | CA | 346 | 357 | 620 | 34 |
| 152 | S | CB | 334 | 348 | 623 | 36 |
| 152 | S | OG | 334 | 346 | 636 | 42 |
| 152 | S | C | 342 | 371 | 620 | 35 |
| 152 | S | O | 337 | 376 | 610 | 36 |
| 153 | L | N | 343 | 378 | 631 | 35 |
| 153 | L | CA | 339 | 392 | 632 | 38 |
| 153 | L | CB | 341 | 397 | 647 | 40 |
| 153 | L | CG | 330 | 406 | 653 | 43 |
| 153 | L | CD1 | 317 | 407 | 646 | 47 |
| 153 | L | CD2 | 329 | 400 | 667 | 48 |
| 153 | L | C | 348 | 401 | 624 | 39 |
| 153 | L | O | 343 | 409 | 616 | 39 |
| 154 | S | N | 361 | 398 | 625 | 37 |
| 154 | S | CA | 372 | 406 | 618 | 39 |
| 154 | S | CB | 385 | 403 | 624 | 36 |
| 154 | S | OG | 390 | 391 | 619 | 41 |
| 154 | S | C | 371 | 404 | 603 | 41 |
| 154 | S | O | 375 | 413 | 595 | 42 |
| 155 | T | N | 366 | 393 | 598 | 42 |
| 155 | T | CA | 365 | 391 | 584 | 45 |
| 155 | T | CB | 370 | 377 | 580 | 44 |
| 155 | T | OG1 | 363 | 367 | 587 | 41 |
| 155 | T | CG2 | 384 | 374 | 584 | 40 |
| 155 | T | C | 351 | 393 | 578 | 48 |
| 155 | T | O | 350 | 394 | 566 | 49 |
| 156 | N | N | 341 | 393 | 586 | 51 |
| 156 | N | CA | 327 | 395 | 581 | 55 |
| 156 | N | CB | 317 | 384 | 587 | 57 |
| 156 | N | CG | 321 | 369 | 584 | 62 |
| 156 | N | OD1 | 315 | 360 | 591 | 67 |
| 156 | N | ND2 | 330 | 367 | 575 | 68 |
| 156 | N | C | 321 | 409 | 584 | 56 |
| 156 | N | O | 326 | 419 | 580 | 57 |
| 6 | A | N | 624 | 164 | 488 | 83 |
| 6 | A | CA | 619 | 173 | 499 | 83 |
| 6 | A | CB | 621 | 166 | 513 | 83 |
| 6 | A | C | 626 | 187 | 499 | 83 |
| 6 | A | O | 633 | 191 | 508 | 83 |
| 7 | H | N | 623 | 194 | 488 | 82 |
| 7 | H | CA | 624 | 208 | 488 | 81 |
| 7 | H | CB | 630 | 213 | 474 | 81 |
| 7 | H | CG | 645 | 215 | 475 | 79 |
| 7 | H | ND1 | 652 | 223 | 483 | 78 |
| 7 | H | CE1 | 665 | 222 | 481 | 77 |
| 7 | H | NE2 | 667 | 213 | 472 | 75 |
| 7 | H | CD2 | 655 | 208 | 467 | 77 |
| 7 | H | C | 610 | 214 | 490 | 81 |
| 7 | H | O | 609 | 225 | 493 | 81 |
| 8 | A | N | 601 | 205 | 487 | 80 |
| 8 | A | CA | 586 | 207 | 490 | 79 |
| 8 | A | CB | 578 | 196 | 483 | 79 |
| 8 | A | C | 583 | 208 | 505 | 77 |
| 8 | A | O | 577 | 218 | 509 | 78 |
| 9 | A | N | 587 | 198 | 513 | 75 |
| 9 | A | CA | 584 | 198 | 527 | 73 |
| 9 | A | CB | 580 | 184 | 532 | 74 |
| 9 | A | C | 595 | 204 | 536 | 71 |
| 9 | A | O | 592 | 207 | 548 | 71 |
| 10 | G | N | 607 | 205 | 531 | 68 |
| 10 | G | CA | 618 | 211 | 538 | 64 |
| 10 | G | C | 616 | 226 | 540 | 61 |
| 10 | G | O | 620 | 233 | 550 | 61 |
| 11 | S | N | 611 | 232 | 529 | 58 |
| 11 | S | CA | 608 | 246 | 529 | 56 |
| 11 | S | CB | 605 | 250 | 514 | 56 |
| 11 | S | OG | 595 | 243 | 509 | 58 |
| 11 | S | C | 597 | 251 | 538 | 54 |
| 11 | S | O | 596 | 262 | 541 | 53 |
| 12 | R | N | 588 | 241 | 542 | 52 |
| 12 | R | CA | 577 | 245 | 550 | 48 |
| 12 | R | CB | 567 | 233 | 551 | 51 |
| 12 | R | CG | 560 | 228 | 539 | 53 |
| 12 | R | CD | 546 | 235 | 537 | 61 |
| 12 | R | NE | 536 | 232 | 548 | 63 |
| 12 | R | CZ | 525 | 240 | 549 | 64 |
| 12 | R | NH1 | 523 | 250 | 540 | 63 |
| 12 | R | NH2 | 516 | 237 | 558 | 55 |
| 12 | R | C | 582 | 249 | 563 | 46 |
| 12 | R | O | 577 | 259 | 568 | 44 |
| 13 | R | N | 591 | 242 | 569 | 43 |
| 13 | R | CA | 596 | 246 | 582 | 42 |
| 13 | R | CB | 605 | 235 | 588 | 43 |
| 13 | R | CG | 599 | 221 | 590 | 50 |
| 13 | R | CD | 608 | 209 | 594 | 57 |
| 13 | R | NE | 617 | 206 | 582 | 64 |
| 13 | R | CZ | 621 | 194 | 580 | 69 |
| 13 | R | NH1 | 618 | 183 | 588 | 72 |
| 13 | R | NH2 | 629 | 191 | 569 | 69 |
| 13 | R | C | 603 | 259 | 581 | 39 |
| 13 | R | O | 603 | 267 | 591 | 37 |
| 14 | T | N | 610 | 261 | 570 | 38 |
| 14 | T | CA | 618 | 274 | 568 | 38 |
| 14 | T | CB | 625 | 273 | 555 | 38 |
| 14 | T | OG1 | 635 | 263 | 555 | 41 |
| 14 | T | CG2 | 634 | 286 | 553 | 35 |
| 14 | T | C | 609 | 286 | 568 | 36 |
| 14 | T | O | 611 | 296 | 574 | 36 |
| 15 | L | N | 598 | 285 | 559 | 37 |
| 15 | L | CA | 587 | 295 | 559 | 39 |
| 15 | L | CB | 577 | 291 | 549 | 41 |
| 15 | L | CG | 582 | 291 | 535 | 43 |
| 15 | L | CD1 | 585 | 306 | 531 | 48 |
| 15 | L | CD2 | 572 | 285 | 525 | 45 |
| 15 | L | C | 581 | 299 | 572 | 38 |
| 15 | L | O | 579 | 310 | 576 | 37 |
| 16 | M | N | 578 | 288 | 580 | 38 |

-continued

| | | | | | | |
|---|---|---|---|---|---|---|
| 16 | M | CA | 572 | 290 | 594 | 37 |
| 16 | M | CB | 569 | 277 | 601 | 38 |
| 16 | M | CG | 565 | 279 | 616 | 39 |
| 16 | M | SD | 561 | 263 | 625 | 49 |
| 16 | M | CE | 547 | 258 | 615 | 44 |
| 16 | M | C | 582 | 298 | 602 | 36 |
| 16 | M | O | 578 | 307 | 610 | 35 |
| 17 | L | N | 595 | 294 | 601 | 35 |
| 17 | L | CA | 604 | 302 | 609 | 34 |
| 17 | L | CB | 617 | 295 | 610 | 34 |
| 17 | L | CG | 617 | 282 | 618 | 38 |
| 17 | L | CD1 | 629 | 273 | 612 | 40 |
| 17 | L | CD2 | 620 | 286 | 632 | 37 |
| 17 | L | C | 604 | 316 | 605 | 30 |
| 17 | L | O | 605 | 325 | 613 | 31 |
| 18 | L | N | 605 | 319 | 592 | 32 |
| 18 | L | CA | 606 | 333 | 587 | 33 |
| 18 | L | CB | 607 | 333 | 572 | 33 |
| 18 | L | CG | 621 | 332 | 566 | 36 |
| 18 | L | CD1 | 619 | 328 | 551 | 37 |
| 18 | L | CD2 | 629 | 345 | 568 | 37 |
| 18 | L | C | 593 | 340 | 591 | 34 |
| 18 | L | O | 593 | 352 | 595 | 35 |
| 19 | A | N | 582 | 333 | 590 | 35 |
| 19 | A | CA | 569 | 339 | 596 | 36 |
| 19 | A | CB | 557 | 330 | 592 | 38 |
| 19 | A | C | 570 | 342 | 610 | 36 |
| 19 | A | O | 566 | 354 | 613 | 37 |
| 20 | Q | N | 575 | 334 | 618 | 35 |
| 20 | Q | CA | 576 | 336 | 633 | 34 |
| 20 | Q | CB | 580 | 324 | 641 | 36 |
| 20 | Q | CG | 569 | 313 | 640 | 38 |
| 20 | Q | CD | 573 | 299 | 646 | 42 |
| 20 | Q | OE1 | 585 | 296 | 645 | 45 |
| 20 | Q | NE2 | 564 | 292 | 651 | 39 |
| 20 | Q | C | 586 | 347 | 636 | 34 |
| 20 | Q | O | 586 | 353 | 647 | 32 |
| 21 | M | N | 596 | 349 | 627 | 31 |
| 21 | M | CA | 606 | 359 | 630 | 30 |
| 21 | M | CB | 619 | 358 | 620 | 30 |
| 21 | M | CG | 627 | 346 | 624 | 32 |
| 21 | M | SD | 638 | 341 | 609 | 37 |
| 21 | M | CE | 646 | 356 | 608 | 33 |
| 21 | M | C | 602 | 374 | 629 | 30 |
| 21 | M | O | 608 | 382 | 635 | 32 |
| 22 | R | N | 590 | 376 | 622 | 33 |
| 22 | R | CA | 585 | 389 | 620 | 34 |
| 22 | R | CB | 571 | 387 | 613 | 36 |
| 22 | R | CG | 564 | 401 | 609 | 38 |
| 22 | R | CD | 552 | 404 | 617 | 38 |
| 22 | R | NE | 541 | 411 | 611 | 37 |
| 22 | R | CZ | 531 | 417 | 618 | 34 |
| 22 | R | NH1 | 531 | 415 | 631 | 31 |
| 22 | R | NH2 | 522 | 424 | 612 | 35 |
| 22 | R | C | 583 | 397 | 633 | 36 |
| 22 | R | O | 577 | 392 | 643 | 35 |
| 23 | R | N | 587 | 410 | 634 | 35 |
| 23 | R | CA | 586 | 417 | 647 | 36 |
| 23 | R | CB | 599 | 421 | 653 | 37 |
| 23 | R | CG | 609 | 409 | 655 | 41 |
| 23 | R | CD | 623 | 414 | 657 | 46 |
| 23 | R | NE | 623 | 423 | 669 | 54 |
| 23 | R | CZ | 634 | 429 | 673 | 60 |
| 23 | R | NH1 | 633 | 436 | 684 | 64 |
| 23 | R | NH2 | 646 | 427 | 668 | 61 |
| 23 | R | C | 577 | 429 | 644 | 38 |
| 23 | R | O | 569 | 433 | 654 | 37 |
| 24 | I | N | 576 | 435 | 632 | 35 |
| 24 | I | CA | 568 | 447 | 630 | 35 |
| 24 | I | CB | 575 | 460 | 630 | 33 |
| 24 | I | CG1 | 585 | 460 | 619 | 35 |
| 24 | I | CD1 | 594 | 475 | 617 | 34 |
| 24 | I | CG2 | 581 | 462 | 644 | 36 |
| 24 | I | C | 561 | 445 | 617 | 34 |
| 24 | I | O | 564 | 436 | 609 | 34 |
| 25 | S | N | 551 | 453 | 614 | 33 |
| 25 | S | CA | 542 | 451 | 603 | 35 |
| 25 | S | CB | 528 | 457 | 605 | 33 |
| 25 | S | OG | 521 | 457 | 594 | 33 |
| 25 | S | C | 548 | 458 | 590 | 35 |
| 25 | S | O | 553 | 469 | 591 | 36 |
| 26 | L | N | 548 | 451 | 579 | 35 |
| 26 | L | CA | 551 | 458 | 566 | 37 |
| 26 | L | CB | 546 | 449 | 555 | 37 |
| 26 | L | CG | 555 | 438 | 551 | 44 |
| 26 | L | CD1 | 547 | 427 | 543 | 44 |
| 26 | L | CD2 | 566 | 445 | 542 | 47 |
| 26 | L | C | 542 | 470 | 564 | 38 |
| 26 | L | O | 546 | 479 | 556 | 36 |
| 27 | F | N | 530 | 470 | 570 | 36 |
| 27 | F | CA | 521 | 482 | 568 | 37 |
| 27 | F | CB | 506 | 479 | 570 | 34 |
| 27 | F | CG | 501 | 469 | 560 | 34 |
| 27 | F | CD1 | 495 | 474 | 548 | 38 |
| 27 | F | CE1 | 490 | 466 | 539 | 38 |
| 27 | F | CZ | 490 | 452 | 541 | 34 |
| 27 | F | CE2 | 496 | 447 | 553 | 31 |
| 27 | F | CD2 | 501 | 456 | 562 | 30 |
| 27 | F | C | 525 | 494 | 577 | 36 |
| 27 | F | O | 521 | 505 | 575 | 39 |
| 28 | S | N | 534 | 492 | 586 | 36 |
| 28 | S | CA | 541 | 503 | 594 | 37 |
| 28 | S | CB | 544 | 499 | 608 | 36 |
| 28 | S | OG | 533 | 492 | 614 | 39 |
| 28 | S | C | 553 | 508 | 587 | 37 |
| 28 | S | O | 560 | 517 | 592 | 38 |
| 29 | C | N | 556 | 503 | 575 | 37 |
| 29 | C | CA | 569 | 505 | 568 | 37 |
| 29 | C | CB | 577 | 491 | 569 | 37 |
| 29 | C | SG | 583 | 488 | 587 | 41 |
| 29 | C | C | 567 | 508 | 553 | 36 |
| 29 | C | O | 576 | 505 | 545 | 36 |
| 30 | L | N | 556 | 514 | 550 | 37 |
| 30 | L | CA | 552 | 516 | 536 | 39 |
| 30 | L | CB | 538 | 521 | 535 | 40 |
| 30 | L | CG | 526 | 511 | 539 | 44 |
| 30 | L | CD1 | 514 | 520 | 540 | 49 |
| 30 | L | CD2 | 525 | 500 | 529 | 46 |
| 30 | L | C | 561 | 525 | 529 | 39 |
| 30 | L | O | 564 | 523 | 517 | 39 |
| 31 | K | N | 567 | 535 | 535 | 41 |
| 31 | K | CA | 577 | 544 | 529 | 42 |
| 31 | K | CB | 581 | 555 | 539 | 43 |
| 31 | K | CG | 590 | 550 | 550 | 48 |
| 31 | K | CD | 591 | 559 | 562 | 52 |
| 31 | K | CE | 603 | 555 | 572 | 55 |
| 31 | K | NZ | 601 | 542 | 579 | 55 |
| 31 | K | C | 590 | 536 | 525 | 42 |
| 31 | K | O | 597 | 541 | 517 | 41 |
| 32 | D | N | 592 | 524 | 531 | 40 |
| 32 | D | CA | 604 | 516 | 527 | 40 |
| 32 | D | CB | 611 | 510 | 539 | 41 |
| 32 | D | CG | 614 | 520 | 550 | 44 |
| 32 | D | OD1 | 623 | 528 | 547 | 45 |
| 32 | D | OD2 | 608 | 522 | 561 | 46 |
| 32 | D | C | 601 | 505 | 517 | 39 |
| 32 | D | O | 610 | 497 | 514 | 38 |
| 33 | A | N | 589 | 505 | 512 | 38 |
| 33 | A | CA | 585 | 495 | 501 | 38 |
| 33 | A | CB | 571 | 499 | 495 | 40 |
| 33 | A | C | 595 | 496 | 490 | 39 |
| 33 | A | O | 599 | 506 | 486 | 39 |
| 34 | H | N | 598 | 484 | 484 | 37 |
| 34 | H | CA | 608 | 484 | 473 | 39 |
| 34 | H | CB | 622 | 484 | 480 | 39 |
| 34 | H | CG | 634 | 486 | 471 | 41 |
| 34 | H | ND1 | 641 | 498 | 469 | 46 |
| 34 | H | CE1 | 650 | 496 | 460 | 46 |
| 34 | H | NE2 | 649 | 484 | 455 | 43 |
| 34 | H | CD2 | 639 | 477 | 462 | 40 |
| 34 | H | C | 606 | 471 | 465 | 40 |
| 34 | H | O | 603 | 461 | 471 | 41 |
| 35 | D | N | 605 | 472 | 452 | 39 |
| 35 | D | CA | 604 | 461 | 443 | 38 |
| 35 | D | CB | 595 | 462 | 431 | 41 |
| 35 | D | CG | 590 | 449 | 426 | 44 |
| 35 | D | OD1 | 578 | 449 | 421 | 51 |
| 35 | D | OD2 | 597 | 438 | 424 | 43 |
| 35 | D | C | 618 | 457 | 439 | 38 |
| 35 | D | O | 625 | 465 | 432 | 35 |

| 36 | F | N | 622 | 445 | 443 | 36 |
| --- | --- | --- | --- | --- | --- | --- |
| 36 | F | CA | 636 | 440 | 441 | 34 |
| 36 | F | CB | 640 | 431 | 453 | 32 |
| 36 | F | CG | 642 | 438 | 466 | 32 |
| 36 | F | CD1 | 632 | 438 | 475 | 28 |
| 36 | F | CE1 | 633 | 445 | 487 | 31 |
| 36 | F | CZ | 644 | 452 | 490 | 32 |
| 36 | F | CE2 | 655 | 453 | 480 | 30 |
| 36 | F | CD2 | 653 | 446 | 468 | 29 |
| 36 | F | C | 637 | 433 | 428 | 33 |
| 36 | F | O | 648 | 429 | 425 | 32 |
| 37 | G | N | 626 | 430 | 422 | 33 |
| 37 | G | CA | 626 | 423 | 409 | 35 |
| 37 | G | C | 631 | 408 | 410 | 36 |
| 37 | G | O | 639 | 404 | 402 | 33 |
| 38 | F | N | 625 | 400 | 419 | 36 |
| 38 | F | CA | 630 | 387 | 420 | 37 |
| 38 | F | CB | 621 | 380 | 430 | 36 |
| 38 | F | CG | 624 | 365 | 432 | 38 |
| 38 | F | CD1 | 636 | 361 | 436 | 39 |
| 38 | F | CE1 | 639 | 347 | 437 | 44 |
| 38 | F | CZ | 630 | 338 | 435 | 41 |
| 38 | F | CE2 | 617 | 342 | 431 | 42 |
| 38 | F | CD2 | 614 | 355 | 429 | 38 |
| 38 | F | C | 628 | 379 | 406 | 38 |
| 38 | F | O | 617 | 379 | 401 | 39 |
| 39 | P | N | 638 | 372 | 401 | 38 |
| 39 | P | CA | 636 | 365 | 388 | 39 |
| 39 | P | CB | 651 | 363 | 383 | 38 |
| 39 | P | CG | 659 | 363 | 396 | 39 |
| 39 | P | CD | 652 | 372 | 406 | 36 |
| 39 | P | C | 629 | 351 | 390 | 39 |
| 39 | P | O | 634 | 340 | 387 | 41 |
| 40 | Q | N | 616 | 352 | 393 | 41 |
| 40 | Q | CA | 608 | 340 | 396 | 43 |
| 40 | Q | CB | 594 | 344 | 401 | 44 |
| 40 | Q | CG | 585 | 351 | 391 | 49 |
| 40 | Q | CD | 571 | 353 | 396 | 54 |
| 40 | Q | OE1 | 568 | 361 | 405 | 57 |
| 40 | Q | NE2 | 562 | 345 | 391 | 59 |
| 40 | Q | C | 607 | 331 | 384 | 45 |
| 40 | Q | O | 605 | 319 | 385 | 45 |
| 41 | E | N | 609 | 336 | 372 | 46 |
| 41 | E | CA | 609 | 328 | 359 | 47 |
| 41 | E | CB | 608 | 337 | 347 | 45 |
| 41 | E | CG | 622 | 344 | 344 | 43 |
| 41 | E | CD | 625 | 357 | 352 | 38 |
| 41 | E | OE1 | 616 | 361 | 360 | 38 |
| 41 | E | OE2 | 635 | 363 | 350 | 39 |
| 41 | E | C | 620 | 318 | 358 | 50 |
| 41 | E | O | 619 | 308 | 350 | 50 |
| 42 | E | N | 631 | 320 | 365 | 52 |
| 42 | E | CA | 642 | 310 | 365 | 55 |
| 42 | E | CB | 655 | 315 | 373 | 55 |
| 42 | E | CG | 660 | 329 | 369 | 59 |
| 42 | E | CD | 661 | 332 | 354 | 62 |
| 42 | E | OE1 | 650 | 336 | 349 | 68 |
| 42 | E | OE2 | 671 | 330 | 348 | 62 |
| 42 | E | C | 638 | 297 | 372 | 57 |
| 42 | E | O | 644 | 287 | 371 | 58 |
| 43 | F | N | 627 | 298 | 380 | 60 |
| 43 | F | CA | 623 | 286 | 388 | 63 |
| 43 | F | CB | 620 | 290 | 403 | 62 |
| 43 | F | CG | 632 | 296 | 409 | 60 |
| 43 | F | CD1 | 635 | 310 | 408 | 58 |
| 43 | F | CE1 | 646 | 316 | 415 | 56 |
| 43 | F | CZ | 655 | 308 | 422 | 57 |
| 43 | F | CE2 | 652 | 294 | 423 | 57 |
| 43 | F | CD2 | 641 | 288 | 416 | 58 |
| 43 | F | C | 610 | 280 | 382 | 67 |
| 43 | F | O | 604 | 271 | 388 | 69 |
| 44 | G | N | 605 | 285 | 371 | 71 |
| 44 | G | CA | 592 | 281 | 366 | 75 |
| 44 | G | C | 592 | 269 | 357 | 78 |
| 44 | G | O | 602 | 262 | 355 | 78 |
| 45 | N | N | 579 | 266 | 352 | 82 |
| 45 | N | CA | 576 | 254 | 344 | 85 |
| 45 | N | CB | 561 | 253 | 342 | 85 |
| 45 | N | CG | 555 | 266 | 337 | 88 |
| 45 | N | OD1 | 554 | 269 | 325 | 90 |
| 45 | N | ND2 | 551 | 275 | 347 | 88 |
| 45 | N | C | 583 | 253 | 331 | 86 |
| 45 | N | O | 585 | 242 | 325 | 87 |
| 46 | Q | N | 587 | 264 | 325 | 88 |
| 46 | Q | CA | 594 | 264 | 312 | 89 |
| 46 | Q | CB | 594 | 278 | 305 | 89 |
| 46 | Q | CG | 602 | 290 | 312 | 90 |
| 46 | Q | CD | 602 | 303 | 304 | 92 |
| 46 | Q | OE1 | 592 | 309 | 303 | 91 |
| 46 | Q | NE2 | 614 | 307 | 300 | 92 |
| 46 | Q | C | 608 | 258 | 312 | 89 |
| 46 | Q | O | 615 | 257 | 302 | 90 |
| 47 | F | N | 612 | 253 | 324 | 90 |
| 47 | F | CA | 625 | 246 | 326 | 90 |
| 47 | F | CB | 635 | 254 | 334 | 91 |
| 47 | F | CG | 639 | 267 | 327 | 92 |
| 47 | F | CD1 | 646 | 267 | 315 | 93 |
| 47 | F | CE1 | 650 | 279 | 309 | 94 |
| 47 | F | CZ | 647 | 291 | 315 | 94 |
| 47 | F | CE2 | 640 | 292 | 327 | 93 |
| 47 | F | CD2 | 636 | 279 | 333 | 92 |
| 47 | F | C | 623 | 233 | 333 | 90 |
| 47 | F | O | 614 | 231 | 341 | 90 |
| 48 | A | N | 631 | 223 | 329 | 90 |
| 48 | A | CA | 631 | 210 | 336 | 89 |
| 48 | A | CB | 638 | 199 | 327 | 89 |
| 48 | A | C | 637 | 211 | 350 | 89 |
| 48 | A | O | 646 | 219 | 352 | 88 |
| 49 | A | N | 631 | 203 | 359 | 88 |
| 49 | A | CA | 636 | 203 | 373 | 87 |
| 49 | A | CB | 629 | 192 | 381 | 87 |
| 49 | A | C | 651 | 202 | 375 | 86 |
| 49 | A | O | 657 | 209 | 383 | 86 |
| 50 | A | N | 658 | 195 | 366 | 84 |
| 50 | A | CA | 672 | 194 | 366 | 82 |
| 50 | A | CB | 677 | 182 | 357 | 83 |
| 50 | A | C | 679 | 207 | 361 | 81 |
| 50 | A | O | 691 | 208 | 362 | 81 |
| 51 | A | N | 671 | 216 | 356 | 78 |
| 51 | A | CA | 677 | 229 | 352 | 76 |
| 51 | A | CB | 669 | 235 | 339 | 76 |
| 51 | A | C | 676 | 238 | 364 | 74 |
| 51 | A | O | 685 | 247 | 365 | 74 |
| 52 | T | N | 666 | 237 | 372 | 71 |
| 52 | T | CA | 663 | 247 | 382 | 68 |
| 52 | T | CB | 647 | 248 | 385 | 68 |
| 52 | T | OG1 | 642 | 236 | 390 | 70 |
| 52 | T | CG2 | 640 | 251 | 372 | 68 |
| 52 | T | C | 670 | 244 | 396 | 66 |
| 52 | T | O | 670 | 252 | 405 | 65 |
| 53 | I | N | 676 | 232 | 397 | 63 |
| 53 | I | CA | 682 | 228 | 410 | 61 |
| 53 | I | CB | 684 | 213 | 410 | 61 |
| 53 | I | CG1 | 670 | 206 | 414 | 62 |
| 53 | I | CD1 | 669 | 192 | 408 | 65 |
| 53 | I | CG2 | 695 | 209 | 420 | 60 |
| 53 | I | C | 694 | 236 | 413 | 58 |
| 53 | I | O | 695 | 242 | 424 | 58 |
| 54 | P | N | 704 | 238 | 404 | 56 |
| 54 | P | CA | 715 | 247 | 406 | 54 |
| 54 | P | CB | 722 | 247 | 392 | 55 |
| 54 | P | CG | 718 | 234 | 386 | 55 |
| 54 | P | CD | 704 | 232 | 390 | 55 |
| 54 | P | C | 710 | 261 | 409 | 53 |
| 54 | P | O | 717 | 268 | 418 | 52 |
| 55 | V | N | 699 | 266 | 404 | 50 |
| 55 | V | CA | 694 | 279 | 407 | 48 |
| 55 | V | CB | 683 | 284 | 396 | 49 |
| 55 | V | CG1 | 683 | 300 | 397 | 48 |
| 55 | V | CG2 | 687 | 280 | 382 | 48 |
| 55 | V | C | 688 | 279 | 421 | 47 |
| 55 | V | O | 691 | 288 | 428 | 45 |
| 56 | L | N | 680 | 269 | 424 | 46 |
| 56 | L | CA | 675 | 268 | 437 | 46 |
| 56 | L | CB | 665 | 256 | 437 | 46 |
| 56 | L | CG | 659 | 252 | 451 | 48 |
| 56 | L | CD1 | 651 | 264 | 458 | 51 |
| 56 | L | CD2 | 650 | 240 | 449 | 52 |
| 56 | L | C | 686 | 267 | 448 | 45 |
| 56 | L | O | 685 | 273 | 459 | 45 |

| | | | | | |
|---|---|---|---|---|---|
| 57 | H | N | 696 | 260 | 445 | 46 |
| 57 | H | CA | 708 | 259 | 455 | 45 |
| 57 | H | CB | 717 | 247 | 452 | 46 |
| 57 | H | CG | 710 | 234 | 454 | 48 |
| 57 | H | ND1 | 716 | 221 | 451 | 48 |
| 57 | H | CE1 | 707 | 212 | 454 | 52 |
| 57 | H | NE2 | 696 | 217 | 459 | 50 |
| 57 | H | CD2 | 698 | 231 | 459 | 48 |
| 57 | H | C | 715 | 272 | 457 | 43 |
| 57 | H | O | 719 | 275 | 468 | 42 |
| 58 | E | N | 716 | 280 | 446 | 42 |
| 58 | E | CA | 721 | 293 | 448 | 41 |
| 58 | E | CB | 723 | 300 | 434 | 42 |
| 58 | E | CG | 730 | 314 | 435 | 41 |
| 58 | E | CD | 744 | 313 | 439 | 45 |
| 58 | E | OE1 | 749 | 323 | 445 | 41 |
| 58 | E | OE2 | 751 | 303 | 437 | 48 |
| 58 | E | C | 712 | 302 | 457 | 40 |
| 58 | E | O | 717 | 310 | 465 | 40 |
| 59 | M | N | 699 | 301 | 455 | 40 |
| 59 | M | CA | 690 | 308 | 464 | 41 |
| 59 | M | CB | 676 | 303 | 460 | 41 |
| 59 | M | CG | 664 | 310 | 467 | 47 |
| 59 | M | SD | 661 | 326 | 460 | 54 |
| 59 | M | CE | 647 | 331 | 471 | 48 |
| 59 | M | C | 692 | 304 | 479 | 39 |
| 59 | M | O | 694 | 313 | 487 | 38 |
| 60 | I | N | 693 | 291 | 482 | 39 |
| 60 | I | CA | 696 | 287 | 496 | 38 |
| 60 | I | CB | 695 | 271 | 497 | 39 |
| 60 | I | CG1 | 682 | 266 | 491 | 42 |
| 60 | I | CD1 | 670 | 269 | 500 | 47 |
| 60 | I | CG2 | 699 | 267 | 512 | 39 |
| 60 | I | C | 709 | 293 | 501 | 37 |
| 60 | I | O | 710 | 298 | 512 | 37 |
| 61 | Q | N | 720 | 291 | 493 | 37 |
| 61 | Q | CA | 732 | 297 | 497 | 37 |
| 61 | Q | CB | 743 | 296 | 486 | 38 |
| 61 | Q | CG | 756 | 303 | 490 | 38 |
| 61 | Q | CD | 763 | 295 | 500 | 47 |
| 61 | Q | OE1 | 767 | 300 | 511 | 45 |
| 61 | Q | NE2 | 765 | 283 | 497 | 46 |
| 61 | Q | C | 732 | 312 | 500 | 36 |
| 61 | Q | O | 738 | 317 | 509 | 35 |
| 62 | Q | N | 725 | 320 | 491 | 35 |
| 62 | Q | CA | 724 | 335 | 493 | 32 |
| 62 | Q | CB | 717 | 341 | 481 | 33 |
| 62 | Q | CG | 726 | 340 | 468 | 32 |
| 62 | Q | CD | 738 | 348 | 469 | 34 |
| 62 | Q | OE1 | 739 | 359 | 475 | 37 |
| 62 | Q | NE2 | 750 | 342 | 464 | 35 |
| 62 | Q | C | 716 | 338 | 505 | 31 |
| 62 | Q | O | 718 | 347 | 512 | 32 |
| 63 | I | N | 705 | 330 | 508 | 31 |
| 63 | I | CA | 697 | 332 | 520 | 33 |
| 63 | I | CB | 685 | 324 | 520 | 34 |
| 63 | I | CG1 | 674 | 328 | 510 | 36 |
| 63 | I | CD1 | 664 | 318 | 506 | 36 |
| 63 | I | CG2 | 678 | 324 | 534 | 32 |
| 63 | I | C | 706 | 330 | 532 | 33 |
| 63 | I | O | 707 | 337 | 542 | 32 |
| 64 | F | N | 714 | 319 | 531 | 34 |
| 64 | F | CA | 724 | 316 | 542 | 34 |
| 64 | F | CB | 733 | 303 | 540 | 35 |
| 64 | F | CG | 745 | 302 | 550 | 37 |
| 64 | F | CD1 | 743 | 295 | 561 | 45 |
| 64 | F | CE1 | 754 | 295 | 571 | 41 |
| 64 | F | CZ | 765 | 302 | 569 | 40 |
| 64 | F | CE2 | 767 | 310 | 557 | 42 |
| 64 | F | CD2 | 756 | 310 | 548 | 38 |
| 64 | F | C | 732 | 328 | 544 | 34 |
| 64 | F | O | 733 | 333 | 556 | 35 |
| 65 | N | N | 738 | 333 | 534 | 34 |
| 65 | N | CA | 747 | 345 | 534 | 34 |
| 65 | N | CB | 753 | 349 | 520 | 34 |
| 65 | N | CG | 761 | 338 | 513 | 41 |
| 65 | N | OD1 | 763 | 338 | 500 | 43 |
| 65 | N | ND2 | 766 | 328 | 520 | 30 |
| 65 | N | C | 740 | 357 | 540 | 34 |
| 65 | N | O | 745 | 363 | 549 | 35 |
| 66 | L | N | 728 | 361 | 535 | 33 |
| 66 | L | CA | 721 | 373 | 540 | 32 |
| 66 | L | CB | 708 | 374 | 533 | 32 |
| 66 | L | CG | 698 | 385 | 537 | 32 |
| 66 | L | CD1 | 704 | 398 | 535 | 34 |
| 66 | L | CD2 | 685 | 383 | 527 | 33 |
| 66 | L | C | 718 | 372 | 555 | 30 |
| 66 | L | O | 719 | 382 | 562 | 32 |
| 67 | F | N | 713 | 361 | 560 | 32 |
| 67 | F | CA | 709 | 360 | 575 | 33 |
| 67 | F | CB | 697 | 351 | 576 | 34 |
| 67 | F | CG | 684 | 357 | 571 | 35 |
| 67 | F | CD1 | 680 | 355 | 558 | 34 |
| 67 | F | CE1 | 668 | 361 | 553 | 36 |
| 67 | F | CZ | 661 | 369 | 561 | 35 |
| 67 | F | CE2 | 665 | 371 | 574 | 38 |
| 67 | F | CD2 | 677 | 365 | 579 | 35 |
| 67 | F | C | 720 | 357 | 584 | 38 |
| 67 | F | O | 717 | 355 | 596 | 37 |
| 68 | S | N | 733 | 357 | 580 | 42 |
| 68 | S | CA | 744 | 351 | 588 | 44 |
| 68 | S | CB | 751 | 340 | 581 | 45 |
| 68 | S | OG | 759 | 344 | 569 | 49 |
| 68 | S | C | 753 | 362 | 593 | 45 |
| 68 | S | O | 762 | 360 | 601 | 48 |
| 69 | T | N | 750 | 374 | 589 | 45 |
| 69 | T | CA | 758 | 386 | 593 | 44 |
| 69 | T | CB | 755 | 398 | 584 | 44 |
| 69 | T | OG1 | 741 | 402 | 586 | 41 |
| 69 | T | CG2 | 755 | 394 | 569 | 41 |
| 69 | T | C | 755 | 390 | 607 | 46 |
| 69 | T | O | 745 | 386 | 613 | 44 |
| 70 | K | N | 764 | 399 | 612 | 47 |
| 70 | K | CA | 762 | 406 | 625 | 49 |
| 70 | K | CB | 774 | 415 | 627 | 50 |
| 70 | K | CG | 785 | 409 | 635 | 55 |
| 70 | K | CD | 797 | 419 | 639 | 62 |
| 70 | K | CE | 810 | 412 | 641 | 66 |
| 70 | K | NZ | 809 | 402 | 653 | 67 |
| 70 | K | C | 749 | 413 | 625 | 48 |
| 70 | K | O | 742 | 415 | 635 | 48 |
| 71 | D | N | 746 | 419 | 613 | 46 |
| 71 | D | CA | 734 | 427 | 611 | 44 |
| 71 | D | CB | 735 | 435 | 598 | 45 |
| 71 | D | CG | 746 | 444 | 598 | 48 |
| 71 | D | OD1 | 745 | 455 | 604 | 52 |
| 71 | D | OD2 | 757 | 442 | 592 | 53 |
| 71 | D | C | 722 | 419 | 613 | 43 |
| 71 | D | O | 713 | 423 | 620 | 43 |
| 72 | S | N | 722 | 407 | 607 | 40 |
| 72 | S | CA | 711 | 398 | 609 | 39 |
| 72 | S | CB | 712 | 386 | 600 | 39 |
| 72 | S | OG | 702 | 377 | 602 | 37 |
| 72 | S | C | 709 | 394 | 623 | 41 |
| 72 | S | O | 698 | 394 | 629 | 40 |
| 73 | S | N | 721 | 391 | 630 | 42 |
| 73 | S | CA | 720 | 388 | 644 | 45 |
| 73 | S | CB | 734 | 382 | 650 | 46 |
| 73 | S | OG | 736 | 369 | 643 | 47 |
| 73 | S | C | 715 | 399 | 653 | 45 |
| 73 | S | O | 708 | 396 | 663 | 47 |
| 74 | A | N | 717 | 411 | 650 | 46 |
| 74 | A | CA | 711 | 422 | 657 | 45 |
| 74 | A | CB | 719 | 436 | 655 | 46 |
| 74 | A | C | 697 | 425 | 654 | 46 |
| 74 | A | O | 690 | 431 | 662 | 48 |
| 75 | A | N | 692 | 419 | 643 | 44 |
| 75 | A | CA | 678 | 422 | 638 | 41 |
| 75 | A | CB | 678 | 422 | 623 | 40 |
| 75 | A | C | 668 | 412 | 643 | 40 |
| 75 | A | O | 656 | 415 | 644 | 39 |
| 76 | W | N | 672 | 399 | 645 | 39 |
| 76 | W | CA | 663 | 388 | 646 | 38 |
| 76 | W | CB | 664 | 379 | 634 | 37 |
| 76 | W | CG | 661 | 386 | 621 | 37 |
| 76 | W | CD1 | 670 | 388 | 611 | 35 |
| 76 | W | NE1 | 664 | 395 | 600 | 36 |
| 76 | W | CE2 | 651 | 398 | 604 | 36 |
| 76 | W | CD2 | 649 | 393 | 617 | 36 |
| 76 | W | CE3 | 636 | 395 | 622 | 34 |

-continued

| | | | | | | | | | | | | |
|---|---|---|---|---|---|---|---|---|---|---|---|---|
| 76 | W | CZ3 | 626 | 401 | 615 | 35 | 85 | Y | OH | 723 | 331 | 579 | 57 |
| 76 | W | CH2 | 629 | 406 | 602 | 36 | 85 | Y | CE2 | 713 | 320 | 599 | 46 |
| 76 | W | CZ2 | 642 | 405 | 596 | 34 | 85 | Y | CD2 | 710 | 308 | 605 | 43 |
| 76 | W | C | 665 | 380 | 659 | 38 | 85 | Y | C | 699 | 264 | 598 | 38 |
| 76 | W | O | 676 | 381 | 665 | 37 | 85 | Y | O | 703 | 258 | 588 | 39 |
| 77 | D | N | 655 | 373 | 664 | 38 | 86 | T | N | 694 | 257 | 608 | 39 |
| 77 | D | CA | 656 | 365 | 676 | 39 | 86 | T | CA | 692 | 243 | 608 | 41 |
| 77 | D | CB | 642 | 359 | 679 | 38 | 86 | T | CB | 686 | 238 | 621 | 40 |
| 77 | D | CG | 642 | 350 | 691 | 44 | 86 | T | OG1 | 696 | 240 | 632 | 44 |
| 77 | D | OD1 | 639 | 338 | 691 | 46 | 86 | T | CG2 | 685 | 223 | 622 | 46 |
| 77 | D | OD2 | 646 | 355 | 703 | 50 | 86 | T | C | 685 | 238 | 596 | 42 |
| 77 | D | C | 666 | 354 | 674 | 39 | 86 | T | O | 689 | 228 | 589 | 42 |
| 77 | D | O | 664 | 346 | 664 | 36 | 87 | E | N | 674 | 245 | 593 | 40 |
| 78 | E | N | 675 | 352 | 683 | 40 | 87 | E | CA | 667 | 241 | 580 | 39 |
| 78 | E | CA | 686 | 342 | 682 | 42 | 87 | E | CB | 654 | 249 | 579 | 40 |
| 78 | E | CB | 697 | 343 | 692 | 43 | 87 | E | CG | 644 | 246 | 591 | 42 |
| 78 | E | CG | 707 | 331 | 691 | 49 | 87 | E | CD | 642 | 231 | 592 | 47 |
| 78 | E | CD | 719 | 333 | 681 | 58 | 87 | E | OE1 | 638 | 225 | 582 | 45 |
| 78 | E | OE1 | 728 | 324 | 680 | 57 | 87 | E | OE2 | 643 | 226 | 603 | 49 |
| 78 | E | OE2 | 719 | 344 | 674 | 62 | 87 | E | C | 676 | 244 | 567 | 38 |
| 78 | E | C | 680 | 327 | 681 | 42 | 87 | E | O | 676 | 236 | 558 | 38 |
| 78 | E | O | 684 | 320 | 673 | 43 | 88 | L | N | 683 | 255 | 567 | 36 |
| 79 | T | N | 671 | 324 | 690 | 41 | 88 | L | CA | 690 | 258 | 555 | 38 |
| 79 | T | CA | 664 | 311 | 690 | 41 | 88 | L | CB | 697 | 272 | 555 | 37 |
| 79 | T | CB | 653 | 311 | 701 | 42 | 88 | L | CG | 687 | 284 | 557 | 38 |
| 79 | T | OG1 | 659 | 313 | 714 | 44 | 88 | L | CD1 | 695 | 296 | 559 | 33 |
| 79 | T | CG2 | 646 | 297 | 702 | 43 | 88 | L | CD2 | 677 | 284 | 545 | 40 |
| 79 | T | C | 658 | 308 | 676 | 40 | 88 | L | C | 701 | 248 | 552 | 37 |
| 79 | T | O | 660 | 296 | 671 | 39 | 88 | L | O | 704 | 245 | 540 | 38 |
| 80 | L | N | 651 | 317 | 670 | 38 | 89 | Y | N | 708 | 243 | 562 | 40 |
| 80 | L | CA | 645 | 314 | 658 | 35 | 89 | Y | CA | 719 | 232 | 560 | 40 |
| 80 | L | CB | 634 | 325 | 654 | 37 | 89 | Y | CB | 725 | 228 | 574 | 39 |
| 80 | L | CG | 622 | 325 | 664 | 40 | 89 | Y | CG | 732 | 239 | 581 | 36 |
| 80 | L | CD1 | 613 | 337 | 660 | 45 | 89 | Y | CD1 | 739 | 249 | 574 | 38 |
| 80 | L | CD2 | 614 | 311 | 662 | 42 | 89 | Y | CE1 | 744 | 260 | 581 | 39 |
| 80 | L | C | 655 | 314 | 646 | 34 | 89 | Y | CZ | 743 | 261 | 594 | 37 |
| 80 | L | O | 655 | 306 | 638 | 32 | 89 | Y | OH | 748 | 272 | 601 | 36 |
| 81 | L | N | 665 | 323 | 647 | 35 | 89 | Y | CE2 | 735 | 252 | 601 | 34 |
| 81 | L | CA | 676 | 322 | 636 | 36 | 89 | Y | CD2 | 730 | 241 | 595 | 35 |
| 81 | L | CB | 686 | 332 | 639 | 37 | 89 | Y | C | 714 | 220 | 553 | 41 |
| 81 | L | CG | 685 | 346 | 632 | 40 | 89 | Y | O | 721 | 215 | 544 | 41 |
| 81 | L | CD1 | 697 | 353 | 637 | 42 | 90 | Q | N | 701 | 216 | 555 | 42 |
| 81 | L | CD2 | 684 | 343 | 617 | 34 | 90 | Q | CA | 695 | 204 | 549 | 44 |
| 81 | L | C | 683 | 309 | 636 | 37 | 90 | Q | CB | 683 | 199 | 556 | 45 |
| 81 | L | O | 686 | 303 | 625 | 37 | 90 | Q | CG | 684 | 199 | 571 | 49 |
| 82 | D | N | 686 | 304 | 648 | 38 | 90 | Q | CD | 671 | 192 | 577 | 58 |
| 82 | D | CA | 694 | 291 | 649 | 37 | 90 | Q | OE1 | 666 | 197 | 588 | 62 |
| 82 | D | CB | 697 | 287 | 663 | 37 | 90 | Q | NE2 | 666 | 182 | 571 | 59 |
| 82 | D | CG | 708 | 296 | 669 | 40 | 90 | Q | C | 692 | 206 | 534 | 45 |
| 82 | D | OD1 | 712 | 296 | 681 | 35 | 90 | Q | O | 690 | 196 | 526 | 45 |
| 82 | D | OD2 | 714 | 304 | 661 | 42 | 91 | Q | N | 691 | 219 | 530 | 44 |
| 82 | D | C | 686 | 280 | 642 | 37 | 91 | Q | CA | 686 | 222 | 517 | 45 |
| 82 | D | O | 691 | 271 | 635 | 38 | 91 | Q | CB | 676 | 233 | 517 | 44 |
| 83 | K | N | 673 | 279 | 645 | 37 | 91 | Q | CG | 663 | 229 | 525 | 47 |
| 83 | K | CA | 664 | 269 | 639 | 37 | 91 | Q | CD | 654 | 241 | 528 | 48 |
| 83 | K | CB | 651 | 270 | 646 | 38 | 91 | Q | OE1 | 646 | 245 | 520 | 49 |
| 83 | K | CG | 652 | 264 | 660 | 44 | 91 | Q | NE2 | 654 | 246 | 541 | 48 |
| 83 | K | CD | 638 | 261 | 667 | 54 | 91 | Q | C | 698 | 226 | 508 | 45 |
| 83 | K | CE | 639 | 258 | 682 | 58 | 91 | Q | O | 696 | 227 | 495 | 46 |
| 83 | K | NZ | 626 | 259 | 688 | 62 | 92 | L | N | 710 | 228 | 513 | 45 |
| 83 | K | C | 663 | 271 | 623 | 37 | 92 | L | CA | 721 | 234 | 505 | 44 |
| 83 | K | O | 663 | 261 | 615 | 36 | 92 | L | CB | 733 | 237 | 514 | 45 |
| 84 | F | N | 662 | 283 | 619 | 35 | 92 | L | CG | 733 | 250 | 522 | 46 |
| 84 | F | CA | 662 | 287 | 605 | 35 | 92 | L | CD1 | 745 | 250 | 532 | 47 |
| 84 | F | CB | 662 | 302 | 604 | 35 | 92 | L | CD2 | 735 | 263 | 512 | 48 |
| 84 | F | CG | 661 | 308 | 590 | 35 | 92 | L | C | 726 | 225 | 494 | 46 |
| 84 | F | CD1 | 651 | 305 | 581 | 33 | 92 | L | O | 731 | 229 | 484 | 45 |
| 84 | F | CE1 | 650 | 311 | 568 | 34 | 93 | N | N | 726 | 212 | 498 | 47 |
| 84 | F | CZ | 660 | 320 | 564 | 33 | 93 | N | CA | 734 | 202 | 489 | 49 |
| 84 | F | CE2 | 671 | 323 | 573 | 34 | 93 | N | CB | 749 | 203 | 493 | 47 |
| 84 | F | CD2 | 671 | 317 | 586 | 37 | 93 | N | CG | 757 | 194 | 484 | 48 |
| 84 | F | C | 675 | 282 | 598 | 35 | 93 | N | OD1 | 753 | 190 | 473 | 44 |
| 84 | F | O | 676 | 274 | 589 | 33 | 93 | N | ND2 | 769 | 190 | 490 | 47 |
| 85 | Y | N | 687 | 285 | 605 | 36 | 93 | N | C | 728 | 188 | 492 | 51 |
| 85 | Y | CA | 699 | 279 | 599 | 38 | 93 | N | O | 734 | 180 | 499 | 51 |
| 85 | Y | CB | 711 | 284 | 607 | 38 | 94 | D | N | 716 | 186 | 487 | 53 |
| 85 | Y | CG | 715 | 296 | 601 | 43 | 94 | D | CA | 708 | 174 | 491 | 56 |
| 85 | Y | CD1 | 722 | 296 | 588 | 47 | 94 | D | CB | 694 | 177 | 495 | 56 |
| 85 | Y | CE1 | 725 | 308 | 581 | 51 | 94 | D | CG | 686 | 184 | 484 | 58 |
| 85 | Y | CZ | 720 | 319 | 587 | 51 | 94 | D | OD1 | 674 | 181 | 482 | 61 |

| | | | | | | |
|---|---|---|---|---|---|---|
| 94 | D | OD2 | 692 | 193 | 478 | 60 |
| 94 | D | C | 708 | 163 | 480 | 57 |
| 94 | D | O | 701 | 153 | 482 | 57 |
| 95 | L | N | 716 | 165 | 469 | 59 |
| 95 | L | CA | 720 | 154 | 460 | 61 |
| 95 | L | CB | 730 | 145 | 466 | 61 |
| 95 | L | CG | 742 | 152 | 472 | 62 |
| 95 | L | CD1 | 750 | 143 | 482 | 60 |
| 95 | L | CD2 | 752 | 158 | 462 | 60 |
| 95 | L | C | 708 | 146 | 453 | 63 |
| 95 | L | O | 708 | 134 | 453 | 63 |
| 96 | E | N | 699 | 154 | 448 | 64 |
| 96 | E | CA | 687 | 149 | 441 | 65 |
| 96 | E | CB | 683 | 158 | 430 | 65 |
| 96 | E | CG | 674 | 169 | 434 | 66 |
| 96 | E | CD | 680 | 179 | 445 | 67 |
| 96 | E | OE1 | 672 | 186 | 451 | 67 |
| 96 | E | OE2 | 692 | 179 | 447 | 66 |
| 96 | E | C | 686 | 134 | 437 | 66 |
| 96 | E | O | 688 | 130 | 425 | 66 |
| 112 | A | N | 740 | 266 | 337 | 59 |
| 112 | A | CA | 730 | 277 | 337 | 59 |
| 112 | A | CB | 716 | 272 | 342 | 59 |
| 112 | A | C | 736 | 289 | 345 | 57 |
| 112 | A | O | 729 | 294 | 354 | 57 |
| 113 | E | N | 747 | 294 | 340 | 56 |
| 113 | E | CA | 754 | 305 | 346 | 55 |
| 113 | E | CB | 767 | 307 | 337 | 56 |
| 113 | E | CG | 777 | 317 | 342 | 62 |
| 113 | E | CD | 789 | 318 | 332 | 72 |
| 113 | E | OE1 | 795 | 329 | 331 | 73 |
| 113 | E | OE2 | 793 | 308 | 326 | 74 |
| 113 | E | C | 746 | 318 | 346 | 53 |
| 113 | E | O | 748 | 326 | 356 | 52 |
| 114 | D | N | 738 | 322 | 336 | 50 |
| 114 | D | CA | 732 | 335 | 336 | 49 |
| 114 | D | CB | 726 | 338 | 322 | 50 |
| 114 | D | CG | 736 | 340 | 311 | 56 |
| 114 | D | OD1 | 734 | 336 | 300 | 61 |
| 114 | D | OD2 | 746 | 347 | 313 | 61 |
| 114 | D | C | 721 | 336 | 346 | 46 |
| 114 | D | O | 719 | 346 | 352 | 45 |
| 115 | S | N | 714 | 324 | 348 | 44 |
| 115 | S | CA | 704 | 323 | 358 | 44 |
| 115 | S | CB | 697 | 309 | 356 | 45 |
| 115 | S | OG | 688 | 309 | 345 | 49 |
| 115 | S | C | 709 | 324 | 372 | 44 |
| 115 | S | O | 703 | 330 | 380 | 43 |
| 116 | I | N | 721 | 317 | 375 | 43 |
| 116 | I | CA | 726 | 318 | 388 | 42 |
| 116 | I | CB | 739 | 309 | 389 | 43 |
| 116 | I | CG1 | 734 | 294 | 391 | 45 |
| 116 | I | CD1 | 744 | 284 | 386 | 50 |
| 116 | I | CG2 | 748 | 313 | 401 | 44 |
| 116 | I | C | 731 | 333 | 391 | 42 |
| 116 | I | O | 729 | 338 | 401 | 40 |
| 117 | L | N | 736 | 339 | 380 | 41 |
| 117 | L | CA | 740 | 353 | 382 | 41 |
| 117 | L | CB | 747 | 357 | 369 | 41 |
| 117 | L | CG | 753 | 371 | 371 | 46 |
| 117 | L | CD1 | 765 | 371 | 381 | 51 |
| 117 | L | CD2 | 757 | 378 | 358 | 50 |
| 117 | L | C | 728 | 363 | 385 | 38 |
| 117 | L | O | 730 | 373 | 392 | 39 |
| 118 | A | N | 717 | 360 | 379 | 36 |
| 118 | A | CA | 704 | 367 | 381 | 36 |
| 118 | A | CB | 693 | 360 | 372 | 35 |
| 118 | A | C | 700 | 366 | 395 | 35 |
| 118 | A | O | 696 | 376 | 401 | 32 |
| 119 | V | N | 701 | 354 | 401 | 35 |
| 119 | V | CA | 698 | 352 | 415 | 35 |
| 119 | V | CB | 698 | 337 | 419 | 35 |
| 119 | V | CG1 | 698 | 335 | 434 | 34 |
| 119 | V | CG2 | 687 | 331 | 412 | 34 |
| 119 | V | C | 708 | 360 | 424 | 36 |
| 119 | V | O | 704 | 367 | 433 | 35 |
| 120 | R | N | 721 | 359 | 420 | 35 |
| 120 | R | CA | 731 | 366 | 428 | 35 |
| 120 | R | CB | 745 | 364 | 424 | 35 |
| 120 | R | CG | 751 | 350 | 427 | 40 |
| 120 | R | CD | 765 | 348 | 423 | 40 |
| 120 | R | NE | 768 | 333 | 425 | 41 |
| 120 | R | CZ | 778 | 326 | 419 | 46 |
| 120 | R | NH1 | 787 | 333 | 412 | 50 |
| 120 | R | NH2 | 779 | 313 | 422 | 48 |
| 120 | R | C | 728 | 381 | 428 | 34 |
| 120 | R | O | 730 | 388 | 437 | 32 |
| 121 | K | N | 723 | 386 | 416 | 33 |
| 121 | K | CA | 722 | 401 | 415 | 32 |
| 121 | K | CB | 720 | 405 | 400 | 31 |
| 121 | K | CG | 733 | 406 | 391 | 36 |
| 121 | K | CD | 731 | 409 | 376 | 45 |
| 121 | K | CE | 745 | 411 | 369 | 49 |
| 121 | K | NZ | 746 | 415 | 354 | 54 |
| 121 | K | C | 710 | 405 | 423 | 30 |
| 121 | K | O | 709 | 416 | 428 | 31 |
| 122 | Y | N | 700 | 397 | 423 | 30 |
| 122 | Y | CA | 688 | 400 | 432 | 31 |
| 122 | Y | CB | 678 | 388 | 430 | 28 |
| 122 | Y | CG | 667 | 387 | 441 | 32 |
| 122 | Y | CD1 | 668 | 376 | 450 | 32 |
| 122 | Y | CE1 | 658 | 375 | 460 | 29 |
| 122 | Y | CZ | 647 | 383 | 460 | 32 |
| 122 | Y | OH | 637 | 381 | 468 | 33 |
| 122 | Y | CE2 | 646 | 394 | 450 | 33 |
| 122 | Y | CD2 | 656 | 396 | 441 | 30 |
| 122 | Y | C | 692 | 401 | 446 | 30 |
| 122 | Y | O | 689 | 411 | 453 | 30 |
| 123 | F | N | 701 | 392 | 452 | 30 |
| 123 | F | CA | 706 | 394 | 465 | 31 |
| 123 | F | CB | 712 | 380 | 470 | 31 |
| 123 | F | CG | 702 | 370 | 474 | 31 |
| 123 | F | CD1 | 696 | 370 | 487 | 30 |
| 123 | F | CE1 | 686 | 361 | 491 | 27 |
| 123 | F | CZ | 682 | 352 | 481 | 28 |
| 123 | F | CE2 | 687 | 352 | 468 | 32 |
| 123 | F | CD2 | 697 | 361 | 465 | 29 |
| 123 | F | C | 715 | 406 | 468 | 29 |
| 123 | F | O | 714 | 413 | 478 | 29 |
| 124 | Q | N | 722 | 410 | 457 | 31 |
| 124 | Q | CA | 731 | 422 | 458 | 30 |
| 124 | Q | CB | 740 | 424 | 446 | 32 |
| 124 | Q | CG | 750 | 413 | 444 | 36 |
| 124 | Q | CD | 756 | 413 | 429 | 43 |
| 124 | Q | OE1 | 753 | 421 | 421 | 43 |
| 124 | Q | NE2 | 765 | 403 | 427 | 46 |
| 124 | Q | C | 722 | 434 | 460 | 28 |
| 124 | Q | O | 725 | 443 | 467 | 30 |
| 125 | R | N | 710 | 434 | 452 | 28 |
| 125 | R | CA | 701 | 445 | 454 | 29 |
| 125 | R | CB | 690 | 445 | 443 | 28 |
| 125 | R | CG | 694 | 445 | 429 | 32 |
| 125 | R | CD | 683 | 447 | 418 | 27 |
| 125 | R | NE | 675 | 436 | 416 | 29 |
| 125 | R | CZ | 677 | 426 | 408 | 28 |
| 125 | R | NH1 | 688 | 425 | 401 | 30 |
| 125 | R | NH2 | 668 | 416 | 407 | 27 |
| 125 | R | C | 695 | 445 | 468 | 28 |
| 125 | R | O | 693 | 456 | 474 | 28 |
| 126 | I | N | 692 | 434 | 473 | 29 |
| 126 | I | CA | 687 | 433 | 487 | 30 |
| 126 | I | CB | 682 | 419 | 491 | 29 |
| 126 | I | CG1 | 668 | 416 | 485 | 32 |
| 126 | I | CD1 | 665 | 402 | 484 | 31 |
| 126 | I | CG2 | 681 | 417 | 506 | 31 |
| 126 | I | C | 697 | 439 | 497 | 29 |
| 126 | I | O | 695 | 447 | 506 | 27 |
| 127 | T | N | 710 | 433 | 496 | 30 |
| 127 | T | CA | 721 | 438 | 504 | 33 |
| 127 | T | CB | 733 | 430 | 500 | 33 |
| 127 | T | OG1 | 732 | 417 | 505 | 40 |
| 127 | T | CG2 | 746 | 435 | 508 | 39 |
| 127 | T | C | 723 | 453 | 504 | 32 |
| 127 | T | O | 726 | 459 | 514 | 32 |
| 128 | L | N | 723 | 458 | 492 | 33 |
| 128 | L | CA | 725 | 473 | 491 | 34 |
| 128 | L | CB | 727 | 476 | 476 | 36 |
| 128 | L | CG | 730 | 490 | 472 | 41 |
| 128 | L | CD1 | 743 | 496 | 478 | 41 |
| 128 | L | CD2 | 730 | 491 | 457 | 46 |

| | | | | | | | | | | | |
|---|---|---|---|---|---|---|---|---|---|---|---|
| 128 | L | C | 714 | 481 | 497 | 33 | 137 | P | CD | 650 | 496 | 626 | 37 |
| 128 | L | O | 716 | 491 | 503 | 35 | 137 | P | C | 629 | 476 | 604 | 34 |
| 129 | Y | N | 702 | 476 | 495 | 33 | 137 | P | O | 625 | 465 | 600 | 33 |
| 129 | Y | CA | 690 | 483 | 501 | 31 | 138 | C | N | 625 | 487 | 598 | 34 |
| 129 | Y | CB | 678 | 475 | 497 | 31 | 138 | C | CA | 615 | 487 | 587 | 33 |
| 129 | Y | CG | 665 | 478 | 505 | 31 | 138 | C | CB | 610 | 501 | 583 | 35 |
| 129 | Y | CD1 | 656 | 488 | 501 | 32 | 138 | C | SG | 595 | 504 | 593 | 40 |
| 129 | Y | CE1 | 644 | 490 | 508 | 34 | 138 | C | C | 622 | 480 | 575 | 32 |
| 129 | Y | CZ | 641 | 483 | 520 | 34 | 138 | C | O | 616 | 473 | 567 | 32 |
| 129 | Y | OH | 629 | 486 | 526 | 35 | 139 | A | N | 635 | 483 | 573 | 31 |
| 129 | Y | CE2 | 650 | 473 | 524 | 31 | 139 | A | CA | 641 | 477 | 561 | 31 |
| 129 | Y | CD2 | 662 | 470 | 517 | 30 | 139 | A | CB | 655 | 484 | 558 | 30 |
| 129 | Y | C | 692 | 483 | 516 | 30 | 139 | A | C | 643 | 462 | 562 | 29 |
| 129 | Y | O | 690 | 494 | 523 | 32 | 139 | A | O | 640 | 454 | 553 | 30 |
| 130 | L | N | 696 | 472 | 522 | 31 | 140 | W | N | 645 | 458 | 574 | 29 |
| 130 | L | CA | 698 | 472 | 537 | 33 | 140 | W | CA | 646 | 443 | 578 | 29 |
| 130 | L | CB | 700 | 458 | 542 | 32 | 140 | W | CB | 652 | 441 | 591 | 28 |
| 130 | L | CG | 689 | 447 | 542 | 31 | 140 | W | CG | 667 | 439 | 591 | 33 |
| 130 | L | CD1 | 694 | 432 | 542 | 29 | 140 | W | CD1 | 677 | 446 | 598 | 29 |
| 130 | L | CD2 | 679 | 450 | 554 | 31 | 140 | W | NE1 | 689 | 441 | 595 | 32 |
| 130 | L | C | 709 | 481 | 541 | 35 | 140 | W | CE2 | 688 | 429 | 587 | 35 |
| 130 | L | O | 707 | 489 | 551 | 34 | 140 | W | CD2 | 674 | 428 | 584 | 32 |
| 131 | K | N | 720 | 481 | 534 | 37 | 140 | W | CE3 | 670 | 418 | 576 | 34 |
| 131 | K | CA | 731 | 490 | 537 | 39 | 140 | W | CZ3 | 679 | 409 | 571 | 35 |
| 131 | K | CB | 742 | 488 | 527 | 39 | 140 | W | CH2 | 693 | 411 | 575 | 34 |
| 131 | K | CG | 754 | 496 | 531 | 43 | 140 | W | CZ2 | 697 | 421 | 582 | 31 |
| 131 | K | CD | 766 | 495 | 520 | 50 | 140 | W | C | 633 | 436 | 576 | 28 |
| 131 | K | CE | 777 | 505 | 524 | 54 | 140 | W | O | 633 | 425 | 571 | 28 |
| 131 | K | NZ | 790 | 499 | 518 | 59 | 141 | E | N | 622 | 443 | 580 | 27 |
| 131 | K | C | 726 | 505 | 536 | 38 | 141 | E | CA | 609 | 437 | 577 | 28 |
| 131 | K | O | 728 | 513 | 545 | 39 | 141 | E | CB | 598 | 445 | 585 | 27 |
| 132 | E | N | 719 | 509 | 525 | 40 | 141 | E | CG | 583 | 441 | 581 | 26 |
| 132 | E | CA | 714 | 522 | 523 | 40 | 141 | E | CD | 581 | 426 | 584 | 27 |
| 132 | E | CB | 707 | 524 | 509 | 41 | 141 | E | OE1 | 588 | 420 | 591 | 30 |
| 132 | E | CG | 717 | 523 | 497 | 49 | 141 | E | OE2 | 571 | 420 | 578 | 33 |
| 132 | E | CD | 711 | 524 | 484 | 59 | 141 | E | C | 605 | 436 | 563 | 28 |
| 132 | E | OE1 | 699 | 520 | 481 | 62 | 141 | E | O | 601 | 425 | 558 | 28 |
| 132 | E | OE2 | 718 | 530 | 475 | 62 | 142 | V | N | 608 | 446 | 555 | 29 |
| 132 | E | C | 704 | 527 | 533 | 41 | 142 | V | CA | 606 | 446 | 540 | 28 |
| 132 | E | O | 703 | 539 | 537 | 40 | 142 | V | CB | 610 | 459 | 534 | 31 |
| 133 | K | N | 696 | 517 | 538 | 38 | 142 | V | CG1 | 612 | 457 | 518 | 28 |
| 133 | K | CA | 687 | 520 | 548 | 38 | 142 | V | CG2 | 601 | 470 | 538 | 31 |
| 133 | K | CB | 675 | 510 | 547 | 37 | 142 | V | C | 614 | 434 | 535 | 26 |
| 133 | K | CG | 666 | 511 | 535 | 38 | 142 | V | O | 609 | 427 | 527 | 28 |
| 133 | K | CD | 657 | 523 | 535 | 42 | 143 | V | N | 626 | 432 | 539 | 28 |
| 133 | K | CE | 648 | 524 | 523 | 43 | 143 | V | CA | 634 | 422 | 533 | 28 |
| 133 | K | NZ | 640 | 536 | 525 | 47 | 143 | V | CB | 649 | 424 | 537 | 29 |
| 133 | K | C | 693 | 518 | 562 | 39 | 143 | V | CG1 | 658 | 411 | 536 | 28 |
| 133 | K | O | 685 | 520 | 572 | 40 | 143 | V | CG2 | 655 | 436 | 528 | 27 |
| 134 | K | N | 706 | 516 | 563 | 39 | 143 | V | C | 629 | 408 | 537 | 29 |
| 134 | K | CA | 713 | 515 | 576 | 40 | 143 | V | O | 629 | 398 | 530 | 28 |
| 134 | K | CB | 713 | 528 | 584 | 42 | 144 | R | N | 625 | 407 | 550 | 30 |
| 134 | K | CG | 717 | 541 | 575 | 46 | 144 | R | CA | 620 | 394 | 555 | 29 |
| 134 | K | CD | 717 | 553 | 583 | 57 | 144 | R | CB | 618 | 395 | 570 | 28 |
| 134 | K | CE | 728 | 563 | 578 | 63 | 144 | R | CG | 613 | 382 | 578 | 29 |
| 134 | K | NZ | 722 | 577 | 578 | 69 | 144 | R | CD | 603 | 384 | 590 | 27 |
| 134 | K | C | 706 | 504 | 586 | 40 | 144 | R | NE | 591 | 390 | 586 | 29 |
| 134 | K | O | 706 | 505 | 598 | 40 | 144 | R | CZ | 580 | 385 | 580 | 28 |
| 135 | Y | N | 701 | 493 | 579 | 38 | 144 | R | NH1 | 579 | 372 | 578 | 29 |
| 135 | Y | CA | 696 | 481 | 586 | 38 | 144 | R | NH2 | 571 | 393 | 576 | 28 |
| 135 | Y | CB | 707 | 474 | 593 | 37 | 144 | R | C | 608 | 389 | 548 | 29 |
| 135 | Y | CG | 718 | 470 | 583 | 39 | 144 | R | O | 607 | 378 | 543 | 31 |
| 135 | Y | CD1 | 729 | 478 | 582 | 43 | 145 | A | N | 599 | 399 | 546 | 32 |
| 135 | Y | CE1 | 739 | 475 | 572 | 45 | 145 | A | CA | 587 | 396 | 539 | 30 |
| 135 | Y | CZ | 738 | 463 | 565 | 43 | 145 | A | CB | 577 | 408 | 539 | 32 |
| 135 | Y | OH | 748 | 460 | 557 | 44 | 145 | A | C | 590 | 392 | 525 | 31 |
| 135 | Y | CE2 | 727 | 455 | 567 | 41 | 145 | A | O | 583 | 384 | 519 | 33 |
| 135 | Y | CD2 | 717 | 458 | 576 | 37 | 146 | E | N | 600 | 399 | 519 | 29 |
| 135 | Y | C | 685 | 485 | 595 | 37 | 146 | E | CA | 603 | 396 | 505 | 30 |
| 135 | Y | O | 684 | 480 | 607 | 36 | 146 | E | CB | 614 | 407 | 500 | 28 |
| 136 | S | N | 676 | 495 | 592 | 35 | 146 | E | CG | 622 | 404 | 488 | 31 |
| 136 | S | CA | 666 | 499 | 601 | 36 | 146 | E | CD | 614 | 404 | 475 | 34 |
| 136 | S | CB | 657 | 510 | 594 | 35 | 146 | E | OE1 | 617 | 397 | 466 | 34 |
| 136 | S | OG | 651 | 506 | 583 | 36 | 146 | E | OE2 | 604 | 412 | 475 | 35 |
| 136 | S | C | 656 | 487 | 603 | 36 | 146 | E | C | 609 | 383 | 503 | 29 |
| 136 | S | O | 655 | 478 | 594 | 33 | 146 | E | O | 606 | 375 | 494 | 31 |
| 137 | P | N | 649 | 487 | 614 | 37 | 147 | I | N | 619 | 379 | 512 | 30 |
| 137 | P | CA | 638 | 477 | 616 | 36 | 147 | I | CA | 625 | 366 | 511 | 32 |
| 137 | P | CB | 630 | 482 | 629 | 37 | 147 | I | CB | 636 | 364 | 521 | 33 |
| 137 | P | CG | 641 | 489 | 637 | 39 | 147 | I | CG1 | 647 | 374 | 518 | 32 |

| | | | | | | | | | | | | |
|---|---|---|---|---|---|---|---|---|---|---|---|---|
| 147 | I | CD1 | 652 | 372 | 504 | 36 | 9 | A | O | 475 | 606 | 125 | 58 |
| 147 | I | CG2 | 641 | 349 | 522 | 32 | 10 | G | N | 464 | 611 | 105 | 58 |
| 147 | I | C | 614 | 355 | 513 | 32 | 10 | G | CA | 452 | 603 | 109 | 56 |
| 147 | I | O | 613 | 345 | 507 | 33 | 10 | G | C | 456 | 588 | 110 | 55 |
| 148 | M | N | 605 | 358 | 523 | 34 | 10 | G | O | 452 | 581 | 119 | 54 |
| 148 | M | CA | 595 | 348 | 525 | 38 | 11 | S | N | 464 | 583 | 100 | 53 |
| 148 | M | CB | 587 | 352 | 538 | 37 | 11 | S | CA | 467 | 569 | 101 | 52 |
| 148 | M | CG | 573 | 348 | 538 | 45 | 11 | S | CB | 472 | 565 | 87 | 51 |
| 148 | M | SD | 571 | 345 | 555 | 49 | 11 | S | OG | 484 | 571 | 84 | 55 |
| 148 | M | CE | 564 | 329 | 554 | 45 | 11 | S | C | 477 | 566 | 112 | 50 |
| 148 | M | C | 586 | 346 | 513 | 39 | 11 | S | O | 476 | 555 | 118 | 49 |
| 148 | M | O | 584 | 334 | 509 | 39 | 12 | R | N | 487 | 575 | 114 | 50 |
| 149 | R | N | 582 | 357 | 507 | 40 | 12 | R | CA | 496 | 573 | 126 | 49 |
| 149 | R | CA | 576 | 356 | 494 | 42 | 12 | R | CB | 506 | 585 | 126 | 50 |
| 149 | R | CB | 572 | 370 | 489 | 42 | 12 | R | CG | 518 | 582 | 116 | 53 |
| 149 | R | CG | 561 | 371 | 478 | 49 | 12 | R | CD | 529 | 593 | 117 | 61 |
| 149 | R | CD | 557 | 386 | 475 | 57 | 12 | R | NE | 523 | 606 | 117 | 68 |
| 149 | R | NE | 556 | 394 | 487 | 61 | 12 | R | CZ | 529 | 617 | 112 | 72 |
| 149 | R | CZ | 564 | 405 | 490 | 65 | 12 | R | NH1 | 541 | 617 | 107 | 73 |
| 149 | R | NH1 | 562 | 412 | 502 | 65 | 12 | R | NH2 | 522 | 629 | 113 | 74 |
| 149 | R | NH2 | 574 | 408 | 482 | 68 | 12 | R | C | 488 | 573 | 139 | 46 |
| 149 | R | C | 584 | 349 | 483 | 41 | 12 | R | O | 491 | 564 | 147 | 47 |
| 149 | R | O | 579 | 340 | 476 | 43 | 13 | R | N | 478 | 581 | 141 | 44 |
| 150 | S | N | 597 | 353 | 481 | 40 | 13 | R | CA | 470 | 580 | 153 | 44 |
| 150 | S | CA | 604 | 347 | 470 | 40 | 13 | R | CB | 461 | 593 | 154 | 45 |
| 150 | S | CB | 616 | 356 | 466 | 40 | 13 | R | CG | 452 | 594 | 166 | 52 |
| 150 | S | OG | 626 | 357 | 476 | 43 | 13 | R | CD | 460 | 594 | 180 | 63 |
| 150 | S | C | 609 | 333 | 473 | 41 | 13 | R | NE | 451 | 595 | 191 | 71 |
| 150 | S | O | 611 | 324 | 464 | 40 | 13 | R | CZ | 455 | 593 | 204 | 75 |
| 151 | F | N | 611 | 330 | 486 | 41 | 13 | R | NH1 | 467 | 590 | 207 | 76 |
| 151 | F | CA | 615 | 316 | 489 | 43 | 13 | R | NH2 | 446 | 594 | 214 | 78 |
| 151 | F | CB | 620 | 314 | 503 | 42 | 13 | R | C | 461 | 567 | 154 | 41 |
| 151 | F | CG | 624 | 300 | 507 | 45 | 13 | R | O | 460 | 562 | 166 | 39 |
| 151 | F | CD1 | 634 | 294 | 500 | 49 | 14 | T | N | 457 | 562 | 143 | 38 |
| 151 | F | CE1 | 638 | 281 | 504 | 50 | 14 | T | CA | 450 | 549 | 143 | 37 |
| 151 | F | CZ | 631 | 274 | 513 | 49 | 14 | T | CB | 446 | 546 | 128 | 38 |
| 151 | F | CE2 | 620 | 280 | 519 | 51 | 14 | T | OG1 | 437 | 556 | 124 | 39 |
| 151 | F | CD2 | 616 | 293 | 516 | 49 | 14 | T | CG2 | 438 | 533 | 127 | 38 |
| 151 | F | C | 602 | 306 | 487 | 45 | 14 | T | C | 460 | 538 | 147 | 36 |
| 151 | F | O | 604 | 296 | 481 | 44 | 14 | T | O | 456 | 530 | 156 | 36 |
| 152 | S | N | 590 | 311 | 490 | 48 | 15 | L | N | 472 | 538 | 142 | 35 |
| 152 | S | CA | 578 | 303 | 486 | 52 | 15 | L | CA | 482 | 528 | 146 | 37 |
| 152 | S | CB | 565 | 309 | 490 | 52 | 15 | L | CB | 495 | 530 | 138 | 37 |
| 152 | S | OG | 565 | 317 | 502 | 53 | 15 | L | CG | 494 | 525 | 124 | 39 |
| 152 | S | C | 578 | 300 | 472 | 54 | 15 | L | CD1 | 506 | 528 | 116 | 43 |
| 152 | S | O | 574 | 290 | 468 | 55 | 15 | L | CD2 | 490 | 509 | 123 | 38 |
| 153 | L | N | 582 | 310 | 463 | 57 | 15 | L | C | 485 | 529 | 161 | 34 |
| 153 | L | CA | 581 | 309 | 449 | 60 | 15 | L | O | 486 | 519 | 168 | 36 |
| 153 | L | CB | 582 | 322 | 442 | 59 | 16 | M | N | 487 | 541 | 166 | 35 |
| 153 | L | CG | 570 | 332 | 442 | 60 | 16 | M | CA | 489 | 543 | 180 | 35 |
| 153 | L | CD1 | 575 | 345 | 437 | 59 | 16 | M | CB | 491 | 558 | 183 | 34 |
| 153 | L | CD2 | 558 | 326 | 433 | 60 | 16 | M | CG | 492 | 561 | 198 | 39 |
| 153 | L | C | 592 | 300 | 442 | 62 | 16 | M | SD | 496 | 578 | 202 | 47 |
| 153 | L | O | 590 | 296 | 430 | 62 | 16 | M | CE | 507 | 581 | 193 | 48 |
| 154 | S | N | 603 | 299 | 448 | 64 | 16 | M | C | 478 | 537 | 189 | 34 |
| 154 | S | CA | 614 | 292 | 442 | 67 | 16 | M | O | 481 | 530 | 199 | 33 |
| 154 | S | CB | 628 | 297 | 446 | 66 | 17 | L | N | 466 | 539 | 185 | 34 |
| 154 | S | OG | 629 | 296 | 460 | 66 | 17 | L | CA | 454 | 534 | 193 | 34 |
| 154 | S | C | 613 | 277 | 445 | 69 | 17 | L | CB | 441 | 541 | 189 | 34 |
| 154 | S | O | 618 | 268 | 438 | 69 | 17 | L | CG | 441 | 556 | 192 | 38 |
| 155 | T | N | 605 | 274 | 456 | 71 | 17 | L | CD1 | 430 | 564 | 184 | 37 |
| 155 | T | CA | 602 | 261 | 461 | 74 | 17 | L | CD2 | 439 | 559 | 208 | 37 |
| 155 | T | CB | 599 | 264 | 476 | 74 | 17 | L | C | 453 | 519 | 192 | 33 |
| 155 | T | OG1 | 611 | 261 | 484 | 74 | 17 | L | O | 451 | 512 | 202 | 35 |
| 155 | T | CG2 | 588 | 255 | 482 | 75 | 18 | L | N | 456 | 513 | 181 | 32 |
| 155 | T | C | 590 | 256 | 454 | 76 | 18 | L | CA | 456 | 498 | 180 | 33 |
| 155 | T | O | 590 | 247 | 446 | 77 | 18 | L | CB | 458 | 495 | 165 | 34 |
| 156 | N | N | 579 | 264 | 456 | 78 | 18 | L | CG | 446 | 492 | 156 | 35 |
| 156 | N | CA | 565 | 262 | 450 | 81 | 18 | L | CD1 | 451 | 490 | 142 | 37 |
| 156 | N | CB | 564 | 251 | 440 | 81 | 18 | L | CD2 | 439 | 479 | 161 | 37 |
| 156 | N | CG | 570 | 254 | 427 | 84 | 18 | L | C | 467 | 492 | 188 | 33 |
| 156 | N | OD1 | 568 | 265 | 421 | 86 | 18 | L | O | 466 | 482 | 194 | 35 |
| 156 | N | ND2 | 578 | 244 | 421 | 86 | 19 | A | N | 479 | 499 | 188 | 34 |
| 156 | N | C | 555 | 262 | 461 | 81 | 19 | A | CA | 490 | 494 | 196 | 35 |
| 156 | N | O | 544 | 267 | 459 | 82 | 19 | A | CB | 503 | 503 | 192 | 34 |
| 156 | N | OXT | 557 | 256 | 472 | 82 | 19 | A | C | 487 | 495 | 211 | 35 |
| 9 | A | N | 490 | 613 | 95 | 59 | 19 | A | O | 492 | 487 | 219 | 36 |
| 9 | A | CA | 486 | 619 | 108 | 59 | 20 | Q | N | 480 | 505 | 215 | 36 |
| 9 | A | CB | 483 | 634 | 107 | 60 | 20 | Q | CA | 476 | 507 | 230 | 36 |
| 9 | A | C | 474 | 611 | 114 | 59 | 20 | Q | CB | 472 | 522 | 232 | 37 |

| | | | | | | | | | | | | |
|---|---|---|---|---|---|---|---|---|---|---|---|---|
| 20 | Q | CG | 483 | 532 | 231 | 37 | 29 | C | O | 480 | 321 | 187 | 42 |
| 20 | Q | CD | 479 | 547 | 233 | 45 | 30 | L | N | 500 | 314 | 197 | 42 |
| 20 | Q | OE1 | 468 | 551 | 229 | 48 | 30 | L | CA | 505 | 308 | 184 | 42 |
| 20 | Q | NE2 | 488 | 555 | 238 | 43 | 30 | L | CB | 519 | 303 | 185 | 42 |
| 20 | Q | C | 465 | 498 | 234 | 38 | 30 | L | CG | 530 | 314 | 187 | 47 |
| 20 | Q | O | 463 | 496 | 246 | 37 | 30 | L | CD1 | 543 | 308 | 191 | 48 |
| 21 | M | N | 456 | 493 | 225 | 35 | 30 | L | CD2 | 531 | 322 | 174 | 46 |
| 21 | M | CA | 446 | 484 | 229 | 35 | 30 | L | C | 495 | 297 | 179 | 44 |
| 21 | M | CB | 436 | 483 | 217 | 35 | 30 | L | O | 494 | 296 | 166 | 44 |
| 21 | M | CG | 429 | 496 | 214 | 35 | 31 | K | N | 489 | 290 | 187 | 44 |
| 21 | M | SD | 418 | 496 | 199 | 43 | 31 | K | CA | 479 | 280 | 183 | 47 |
| 21 | M | CE | 414 | 480 | 197 | 38 | 31 | K | CB | 473 | 271 | 194 | 47 |
| 21 | M | C | 451 | 471 | 232 | 34 | 31 | K | CG | 467 | 280 | 204 | 50 |
| 21 | M | O | 445 | 463 | 238 | 33 | 31 | K | CD | 458 | 273 | 215 | 57 |
| 22 | R | N | 463 | 467 | 227 | 34 | 31 | K | CE | 445 | 280 | 218 | 58 |
| 22 | R | CA | 469 | 454 | 229 | 36 | 31 | K | NZ | 448 | 294 | 225 | 58 |
| 22 | R | CB | 483 | 453 | 224 | 37 | 31 | K | C | 468 | 286 | 174 | 46 |
| 22 | R | CG | 487 | 439 | 223 | 38 | 31 | K | O | 462 | 279 | 166 | 45 |
| 22 | R | CD | 502 | 436 | 222 | 46 | 32 | D | N | 465 | 299 | 176 | 45 |
| 22 | R | NE | 508 | 435 | 235 | 42 | 32 | D | CA | 454 | 306 | 169 | 44 |
| 22 | R | CZ | 519 | 428 | 239 | 41 | 32 | D | CB | 446 | 315 | 178 | 44 |
| 22 | R | NH1 | 523 | 430 | 251 | 38 | 32 | D | CG | 440 | 307 | 190 | 49 |
| 22 | R | NH2 | 526 | 420 | 231 | 43 | 32 | D | OD1 | 431 | 299 | 189 | 52 |
| 22 | R | C | 469 | 450 | 244 | 37 | 32 | D | OD2 | 445 | 310 | 201 | 50 |
| 22 | R | O | 472 | 459 | 252 | 37 | 32 | D | C | 458 | 313 | 156 | 42 |
| 23 | R | N | 464 | 438 | 247 | 38 | 32 | D | O | 450 | 320 | 150 | 42 |
| 23 | R | CA | 464 | 433 | 261 | 41 | 33 | A | N | 471 | 312 | 153 | 42 |
| 23 | R | CB | 450 | 428 | 264 | 41 | 33 | A | CA | 477 | 319 | 141 | 42 |
| 23 | R | CG | 440 | 439 | 265 | 47 | 33 | A | CB | 491 | 316 | 138 | 41 |
| 23 | R | CD | 426 | 435 | 268 | 53 | 33 | A | C | 468 | 315 | 129 | 42 |
| 23 | R | NE | 419 | 446 | 272 | 58 | 33 | A | O | 463 | 304 | 128 | 41 |
| 23 | R | CZ | 406 | 446 | 277 | 64 | 34 | H | N | 467 | 325 | 120 | 41 |
| 23 | R | NH1 | 400 | 457 | 281 | 63 | 34 | H | CA | 458 | 323 | 108 | 40 |
| 23 | R | NH2 | 400 | 434 | 278 | 63 | 34 | H | CB | 443 | 325 | 112 | 40 |
| 23 | R | C | 474 | 422 | 263 | 40 | 34 | H | CG | 433 | 321 | 102 | 43 |
| 23 | R | O | 481 | 422 | 274 | 40 | 34 | H | ND1 | 427 | 309 | 101 | 46 |
| 24 | I | N | 474 | 412 | 254 | 39 | 34 | H | CE1 | 419 | 309 | 91 | 49 |
| 24 | I | CA | 484 | 401 | 255 | 38 | 34 | H | NE2 | 420 | 320 | 84 | 46 |
| 24 | I | CB | 475 | 388 | 258 | 39 | 34 | H | CD2 | 429 | 328 | 91 | 42 |
| 24 | I | CG1 | 466 | 385 | 246 | 37 | 34 | H | C | 462 | 332 | 97 | 39 |
| 24 | I | CD1 | 458 | 372 | 246 | 38 | 34 | H | O | 464 | 344 | 100 | 40 |
| 24 | I | CG2 | 468 | 389 | 272 | 37 | 35 | D | N | 462 | 327 | 85 | 39 |
| 24 | I | C | 492 | 400 | 243 | 38 | 35 | D | CA | 466 | 336 | 73 | 37 |
| 24 | I | O | 490 | 406 | 232 | 37 | 35 | D | CB | 476 | 328 | 64 | 36 |
| 25 | S | N | 502 | 391 | 243 | 37 | 35 | D | CG | 481 | 337 | 53 | 36 |
| 25 | S | CA | 511 | 389 | 232 | 36 | 35 | D | OD1 | 491 | 333 | 46 | 40 |
| 25 | S | CB | 525 | 383 | 237 | 36 | 35 | D | OD2 | 475 | 347 | 49 | 36 |
| 25 | S | OG | 533 | 382 | 226 | 37 | 35 | D | C | 454 | 340 | 66 | 37 |
| 25 | S | C | 506 | 379 | 222 | 37 | 35 | D | O | 447 | 332 | 61 | 34 |
| 25 | S | O | 501 | 369 | 226 | 35 | 36 | F | N | 450 | 353 | 68 | 35 |
| 26 | L | N | 508 | 382 | 209 | 35 | 36 | F | CA | 438 | 358 | 62 | 34 |
| 26 | L | CA | 505 | 373 | 199 | 38 | 36 | F | CB | 433 | 370 | 71 | 34 |
| 26 | L | CB | 506 | 379 | 185 | 38 | 36 | F | CG | 429 | 366 | 84 | 34 |
| 26 | L | CG | 518 | 381 | 177 | 43 | 36 | F | CD1 | 438 | 367 | 95 | 36 |
| 26 | L | CD1 | 525 | 368 | 171 | 49 | 36 | F | CE1 | 434 | 364 | 108 | 35 |
| 26 | L | CD2 | 515 | 389 | 164 | 46 | 36 | F | CZ | 421 | 359 | 111 | 35 |
| 26 | L | C | 513 | 360 | 200 | 38 | 36 | F | CE2 | 412 | 358 | 100 | 37 |
| 26 | L | O | 510 | 350 | 195 | 37 | 36 | F | CD2 | 416 | 361 | 87 | 36 |
| 27 | F | N | 525 | 361 | 206 | 38 | 36 | F | C | 438 | 361 | 48 | 34 |
| 27 | F | CA | 533 | 349 | 209 | 39 | 36 | F | O | 428 | 366 | 42 | 34 |
| 27 | F | CB | 548 | 353 | 212 | 39 | 37 | G | N | 450 | 360 | 42 | 34 |
| 27 | F | CG | 555 | 359 | 200 | 40 | 37 | G | CA | 451 | 363 | 27 | 35 |
| 27 | F | CD1 | 560 | 351 | 190 | 43 | 37 | G | C | 448 | 378 | 24 | 35 |
| 27 | F | CE1 | 567 | 357 | 179 | 45 | 37 | G | O | 440 | 381 | 14 | 34 |
| 27 | F | CZ | 567 | 371 | 178 | 46 | 38 | F | N | 454 | 387 | 31 | 34 |
| 27 | F | CE2 | 562 | 379 | 187 | 40 | 38 | F | CA | 452 | 401 | 29 | 33 |
| 27 | F | CD2 | 556 | 373 | 198 | 41 | 38 | F | CB | 460 | 410 | 38 | 32 |
| 27 | F | C | 528 | 340 | 220 | 40 | 38 | F | CG | 458 | 425 | 36 | 33 |
| 27 | F | O | 532 | 329 | 221 | 42 | 38 | F | CD1 | 446 | 431 | 37 | 32 |
| 28 | S | N | 518 | 345 | 228 | 40 | 38 | F | CE1 | 444 | 445 | 35 | 34 |
| 28 | S | CA | 510 | 336 | 236 | 40 | 38 | F | CZ | 455 | 452 | 31 | 33 |
| 28 | S | CB | 505 | 344 | 249 | 41 | 38 | F | CE2 | 467 | 446 | 29 | 32 |
| 28 | S | OG | 516 | 351 | 255 | 42 | 38 | F | CD2 | 469 | 433 | 32 | 37 |
| 28 | S | C | 498 | 329 | 230 | 41 | 38 | F | C | 456 | 405 | 14 | 34 |
| 28 | S | O | 490 | 323 | 237 | 42 | 38 | F | O | 467 | 402 | 10 | 33 |
| 29 | C | N | 496 | 331 | 217 | 41 | 39 | P | N | 447 | 411 | 7 | 34 |
| 29 | C | CA | 484 | 328 | 210 | 42 | 39 | P | CA | 451 | 415 | −7 | 36 |
| 29 | C | CB | 477 | 341 | 206 | 42 | 39 | P | CB | 437 | 415 | −14 | 37 |
| 29 | C | SG | 472 | 351 | 221 | 47 | 39 | P | CG | 428 | 421 | −3 | 33 |
| 29 | C | C | 488 | 321 | 197 | 42 | 39 | P | CD | 433 | 414 | 10 | 35 |

| | | | | | | | | | | | | |
|---|---|---|---|---|---|---|---|---|---|---|---|---|
| 39 | P | C | 459 | 427 | −8 | 36 | 49 | A | C | 459 | 573 | −55 | 74 |
| 39 | P | O | 455 | 438 | −14 | 37 | 49 | A | O | 453 | 567 | −46 | 74 |
| 40 | Q | N | 472 | 426 | −4 | 38 | 50 | A | N | 453 | 580 | −64 | 71 |
| 40 | Q | CA | 481 | 438 | −4 | 39 | 50 | A | CA | 439 | 583 | −64 | 68 |
| 40 | Q | CB | 494 | 435 | 3 | 39 | 50 | A | CB | 436 | 595 | −73 | 69 |
| 40 | Q | CG | 502 | 423 | −3 | 46 | 50 | A | C | 431 | 571 | −67 | 66 |
| 40 | Q | CD | 515 | 422 | 3 | 52 | 50 | A | O | 419 | 571 | −64 | 66 |
| 40 | Q | OE1 | 517 | 416 | 14 | 53 | 51 | A | N | 437 | 561 | −74 | 63 |
| 40 | Q | NE2 | 525 | 429 | −2 | 56 | 51 | A | CA | 430 | 549 | −77 | 60 |
| 40 | Q | C | 483 | 444 | −18 | 39 | 51 | A | CB | 438 | 541 | −88 | 60 |
| 40 | Q | O | 486 | 456 | −19 | 37 | 51 | A | C | 427 | 540 | −65 | 57 |
| 41 | E | N | 482 | 435 | −28 | 38 | 51 | A | O | 418 | 532 | −66 | 57 |
| 41 | E | CA | 483 | 440 | −42 | 40 | 52 | T | N | 436 | 541 | −55 | 54 |
| 41 | E | CB | 483 | 428 | −52 | 40 | 52 | T | CA | 434 | 533 | −43 | 53 |
| 41 | E | CG | 470 | 421 | −54 | 36 | 52 | T | CB | 448 | 529 | −36 | 52 |
| 41 | E | CD | 466 | 411 | −43 | 39 | 52 | T | OG1 | 455 | 541 | −33 | 57 |
| 41 | E | OE1 | 474 | 409 | −33 | 37 | 52 | T | CG2 | 457 | 522 | −46 | 55 |
| 41 | E | OE2 | 455 | 406 | −44 | 37 | 52 | T | C | 426 | 539 | −32 | 50 |
| 41 | E | C | 473 | 450 | −46 | 41 | 52 | T | O | 423 | 533 | −22 | 50 |
| 41 | E | O | 475 | 457 | −56 | 40 | 53 | I | N | 422 | 552 | −33 | 47 |
| 42 | E | N | 462 | 451 | −39 | 41 | 53 | I | CA | 413 | 559 | −24 | 46 |
| 42 | E | CA | 452 | 461 | −43 | 45 | 53 | I | CB | 408 | 573 | −29 | 46 |
| 42 | E | CB | 438 | 459 | −35 | 45 | 53 | I | CG1 | 420 | 583 | −29 | 49 |
| 42 | E | CG | 430 | 447 | −39 | 49 | 53 | I | CD1 | 428 | 583 | −16 | 52 |
| 42 | E | CD | 433 | 441 | −52 | 54 | 53 | I | CG2 | 397 | 579 | −20 | 46 |
| 42 | E | OE1 | 430 | 446 | −63 | 55 | 53 | I | C | 401 | 550 | −20 | 43 |
| 42 | E | OE2 | 439 | 430 | −51 | 60 | 53 | I | O | 399 | 547 | −9 | 43 |
| 42 | E | C | 456 | 475 | −39 | 46 | 54 | P | N | 393 | 545 | −30 | 42 |
| 42 | E | O | 451 | 485 | −44 | 46 | 54 | P | CA | 382 | 536 | −27 | 41 |
| 43 | F | N | 467 | 489 | −87 | 80 | 54 | P | CB | 376 | 532 | −41 | 40 |
| 43 | F | CA | 472 | 476 | −30 | 47 | 54 | P | CG | 382 | 544 | −50 | 41 |
| 43 | F | CB | 474 | 489 | −26 | 52 | 54 | P | CD | 395 | 547 | −45 | 41 |
| 43 | F | CG | 461 | 489 | −11 | 50 | 54 | P | C | 385 | 523 | −19 | 39 |
| 43 | F | CD1 | 456 | 487 | −4 | 47 | 54 | P | O | 376 | 519 | −11 | 38 |
| 43 | F | CE1 | 444 | 474 | −1 | 44 | 55 | V | N | 396 | 517 | −21 | 38 |
| 43 | F | CZ | 437 | 472 | 6 | 42 | 55 | V | CA | 400 | 505 | −13 | 38 |
| 43 | F | CE2 | 441 | 484 | 9 | 44 | 55 | V | CB | 411 | 495 | −19 | 38 |
| 43 | F | CD2 | 453 | 496 | 6 | 40 | 55 | V | CG1 | 406 | 489 | −31 | 42 |
| 43 | F | C | 486 | 498 | 0 | 42 | 55 | V | CG2 | 424 | 502 | −23 | 43 |
| 43 | F | O | 491 | 492 | −32 | 56 | 55 | V | C | 405 | 509 | 1 | 36 |
| 44 | G | N | 492 | 503 | −30 | 58 | 55 | V | O | 402 | 502 | 10 | 36 |
| 44 | G | CA | 505 | 483 | −40 | 61 | 56 | L | N | 412 | 520 | 2 | 36 |
| 44 | G | C | 508 | 484 | −44 | 66 | 56 | L | CA | 416 | 525 | 15 | 36 |
| 44 | G | O | 499 | 494 | −55 | 70 | 56 | L | CB | 426 | 536 | 15 | 37 |
| 45 | N | N | 520 | 502 | −59 | 71 | 56 | L | CG | 429 | 542 | 29 | 41 |
| 45 | N | CA | 525 | 494 | −60 | 74 | 56 | L | CD1 | 436 | 531 | 38 | 41 |
| 45 | N | CB | 541 | 504 | −70 | 77 | 56 | L | CD2 | 438 | 555 | 29 | 42 |
| 45 | N | CG | 545 | 505 | −69 | 78 | 56 | L | C | 403 | 528 | 24 | 34 |
| 45 | N | OD1 | 542 | 518 | −62 | 81 | 56 | L | O | 402 | 524 | 35 | 34 |
| 45 | N | ND2 | 552 | 519 | −50 | 83 | 57 | H | N | 394 | 535 | 17 | 34 |
| 45 | N | C | 521 | 527 | −69 | 83 | 57 | H | CA | 381 | 539 | 23 | 34 |
| 45 | N | O | 523 | 501 | −85 | 79 | 57 | H | CB | 372 | 546 | 13 | 35 |
| 46 | Q | N | 516 | 510 | −93 | 80 | 57 | H | CG | 359 | 550 | 18 | 37 |
| 46 | Q | CA | 509 | 486 | −100 | 81 | 57 | H | ND1 | 347 | 542 | 16 | 38 |
| 46 | Q | CB | 506 | 471 | −102 | 81 | 57 | H | CE1 | 337 | 548 | 21 | 38 |
| 46 | Q | CG | 494 | 466 | −94 | 81 | 57 | H | NE2 | 341 | 559 | 27 | 38 |
| 46 | Q | CD | 497 | 463 | −79 | 79 | 57 | H | CD2 | 354 | 561 | 25 | 41 |
| 46 | Q | OE1 | 488 | 464 | −71 | 80 | 57 | H | C | 374 | 526 | 28 | 34 |
| 46 | Q | NE2 | 509 | 460 | −76 | 79 | 57 | H | O | 369 | 526 | 39 | 33 |
| 46 | Q | C | 496 | 495 | −101 | 82 | 58 | E | N | 373 | 516 | 19 | 33 |
| 46 | Q | O | 490 | 495 | −112 | 82 | 58 | E | CA | 366 | 503 | 23 | 35 |
| 47 | F | N | 494 | 503 | −91 | 82 | 58 | E | CB | 366 | 493 | 11 | 34 |
| 47 | F | CA | 482 | 513 | −90 | 82 | 58 | E | CG | 360 | 480 | 14 | 35 |
| 47 | F | CB | 472 | 508 | −81 | 82 | 58 | E | CD | 344 | 481 | 15 | 36 |
| 47 | F | CG | 464 | 496 | −85 | 83 | 58 | E | OE1 | 338 | 473 | 23 | 37 |
| 47 | F | CD1 | 458 | 495 | −97 | 85 | 58 | E | OE2 | 339 | 490 | 9 | 36 |
| 47 | F | CE1 | 451 | 483 | −101 | 86 | 58 | E | C | 373 | 497 | 35 | 35 |
| 47 | F | CZ | 451 | 472 | −92 | 85 | 58 | E | O | 366 | 492 | 44 | 34 |
| 47 | F | CE2 | 457 | 473 | −80 | 85 | 59 | M | N | 386 | 497 | 35 | 34 |
| 47 | F | CD2 | 464 | 485 | −76 | 84 | 59 | M | CA | 393 | 492 | 47 | 34 |
| 47 | F | C | 487 | 527 | −86 | 81 | 59 | M | CB | 408 | 494 | 44 | 36 |
| 47 | F | O | 498 | 529 | −80 | 81 | 59 | M | CG | 417 | 490 | 56 | 45 |
| 48 | A | N | 479 | 537 | −90 | 80 | 59 | M | SD | 432 | 483 | 51 | 58 |
| 48 | A | CA | 481 | 551 | −87 | 79 | 59 | M | CE | 424 | 468 | 49 | 49 |
| 48 | A | CB | 475 | 560 | −98 | 80 | 59 | M | C | 390 | 499 | 60 | 33 |
| 48 | A | C | 476 | 555 | −73 | 79 | 59 | M | O | 388 | 493 | 70 | 32 |
| 48 | A | O | 469 | 547 | −66 | 79 | 60 | I | N | 390 | 512 | 59 | 33 |
| 49 | A | N | 479 | 567 | −68 | 77 | 60 | I | CA | 387 | 520 | 71 | 33 |
| 49 | A | CA | 474 | 572 | −55 | 75 | 60 | I | CB | 391 | 535 | 68 | 35 |
| 49 | A | CB | 481 | 585 | −52 | 75 | 60 | I | CG1 | 406 | 536 | 67 | 38 |

| | | | | | | | | | | | | |
|---|---|---|---|---|---|---|---|---|---|---|---|---|
| 60 | I | CD1 | 411 | 549 | 62 | 40 | 69 | T | O | 313 | 461 | 199 | 43 |
| 60 | I | CG2 | 386 | 544 | 80 | 32 | 70 | L | N | 294 | 449 | 198 | 47 |
| 60 | I | C | 373 | 518 | 76 | 33 | 70 | L | CA | 294 | 447 | 213 | 49 |
| 60 | I | O | 371 | 517 | 88 | 34 | 70 | L | CB | 280 | 442 | 217 | 50 |
| 61 | Q | N | 364 | 517 | 67 | 32 | 70 | L | CG | 277 | 441 | 232 | 55 |
| 61 | Q | CA | 350 | 515 | 71 | 33 | 70 | L | CD1 | 278 | 454 | 241 | 62 |
| 61 | Q | CB | 341 | 516 | 59 | 32 | 70 | L | CD2 | 263 | 434 | 235 | 61 |
| 61 | Q | CG | 326 | 512 | 62 | 34 | 70 | L | C | 305 | 438 | 217 | 47 |
| 61 | Q | CD | 318 | 522 | 69 | 35 | 70 | L | O | 310 | 439 | 228 | 48 |
| 61 | Q | OE1 | 312 | 519 | 80 | 41 | 71 | D | N | 308 | 428 | 209 | 46 |
| 61 | Q | NE2 | 318 | 534 | 65 | 33 | 71 | D | CA | 318 | 418 | 211 | 45 |
| 61 | Q | C | 349 | 501 | 77 | 32 | 71 | D | CB | 319 | 408 | 199 | 45 |
| 61 | Q | O | 341 | 500 | 87 | 33 | 71 | D | CG | 307 | 399 | 198 | 49 |
| 62 | Q | N | 355 | 491 | 71 | 31 | 71 | D | OD1 | 305 | 390 | 206 | 48 |
| 62 | Q | CA | 355 | 477 | 77 | 32 | 71 | D | OD2 | 299 | 400 | 188 | 52 |
| 62 | Q | CB | 361 | 467 | 67 | 31 | 71 | D | C | 332 | 426 | 212 | 44 |
| 62 | Q | CG | 353 | 466 | 54 | 32 | 71 | D | O | 340 | 422 | 220 | 43 |
| 62 | Q | CD | 339 | 460 | 56 | 36 | 72 | S | N | 334 | 436 | 204 | 42 |
| 62 | Q | OE1 | 337 | 453 | 66 | 35 | 72 | S | CA | 346 | 444 | 205 | 41 |
| 62 | Q | NE2 | 330 | 463 | 47 | 32 | 72 | S | CB | 347 | 454 | 192 | 41 |
| 62 | Q | C | 362 | 476 | 91 | 32 | 72 | S | OG | 358 | 462 | 194 | 36 |
| 62 | Q | O | 358 | 469 | 99 | 32 | 72 | S | C | 346 | 452 | 218 | 42 |
| 63 | I | N | 373 | 484 | 93 | 31 | 72 | S | O | 357 | 453 | 224 | 39 |
| 63 | I | CA | 379 | 484 | 106 | 30 | 73 | S | N | 334 | 458 | 221 | 42 |
| 63 | I | CB | 392 | 493 | 106 | 29 | 73 | S | CA | 333 | 465 | 233 | 46 |
| 63 | I | CG1 | 403 | 485 | 98 | 30 | 73 | S | CB | 319 | 472 | 234 | 47 |
| 63 | I | CD1 | 415 | 492 | 94 | 32 | 73 | S | OG | 319 | 485 | 228 | 50 |
| 63 | I | CG2 | 397 | 495 | 120 | 30 | 73 | S | C | 337 | 457 | 246 | 45 |
| 63 | I | C | 369 | 490 | 116 | 30 | 73 | S | O | 342 | 463 | 256 | 48 |
| 63 | I | O | 367 | 485 | 127 | 31 | 74 | A | N | 335 | 444 | 246 | 46 |
| 64 | F | N | 362 | 501 | 112 | 31 | 74 | A | CA | 339 | 434 | 256 | 47 |
| 64 | F | CA | 352 | 507 | 120 | 33 | 74 | A | CB | 330 | 422 | 255 | 47 |
| 64 | F | CB | 346 | 519 | 113 | 32 | 74 | A | C | 354 | 430 | 256 | 47 |
| 64 | F | CG | 336 | 526 | 121 | 35 | 74 | A | O | 359 | 426 | 266 | 47 |
| 64 | F | CD1 | 339 | 536 | 130 | 40 | 75 | A | N | 360 | 432 | 244 | 45 |
| 64 | F | CE1 | 329 | 543 | 138 | 43 | 75 | A | CA | 374 | 428 | 242 | 44 |
| 64 | F | CZ | 316 | 538 | 138 | 37 | 75 | A | CB | 376 | 422 | 228 | 43 |
| 64 | F | CE2 | 313 | 527 | 129 | 37 | 75 | A | C | 384 | 439 | 245 | 43 |
| 64 | F | CD2 | 323 | 521 | 121 | 35 | 75 | A | O | 396 | 436 | 249 | 45 |
| 64 | F | C | 341 | 497 | 124 | 34 | 76 | W | N | 380 | 451 | 243 | 43 |
| 64 | F | O | 337 | 495 | 135 | 34 | 76 | W | CA | 390 | 462 | 243 | 42 |
| 65 | N | N | 337 | 489 | 114 | 34 | 76 | W | CB | 392 | 468 | 229 | 39 |
| 65 | N | CA | 325 | 480 | 116 | 35 | 76 | W | CG | 395 | 457 | 219 | 38 |
| 65 | N | CB | 321 | 474 | 103 | 36 | 76 | W | CD1 | 387 | 453 | 209 | 35 |
| 65 | N | CG | 312 | 483 | 94 | 38 | 76 | W | NE1 | 393 | 442 | 202 | 36 |
| 65 | N | OD1 | 309 | 479 | 83 | 45 | 76 | W | CE2 | 405 | 440 | 207 | 37 |
| 65 | N | ND2 | 310 | 495 | 98 | 37 | 76 | W | CD2 | 407 | 449 | 218 | 38 |
| 65 | N | C | 329 | 469 | 126 | 36 | 76 | W | CE3 | 418 | 448 | 226 | 38 |
| 65 | N | O | 321 | 464 | 134 | 34 | 76 | W | C23 | 428 | 439 | 222 | 36 |
| 66 | L | N | 342 | 465 | 124 | 35 | 76 | W | CH2 | 427 | 430 | 211 | 36 |
| 66 | L | CA | 347 | 453 | 132 | 35 | 76 | W | CZ2 | 415 | 431 | 204 | 35 |
| 66 | L | CB | 361 | 449 | 126 | 34 | 76 | W | C | 386 | 473 | 252 | 44 |
| 66 | L | CG | 368 | 438 | 134 | 37 | 76 | W | O | 374 | 475 | 256 | 45 |
| 66 | L | CD1 | 361 | 425 | 134 | 37 | 77 | D | N | 396 | 481 | 256 | 44 |
| 66 | L | CD2 | 382 | 436 | 128 | 39 | 77 | D | CA | 393 | 493 | 265 | 46 |
| 66 | L | C | 348 | 457 | 147 | 34 | 77 | D | CB | 406 | 500 | 269 | 45 |
| 66 | L | O | 345 | 449 | 156 | 34 | 77 | D | CG | 404 | 511 | 278 | 48 |
| 67 | F | N | 353 | 469 | 150 | 34 | 77 | D | OD1 | 405 | 523 | 274 | 46 |
| 67 | F | CA | 356 | 473 | 163 | 35 | 77 | D | OD2 | 401 | 509 | 290 | 52 |
| 67 | F | CB | 369 | 481 | 163 | 35 | 77 | D | C | 383 | 503 | 259 | 46 |
| 67 | F | CG | 381 | 473 | 162 | 37 | 77 | D | O | 386 | 509 | 248 | 44 |
| 67 | F | CD1 | 387 | 471 | 149 | 35 | 78 | E | N | 373 | 507 | 267 | 47 |
| 67 | F | CE1 | 399 | 463 | 147 | 36 | 78 | E | CA | 363 | 516 | 263 | 47 |
| 67 | F | CZ | 405 | 457 | 159 | 38 | 78 | E | CB | 352 | 518 | 275 | 48 |
| 67 | F | CE2 | 399 | 459 | 171 | 37 | 78 | E | CG | 339 | 524 | 270 | 53 |
| 67 | F | CD2 | 388 | 467 | 173 | 38 | 78 | E | CD | 330 | 530 | 280 | 61 |
| 67 | F | C | 345 | 480 | 170 | 36 | 78 | E | OE1 | 331 | 525 | 292 | 59 |
| 67 | F | O | 345 | 482 | 182 | 35 | 78 | E | OE2 | 323 | 539 | 277 | 65 |
| 68 | S | N | 334 | 483 | 163 | 37 | 78 | E | C | 368 | 530 | 259 | 46 |
| 68 | S | CA | 323 | 489 | 169 | 38 | 78 | E | O | 364 | 536 | 249 | 47 |
| 68 | S | CB | 317 | 500 | 159 | 38 | 79 | T | N | 378 | 535 | 267 | 46 |
| 68 | S | OG | 312 | 494 | 148 | 39 | 79 | T | CA | 383 | 549 | 264 | 46 |
| 68 | S | C | 312 | 479 | 174 | 38 | 79 | T | CB | 392 | 555 | 275 | 47 |
| 68 | S | O | 302 | 483 | 179 | 41 | 79 | T | OG1 | 384 | 555 | 287 | 51 |
| 69 | T | N | 314 | 466 | 172 | 41 | 79 | T | CG2 | 395 | 569 | 272 | 48 |
| 69 | T | CA | 304 | 457 | 177 | 42 | 79 | T | C | 391 | 549 | 251 | 45 |
| 69 | T | CB | 306 | 442 | 172 | 43 | 79 | T | O | 390 | 558 | 243 | 44 |
| 69 | T | OG1 | 319 | 437 | 177 | 42 | 80 | L | N | 398 | 538 | 249 | 43 |
| 69 | T | CG2 | 308 | 442 | 156 | 41 | 80 | L | CA | 406 | 537 | 236 | 42 |
| 69 | T | C | 304 | 456 | 193 | 45 | 80 | L | CB | 416 | 526 | 237 | 42 |

-continued

| | | | | | | |
|---|---|---|---|---|---|---|
| 80 | L | CG | 428 | 528 | 247 | 43 |
| 80 | L | CD1 | 436 | 515 | 247 | 39 |
| 80 | L | CD2 | 437 | 540 | 243 | 42 |
| 80 | L | C | 397 | 535 | 224 | 40 |
| 80 | L | O | 399 | 541 | 213 | 40 |
| 81 | L | N | 388 | 526 | 225 | 40 |
| 81 | L | CA | 378 | 523 | 214 | 41 |
| 81 | L | CB | 368 | 513 | 218 | 39 |
| 81 | L | CG | 372 | 498 | 217 | 41 |
| 81 | L | CD1 | 361 | 489 | 223 | 38 |
| 81 | L | CD2 | 376 | 494 | 203 | 38 |
| 81 | L | C | 370 | 536 | 210 | 41 |
| 81 | L | O | 368 | 539 | 199 | 40 |
| 82 | D | N | 367 | 545 | 220 | 42 |
| 82 | D | CA | 360 | 557 | 218 | 43 |
| 82 | D | CB | 354 | 563 | 230 | 46 |
| 82 | D | CG | 339 | 560 | 233 | 54 |
| 82 | D | OD1 | 334 | 563 | 244 | 63 |
| 82 | D | OD2 | 331 | 554 | 224 | 58 |
| 82 | D | C | 369 | 566 | 210 | 42 |
| 82 | D | 0 | 364 | 573 | 200 | 41 |
| 83 | K | N | 381 | 567 | 213 | 39 |
| 83 | K | CA | 390 | 576 | 205 | 39 |
| 83 | K | CB | 404 | 579 | 212 | 40 |
| 83 | K | CG | 402 | 586 | 226 | 43 |
| 83 | K | CD | 416 | 587 | 233 | 54 |
| 83 | K | CE | 415 | 595 | 246 | 60 |
| 83 | K | NZ | 426 | 606 | 246 | 63 |
| 83 | K | C | 393 | 570 | 191 | 37 |
| 83 | K | O | 395 | 577 | 182 | 38 |
| 84 | F | N | 393 | 557 | 190 | 36 |
| 84 | F | CA | 395 | 550 | 177 | 36 |
| 84 | F | CB | 395 | 535 | 180 | 35 |
| 84 | F | CG | 401 | 525 | 169 | 33 |
| 84 | F | CD1 | 413 | 528 | 163 | 33 |
| 84 | F | CE1 | 418 | 518 | 154 | 34 |
| 84 | F | CZ | 411 | 507 | 151 | 31 |
| 84 | F | CE2 | 399 | 504 | 158 | 34 |
| 84 | F | CD2 | 394 | 514 | 167 | 31 |
| 84 | F | C | 384 | 553 | 167 | 36 |
| 84 | F | O | 386 | 557 | 156 | 36 |
| 85 | Y | N | 371 | 552 | 172 | 38 |
| 85 | Y | CA | 359 | 556 | 164 | 39 |
| 85 | Y | CB | 347 | 555 | 172 | 40 |
| 85 | Y | CG | 344 | 542 | 178 | 38 |
| 85 | Y | CD1 | 348 | 530 | 172 | 34 |
| 85 | Y | CE1 | 346 | 518 | 178 | 36 |
| 85 | Y | CZ | 339 | 517 | 190 | 36 |
| 85 | Y | OH | 337 | 505 | 197 | 39 |
| 85 | Y | CE2 | 335 | 529 | 196 | 37 |
| 85 | Y | CD2 | 338 | 541 | 190 | 35 |
| 85 | Y | C | 361 | 570 | 158 | 41 |
| 85 | Y | O | 359 | 572 | 146 | 42 |
| 86 | T | N | 364 | 579 | 167 | 42 |
| 86 | T | CA | 366 | 593 | 162 | 41 |
| 86 | T | CB | 370 | 601 | 175 | 43 |
| 86 | T | OG1 | 360 | 602 | 184 | 44 |
| 86 | T | CG2 | 374 | 616 | 171 | 43 |
| 86 | T | C | 376 | 594 | 151 | 42 |
| 86 | T | O | 374 | 601 | 141 | 42 |
| 87 | E | N | 388 | 588 | 154 | 42 |
| 87 | E | CA | 398 | 588 | 143 | 42 |
| 87 | E | CB | 411 | 581 | 149 | 44 |
| 87 | E | CG | 424 | 588 | 144 | 50 |
| 87 | E | CD | 424 | 603 | 148 | 55 |
| 87 | E | OE1 | 422 | 606 | 160 | 60 |
| 87 | E | OE2 | 428 | 611 | 139 | 59 |
| 87 | E | C | 394 | 581 | 130 | 39 |
| 87 | E | O | 397 | 586 | 119 | 39 |
| 88 | L | N | 386 | 570 | 131 | 39 |
| 88 | L | CA | 382 | 563 | 119 | 39 |
| 88 | L | CB | 377 | 549 | 122 | 38 |
| 88 | L | CG | 387 | 539 | 128 | 39 |
| 88 | L | CD1 | 380 | 527 | 134 | 34 |
| 88 | L | CD2 | 397 | 535 | 118 | 37 |
| 88 | L | C | 371 | 572 | 111 | 40 |
| 88 | L | O | 372 | 573 | 99 | 39 |
| 89 | Y | N | 362 | 577 | 119 | 43 |
| 89 | Y | CA | 352 | 587 | 113 | 46 |
| 89 | Y | CB | 345 | 595 | 124 | 47 |
| 89 | Y | CG | 333 | 589 | 130 | 53 |
| 89 | Y | CD1 | 323 | 584 | 122 | 56 |
| 89 | Y | CE1 | 312 | 578 | 127 | 60 |
| 89 | Y | CZ | 310 | 578 | 141 | 64 |
| 89 | Y | OH | 299 | 572 | 148 | 69 |
| 89 | Y | CE2 | 321 | 583 | 149 | 63 |
| 89 | Y | CD2 | 332 | 588 | 143 | 58 |
| 89 | Y | C | 358 | 598 | 104 | 47 |
| 89 | Y | O | 355 | 600 | 93 | 47 |
| 90 | Q | N | 368 | 605 | 111 | 46 |
| 90 | Q | CA | 375 | 615 | 104 | 47 |
| 90 | Q | CB | 384 | 623 | 114 | 48 |
| 90 | Q | CG | 393 | 633 | 107 | 55 |
| 90 | Q | CD | 386 | 644 | 100 | 64 |
| 90 | Q | OE1 | 374 | 646 | 100 | 66 |
| 90 | Q | NE2 | 394 | 652 | 93 | 67 |
| 90 | Q | C | 382 | 610 | 91 | 46 |
| 90 | Q | O | 383 | 617 | 81 | 45 |
| 91 | Q | N | 388 | 599 | 92 | 45 |
| 91 | Q | CA | 395 | 594 | 80 | 44 |
| 91 | Q | CB | 404 | 582 | 83 | 45 |
| 91 | Q | CG | 417 | 585 | 89 | 47 |
| 91 | Q | CD | 425 | 573 | 93 | 51 |
| 91 | Q | OE1 | 433 | 569 | 86 | 53 |
| 91 | Q | NE2 | 422 | 568 | 105 | 53 |
| 91 | Q | C | 385 | 591 | 68 | 44 |
| 91 | Q | O | 387 | 594 | 57 | 43 |
| 92 | L | N | 373 | 585 | 72 | 45 |
| 92 | L | CA | 363 | 583 | 62 | 45 |
| 92 | L | CB | 351 | 576 | 69 | 44 |
| 92 | L | CG | 353 | 561 | 73 | 46 |
| 92 | L | CD1 | 342 | 556 | 82 | 46 |
| 92 | L | CD2 | 355 | 552 | 60 | 45 |
| 92 | L | C | 358 | 596 | 56 | 47 |
| 92 | L | O | 358 | 597 | 43 | 46 |
| 93 | N | N | 355 | 605 | 64 | 49 |
| 93 | N | CA | 351 | 618 | 60 | 52 |
| 93 | N | CB | 348 | 626 | 73 | 52 |
| 93 | N | CG | 339 | 637 | 70 | 58 |
| 93 | N | OD1 | 343 | 649 | 69 | 62 |
| 93 | N | ND2 | 326 | 634 | 69 | 60 |
| 93 | N | C | 361 | 625 | 51 | 52 |
| 93 | N | O | 358 | 630 | 39 | 52 |
| 94 | D | N | 374 | 625 | 54 | 53 |
| 94 | D | CA | 384 | 630 | 45 | 54 |
| 94 | D | CB | 398 | 628 | 51 | 55 |
| 94 | D | CG | 401 | 637 | 62 | 60 |
| 94 | D | OD1 | 393 | 646 | 65 | 64 |
| 94 | D | OD2 | 412 | 637 | 68 | 66 |
| 94 | D | C | 385 | 624 | 32 | 54 |
| 94 | D | O | 387 | 630 | 22 | 54 |
| 95 | L | N | 384 | 610 | 32 | 54 |
| 95 | L | CA | 385 | 603 | 19 | 53 |
| 95 | L | CB | 387 | 588 | 22 | 52 |
| 95 | L | CG | 401 | 584 | 28 | 53 |
| 95 | L | CD1 | 400 | 570 | 34 | 50 |
| 95 | L | CD2 | 412 | 585 | 18 | 52 |
| 95 | L | C | 373 | 604 | 11 | 54 |
| 95 | L | O | 373 | 604 | -1 | 53 |
| 96 | E | N | 361 | 606 | 18 | 56 |
| 96 | E | CA | 349 | 608 | 11 | 58 |
| 96 | E | CB | 337 | 606 | 20 | 56 |
| 96 | E | CG | 333 | 592 | 22 | 55 |
| 96 | E | CD | 324 | 589 | 34 | 52 |
| 96 | E | OE1 | 317 | 599 | 38 | 48 |
| 96 | E | OE2 | 323 | 578 | 39 | 52 |
| 96 | E | C | 348 | 621 | 4 | 61 |
| 96 | E | O | 340 | 623 | -6 | 61 |
| 97 | A | N | 357 | 631 | 8 | 65 |
| 97 | A | CA | 357 | 644 | 2 | 70 |
| 97 | A | CB | 367 | 653 | 10 | 69 |
| 97 | A | C | 361 | 644 | -12 | 73 |
| 97 | A | O | 356 | 651 | -20 | 74 |
| 98 | C | N | 370 | 634 | -15 | 78 |
| 98 | C | CA | 376 | 633 | -28 | 82 |
| 98 | C | CB | 386 | 621 | -28 | 81 |
| 98 | C | SG | 401 | 625 | -20 | 84 |
| 98 | C | C | 366 | 633 | -40 | 83 |
| 98 | C | O | 369 | 639 | -51 | 84 |
| 99 | A | N | 355 | 626 | -38 | 86 |

| | | | | | | | | | | | | |
|---|---|---|---|---|---|---|---|---|---|---|---|---|
| 99 | A | CA | 345 | 625 | −49 | 88 | 119 | V | CA | 389 | 441 | 9 | 33 |
| 99 | A | CB | 347 | 611 | −56 | 88 | 119 | V | CB | 391 | 456 | 8 | 33 |
| 99 | A | C | 330 | 627 | −45 | 89 | 119 | V | CG1 | 391 | 462 | 22 | 32 |
| 99 | A | O | 321 | 624 | −52 | 89 | 119 | V | CG2 | 404 | 459 | 2 | 30 |
| 100 | I | N | 328 | 634 | −33 | 91 | 119 | V | C | 378 | 437 | 18 | 33 |
| 100 | I | CA | 315 | 639 | −30 | 92 | 119 | V | O | 380 | 432 | 29 | 31 |
| 100 | I | CB | 311 | 635 | −15 | 92 | 120 | R | N | 366 | 440 | 13 | 32 |
| 100 | I | CG1 | 296 | 632 | −14 | 92 | 120 | R | CA | 354 | 434 | 20 | 32 |
| 100 | I | CD1 | 293 | 619 | −5 | 92 | 120 | R | CB | 341 | 438 | 12 | 31 |
| 100 | I | CG2 | 315 | 646 | −4 | 92 | 120 | R | CG | 328 | 437 | 20 | 33 |
| 100 | I | C | 314 | 654 | −33 | 93 | 120 | R | CD | 316 | 443 | 12 | 35 |
| 100 | I | O | 303 | 660 | −30 | 93 | 120 | R | NE | 319 | 457 | 9 | 35 |
| 101 | A | N | 325 | 660 | −38 | 94 | 120 | R | CZ | 314 | 463 | −2 | 37 |
| 101 | A | CA | 324 | 673 | −44 | 94 | 120 | R | NH1 | 305 | 456 | −10 | 34 |
| 101 | A | CB | 330 | 684 | −34 | 94 | 120 | R | NH2 | 317 | 476 | −4 | 33 |
| 101 | A | C | 332 | 673 | −57 | 95 | 120 | R | C | 354 | 420 | 24 | 33 |
| 101 | A | O | 326 | 673 | −68 | 95 | 120 | R | O | 351 | 416 | 35 | 33 |
| 102 | G | N | 346 | 672 | −56 | 95 | 121 | K | N | 359 | 411 | 15 | 33 |
| 102 | G | CA | 355 | 672 | −67 | 95 | 121 | K | CA | 359 | 397 | 18 | 33 |
| 102 | G | C | 354 | 660 | −76 | 95 | 121 | K | CB | 362 | 388 | 6 | 34 |
| 102 | G | O | 365 | 653 | −77 | 96 | 121 | K | CG | 349 | 387 | −3 | 37 |
| 111 | A | N | 367 | 520 | −127 | 63 | 121 | K | CD | 354 | 380 | −16 | 40 |
| 111 | A | CA | 367 | 520 | −112 | 63 | 121 | K | CE | 342 | 373 | −23 | 49 |
| 111 | A | CB | 356 | 529 | −107 | 64 | 121 | K | NZ | 335 | 384 | −31 | 51 |
| 111 | A | C | 367 | 506 | −106 | 62 | 121 | K | C | 371 | 393 | 28 | 33 |
| 111 | A | O | 360 | 497 | −111 | 63 | 121 | K | O | 369 | 384 | 37 | 33 |
| 112 | K | N | 374 | 505 | −94 | 60 | 122 | Y | N | 382 | 400 | 28 | 33 |
| 112 | K | CA | 378 | 492 | −89 | 58 | 122 | Y | CA | 392 | 399 | 38 | 32 |
| 112 | K | CB | 392 | 495 | −81 | 59 | 122 | Y | CB | 403 | 409 | 35 | 31 |
| 112 | K | CG | 402 | 505 | −87 | 62 | 122 | Y | CG | 413 | 411 | 46 | 30 |
| 112 | K | CD | 412 | 499 | −97 | 66 | 122 | Y | CD1 | 413 | 424 | 53 | 31 |
| 112 | K | CE | 407 | 501 | −111 | 69 | 122 | Y | CE1 | 422 | 427 | 62 | 30 |
| 112 | K | NZ | 417 | 499 | −122 | 70 | 122 | Y | CZ | 431 | 417 | 66 | 30 |
| 112 | K | C | 369 | 484 | −80 | 56 | 122 | Y | OH | 440 | 421 | 76 | 30 |
| 112 | K | O | 372 | 480 | −69 | 55 | 122 | Y | CE2 | 431 | 405 | 61 | 28 |
| 113 | E | N | 357 | 480 | −86 | 53 | 122 | Y | CD2 | 422 | 402 | 50 | 28 |
| 113 | E | CA | 347 | 473 | −78 | 50 | 122 | Y | C | 386 | 401 | 52 | 32 |
| 113 | E | CB | 335 | 470 | −87 | 50 | 122 | Y | O | 388 | 392 | 61 | 33 |
| 113 | E | CG | 328 | 483 | −91 | 56 | 123 | F | N | 378 | 412 | 54 | 31 |
| 113 | E | CD | 323 | 491 | −79 | 62 | 123 | F | CA | 372 | 414 | 67 | 33 |
| 113 | E | OE1 | 318 | 485 | −70 | 63 | 123 | F | CB | 366 | 429 | 67 | 32 |
| 113 | E | OE2 | 325 | 504 | −80 | 64 | 123 | F | CG | 377 | 438 | 70 | 31 |
| 113 | E | C | 351 | 459 | −72 | 48 | 123 | F | CD1 | 381 | 441 | 83 | 37 |
| 113 | E | O | 347 | 455 | −61 | 46 | 123 | F | CE1 | 392 | 449 | 86 | 31 |
| 114 | D | N | 360 | 452 | −80 | 45 | 123 | F | CZ | 399 | 456 | 76 | 31 |
| 114 | D | CA | 364 | 439 | −75 | 42 | 123 | F | CE2 | 395 | 453 | 62 | 28 |
| 114 | D | CB | 369 | 430 | −87 | 43 | 123 | F | CD2 | 384 | 444 | 60 | 30 |
| 114 | D | CG | 358 | 426 | −96 | 47 | 123 | F | C | 361 | 404 | 70 | 34 |
| 114 | D | OD1 | 361 | 426 | −108 | 54 | 123 | F | O | 359 | 400 | 82 | 33 |
| 114 | D | OD2 | 346 | 423 | −93 | 49 | 124 | Q | N | 354 | 399 | 60 | 35 |
| 114 | D | C | 374 | 440 | −64 | 39 | 124 | Q | CA | 345 | 388 | 62 | 37 |
| 114 | D | O | 375 | 431 | −55 | 37 | 124 | Q | CB | 337 | 384 | 49 | 39 |
| 115 | S | N | 382 | 450 | −65 | 38 | 124 | Q | CG | 326 | 395 | 47 | 39 |
| 115 | S | CA | 392 | 454 | −54 | 38 | 124 | Q | CD | 320 | 394 | 32 | 47 |
| 115 | S | CB | 401 | 465 | −59 | 39 | 124 | Q | OE1 | 324 | 384 | 25 | 45 |
| 115 | S | OG | 411 | 460 | −67 | 46 | 124 | Q | NE2 | 312 | 403 | 29 | 47 |
| 115 | S | C | 385 | 458 | −42 | 38 | 124 | Q | C | 352 | 376 | 68 | 37 |
| 115 | S | O | 389 | 454 | −31 | 38 | 124 | Q | O | 347 | 369 | 77 | 37 |
| 116 | I | N | 375 | 467 | −43 | 36 | 125 | R | N | 364 | 373 | 63 | 35 |
| 116 | I | CA | 366 | 470 | −31 | 36 | 125 | R | CA | 372 | 362 | 68 | 37 |
| 116 | I | CB | 355 | 480 | −35 | 37 | 125 | R | CB | 385 | 359 | 60 | 37 |
| 116 | I | CG1 | 361 | 494 | −38 | 37 | 125 | R | CG | 381 | 355 | 46 | 38 |
| 116 | I | CD1 | 351 | 504 | −45 | 39 | 125 | R | CD | 392 | 350 | 37 | 36 |
| 116 | I | CG2 | 343 | 480 | −24 | 37 | 125 | R | NE | 402 | 360 | 33 | 35 |
| 116 | I | C | 361 | 457 | −25 | 36 | 125 | R | CZ | 401 | 367 | 22 | 34 |
| 116 | I | O | 362 | 455 | −12 | 34 | 125 | R | NH1 | 390 | 367 | 15 | 33 |
| 117 | L | N | 356 | 448 | −33 | 35 | 125 | R | NH2 | 411 | 375 | 19 | 32 |
| 117 | L | CA | 350 | 436 | −28 | 35 | 125 | R | C | 376 | 364 | 83 | 36 |
| 117 | L | CB | 344 | 428 | −40 | 36 | 125 | R | O | 375 | 355 | 91 | 36 |
| 117 | L | CG | 330 | 433 | −44 | 40 | 126 | I | N | 380 | 377 | 86 | 36 |
| 117 | L | CD1 | 325 | 424 | −55 | 46 | 126 | I | CA | 383 | 380 | 100 | 35 |
| 117 | L | CD2 | 321 | 433 | −32 | 42 | 126 | I | CB | 388 | 395 | 101 | 34 |
| 117 | L | C | 361 | 427 | −22 | 34 | 126 | I | CG1 | 403 | 395 | 95 | 34 |
| 117 | L | O | 358 | 420 | −13 | 34 | 126 | I | CD1 | 408 | 409 | 94 | 33 |
| 118 | A | N | 373 | 428 | −27 | 32 | 126 | I | CG2 | 388 | 400 | 115 | 34 |
| 118 | A | CA | 384 | 419 | −22 | 33 | 126 | I | C | 371 | 378 | 109 | 36 |
| 118 | A | CB | 397 | 419 | −30 | 32 | 126 | I | O | 372 | 372 | 120 | 35 |
| 118 | A | C | 387 | 423 | −7 | 32 | 127 | T | N | 359 | 383 | 105 | 37 |
| 118 | A | O | 388 | 415 | 1 | 31 | 127 | T | CA | 347 | 383 | 113 | 40 |
| 119 | V | N | 386 | 436 | −5 | 32 | 127 | T | CB | 336 | 390 | 105 | 40 |

-continued

| | | | | | | |
|---|---|---|---|---|---|---|
| 127 | T | OG1 | 337 | 404 | 108 | 45 |
| 127 | T | CG2 | 322 | 387 | 111 | 44 |
| 127 | T | C | 343 | 368 | 116 | 41 |
| 127 | T | O | 340 | 365 | 128 | 43 |
| 128 | L | N | 343 | 360 | 106 | 42 |
| 128 | L | CA | 341 | 346 | 108 | 44 |
| 128 | L | CB | 342 | 339 | 94 | 44 |
| 128 | L | CG | 335 | 326 | 91 | 49 |
| 128 | L | CD1 | 324 | 330 | 81 | 52 |
| 128 | L | CD2 | 344 | 315 | 86 | 54 |
| 128 | L | C | 350 | 339 | 117 | 44 |
| 128 | L | O | 346 | 331 | 126 | 43 |
| 129 | Y | N | 363 | 341 | 115 | 42 |
| 129 | Y | CA | 374 | 336 | 124 | 41 |
| 129 | Y | CB | 388 | 341 | 119 | 41 |
| 129 | Y | CG | 399 | 339 | 130 | 39 |
| 129 | Y | CD1 | 408 | 329 | 130 | 41 |
| 129 | Y | CE1 | 418 | 327 | 139 | 40 |
| 129 | Y | CZ | 420 | 337 | 149 | 40 |
| 129 | Y | OH | 430 | 336 | 159 | 39 |
| 129 | Y | CE2 | 411 | 348 | 149 | 41 |
| 129 | Y | CD2 | 401 | 349 | 140 | 39 |
| 129 | Y | C | 370 | 339 | 138 | 42 |
| 129 | Y | O | 370 | 329 | 147 | 42 |
| 130 | L | N | 367 | 351 | 141 | 41 |
| 130 | L | CA | 363 | 355 | 155 | 43 |
| 130 | L | CB | 360 | 370 | 156 | 42 |
| 130 | L | CG | 373 | 379 | 155 | 41 |
| 130 | L | CD1 | 369 | 393 | 153 | 37 |
| 130 | L | CD2 | 381 | 378 | 169 | 39 |
| 130 | L | C | 351 | 348 | 161 | 46 |
| 130 | L | O | 351 | 344 | 173 | 46 |
| 131 | K | N | 341 | 346 | 152 | 48 |
| 131 | K | CA | 329 | 338 | 156 | 50 |
| 131 | K | CB | 318 | 338 | 145 | 50 |
| 131 | K | CG | 311 | 351 | 143 | 55 |
| 131 | K | CD | 300 | 350 | 132 | 62 |
| 131 | K | CE | 288 | 341 | 137 | 65 |
| 131 | K | NZ | 276 | 341 | 127 | 67 |
| 131 | K | C | 333 | 324 | 160 | 50 |
| 131 | K | O | 329 | 319 | 170 | 52 |
| 132 | E | N | 340 | 318 | 150 | 50 |
| 132 | E | CA | 345 | 304 | 152 | 52 |
| 132 | E | CB | 352 | 299 | 140 | 52 |
| 132 | E | CG | 343 | 300 | 128 | 60 |
| 132 | E | CD | 348 | 293 | 116 | 67 |
| 132 | E | OE1 | 360 | 295 | 111 | 71 |
| 132 | E | OE2 | 340 | 285 | 110 | 71 |
| 132 | E | C | 353 | 301 | 165 | 52 |
| 132 | E | O | 352 | 291 | 171 | 52 |
| 133 | K | N | 362 | 311 | 168 | 52 |
| 133 | K | CA | 371 | 310 | 180 | 51 |
| 133 | K | CB | 383 | 319 | 178 | 51 |
| 133 | K | CG | 393 | 315 | 167 | 49 |
| 133 | K | CD | 400 | 302 | 170 | 50 |
| 133 | K | CE | 410 | 298 | 160 | 51 |
| 133 | K | NZ | 420 | 288 | 165 | 55 |
| 133 | K | C | 364 | 314 | 192 | 50 |
| 133 | K | O | 369 | 315 | 203 | 52 |
| 134 | K | N | 351 | 318 | 190 | 51 |
| 134 | K | CA | 342 | 323 | 200 | 50 |
| 134 | K | CB | 339 | 312 | 211 | 52 |
| 134 | K | CG | 331 | 300 | 204 | 56 |
| 134 | K | CD | 325 | 291 | 215 | 66 |
| 134 | K | CE | 314 | 298 | 223 | 71 |
| 134 | K | NZ | 303 | 288 | 226 | 76 |
| 134 | K | C | 347 | 335 | 207 | 49 |
| 134 | K | O | 345 | 337 | 219 | 48 |
| 135 | Y | N | 354 | 344 | 199 | 47 |
| 135 | Y | CA | 359 | 357 | 204 | 45 |
| 135 | Y | CB | 347 | 366 | 208 | 45 |
| 135 | Y | CG | 338 | 369 | 197 | 48 |
| 135 | Y | CD1 | 325 | 362 | 196 | 51 |
| 135 | Y | CE1 | 316 | 364 | 186 | 49 |
| 135 | Y | CZ | 320 | 373 | 176 | 49 |
| 135 | Y | OH | 311 | 375 | 165 | 50 |
| 135 | Y | CE2 | 332 | 380 | 176 | 47 |
| 135 | Y | CD2 | 341 | 378 | 186 | 49 |
| 135 | Y | C | 369 | 356 | 216 | 43 |
| 135 | Y | O | 369 | 364 | 225 | 42 |
| 136 | S | N | 377 | 345 | 216 | 43 |
| 136 | S | CA | 387 | 344 | 227 | 43 |
| 136 | S | CB | 394 | 330 | 226 | 43 |
| 136 | S | OG | 403 | 330 | 215 | 44 |
| 136 | S | C | 396 | 355 | 228 | 43 |
| 136 | S | O | 398 | 362 | 217 | 43 |
| 137 | P | N | 402 | 358 | 239 | 43 |
| 137 | P | CA | 413 | 368 | 240 | 42 |
| 137 | P | CB | 419 | 365 | 255 | 42 |
| 137 | P | CG | 406 | 362 | 262 | 42 |
| 137 | P | CD | 399 | 353 | 253 | 42 |
| 137 | P | C | 424 | 366 | 230 | 40 |
| 137 | P | O | 429 | 376 | 224 | 39 |
| 138 | C | N | 427 | 353 | 228 | 38 |
| 138 | C | CA | 438 | 350 | 218 | 41 |
| 138 | C | CB | 442 | 335 | 219 | 40 |
| 138 | C | SG | 454 | 333 | 232 | 48 |
| 138 | C | C | 434 | 353 | 204 | 40 |
| 138 | C | O | 442 | 358 | 196 | 39 |
| 139 | A | N | 421 | 349 | 200 | 38 |
| 139 | A | CA | 416 | 352 | 187 | 37 |
| 139 | A | CB | 402 | 346 | 185 | 37 |
| 139 | A | C | 416 | 367 | 184 | 36 |
| 139 | A | O | 420 | 371 | 173 | 36 |
| 140 | W | N | 411 | 375 | 193 | 36 |
| 140 | W | CA | 411 | 389 | 192 | 37 |
| 140 | W | CB | 404 | 395 | 205 | 37 |
| 140 | W | CG | 389 | 399 | 202 | 40 |
| 140 | W | CD1 | 378 | 394 | 209 | 40 |
| 140 | W | NE1 | 366 | 400 | 204 | 39 |
| 140 | W | CE2 | 370 | 408 | 194 | 42 |
| 140 | W | CD2 | 384 | 408 | 192 | 39 |
| 140 | W | CE3 | 390 | 416 | 182 | 40 |
| 140 | W | C23 | 381 | 424 | 174 | 38 |
| 140 | W | CH2 | 367 | 424 | 176 | 39 |
| 140 | W | CZ2 | 361 | 416 | 186 | 41 |
| 140 | W | C | 425 | 395 | 191 | 36 |
| 140 | W | O | 426 | 405 | 185 | 35 |
| 141 | E | N | 435 | 390 | 198 | 35 |
| 141 | E | CA | 448 | 395 | 197 | 35 |
| 141 | E | CB | 457 | 389 | 208 | 34 |
| 141 | E | CG | 472 | 393 | 206 | 30 |
| 141 | E | CD | 475 | 408 | 204 | 32 |
| 141 | E | OE1 | 466 | 416 | 208 | 34 |
| 141 | E | OE2 | 485 | 411 | 198 | 32 |
| 141 | E | C | 454 | 392 | 183 | 34 |
| 141 | E | O | 461 | 400 | 177 | 34 |
| 142 | V | N | 451 | 380 | 178 | 34 |
| 142 | V | CA | 456 | 377 | 165 | 35 |
| 142 | V | CB | 452 | 362 | 162 | 35 |
| 142 | V | CG1 | 452 | 360 | 146 | 37 |
| 142 | V | CG2 | 460 | 352 | 169 | 36 |
| 142 | V | C | 450 | 387 | 155 | 33 |
| 142 | V | O | 457 | 392 | 146 | 33 |
| 143 | V | N | 437 | 390 | 157 | 33 |
| 143 | V | CA | 430 | 399 | 148 | 31 |
| 143 | V | CB | 415 | 398 | 150 | 32 |
| 143 | V | CG1 | 407 | 411 | 144 | 32 |
| 143 | V | CG2 | 410 | 385 | 144 | 31 |
| 143 | V | C | 436 | 413 | 149 | 30 |
| 143 | V | O | 438 | 420 | 139 | 30 |
| 144 | R | N | 438 | 418 | 162 | 31 |
| 144 | R | CA | 442 | 431 | 164 | 30 |
| 144 | R | CB | 442 | 435 | 179 | 31 |
| 144 | R | CG | 448 | 449 | 182 | 30 |
| 144 | R | CD | 455 | 450 | 196 | 32 |
| 144 | R | NE | 468 | 442 | 196 | 32 |
| 144 | R | CZ | 479 | 447 | 190 | 28 |
| 144 | R | NH1 | 480 | 459 | 185 | 29 |
| 144 | R | NH2 | 489 | 438 | 189 | 30 |
| 144 | R | C | 456 | 433 | 157 | 30 |
| 144 | R | O | 458 | 443 | 150 | 30 |
| 145 | A | N | 465 | 423 | 160 | 29 |
| 145 | A | CA | 479 | 423 | 154 | 30 |
| 145 | A | CB | 487 | 412 | 159 | 31 |
| 145 | A | C | 478 | 423 | 139 | 30 |
| 145 | A | O | 486 | 430 | 132 | 29 |
| 146 | E | N | 469 | 414 | 133 | 30 |
| 146 | E | CA | 468 | 413 | 119 | 29 |
| 146 | E | CB | 456 | 403 | 116 | 29 |

-continued

| 146 | E | CG  | 450 | 403 | 102 | 32 |
| --- | - | --- | --- | --- | --- | -- |
| 146 | E | CD  | 461 | 399 | 91  | 34 |
| 146 | E | OE1 | 459 | 404 | 79  | 31 |
| 146 | E | OE2 | 470 | 392 | 94  | 34 |
| 146 | E | C   | 464 | 427 | 112 | 30 |
| 146 | E | O   | 469 | 430 | 101 | 31 |
| 147 | I | N   | 454 | 434 | 118 | 28 |
| 147 | I | CA  | 449 | 447 | 113 | 28 |
| 147 | I | CB  | 436 | 451 | 121 | 27 |
| 147 | I | CG1 | 424 | 442 | 117 | 29 |
| 147 | I | CD1 | 421 | 442 | 102 | 35 |
| 147 | I | CG2 | 432 | 466 | 118 | 28 |
| 147 | I | C   | 460 | 457 | 115 | 29 |
| 147 | I | O   | 462 | 466 | 106 | 28 |
| 148 | M | N   | 468 | 456 | 126 | 29 |
| 148 | M | CA  | 479 | 465 | 128 | 31 |
| 148 | M | CB  | 487 | 462 | 141 | 31 |
| 148 | M | CG  | 499 | 471 | 143 | 41 |
| 148 | M | SD  | 493 | 485 | 153 | 53 |
| 148 | M | CE  | 509 | 495 | 154 | 47 |
| 148 | M | C   | 489 | 464 | 115 | 31 |
| 148 | M | O   | 493 | 474 | 109 | 30 |
| 149 | R | N   | 491 | 451 | 112 | 31 |
| 149 | R | CA  | 500 | 448 | 101 | 31 |
| 149 | R | CB  | 503 | 433 | 100 | 32 |
| 149 | R | CG  | 513 | 429 | 112 | 37 |
| 149 | R | CD  | 519 | 415 | 110 | 40 |
| 149 | R | NE  | 508 | 405 | 109 | 38 |
| 149 | R | CZ  | 502 | 398 | 118 | 38 |
| 149 | R | NH1 | 493 | 389 | 115 | 38 |
| 149 | R | NH2 | 506 | 400 | 131 | 34 |
| 149 | R | C   | 494 | 452 | 87  | 32 |
| 149 | R | O   | 501 | 458 | 79  | 30 |
| 150 | S | N   | 481 | 449 | 85  | 31 |
| 150 | S | CA  | 476 | 452 | 71  | 33 |
| 150 | S | CB  | 464 | 443 | 68  | 33 |
| 150 | S | OG  | 453 | 447 | 77  | 34 |
| 150 | S | C   | 473 | 466 | 69  | 33 |
| 150 | S | O   | 474 | 472 | 58  | 34 |
| 151 | F | N   | 468 | 473 | 80  | 33 |
| 151 | F | CA  | 466 | 487 | 79  | 34 |
| 151 | F | CB  | 458 | 492 | 92  | 35 |
| 151 | F | CG  | 455 | 507 | 92  | 38 |
| 151 | F | CD1 | 445 | 512 | 83  | 40 |
| 151 | F | CE1 | 442 | 526 | 83  | 41 |
| 151 | F | CZ  | 450 | 534 | 90  | 39 |
| 151 | F | CE2 | 460 | 530 | 98  | 42 |
| 151 | F | CD2 | 463 | 516 | 99  | 39 |
| 151 | F | C   | 479 | 495 | 77  | 35 |
| 151 | F | O   | 480 | 505 | 69  | 34 |
| 152 | S | N   | 490 | 491 | 84  | 34 |
| 152 | S | CA  | 503 | 497 | 83  | 39 |
| 152 | S | CB  | 514 | 490 | 91  | 37 |
| 152 | S | OG  | 512 | 493 | 104 | 46 |
| 152 | S | C   | 507 | 496 | 68  | 41 |
| 152 | S | O   | 513 | 505 | 63  | 42 |
| 153 | L | N   | 504 | 485 | 63  | 41 |
| 153 | L | CA  | 510 | 481 | 50  | 45 |
| 153 | L | CB  | 508 | 466 | 48  | 44 |
| 153 | L | CG  | 514 | 459 | 35  | 47 |
| 153 | L | CD1 | 528 | 463 | 34  | 48 |
| 153 | L | CD2 | 513 | 444 | 37  | 48 |
| 153 | L | C   | 502 | 489 | 39  | 46 |
| 153 | L | O   | 508 | 495 | 30  | 46 |
| 154 | S | N   | 489 | 490 | 41  | 48 |
| 154 | S | CA  | 480 | 496 | 31  | 51 |
| 154 | S | CB  | 467 | 490 | 32  | 49 |
| 154 | S | OG  | 459 | 497 | 42  | 52 |
| 154 | S | C   | 480 | 512 | 32  | 53 |
| 154 | S | O   | 475 | 518 | 22  | 55 |
| 155 | T | N   | 485 | 518 | 42  | 56 |
| 155 | T | CA  | 487 | 532 | 42  | 59 |
| 155 | T | CB  | 482 | 539 | 55  | 58 |
| 155 | T | OG1 | 489 | 534 | 67  | 58 |
| 155 | T | CG2 | 468 | 536 | 58  | 58 |
| 155 | T | C   | 502 | 535 | 38  | 62 |
| 155 | T | O   | 504 | 544 | 29  | 63 |
| 156 | N | N   | 512 | 529 | 43  | 66 |
| 156 | N | CA  | 526 | 530 | 40  | 70 |
| 156 | N | CB  | 535 | 522 | 49  | 70 |
| 156 | N | CG  | 535 | 527 | 63  | 73 |
| 156 | N | OD1 | 546 | 525 | 70  | 75 |
| 156 | N | ND2 | 524 | 532 | 69  | 74 |
| 156 | N | C   | 529 | 527 | 25  | 72 |
| 156 | N | O   | 540 | 531 | 20  | 72 |
| 157 | L | N   | 519 | 521 | 18  | 73 |
| 157 | L | CA  | 520 | 518 | 4   | 75 |
| 157 | L | CB  | 515 | 504 | 0   | 75 |
| 157 | L | CG  | 523 | 491 | 3   | 76 |
| 157 | L | CD1 | 518 | 479 | −4  | 77 |
| 157 | L | CD2 | 539 | 493 | 0   | 79 |
| 157 | L | C   | 512 | 529 | −4  | 76 |
| 157 | L | O   | 503 | 526 | −12 | 76 |
| 3   | A | N   | 452 | 381 | −264 | 92 |
| 3   | A | CA  | 440 | 389 | −268 | 93 |
| 3   | A | CB  | 443 | 397 | −281 | 93 |
| 3   | A | C   | 426 | 381 | −270 | 92 |
| 3   | A | O   | 416 | 386 | −265 | 92 |
| 4   | P | N   | 426 | 369 | −276 | 92 |
| 4   | P | CA  | 414 | 361 | −277 | 91 |
| 4   | P | CB  | 416 | 351 | −288 | 91 |
| 4   | P | CG  | 431 | 349 | −289 | 91 |
| 4   | P | CD  | 437 | 362 | −282 | 91 |
| 4   | P | C   | 410 | 353 | −264 | 90 |
| 4   | P | O   | 418 | 354 | −254 | 90 |
| 5   | A | N   | 399 | 346 | −263 | 89 |
| 5   | A | CA  | 395 | 338 | −252 | 87 |
| 5   | A | CB  | 380 | 335 | −252 | 87 |
| 5   | A | C   | 404 | 325 | −250 | 85 |
| 5   | A | O   | 413 | 324 | −242 | 86 |
| 6   | A | N   | 400 | 314 | −257 | 83 |
| 6   | A | CA  | 407 | 301 | −259 | 81 |
| 6   | A | CB  | 422 | 304 | −262 | 81 |
| 6   | A | C   | 406 | 291 | −248 | 79 |
| 6   | A | O   | 407 | 279 | −250 | 79 |
| 7   | H | N   | 403 | 295 | −235 | 75 |
| 7   | H | CA  | 403 | 287 | −223 | 71 |
| 7   | H | CB  | 410 | 294 | −212 | 70 |
| 7   | H | CG  | 425 | 295 | −213 | 65 |
| 7   | H | ND1 | 434 | 286 | −206 | 59 |
| 7   | H | CE1 | 446 | 289 | −209 | 57 |
| 7   | H | NE2 | 446 | 300 | −217 | 57 |
| 7   | H | CD2 | 433 | 303 | −220 | 59 |
| 7   | H | C   | 390 | 283 | −218 | 70 |
| 7   | H | O   | 388 | 280 | −206 | 70 |
| 8   | S | N   | 379 | 282 | −227 | 69 |
| 8   | S | CA  | 366 | 279 | −222 | 67 |
| 8   | S | CB  | 355 | 288 | −228 | 67 |
| 8   | S | OG  | 357 | 290 | −242 | 70 |
| 8   | S | C   | 362 | 264 | −224 | 65 |
| 8   | S | O   | 356 | 259 | −215 | 65 |
| 9   | L | N   | 365 | 258 | −235 | 63 |
| 9   | L | CA  | 363 | 244 | −237 | 61 |
| 9   | L | CB  | 364 | 239 | −251 | 62 |
| 9   | L | CG  | 360 | 224 | −254 | 64 |
| 9   | L | CD1 | 346 | 222 | −248 | 67 |
| 9   | L | CD2 | 361 | 220 | −269 | 68 |
| 9   | L | C   | 372 | 236 | −228 | 59 |
| 9   | L | O   | 368 | 226 | −222 | 58 |
| 10  | G | N   | 385 | 240 | −228 | 56 |
| 10  | G | CA  | 395 | 233 | −220 | 53 |
| 10  | G | C   | 391 | 232 | −205 | 51 |
| 10  | G | O   | 392 | 222 | −198 | 50 |
| 11  | S | N   | 387 | 244 | −200 | 50 |
| 11  | S | CA  | 384 | 246 | −186 | 49 |
| 11  | S | CB  | 381 | 261 | −185 | 49 |
| 11  | S | OG  | 374 | 264 | −173 | 56 |
| 11  | S | C   | 372 | 237 | −183 | 47 |
| 11  | S | O   | 372 | 231 | −172 | 44 |
| 12  | R | N   | 362 | 236 | −192 | 45 |
| 12  | R | CA  | 350 | 228 | −188 | 44 |
| 12  | R | CB  | 339 | 230 | −199 | 45 |
| 12  | R | CG  | 329 | 219 | −199 | 51 |
| 12  | R | CD  | 315 | 222 | −207 | 61 |
| 12  | R | NE  | 305 | 214 | −200 | 68 |
| 12  | R | CZ  | 292 | 216 | −202 | 70 |
| 12  | R | NH1 | 287 | 225 | −211 | 75 |
| 12  | R | NH2 | 283 | 208 | −195 | 66 |
| 12  | R | C   | 354 | 213 | −187 | 42 |
| 12  | R | O   | 350 | 207 | −178 | 39 |

| | | | | | | |
|---|---|---|---|---|---|---|
| 13 | R | N | 363 | 208 | −196 | 39 |
| 13 | R | CA | 368 | 194 | −195 | 39 |
| 13 | R | CB | 376 | 190 | −207 | 41 |
| 13 | R | CG | 369 | 193 | −221 | 45 |
| 13 | R | CD | 378 | 189 | −233 | 57 |
| 13 | R | NE | 385 | 200 | −239 | 65 |
| 13 | R | CZ | 397 | 201 | −245 | 69 |
| 13 | R | NH1 | 402 | 212 | −250 | 71 |
| 13 | R | NH2 | 405 | 190 | −245 | 71 |
| 13 | R | C | 375 | 191 | −182 | 38 |
| 13 | R | O | 374 | 181 | −176 | 37 |
| 14 | T | N | 384 | 201 | −178 | 37 |
| 14 | T | CA | 391 | 200 | −166 | 36 |
| 14 | T | CB | 400 | 212 | −164 | 36 |
| 14 | T | OG1 | 409 | 213 | −175 | 38 |
| 14 | T | CG2 | 409 | 212 | −152 | 36 |
| 14 | T | C | 382 | 199 | −153 | 35 |
| 14 | T | O | 385 | 191 | −144 | 34 |
| 15 | L | N | 373 | 208 | −153 | 35 |
| 15 | L | CA | 363 | 209 | −142 | 35 |
| 15 | L | CB | 354 | 221 | −144 | 36 |
| 15 | L | CG | 361 | 234 | −140 | 39 |
| 15 | L | CD1 | 352 | 245 | −145 | 43 |
| 15 | L | CD2 | 363 | 234 | −125 | 40 |
| 15 | L | C | 356 | 196 | −141 | 36 |
| 15 | L | O | 353 | 191 | −130 | 34 |
| 16 | M | N | 352 | 190 | −152 | 37 |
| 16 | M | CA | 344 | 178 | −152 | 38 |
| 16 | M | CB | 340 | 174 | −167 | 40 |
| 16 | M | CG | 324 | 175 | −170 | 50 |
| 16 | M | SD | 315 | 158 | −172 | 65 |
| 16 | M | CE | 328 | 149 | −184 | 56 |
| 16 | M | C | 352 | 166 | −146 | 36 |
| 16 | M | O | 347 | 158 | −139 | 35 |
| 17 | L | N | 365 | 166 | −148 | 35 |
| 17 | L | CA | 374 | 156 | −143 | 34 |
| 17 | L | CB | 387 | 156 | −150 | 36 |
| 17 | L | CG | 386 | 152 | −165 | 38 |
| 17 | L | CD1 | 398 | 156 | −173 | 41 |
| 17 | L | CD2 | 385 | 136 | −165 | 38 |
| 17 | L | C | 376 | 158 | −128 | 33 |
| 17 | L | O | 377 | 149 | −120 | 33 |
| 18 | L | N | 378 | 170 | −124 | 34 |
| 18 | L | CA | 379 | 173 | −109 | 34 |
| 18 | L | CB | 381 | 188 | −107 | 35 |
| 18 | L | CG | 396 | 193 | −108 | 37 |
| 18 | L | CD1 | 396 | 208 | −109 | 35 |
| 18 | L | CD2 | 404 | 187 | −95 | 33 |
| 18 | L | C | 366 | 169 | −102 | 33 |
| 18 | L | O | 366 | 165 | −91 | 33 |
| 19 | A | N | 355 | 171 | −109 | 33 |
| 19 | A | CA | 342 | 167 | −103 | 33 |
| 19 | A | CB | 330 | 172 | −111 | 34 |
| 19 | A | C | 342 | 152 | −101 | 33 |
| 19 | A | O | 338 | 147 | −91 | 34 |
| 20 | Q | N | 347 | 145 | −111 | 34 |
| 20 | Q | CA | 347 | 130 | −111 | 34 |
| 20 | Q | CB | 350 | 124 | −125 | 34 |
| 20 | Q | CG | 339 | 127 | −135 | 35 |
| 20 | Q | CD | 343 | 122 | −148 | 44 |
| 20 | Q | OE1 | 347 | 130 | −157 | 46 |
| 20 | Q | NE2 | 341 | 109 | −151 | 43 |
| 20 | Q | C | 357 | 124 | −101 | 34 |
| 20 | Q | O | 355 | 113 | −97 | 36 |
| 21 | M | N | 367 | 132 | −97 | 35 |
| 21 | M | CA | 377 | 127 | −87 | 35 |
| 21 | M | CB | 389 | 136 | −88 | 35 |
| 21 | M | CG | 397 | 134 | −101 | 40 |
| 21 | M | SD | 409 | 148 | −104 | 48 |
| 21 | M | CE | 418 | 147 | −91 | 35 |
| 21 | M | C | 372 | 127 | −73 | 37 |
| 21 | M | O | 377 | 120 | −65 | 37 |
| 22 | R | N | 361 | 133 | −70 | 37 |
| 22 | R | CA | 355 | 133 | −57 | 37 |
| 22 | R | CB | 341 | 141 | −56 | 37 |
| 22 | R | CG | 336 | 142 | −41 | 39 |
| 22 | R | CD | 322 | 145 | −36 | 46 |
| 22 | R | NE | 316 | 132 | −33 | 42 |
| 22 | R | CZ | 306 | 128 | −26 | 39 |
| 22 | R | NH1 | 304 | 115 | −27 | 35 |
| 22 | R | NH2 | 298 | 135 | −19 | 38 |
| 22 | R | C | 353 | 119 | −51 | 38 |
| 22 | R | O | 346 | 111 | −58 | 38 |
| 23 | R | N | 359 | 116 | −40 | 38 |
| 23 | R | CA | 357 | 103 | −32 | 39 |
| 23 | R | CB | 370 | 97 | −28 | 39 |
| 23 | R | CG | 380 | 96 | −39 | 45 |
| 23 | R | CD | 392 | 90 | −33 | 49 |
| 23 | R | NE | 399 | 82 | −43 | 59 |
| 23 | R | CZ | 411 | 75 | −40 | 62 |
| 23 | R | NH1 | 416 | 68 | −50 | 62 |
| 23 | R | NH2 | 417 | 76 | −28 | 57 |
| 23 | R | C | 348 | 104 | −20 | 39 |
| 23 | R | O | 341 | 94 | −17 | 39 |
| 24 | I | N | 350 | 115 | −12 | 38 |
| 24 | I | CA | 341 | 116 | −1 | 37 |
| 24 | I | CB | 349 | 115 | 13 | 38 |
| 24 | I | CG1 | 360 | 126 | 14 | 38 |
| 24 | I | CD1 | 366 | 127 | 28 | 41 |
| 24 | I | CG2 | 355 | 100 | 14 | 37 |
| 24 | I | C | 334 | 130 | −1 | 38 |
| 24 | I | O | 338 | 139 | −9 | 36 |
| 25 | S | N | 325 | 132 | 8 | 37 |
| 25 | S | CA | 316 | 143 | 9 | 38 |
| 25 | S | CB | 303 | 139 | 15 | 36 |
| 25 | S | OG | 294 | 151 | 16 | 36 |
| 25 | S | C | 322 | 155 | 16 | 36 |
| 25 | S | O | 327 | 152 | 27 | 38 |
| 26 | L | N | 321 | 167 | 12 | 37 |
| 26 | L | CA | 324 | 179 | 19 | 38 |
| 26 | L | CB | 321 | 191 | 12 | 39 |
| 26 | L | CG | 329 | 194 | −1 | 41 |
| 26 | L | CD1 | 321 | 204 | −10 | 43 |
| 26 | L | CD2 | 342 | 200 | 4 | 45 |
| 26 | L | C | 317 | 179 | 33 | 40 |
| 26 | L | O | 321 | 185 | 42 | 40 |
| 27 | F | N | 305 | 172 | 33 | 41 |
| 27 | F | CA | 296 | 173 | 44 | 41 |
| 27 | F | CB | 281 | 170 | 41 | 40 |
| 27 | F | CG | 274 | 181 | 33 | 41 |
| 27 | F | CD1 | 269 | 192 | 40 | 42 |
| 27 | F | CE1 | 263 | 203 | 34 | 39 |
| 27 | F | CZ | 262 | 202 | 20 | 40 |
| 27 | F | CE2 | 267 | 191 | 13 | 38 |
| 27 | F | CD2 | 273 | 180 | 19 | 39 |
| 27 | F | C | 301 | 164 | 55 | 42 |
| 27 | F | O | 297 | 165 | 67 | 44 |
| 28 | S | N | 310 | 155 | 52 | 41 |
| 28 | S | CA | 317 | 146 | 61 | 41 |
| 28 | S | CB | 321 | 133 | 55 | 41 |
| 28 | S | OG | 309 | 126 | 50 | 41 |
| 28 | S | C | 330 | 153 | 67 | 42 |
| 28 | S | O | 337 | 147 | 75 | 41 |
| 29 | C | N | 332 | 165 | 62 | 42 |
| 29 | C | CA | 345 | 172 | 65 | 41 |
| 29 | C | CB | 354 | 172 | 52 | 40 |
| 29 | C | SG | 356 | 156 | 45 | 47 |
| 29 | C | C | 343 | 186 | 70 | 40 |
| 29 | C | O | 352 | 195 | 67 | 40 |
| 30 | L | N | 332 | 189 | 76 | 41 |
| 30 | L | CA | 329 | 203 | 80 | 43 |
| 30 | L | CB | 315 | 204 | 86 | 44 |
| 30 | L | CG | 304 | 200 | 76 | 43 |
| 30 | L | CD1 | 291 | 199 | 83 | 47 |
| 30 | L | CD2 | 303 | 210 | 65 | 45 |
| 30 | L | C | 339 | 209 | 89 | 43 |
| 30 | L | O | 341 | 221 | 89 | 43 |
| 31 | K | N | 346 | 201 | 97 | 43 |
| 31 | K | CA | 356 | 206 | 107 | 44 |
| 31 | K | CB | 359 | 195 | 117 | 45 |
| 31 | K | CG | 366 | 183 | 109 | 49 |
| 31 | K | CD | 372 | 172 | 119 | 58 |
| 31 | K | CE | 381 | 162 | 111 | 60 |
| 31 | K | NZ | 375 | 157 | 98 | 59 |
| 31 | K | C | 368 | 211 | 100 | 44 |
| 31 | K | O | 376 | 218 | 106 | 43 |
| 32 | D | N | 370 | 206 | 87 | 42 |
| 32 | D | CA | 381 | 210 | 79 | 41 |
| 32 | D | CB | 386 | 198 | 71 | 42 |
| 32 | D | CG | 390 | 187 | 80 | 45 |

-continued

| | | | | | | |
|---|---|---|---|---|---|---|
| 32 | D | OD1 | 399 | 188 | 88 | 44 |
| 32 | D | OD2 | 383 | 176 | 81 | 49 |
| 32 | D | C | 379 | 222 | 69 | 40 |
| 32 | D | O | 388 | 226 | 62 | 38 |
| 33 | A | N | 367 | 228 | 70 | 39 |
| 33 | A | CA | 364 | 240 | 62 | 39 |
| 33 | A | CB | 349 | 245 | 64 | 40 |
| 33 | A | C | 374 | 251 | 64 | 39 |
| 33 | A | O | 378 | 254 | 75 | 37 |
| 34 | H | N | 378 | 257 | 53 | 37 |
| 34 | H | CA | 389 | 267 | 54 | 38 |
| 34 | H | CB | 403 | 260 | 52 | 37 |
| 34 | H | CG | 414 | 270 | 55 | 42 |
| 34 | H | ND1 | 420 | 271 | 68 | 46 |
| 34 | H | CE1 | 429 | 280 | 67 | 46 |
| 34 | H | NE2 | 429 | 286 | 55 | 45 |
| 34 | H | CD2 | 420 | 279 | 47 | 43 |
| 34 | H | C | 386 | 277 | 43 | 37 |
| 34 | H | O | 383 | 273 | 32 | 36 |
| 35 | D | N | 388 | 290 | 46 | 37 |
| 35 | D | CA | 387 | 300 | 35 | 36 |
| 35 | D | CB | 377 | 311 | 39 | 39 |
| 35 | D | CG | 374 | 321 | 27 | 41 |
| 35 | D | OD1 | 364 | 328 | 29 | 43 |
| 35 | D | OD2 | 382 | 322 | 17 | 41 |
| 35 | D | C | 401 | 305 | 31 | 36 |
| 35 | D | O | 408 | 311 | 39 | 35 |
| 36 | F | N | 405 | 301 | 19 | 32 |
| 36 | F | CA | 418 | 304 | 14 | 31 |
| 36 | F | CB | 423 | 294 | 4 | 30 |
| 36 | F | CG | 424 | 280 | 9 | 30 |
| 36 | F | CD1 | 412 | 271 | 8 | 31 |
| 36 | F | CE1 | 413 | 258 | 14 | 31 |
| 36 | F | CZ | 425 | 254 | 20 | 31 |
| 36 | F | CE2 | 436 | 262 | 21 | 32 |
| 36 | F | CD2 | 435 | 275 | 16 | 32 |
| 36 | F | C | 420 | 318 | 9 | 31 |
| 36 | F | O | 431 | 322 | 4 | 31 |
| 37 | G | N | 409 | 326 | 8 | 31 |
| 37 | G | CA | 410 | 340 | 3 | 32 |
| 37 | G | C | 416 | 341 | −11 | 33 |
| 37 | G | O | 425 | 348 | −14 | 34 |
| 38 | F | N | 409 | 334 | −21 | 35 |
| 38 | F | CA | 413 | 333 | −34 | 34 |
| 38 | F | CB | 404 | 324 | −43 | 35 |
| 38 | F | CG | 408 | 324 | −57 | 36 |
| 38 | F | CD1 | 420 | 320 | −61 | 37 |
| 38 | F | CE1 | 424 | 320 | −75 | 39 |
| 38 | F | CZ | 414 | 323 | −85 | 42 |
| 38 | F | CE2 | 402 | 328 | −81 | 39 |
| 38 | F | CD2 | 398 | 328 | −67 | 38 |
| 38 | F | C | 412 | 347 | −40 | 35 |
| 38 | F | O | 400 | 353 | −39 | 36 |
| 39 | P | N | 422 | 353 | −47 | 34 |
| 39 | P | CA | 422 | 366 | −52 | 35 |
| 39 | P | CB | 437 | 369 | −55 | 35 |
| 39 | P | CG | 444 | 356 | −57 | 36 |
| 39 | P | CD | 435 | 346 | −49 | 35 |
| 39 | P | C | 414 | 367 | −66 | 36 |
| 39 | P | O | 420 | 369 | −76 | 35 |
| 40 | Q | N | 401 | 364 | −66 | 37 |
| 40 | Q | CA | 393 | 364 | −78 | 38 |
| 40 | Q | CB | 379 | 360 | −76 | 39 |
| 40 | Q | CG | 371 | 368 | −66 | 44 |
| 40 | Q | CD | 357 | 363 | −64 | 50 |
| 40 | Q | OE1 | 354 | 356 | −54 | 53 |
| 40 | Q | NE2 | 348 | 368 | −72 | 53 |
| 40 | Q | C | 394 | 377 | −86 | 40 |
| 40 | Q | O | 393 | 377 | −99 | 40 |
| 41 | E | N | 395 | 388 | −79 | 40 |
| 41 | E | CA | 397 | 401 | −85 | 41 |
| 41 | E | CB | 398 | 412 | −74 | 42 |
| 41 | E | CG | 412 | 413 | −68 | 39 |
| 41 | E | CD | 414 | 403 | −56 | 38 |
| 41 | E | OE1 | 406 | 395 | −53 | 38 |
| 41 | E | OE2 | 425 | 404 | −50 | 40 |
| 41 | E | C | 408 | 403 | −96 | 42 |
| 41 | E | O | 407 | 411 | −105 | 42 |
| 42 | E | N | 419 | 395 | −95 | 42 |
| 42 | E | CA | 430 | 395 | −105 | 45 |
| 42 | E | CB | 441 | 386 | −102 | 45 |
| 42 | E | CG | 448 | 387 | −88 | 48 |
| 42 | E | CD | 448 | 400 | −82 | 49 |
| 42 | E | OE1 | 455 | 410 | −87 | 51 |
| 42 | E | OE2 | 442 | 401 | −71 | 56 |
| 42 | E | C | 425 | 390 | −118 | 47 |
| 42 | E | O | 432 | 391 | −128 | 47 |
| 43 | F | N | 413 | 384 | −119 | 48 |
| 43 | F | CA | 407 | 378 | −131 | 52 |
| 43 | F | CB | 404 | 363 | −129 | 50 |
| 43 | F | CG | 416 | 355 | −125 | 50 |
| 43 | F | CD1 | 419 | 353 | −111 | 46 |
| 43 | F | CE1 | 429 | 346 | −107 | 44 |
| 43 | F | CZ | 438 | 339 | −116 | 45 |
| 43 | F | CE2 | 435 | 341 | −130 | 44 |
| 43 | F | CD2 | 424 | 349 | −134 | 47 |
| 43 | F | C | 395 | 386 | −135 | 55 |
| 43 | F | O | 388 | 381 | −144 | 56 |
| 44 | G | N | 391 | 397 | −128 | 57 |
| 44 | G | CA | 379 | 404 | −130 | 61 |
| 44 | G | C | 379 | 415 | −141 | 63 |
| 44 | G | O | 389 | 418 | −147 | 64 |
| 45 | A | N | 367 | 421 | −142 | 65 |
| 45 | A | CA | 364 | 432 | −152 | 67 |
| 45 | A | CB | 350 | 437 | −150 | 67 |
| 45 | A | C | 374 | 444 | −152 | 68 |
| 45 | A | O | 374 | 452 | −161 | 68 |
| 46 | Q | N | 381 | 447 | −140 | 68 |
| 46 | Q | CA | 390 | 458 | −139 | 68 |
| 46 | Q | CB | 395 | 460 | −125 | 68 |
| 46 | Q | CG | 386 | 454 | −115 | 66 |
| 46 | Q | CD | 390 | 457 | −101 | 64 |
| 46 | Q | OE1 | 383 | 463 | −93 | 60 |
| 46 | Q | NE2 | 403 | 454 | −97 | 63 |
| 46 | Q | C | 402 | 455 | −148 | 69 |
| 46 | Q | O | 411 | 464 | −149 | 69 |
| 47 | F | N | 403 | 443 | −154 | 70 |
| 47 | F | CA | 414 | 439 | −162 | 71 |
| 47 | F | CB | 422 | 428 | −154 | 71 |
| 47 | F | CG | 427 | 433 | −141 | 72 |
| 47 | F | CD1 | 421 | 429 | −129 | 72 |
| 47 | F | CE1 | 426 | 434 | −117 | 71 |
| 47 | F | CZ | 437 | 443 | −116 | 74 |
| 47 | F | CE2 | 443 | 447 | −128 | 75 |
| 47 | F | CD2 | 438 | 442 | −140 | 75 |
| 47 | F | C | 410 | 435 | −176 | 71 |
| 47 | F | O | 400 | 428 | −178 | 70 |
| 48 | A | N | 418 | 439 | −185 | 71 |
| 48 | A | CA | 417 | 435 | −199 | 71 |
| 48 | A | CB | 424 | 445 | −209 | 71 |
| 48 | A | C | 424 | 421 | −201 | 71 |
| 48 | A | O | 433 | 418 | −193 | 71 |
| 49 | A | N | 419 | 413 | −211 | 70 |
| 49 | A | CA | 425 | 400 | −213 | 70 |
| 49 | A | CB | 419 | 394 | −227 | 70 |
| 49 | A | C | 440 | 399 | −213 | 70 |
| 49 | A | O | 446 | 390 | −206 | 70 |
| 50 | A | N | 447 | 409 | −219 | 68 |
| 50 | A | CA | 462 | 409 | −219 | 67 |
| 50 | A | CB | 467 | 420 | −229 | 68 |
| 50 | A | C | 468 | 410 | −206 | 66 |
| 50 | A | O | 480 | 406 | −204 | 66 |
| 51 | E | N | 461 | 415 | −196 | 65 |
| 51 | E | CA | 465 | 415 | −182 | 64 |
| 51 | E | CB | 460 | 427 | −175 | 65 |
| 51 | E | CG | 466 | 441 | −178 | 69 |
| 51 | E | CD | 460 | 452 | −170 | 74 |
| 51 | E | OE1 | 468 | 458 | −162 | 76 |
| 51 | E | OE2 | 448 | 456 | −172 | 75 |
| 51 | E | C | 463 | 402 | −175 | 62 |
| 51 | E | O | 470 | 398 | −166 | 62 |
| 52 | T | N | 451 | 395 | −178 | 59 |
| 52 | T | CA | 447 | 384 | −170 | 56 |
| 52 | T | CB | 432 | 382 | −169 | 56 |
| 52 | T | OG1 | 426 | 381 | −182 | 57 |
| 52 | T | CG2 | 426 | 394 | −162 | 57 |
| 52 | T | C | 454 | 371 | −176 | 55 |
| 52 | T | O | 456 | 362 | −168 | 53 |
| 53 | I | N | 457 | 370 | −189 | 52 |
| 53 | I | CA | 463 | 358 | −194 | 50 |

| | | | | | | | | | | | | |
|---|---|---|---|---|---|---|---|---|---|---|---|---|
| 53 | I | CB | 467 | 360 | −210 | 50 | 62 | Q | O | 494 | 240 | −88 | 30 |
| 53 | I | CG1 | 454 | 362 | −218 | 52 | 63 | I | N | 481 | 247 | −105 | 30 |
| 53 | I | CD1 | 443 | 352 | −216 | 56 | 63 | I | CA | 473 | 235 | −104 | 32 |
| 53 | I | CG2 | 474 | 347 | −215 | 48 | 63 | I | CB | 460 | 237 | −112 | 32 |
| 53 | I | C | 475 | 354 | −186 | 48 | 63 | I | CG1 | 451 | 247 | −105 | 31 |
| 53 | I | O | 476 | 342 | −183 | 48 | 63 | I | CD1 | 441 | 253 | −115 | 36 |
| 54 | P | N | 485 | 362 | −183 | 47 | 63 | I | CG2 | 452 | 224 | −113 | 30 |
| 54 | P | CA | 496 | 358 | −175 | 46 | 63 | I | C | 481 | 222 | −108 | 32 |
| 54 | P | CB | 505 | 370 | −173 | 46 | 63 | I | O | 481 | 212 | −101 | 33 |
| 54 | P | CG | 502 | 378 | −185 | 47 | 64 | F | N | 489 | 224 | −119 | 33 |
| 54 | P | CD | 487 | 376 | −188 | 48 | 64 | F | CA | 498 | 213 | −123 | 34 |
| 54 | P | C | 492 | 352 | −161 | 45 | 64 | F | CB | 507 | 217 | −135 | 34 |
| 54 | P | O | 498 | 342 | −156 | 43 | 64 | F | CG | 518 | 207 | −137 | 38 |
| 55 | V | N | 482 | 358 | −155 | 44 | 64 | F | CD1 | 517 | 196 | −146 | 44 |
| 55 | V | CA | 477 | 353 | −141 | 43 | 64 | F | CE1 | 527 | 186 | −148 | 41 |
| 55 | V | CB | 468 | 364 | −135 | 44 | 64 | F | CZ | 538 | 187 | −140 | 41 |
| 55 | V | CG1 | 467 | 361 | −120 | 45 | 64 | F | CE2 | 540 | 197 | −131 | 40 |
| 55 | V | CG2 | 473 | 378 | −137 | 46 | 64 | F | CD2 | 530 | 207 | −129 | 40 |
| 55 | V | C | 470 | 340 | −143 | 42 | 64 | F | C | 507 | 209 | −111 | 34 |
| 55 | V | O | 472 | 331 | −134 | 41 | 64 | F | O | 508 | 197 | −108 | 34 |
| 56 | L | N | 462 | 338 | −153 | 40 | 65 | N | N | 513 | 219 | −104 | 33 |
| 56 | L | CA | 456 | 326 | −156 | 40 | 65 | N | CA | 522 | 216 | −93 | 34 |
| 56 | L | CB | 446 | 327 | −168 | 41 | 65 | N | CB | 528 | 229 | −87 | 35 |
| 56 | L | CG | 440 | 314 | −172 | 42 | 65 | N | CG | 538 | 236 | −97 | 39 |
| 56 | L | CD1 | 432 | 307 | −160 | 40 | 65 | N | OD1 | 542 | 248 | −95 | 45 |
| 56 | L | CD2 | 432 | 316 | −184 | 42 | 65 | N | ND2 | 542 | 229 | −108 | 39 |
| 56 | L | C | 466 | 315 | −158 | 40 | 65 | N | C | 515 | 210 | −81 | 35 |
| 56 | L | O | 465 | 304 | −153 | 40 | 65 | N | O | 520 | 200 | −75 | 35 |
| 57 | H | N | 476 | 318 | −167 | 40 | 66 | L | N | 503 | 214 | −78 | 35 |
| 57 | H | CA | 486 | 308 | −170 | 40 | 66 | L | CA | 496 | 209 | −67 | 35 |
| 57 | H | CB | 496 | 314 | −181 | 41 | 66 | L | CB | 483 | 217 | −64 | 35 |
| 57 | H | CG | 490 | 313 | −195 | 40 | 66 | L | CG | 474 | 213 | −53 | 35 |
| 57 | H | ND1 | 497 | 315 | −206 | 43 | 66 | L | CD1 | 481 | 213 | −39 | 38 |
| 57 | H | CE1 | 489 | 314 | −217 | 45 | 66 | L | CD2 | 462 | 222 | −53 | 31 |
| 57 | H | NE2 | 477 | 311 | −213 | 43 | 66 | L | C | 492 | 194 | −68 | 35 |
| 57 | H | CD2 | 477 | 310 | −199 | 44 | 66 | L | O | 492 | 187 | −59 | 35 |
| 57 | H | C | 494 | 304 | −157 | 40 | 67 | F | N | 488 | 190 | −80 | 36 |
| 57 | H | O | 498 | 293 | −156 | 39 | 67 | F | CA | 482 | 177 | −82 | 37 |
| 58 | E | N | 496 | 314 | −147 | 39 | 67 | F | CB | 470 | 177 | −91 | 38 |
| 58 | E | CA | 502 | 310 | −134 | 39 | 67 | F | CG | 458 | 182 | −84 | 35 |
| 58 | E | CB | 505 | 322 | −126 | 39 | 67 | F | CD1 | 455 | 196 | −86 | 33 |
| 58 | E | CG | 512 | 319 | −112 | 42 | 67 | F | CE1 | 443 | 202 | −80 | 36 |
| 58 | E | CD | 526 | 314 | −114 | 45 | 67 | F | CZ | 435 | 193 | −72 | 36 |
| 58 | E | OE1 | 531 | 306 | −105 | 44 | 67 | F | CE2 | 438 | 180 | −71 | 39 |
| 58 | E | OE2 | 533 | 318 | −124 | 49 | 67 | F | CD2 | 450 | 174 | −77 | 38 |
| 58 | E | C | 493 | 300 | −126 | 38 | 67 | F | C | 492 | 167 | −88 | 40 |
| 58 | E | O | 498 | 291 | −119 | 38 | 67 | F | O | 488 | 155 | −92 | 40 |
| 59 | M | N | 480 | 303 | −126 | 37 | 68 | S | N | 505 | 170 | −89 | 41 |
| 59 | M | CA | 470 | 294 | −120 | 38 | 68 | S | CA | 515 | 162 | −95 | 43 |
| 59 | M | CB | 456 | 300 | −124 | 38 | 68 | S | CB | 523 | 170 | −106 | 41 |
| 59 | M | CG | 444 | 294 | −118 | 43 | 68 | S | OG | 530 | 181 | −99 | 42 |
| 59 | M | SD | 443 | 300 | −101 | 47 | 68 | S | C | 525 | 156 | −85 | 45 |
| 59 | M | CE | 428 | 290 | −97 | 45 | 68 | S | O | 534 | 149 | −89 | 48 |
| 59 | M | C | 472 | 280 | −125 | 37 | 69 | T | N | 523 | 159 | −72 | 45 |
| 59 | M | O | 472 | 270 | −118 | 37 | 69 | T | CA | 530 | 153 | −62 | 46 |
| 60 | I | N | 473 | 278 | −139 | 38 | 69 | T | CB | 529 | 161 | −49 | 46 |
| 60 | I | CA | 474 | 265 | −145 | 37 | 69 | T | OG1 | 516 | 160 | −44 | 47 |
| 60 | I | CB | 473 | 266 | −160 | 38 | 69 | T | CG2 | 531 | 176 | −51 | 47 |
| 60 | I | CG1 | 461 | 273 | −165 | 38 | 69 | T | C | 526 | 138 | −58 | 46 |
| 60 | I | CD1 | 447 | 266 | −162 | 41 | 69 | T | O | 515 | 134 | −61 | 45 |
| 60 | I | CG2 | 474 | 252 | −166 | 38 | 70 | A | N | 535 | 132 | −52 | 47 |
| 60 | I | C | 487 | 258 | −140 | 36 | 70 | A | CA | 533 | 119 | −46 | 48 |
| 60 | I | O | 487 | 247 | −137 | 34 | 70 | A | CB | 546 | 115 | −38 | 48 |
| 61 | Q | N | 498 | 266 | −140 | 35 | 70 | A | C | 521 | 118 | −37 | 48 |
| 61 | Q | CA | 510 | 261 | −136 | 34 | 70 | A | O | 513 | 108 | −37 | 49 |
| 61 | Q | CB | 521 | 272 | −136 | 35 | 71 | D | N | 519 | 129 | −29 | 47 |
| 61 | Q | CG | 534 | 267 | −129 | 37 | 71 | D | CA | 507 | 130 | −21 | 47 |
| 61 | Q | CD | 541 | 257 | −138 | 43 | 71 | D | CB | 508 | 143 | −12 | 47 |
| 61 | Q | OE1 | 543 | 245 | −136 | 39 | 71 | D | CG | 521 | 144 | −4 | 49 |
| 61 | Q | NE2 | 546 | 262 | −150 | 41 | 71 | D | OD1 | 522 | 136 | 6 | 52 |
| 61 | Q | C | 509 | 256 | −121 | 34 | 71 | D | OD2 | 530 | 151 | −7 | 49 |
| 61 | Q | O | 513 | 245 | −118 | 34 | 71 | D | C | 494 | 130 | −29 | 45 |
| 62 | Q | N | 503 | 264 | −113 | 32 | 71 | D | O | 485 | 123 | −26 | 46 |
| 62 | Q | CA | 501 | 261 | −98 | 32 | 72 | S | N | 494 | 138 | −40 | 45 |
| 62 | Q | CB | 496 | 273 | −90 | 33 | 72 | S | CA | 483 | 139 | −49 | 45 |
| 62 | Q | CG | 506 | 284 | −90 | 35 | 72 | S | CB | 485 | 149 | −60 | 44 |
| 62 | Q | CD | 518 | 281 | −82 | 37 | 72 | S | OG | 475 | 148 | −70 | 46 |
| 62 | Q | OE1 | 518 | 273 | −73 | 38 | 72 | S | C | 480 | 125 | −55 | 46 |
| 62 | Q | NE2 | 530 | 286 | −86 | 37 | 72 | S | O | 469 | 120 | −56 | 44 |
| 62 | Q | C | 492 | 248 | −96 | 31 | 73 | S | N | 491 | 118 | −60 | 45 |

| 73 | S | CA  | 490 | 105 | −66  | 48 |
|----|---|-----|-----|-----|------|----|
| 73 | S | CB  | 504 | 100 | −71  | 48 |
| 73 | S | OG  | 507 | 106 | −83  | 53 |
| 73 | S | C   | 484 | 95  | −57  | 48 |
| 73 | S | O   | 476 | 86  | −61  | 48 |
| 74 | A | N   | 487 | 96  | −44  | 48 |
| 74 | A | CA  | 481 | 87  | −34  | 48 |
| 74 | A | CB  | 489 | 87  | −20  | 48 |
| 74 | A | C   | 466 | 90  | −31  | 48 |
| 74 | A | O   | 459 | 82  | −25  | 50 |
| 75 | A | N   | 462 | 102 | −35  | 47 |
| 75 | A | CA  | 449 | 107 | −30  | 46 |
| 75 | A | CB  | 451 | 122 | −26  | 46 |
| 75 | A | C   | 438 | 105 | −40  | 45 |
| 75 | A | O   | 426 | 104 | −37  | 45 |
| 76 | W | N   | 442 | 105 | −53  | 44 |
| 76 | W | CA  | 432 | 106 | −64  | 43 |
| 76 | W | CB  | 434 | 119 | −72  | 42 |
| 76 | W | CG  | 433 | 131 | −63  | 42 |
| 76 | W | CD1 | 443 | 140 | −60  | 39 |
| 76 | W | NE1 | 438 | 150 | −51  | 37 |
| 76 | W | CE2 | 425 | 147 | −48  | 39 |
| 76 | W | CD2 | 421 | 135 | −55  | 39 |
| 76 | W | CE3 | 408 | 129 | −54  | 37 |
| 76 | W | CZ3 | 399 | 136 | −45  | 36 |
| 76 | W | CH2 | 403 | 148 | −38  | 40 |
| 76 | W | CZ2 | 416 | 153 | −40  | 38 |
| 76 | W | C   | 433 | 94  | −74  | 42 |
| 76 | W | O   | 444 | 88  | −75  | 42 |
| 77 | D | N   | 422 | 90  | −80  | 42 |
| 77 | D | CA  | 422 | 80  | −91  | 43 |
| 77 | D | CB  | 408 | 79  | −97  | 44 |
| 77 | D | CG  | 407 | 68  | −108 | 46 |
| 77 | D | OD1 | 409 | 71  | −120 | 46 |
| 77 | D | OD2 | 405 | 56  | −105 | 48 |
| 77 | D | C   | 433 | 82  | −102 | 42 |
| 77 | D | O   | 432 | 93  | −109 | 42 |
| 78 | E | N   | 441 | 73  | −105 | 43 |
| 78 | E | CA  | 451 | 74  | −115 | 43 |
| 78 | E | CB  | 462 | 63  | −115 | 45 |
| 78 | E | CG  | 471 | 64  | −127 | 45 |
| 78 | E | CD  | 483 | 73  | −124 | 49 |
| 78 | E | OE1 | 493 | 74  | −133 | 52 |
| 78 | E | OE2 | 484 | 79  | −113 | 49 |
| 78 | E | C   | 446 | 77  | −129 | 43 |
| 78 | E | O   | 451 | 86  | −136 | 44 |
| 79 | T | N   | 435 | 70  | −134 | 42 |
| 79 | T | CA  | 430 | 72  | −147 | 42 |
| 79 | T | CB  | 420 | 62  | −151 | 42 |
| 79 | T | OG1 | 426 | 49  | −152 | 45 |
| 79 | T | CG2 | 414 | 64  | −165 | 42 |
| 79 | T | C   | 425 | 86  | −148 | 41 |
| 79 | T | O   | 427 | 93  | −158 | 40 |
| 80 | L | N   | 418 | 91  | −138 | 40 |
| 80 | L | CA  | 413 | 105 | −139 | 40 |
| 80 | L | CB  | 402 | 108 | −128 | 40 |
| 80 | L | CG  | 389 | 100 | −129 | 41 |
| 80 | L | CD1 | 381 | 102 | −115 | 43 |
| 80 | L | CD2 | 381 | 104 | −141 | 40 |
| 80 | L | C   | 424 | 115 | −138 | 37 |
| 80 | L | O   | 423 | 125 | −145 | 39 |
| 81 | L | N   | 434 | 113 | −129 | 37 |
| 81 | L | CA  | 446 | 122 | −129 | 38 |
| 81 | L | CB  | 456 | 117 | −118 | 38 |
| 81 | L | CG  | 454 | 122 | −104 | 40 |
| 81 | L | CD1 | 464 | 115 | −95  | 41 |
| 81 | L | CD2 | 455 | 138 | −103 | 34 |
| 81 | L | C   | 453 | 123 | −142 | 38 |
| 81 | L | O   | 456 | 135 | −146 | 37 |
| 82 | D | N   | 455 | 112 | −149 | 38 |
| 82 | D | CA  | 461 | 113 | −162 | 38 |
| 82 | D | CB  | 464 | 99  | −168 | 39 |
| 82 | D | CG  | 474 | 92  | −160 | 43 |
| 82 | D | OD1 | 476 | 79  | −161 | 44 |
| 82 | D | OD2 | 482 | 98  | −152 | 43 |
| 82 | D | C   | 453 | 121 | −172 | 38 |
| 82 | D | O   | 458 | 129 | −179 | 40 |
| 83 | K | N   | 440 | 119 | −172 | 37 |
| 83 | K | CA  | 432 | 127 | −181 | 37 |
| 83 | K | CB  | 417 | 122 | −180 | 39 |
| 83 | K | CG  | 414 | 109 | −189 | 42 |
| 83 | K | CD  | 400 | 103 | −186 | 52 |
| 83 | K | CE  | 399 | 88  | −191 | 57 |
| 83 | K | NZ  | 385 | 83  | −194 | 61 |
| 83 | K | C   | 433 | 142 | −177 | 37 |
| 83 | K | O   | 433 | 150 | −186 | 35 |
| 84 | F | N   | 433 | 144 | −164 | 35 |
| 84 | F | CA  | 433 | 158 | −159 | 35 |
| 84 | F | CB  | 433 | 157 | −144 | 35 |
| 84 | F | CG  | 434 | 170 | −137 | 35 |
| 84 | F | CD1 | 424 | 179 | −137 | 36 |
| 84 | F | CE1 | 424 | 192 | −130 | 40 |
| 84 | F | CZ  | 435 | 195 | −122 | 34 |
| 84 | F | CE2 | 446 | 186 | −121 | 36 |
| 84 | F | CD2 | 445 | 173 | −129 | 37 |
| 84 | F | C   | 447 | 165 | −164 | 35 |
| 84 | F | O   | 446 | 176 | −169 | 34 |
| 85 | Y | N   | 458 | 158 | −162 | 36 |
| 85 | Y | CA  | 471 | 163 | −168 | 37 |
| 85 | Y | CB  | 482 | 154 | −164 | 37 |
| 85 | Y | CG  | 486 | 159 | −151 | 40 |
| 85 | Y | CD1 | 494 | 170 | −150 | 45 |
| 85 | Y | CE1 | 497 | 176 | −137 | 47 |
| 85 | Y | CZ  | 492 | 170 | −126 | 48 |
| 85 | Y | OH  | 495 | 176 | −114 | 52 |
| 85 | Y | CE2 | 484 | 159 | −127 | 45 |
| 85 | Y | CD2 | 481 | 154 | −139 | 43 |
| 85 | Y | C   | 471 | 166 | −183 | 38 |
| 85 | Y | O   | 476 | 176 | −187 | 39 |
| 86 | T | N   | 465 | 157 | −190 | 38 |
| 86 | T | CA  | 464 | 159 | −205 | 39 |
| 86 | T | CB  | 456 | 147 | −211 | 39 |
| 86 | T | OG1 | 464 | 135 | −209 | 39 |
| 86 | T | CG2 | 456 | 148 | −226 | 42 |
| 86 | T | C   | 456 | 172 | −208 | 39 |
| 86 | T | O   | 461 | 179 | −217 | 40 |
| 87 | E | N   | 446 | 176 | −200 | 39 |
| 87 | E | CA  | 440 | 189 | −202 | 38 |
| 87 | E | CB  | 427 | 190 | −194 | 39 |
| 87 | E | CG  | 416 | 180 | −197 | 41 |
| 87 | E | CD  | 413 | 178 | −212 | 49 |
| 87 | E | OE1 | 411 | 189 | −218 | 48 |
| 87 | E | OE2 | 412 | 167 | −216 | 53 |
| 87 | E | C   | 449 | 200 | −198 | 38 |
| 87 | E | O   | 450 | 210 | −205 | 38 |
| 88 | L | N   | 455 | 198 | −187 | 36 |
| 88 | L | CA  | 464 | 209 | −182 | 37 |
| 88 | L | CB  | 470 | 206 | −169 | 35 |
| 88 | L | CG  | 460 | 206 | −157 | 37 |
| 88 | L | CD1 | 468 | 203 | −145 | 35 |
| 88 | L | CD2 | 453 | 219 | −155 | 36 |
| 88 | L | C   | 475 | 212 | −192 | 36 |
| 88 | L | O   | 478 | 224 | −193 | 36 |
| 89 | Y | N   | 481 | 202 | −199 | 36 |
| 89 | Y | CA  | 492 | 205 | −208 | 36 |
| 89 | Y | CB  | 498 | 193 | −214 | 36 |
| 89 | Y | CG  | 503 | 183 | −204 | 36 |
| 89 | Y | CD1 | 512 | 188 | −194 | 40 |
| 89 | Y | CE1 | 517 | 180 | −184 | 41 |
| 89 | Y | CZ  | 514 | 166 | −185 | 37 |
| 89 | Y | OH  | 519 | 158 | −176 | 39 |
| 89 | Y | CE2 | 506 | 161 | −195 | 35 |
| 89 | Y | CD2 | 501 | 170 | −205 | 39 |
| 89 | Y | C   | 488 | 215 | −219 | 37 |
| 89 | Y | O   | 495 | 225 | −222 | 37 |
| 90 | Q | N   | 475 | 214 | −223 | 36 |
| 90 | Q | CA  | 470 | 222 | −234 | 38 |
| 90 | Q | CB  | 457 | 216 | −239 | 39 |
| 90 | Q | CG  | 459 | 203 | −245 | 42 |
| 90 | Q | CD  | 446 | 197 | −251 | 51 |
| 90 | Q | OE1 | 439 | 204 | −259 | 53 |
| 90 | Q | NE2 | 442 | 185 | −247 | 50 |
| 90 | Q | C   | 467 | 236 | −229 | 39 |
| 90 | Q | O   | 466 | 245 | −238 | 41 |
| 91 | Q | N   | 466 | 239 | −216 | 38 |
| 91 | Q | CA  | 463 | 252 | −212 | 39 |
| 91 | Q | CB  | 452 | 251 | −201 | 39 |
| 91 | Q | CG  | 438 | 247 | −206 | 39 |
| 91 | Q | CD  | 428 | 246 | −195 | 45 |
| 91 | Q | OE1 | 422 | 256 | −191 | 50 |

-continued

| 91 | Q | NE2 | 426 | 234 | −190 | 44 |
|---|---|---|---|---|---|---|
| 91 | Q | C | 475 | 260 | −206 | 39 |
| 91 | Q | O | 474 | 271 | −202 | 39 |
| 92 | L | N | 487 | 253 | −205 | 39 |
| 92 | L | CA | 498 | 260 | −199 | 39 |
| 92 | L | CB | 510 | 250 | −196 | 39 |
| 92 | L | CG | 509 | 240 | −185 | 40 |
| 92 | L | CD1 | 519 | 228 | −187 | 38 |
| 92 | L | CD2 | 511 | 247 | −172 | 40 |
| 92 | L | C | 504 | 272 | −208 | 40 |
| 92 | L | O | 509 | 282 | −202 | 38 |
| 93 | N | N | 504 | 270 | −221 | 39 |
| 93 | N | CA | 512 | 279 | −230 | 41 |
| 93 | N | CB | 526 | 274 | −229 | 40 |
| 93 | N | CG | 536 | 282 | −237 | 42 |
| 93 | N | OD1 | 534 | 294 | −239 | 40 |
| 93 | N | ND2 | 548 | 277 | −240 | 37 |
| 93 | N | C | 505 | 279 | −244 | 42 |
| 93 | N | O | 511 | 274 | −253 | 41 |
| 94 | D | N | 493 | 283 | −244 | 44 |
| 94 | D | CA | 485 | 282 | −257 | 47 |
| 94 | D | CB | 470 | 279 | −255 | 47 |
| 94 | D | CG | 463 | 290 | −247 | 50 |
| 94 | D | OD1 | 469 | 294 | −237 | 46 |
| 94 | D | OD2 | 453 | 296 | −251 | 57 |
| 94 | D | C | 487 | 293 | −267 | 49 |
| 94 | D | O | 481 | 293 | −278 | 49 |
| 95 | L | N | 496 | 302 | −263 | 52 |
| 95 | L | CA | 502 | 313 | −272 | 56 |
| 95 | L | CB | 511 | 307 | −283 | 56 |
| 95 | L | CG | 524 | 300 | −279 | 56 |
| 95 | L | CD1 | 529 | 292 | −291 | 56 |
| 95 | L | CD2 | 534 | 310 | −273 | 56 |
| 95 | L | C | 490 | 321 | −278 | 59 |
| 95 | L | O | 488 | 320 | −290 | 60 |
| 96 | E | N | 483 | 328 | −269 | 61 |
| 96 | E | CA | 473 | 337 | −274 | 63 |
| 96 | E | CB | 467 | 345 | −262 | 62 |
| 96 | E | CG | 456 | 336 | −255 | 60 |
| 96 | E | CD | 462 | 327 | −244 | 57 |
| 96 | E | OE1 | 454 | 322 | −237 | 54 |
| 96 | E | OE2 | 474 | 326 | −243 | 51 |
| 96 | E | C | 478 | 348 | −284 | 65 |
| 96 | E | O | 488 | 354 | −281 | 66 |
| 97 | A | N | 470 | 349 | −294 | 67 |
| 97 | A | CA | 475 | 353 | −308 | 69 |
| 97 | A | CB | 472 | 342 | −318 | 69 |
| 97 | A | C | 469 | 367 | −312 | 70 |
| 97 | A | O | 460 | 373 | −306 | 71 |
| 112 | A | N | 518 | 412 | −148 | 60 |
| 112 | A | CA | 519 | 419 | −135 | 59 |
| 112 | A | CB | 506 | 426 | −131 | 60 |
| 112 | A | C | 524 | 410 | −124 | 58 |
| 112 | A | O | 517 | 401 | −120 | 58 |
| 113 | A | N | 536 | 413 | −119 | 56 |
| 113 | A | CA | 543 | 405 | −109 | 55 |
| 113 | A | CB | 557 | 411 | −106 | 55 |
| 113 | A | C | 535 | 404 | −96 | 54 |
| 113 | A | O | 535 | 393 | −89 | 54 |
| 114 | D | N | 528 | 415 | −92 | 53 |
| 114 | D | CA | 520 | 414 | −79 | 51 |
| 114 | D | CB | 516 | 429 | −76 | 52 |
| 114 | D | CG | 527 | 436 | −68 | 57 |
| 114 | D | OD1 | 524 | 448 | −64 | 60 |
| 114 | D | OD2 | 538 | 431 | −64 | 63 |
| 114 | D | C | 508 | 405 | −80 | 49 |
| 114 | D | O | 504 | 399 | −70 | 47 |
| 115 | S | N | 501 | 405 | −91 | 48 |
| 115 | S | CA | 490 | 396 | −94 | 47 |
| 115 | S | CB | 484 | 399 | −107 | 47 |
| 115 | S | OG | 475 | 410 | −107 | 50 |
| 115 | S | C | 494 | 382 | −94 | 46 |
| 115 | S | O | 488 | 373 | −87 | 45 |
| 116 | I | N | 505 | 379 | −101 | 44 |
| 116 | I | CA | 512 | 366 | −101 | 43 |
| 116 | I | CB | 524 | 366 | −111 | 44 |
| 116 | I | CG1 | 519 | 366 | −126 | 45 |
| 116 | I | CD1 | 530 | 369 | −136 | 50 |
| 116 | I | CG2 | 533 | 354 | −109 | 42 |
| 116 | I | C | 515 | 362 | −88 | 41 |

-continued

| 116 | I | O | 512 | 350 | −84 | 39 |
|---|---|---|---|---|---|---|
| 117 | L | N | 521 | 371 | −80 | 41 |
| 117 | L | CA | 525 | 367 | −66 | 41 |
| 117 | L | CB | 533 | 379 | −59 | 41 |
| 117 | L | CG | 538 | 376 | −45 | 47 |
| 117 | L | CD1 | 548 | 364 | −45 | 51 |
| 117 | L | CD2 | 542 | 388 | −36 | 48 |
| 117 | L | C | 512 | 364 | −57 | 39 |
| 117 | L | O | 513 | 355 | −49 | 39 |
| 118 | A | N | 502 | 372 | −59 | 39 |
| 118 | A | CA | 489 | 369 | −51 | 38 |
| 118 | A | CB | 479 | 379 | −54 | 38 |
| 118 | A | C | 485 | 355 | −54 | 37 |
| 118 | A | O | 480 | 348 | −45 | 37 |
| 119 | V | N | 486 | 350 | −67 | 36 |
| 119 | V | CA | 481 | 337 | −70 | 35 |
| 119 | V | CB | 481 | 335 | −86 | 35 |
| 119 | V | CG1 | 478 | 320 | −89 | 36 |
| 119 | V | CG2 | 470 | 344 | −92 | 36 |
| 119 | V | C | 490 | 327 | −63 | 34 |
| 119 | V | O | 485 | 317 | −58 | 32 |
| 120 | R | N | 503 | 330 | −64 | 34 |
| 120 | R | CA | 513 | 321 | −58 | 35 |
| 120 | R | CB | 527 | 326 | −60 | 36 |
| 120 | R | CG | 532 | 322 | −74 | 40 |
| 120 | R | CD | 547 | 323 | −77 | 45 |
| 120 | R | NE | 549 | 323 | −91 | 47 |
| 120 | R | CZ | 557 | 330 | −98 | 51 |
| 120 | R | NH1 | 565 | 339 | −92 | 50 |
| 120 | R | NH2 | 558 | 329 | −111 | 48 |
| 120 | R | C | 510 | 319 | −43 | 34 |
| 120 | R | O | 511 | 308 | −38 | 34 |
| 121 | K | N | 508 | 330 | −36 | 35 |
| 121 | K | CA | 506 | 329 | −22 | 35 |
| 121 | K | CB | 505 | 343 | −16 | 37 |
| 121 | K | CG | 518 | 352 | −15 | 40 |
| 121 | K | CD | 515 | 366 | −12 | 48 |
| 121 | K | CE | 526 | 375 | −7 | 56 |
| 121 | K | NZ | 519 | 385 | 3 | 60 |
| 121 | K | C | 493 | 322 | −18 | 34 |
| 121 | K | O | 492 | 315 | −8 | 32 |
| 122 | Y | N | 483 | 323 | −27 | 32 |
| 122 | Y | CA | 471 | 315 | −25 | 32 |
| 122 | Y | CB | 461 | 318 | −36 | 31 |
| 122 | Y | CG | 450 | 309 | −38 | 32 |
| 122 | Y | CD1 | 450 | 300 | −50 | 34 |
| 122 | Y | CE1 | 439 | 292 | −52 | 34 |
| 122 | Y | CZ | 428 | 291 | −44 | 35 |
| 122 | Y | OH | 418 | 282 | −46 | 31 |
| 122 | Y | CE2 | 428 | 299 | −32 | 32 |
| 122 | Y | CD2 | 439 | 308 | −30 | 32 |
| 122 | Y | C | 474 | 300 | −25 | 30 |
| 122 | Y | O | 470 | 292 | −16 | 30 |
| 123 | F | N | 482 | 295 | −35 | 31 |
| 123 | F | CA | 486 | 281 | −35 | 31 |
| 123 | F | CB | 492 | 278 | −49 | 31 |
| 123 | F | CG | 481 | 276 | −59 | 32 |
| 123 | F | CD1 | 475 | 263 | −61 | 35 |
| 123 | F | CE1 | 465 | 261 | −71 | 33 |
| 123 | F | CZ | 460 | 271 | −78 | 37 |
| 123 | F | CE2 | 466 | 284 | −77 | 37 |
| 123 | F | CD2 | 476 | 286 | −67 | 32 |
| 123 | F | C | 495 | 277 | −23 | 33 |
| 123 | F | O | 495 | 266 | −19 | 32 |
| 124 | Q | N | 503 | 287 | −19 | 33 |
| 124 | Q | CA | 511 | 284 | −6 | 35 |
| 124 | Q | CB | 520 | 296 | −3 | 35 |
| 124 | Q | CG | 532 | 297 | −13 | 38 |
| 124 | Q | CD | 541 | 309 | −10 | 47 |
| 124 | Q | OE1 | 537 | 320 | −10 | 51 |
| 124 | Q | NE2 | 553 | 305 | −7 | 51 |
| 124 | Q | C | 502 | 281 | 5 | 33 |
| 124 | Q | O | 504 | 273 | 13 | 33 |
| 125 | R | N | 491 | 289 | 6 | 33 |
| 125 | R | CA | 482 | 286 | 18 | 32 |
| 125 | R | CB | 471 | 297 | 19 | 32 |
| 125 | R | CG | 477 | 311 | 21 | 37 |
| 125 | R | CD | 466 | 322 | 24 | 35 |
| 125 | R | NE | 458 | 326 | 13 | 35 |
| 125 | R | CZ | 461 | 336 | 4 | 36 |

| | | | | | | | | | | | | |
|---|---|---|---|---|---|---|---|---|---|---|---|---|
| 125 | R | NH1 | 474 | 341 | 5 | 36 | 134 | K | NZ | 500 | 145 | 132 | 71 |
| 125 | R | NH2 | 453 | 340 | −5 | 35 | 134 | K | C | 481 | 149 | 59 | 47 |
| 125 | R | C | 475 | 273 | 16 | 31 | 134 | K | O | 479 | 137 | 59 | 47 |
| 125 | R | O | 473 | 266 | 26 | 31 | 135 | Y | N | 477 | 157 | 49 | 46 |
| 126 | I | N | 472 | 269 | 4 | 31 | 135 | Y | CA | 471 | 152 | 37 | 44 |
| 126 | I | CA | 466 | 255 | 2 | 31 | 135 | Y | CB | 481 | 145 | 29 | 44 |
| 126 | I | CB | 462 | 254 | −13 | 31 | 135 | Y | CG | 492 | 154 | 25 | 44 |
| 126 | I | CG1 | 449 | 262 | −15 | 33 | 135 | Y | CD1 | 503 | 155 | 34 | 47 |
| 126 | I | CD1 | 442 | 261 | −29 | 35 | 135 | Y | CE1 | 514 | 164 | 31 | 48 |
| 126 | I | CG2 | 460 | 239 | −16 | 29 | 135 | Y | CZ | 513 | 172 | 20 | 47 |
| 126 | I | C | 476 | 244 | 6 | 31 | 135 | Y | OH | 524 | 180 | 17 | 49 |
| 126 | I | O | 472 | 235 | 13 | 32 | 135 | Y | CE2 | 502 | 171 | 11 | 46 |
| 127 | T | N | 488 | 245 | 2 | 33 | 135 | Y | CD2 | 492 | 162 | 14 | 45 |
| 127 | T | CA | 499 | 236 | 4 | 37 | 135 | Y | C | 459 | 142 | 40 | 43 |
| 127 | T | CB | 511 | 241 | −3 | 38 | 135 | Y | O | 458 | 132 | 33 | 44 |
| 127 | T | OG1 | 510 | 237 | −17 | 42 | 136 | S | N | 451 | 145 | 49 | 43 |
| 127 | T | CG2 | 525 | 234 | 1 | 41 | 136 | S | CA | 440 | 137 | 52 | 43 |
| 127 | T | C | 502 | 235 | 19 | 36 | 136 | S | CB | 433 | 141 | 65 | 43 |
| 127 | T | O | 505 | 224 | 24 | 37 | 136 | S | OG | 425 | 153 | 63 | 46 |
| 128 | L | N | 502 | 246 | 26 | 38 | 136 | S | C | 430 | 136 | 41 | 44 |
| 128 | L | CA | 504 | 246 | 41 | 37 | 136 | S | O | 429 | 146 | 32 | 43 |
| 128 | L | CB | 505 | 261 | 46 | 38 | 137 | P | N | 422 | 126 | 40 | 43 |
| 128 | L | CG | 509 | 261 | 61 | 43 | 137 | P | CA | 412 | 125 | 29 | 43 |
| 128 | L | CD1 | 522 | 254 | 65 | 42 | 137 | P | CB | 404 | 112 | 33 | 44 |
| 128 | L | CD2 | 509 | 276 | 65 | 42 | 137 | P | CG | 416 | 103 | 40 | 44 |
| 128 | L | C | 493 | 239 | 48 | 37 | 137 | P | CD | 424 | 113 | 47 | 45 |
| 128 | L | O | 494 | 231 | 58 | 36 | 137 | P | C | 403 | 137 | 30 | 42 |
| 129 | Y | N | 481 | 242 | 43 | 36 | 137 | P | O | 400 | 143 | 19 | 42 |
| 129 | Y | CA | 469 | 236 | 48 | 35 | 138 | C | N | 398 | 141 | 42 | 41 |
| 129 | Y | CB | 456 | 242 | 41 | 35 | 138 | C | CA | 391 | 154 | 43 | 42 |
| 129 | Y | CG | 443 | 234 | 43 | 34 | 138 | C | CB | 386 | 156 | 58 | 42 |
| 129 | Y | CD1 | 435 | 238 | 54 | 31 | 138 | C | SG | 371 | 147 | 61 | 49 |
| 129 | Y | CE1 | 422 | 231 | 56 | 36 | 138 | C | C | 398 | 166 | 38 | 40 |
| 129 | Y | CZ | 419 | 220 | 47 | 34 | 138 | C | O | 391 | 174 | 31 | 38 |
| 129 | Y | OH | 407 | 214 | 49 | 33 | 139 | A | N | 411 | 168 | 41 | 38 |
| 129 | Y | CE2 | 428 | 216 | 37 | 33 | 139 | A | CA | 418 | 180 | 37 | 36 |
| 129 | Y | CD2 | 440 | 223 | 35 | 31 | 139 | A | CB | 432 | 180 | 42 | 36 |
| 129 | Y | C | 470 | 221 | 47 | 35 | 139 | A | C | 418 | 180 | 21 | 36 |
| 129 | Y | O | 467 | 214 | 57 | 36 | 139 | A | O | 416 | 190 | 15 | 34 |
| 130 | L | N | 473 | 215 | 35 | 35 | 140 | W | N | 421 | 168 | 15 | 35 |
| 130 | L | CA | 474 | 201 | 34 | 36 | 140 | W | CA | 421 | 168 | 1 | 35 |
| 130 | L | CB | 478 | 197 | 19 | 35 | 140 | W | CB | 426 | 154 | −3 | 36 |
| 130 | L | CG | 466 | 199 | 10 | 31 | 140 | W | CG | 441 | 154 | −6 | 35 |
| 130 | L | CD1 | 471 | 199 | −4 | 30 | 140 | W | CD1 | 450 | 146 | 1 | 35 |
| 130 | L | CD2 | 455 | 188 | 11 | 31 | 140 | W | NE1 | 463 | 148 | −5 | 37 |
| 130 | L | C | 485 | 195 | 43 | 38 | 140 | W | CE2 | 462 | 157 | −15 | 37 |
| 130 | L | O | 484 | 184 | 49 | 38 | 140 | W | CD2 | 448 | 162 | −16 | 35 |
| 131 | K | N | 496 | 202 | 44 | 40 | 140 | W | CE3 | 445 | 171 | −25 | 30 |
| 131 | K | CA | 508 | 198 | 52 | 44 | 140 | W | CZ3 | 455 | 176 | −33 | 33 |
| 131 | K | CB | 520 | 207 | 49 | 43 | 140 | W | CH2 | 468 | 172 | −32 | 36 |
| 131 | K | CG | 533 | 204 | 56 | 51 | 140 | W | CZ2 | 472 | 163 | −23 | 37 |
| 131 | K | CD | 544 | 211 | 48 | 58 | 140 | W | C | 407 | 170 | −6 | 34 |
| 131 | K | CE | 558 | 208 | 53 | 64 | 140 | W | O | 407 | 177 | −16 | 33 |
| 131 | K | NZ | 568 | 213 | 43 | 67 | 141 | E | N | 397 | 166 | 1 | 33 |
| 131 | K | C | 504 | 198 | 67 | 44 | 141 | E | CA | 383 | 169 | −4 | 34 |
| 131 | K | O | 506 | 188 | 74 | 45 | 141 | E | CB | 372 | 161 | 3 | 34 |
| 132 | E | N | 496 | 208 | 71 | 45 | 141 | E | CG | 358 | 164 | 0 | 34 |
| 132 | E | CA | 492 | 209 | 85 | 47 | 141 | E | CD | 355 | 164 | −16 | 35 |
| 132 | E | CB | 485 | 222 | 88 | 48 | 141 | E | OE1 | 362 | 157 | −23 | 34 |
| 132 | E | CG | 495 | 233 | 92 | 55 | 141 | E | OE2 | 345 | 170 | −20 | 36 |
| 132 | E | CD | 489 | 247 | 92 | 62 | 141 | E | C | 380 | 184 | −4 | 34 |
| 132 | E | OE1 | 477 | 249 | 89 | 67 | 141 | E | O | 375 | 189 | −13 | 32 |
| 132 | E | OE2 | 497 | 256 | 96 | 63 | 142 | V | N | 384 | 190 | 7 | 33 |
| 132 | E | C | 482 | 197 | 88 | 47 | 142 | V | CA | 383 | 205 | 8 | 32 |
| 132 | E | O | 483 | 192 | 99 | 45 | 142 | V | CB | 387 | 210 | 22 | 33 |
| 133 | K | N | 474 | 194 | 78 | 45 | 142 | V | CG1 | 390 | 225 | 21 | 31 |
| 133 | K | CA | 463 | 184 | 80 | 45 | 142 | V | CG2 | 376 | 207 | 33 | 36 |
| 133 | K | CB | 451 | 187 | 71 | 44 | 142 | V | C | 391 | 212 | −3 | 30 |
| 133 | K | CG | 444 | 200 | 74 | 44 | 142 | V | O | 386 | 221 | −9 | 31 |
| 133 | K | CD | 432 | 198 | 85 | 48 | 143 | V | N | 403 | 207 | −6 | 30 |
| 133 | K | CE | 425 | 211 | 88 | 48 | 143 | V | CA | 412 | 213 | −16 | 29 |
| 133 | K | NZ | 414 | 209 | 98 | 50 | 143 | V | CB | 426 | 208 | −14 | 30 |
| 133 | K | C | 468 | 170 | 77 | 45 | 143 | V | CG1 | 435 | 212 | −27 | 28 |
| 133 | K | O | 460 | 161 | 78 | 45 | 143 | V | CG2 | 433 | 214 | −2 | 30 |
| 134 | K | N | 481 | 169 | 74 | 46 | 143 | V | C | 406 | 211 | −30 | 30 |
| 134 | K | CA | 487 | 156 | 71 | 48 | 143 | V | O | 405 | 219 | −39 | 29 |
| 134 | K | CB | 488 | 147 | 83 | 49 | 144 | R | N | 401 | 199 | −32 | 31 |
| 134 | K | CG | 497 | 152 | 95 | 54 | 144 | R | CA | 395 | 196 | −46 | 30 |
| 134 | K | CD | 491 | 148 | 108 | 62 | 144 | R | CB | 391 | 181 | −46 | 30 |
| 134 | K | CE | 499 | 154 | 120 | 68 | 144 | R | CG | 384 | 176 | −60 | 30 |

| | | | | | | | | | | | | |
|---|---|---|---|---|---|---|---|---|---|---|---|---|
| 144 | R | CD | 376 | 163 | −58 | 31 | 154 | S | CA | 395 | 323 | −130 | 49 |
| 144 | R | NE | 364 | 167 | −50 | 34 | 154 | S | CB | 408 | 317 | −126 | 47 |
| 144 | R | CZ | 353 | 173 | −55 | 34 | 154 | S | OG | 409 | 304 | −131 | 51 |
| 144 | R | NH1 | 352 | 176 | −68 | 36 | 154 | S | C | 393 | 322 | −146 | 50 |
| 144 | R | NH2 | 343 | 176 | −47 | 35 | 154 | S | O | 400 | 329 | −153 | 50 |
| 144 | R | C | 383 | 205 | −49 | 29 | 155 | T | N | 384 | 314 | −150 | 52 |
| 144 | R | O | 383 | 212 | −59 | 29 | 155 | T | CA | 381 | 312 | −164 | 55 |
| 145 | A | N | 374 | 207 | −40 | 29 | 155 | T | CB | 382 | 297 | −168 | 54 |
| 145 | A | CA | 363 | 215 | −42 | 29 | 155 | T | OG1 | 376 | 288 | −158 | 51 |
| 145 | A | CB | 352 | 212 | −31 | 30 | 155 | T | CG2 | 397 | 292 | −168 | 52 |
| 145 | A | C | 367 | 230 | −43 | 30 | 155 | T | C | 367 | 318 | −168 | 58 |
| 145 | A | O | 361 | 238 | −51 | 30 | 155 | T | O | 366 | 323 | −179 | 59 |
| 146 | E | N | 377 | 234 | −35 | 29 | 156 | N | N | 357 | 317 | −160 | 62 |
| 146 | E | CA | 382 | 248 | −35 | 29 | 156 | N | CA | 345 | 324 | −162 | 65 |
| 146 | E | CB | 392 | 250 | −24 | 31 | 156 | N | CB | 333 | 314 | −160 | 66 |
| 146 | E | CG | 401 | 262 | −26 | 29 | 156 | N | CG | 336 | 300 | −165 | 69 |
| 146 | E | CD | 394 | 275 | −24 | 33 | 156 | N | OD1 | 344 | 298 | −175 | 73 |
| 146 | E | OE1 | 398 | 284 | −30 | 29 | 156 | N | ND2 | 331 | 290 | −158 | 70 |
| 146 | E | OE2 | 384 | 274 | −16 | 34 | 156 | N | C | 343 | 336 | −152 | 67 |
| 146 | E | C | 388 | 250 | −49 | 30 | 156 | N | O | 337 | 335 | −141 | 68 |
| 146 | E | O | 386 | 261 | −55 | 31 | 156 | N | OXT | 347 | 347 | −154 | 69 |
| 147 | I | N | 396 | 241 | −54 | 29 | 6 | T | N | 734 | 415 | 126 | 71 |
| 147 | I | CA | 402 | 243 | −67 | 30 | 6 | T | CA | 732 | 428 | 118 | 72 |
| 147 | I | CB | 412 | 233 | −70 | 30 | 6 | T | CB | 730 | 425 | 103 | 72 |
| 147 | I | CG1 | 425 | 234 | −61 | 29 | 6 | T | OG1 | 743 | 422 | 97 | 72 |
| 147 | I | CD1 | 431 | 248 | −63 | 31 | 6 | T | CG2 | 726 | 438 | 95 | 73 |
| 147 | I | CG2 | 417 | 234 | −85 | 30 | 6 | T | C | 720 | 436 | 124 | 71 |
| 147 | I | C | 391 | 244 | −78 | 31 | 6 | T | O | 708 | 434 | 120 | 71 |
| 147 | I | O | 392 | 252 | −87 | 33 | 7 | H | N | 724 | 446 | 132 | 69 |
| 148 | M | N | 381 | 236 | −77 | 31 | 7 | H | CA | 714 | 456 | 138 | 68 |
| 148 | M | CA | 371 | 237 | −87 | 33 | 7 | H | CB | 722 | 467 | 145 | 68 |
| 148 | M | CB | 360 | 227 | −86 | 33 | 7 | H | CG | 725 | 464 | 160 | 70 |
| 148 | M | CG | 365 | 213 | −88 | 38 | 7 | H | ND1 | 734 | 455 | 163 | 71 |
| 148 | M | SD | 352 | 202 | −84 | 49 | 7 | H | CE1 | 735 | 454 | 176 | 73 |
| 148 | M | CE | 341 | 205 | −96 | 41 | 7 | H | NE2 | 725 | 462 | 181 | 75 |
| 148 | M | C | 364 | 251 | −87 | 34 | 7 | H | CD2 | 719 | 468 | 171 | 74 |
| 148 | M | O | 361 | 256 | −98 | 32 | 7 | H | C | 705 | 462 | 127 | 66 |
| 149 | R | N | 361 | 256 | −75 | 34 | 7 | H | O | 709 | 465 | 116 | 66 |
| 149 | R | CA | 356 | 270 | −74 | 36 | 8 | S | N | 692 | 463 | 131 | 63 |
| 149 | R | CB | 353 | 273 | −59 | 37 | 8 | S | CA | 683 | 469 | 122 | 59 |
| 149 | R | CG | 340 | 268 | −54 | 45 | 8 | S | CB | 668 | 465 | 126 | 59 |
| 149 | R | CD | 336 | 273 | −40 | 52 | 8 | S | OG | 666 | 467 | 140 | 59 |
| 149 | R | NE | 346 | 271 | −29 | 58 | 8 | S | C | 684 | 484 | 122 | 57 |
| 149 | R | CZ | 347 | 259 | −22 | 59 | 8 | S | O | 688 | 490 | 133 | 57 |
| 149 | R | NH1 | 356 | 259 | −13 | 58 | 9 | L | N | 681 | 491 | 111 | 53 |
| 149 | R | NH2 | 340 | 249 | −25 | 59 | 9 | L | CA | 680 | 505 | 111 | 50 |
| 149 | R | C | 365 | 280 | −79 | 36 | 9 | L | CB | 675 | 511 | 97 | 51 |
| 149 | R | O | 361 | 289 | −87 | 36 | 9 | L | CG | 670 | 525 | 96 | 51 |
| 150 | S | N | 378 | 280 | −75 | 36 | 9 | L | CD1 | 681 | 535 | 98 | 49 |
| 150 | S | CA | 387 | 291 | −79 | 36 | 9 | L | CD2 | 663 | 529 | 83 | 53 |
| 150 | S | CB | 400 | 292 | −72 | 35 | 9 | L | C | 671 | 510 | 123 | 48 |
| 150 | S | OG | 406 | 279 | −71 | 35 | 9 | L | O | 674 | 520 | 129 | 46 |
| 150 | S | C | 390 | 290 | −95 | 37 | 10 | G | N | 661 | 502 | 126 | 45 |
| 150 | S | O | 391 | 300 | −102 | 36 | 10 | G | CA | 651 | 504 | 136 | 42 |
| 151 | F | N | 392 | 278 | −99 | 37 | 10 | G | C | 657 | 505 | 150 | 39 |
| 151 | F | CA | 395 | 276 | −113 | 38 | 10 | G | O | 655 | 515 | 157 | 40 |
| 151 | F | CB | 400 | 262 | −116 | 37 | 11 | S | N | 665 | 495 | 153 | 39 |
| 151 | F | CG | 404 | 259 | −130 | 41 | 11 | S | CA | 671 | 495 | 166 | 39 |
| 151 | F | CD1 | 416 | 265 | −136 | 43 | 11 | S | CB | 678 | 481 | 170 | 39 |
| 151 | F | CE1 | 419 | 263 | −149 | 45 | 11 | S | OG | 689 | 479 | 161 | 43 |
| 151 | F | CZ | 412 | 255 | −157 | 43 | 11 | S | C | 681 | 507 | 168 | 37 |
| 151 | F | CE2 | 400 | 249 | −152 | 44 | 11 | S | O | 680 | 513 | 179 | 36 |
| 151 | F | CD2 | 396 | 252 | −139 | 42 | 12 | R | N | 689 | 510 | 158 | 37 |
| 151 | F | C | 383 | 281 | −122 | 40 | 12 | R | CA | 697 | 521 | 158 | 37 |
| 151 | F | O | 386 | 288 | −132 | 40 | 12 | R | CB | 707 | 523 | 146 | 39 |
| 152 | S | N | 371 | 277 | −119 | 42 | 12 | R | CG | 711 | 509 | 140 | 45 |
| 152 | S | CA | 359 | 282 | −126 | 44 | 12 | R | CD | 723 | 510 | 129 | 53 |
| 152 | S | CB | 346 | 279 | −120 | 45 | 12 | R | NE | 734 | 509 | 137 | 56 |
| 152 | S | OG | 345 | 266 | −116 | 51 | 12 | R | CZ | 742 | 499 | 138 | 56 |
| 152 | S | C | 359 | 297 | −127 | 45 | 12 | R | NH1 | 743 | 489 | 130 | 56 |
| 152 | S | O | 356 | 303 | −137 | 45 | 12 | R | NH2 | 750 | 500 | 149 | 54 |
| 153 | L | N | 362 | 303 | −115 | 46 | 12 | R | C | 690 | 534 | 160 | 35 |
| 153 | L | CA | 362 | 317 | −113 | 47 | 12 | R | O | 694 | 543 | 168 | 34 |
| 153 | L | CB | 364 | 322 | −99 | 47 | 13 | R | N | 680 | 536 | 152 | 34 |
| 153 | L | CG | 352 | 322 | −89 | 47 | 13 | R | CA | 672 | 549 | 153 | 35 |
| 153 | L | CD1 | 358 | 323 | −75 | 50 | 13 | R | CB | 662 | 550 | 141 | 36 |
| 153 | L | CD2 | 343 | 333 | −92 | 50 | 13 | R | CG | 668 | 553 | 128 | 42 |
| 153 | L | C | 372 | 324 | −122 | 48 | 13 | R | CD | 657 | 556 | 117 | 47 |
| 153 | L | O | 371 | 335 | −126 | 48 | 13 | R | NE | 648 | 566 | 122 | 50 |
| 154 | S | N | 384 | 317 | −124 | 47 | 13 | R | CZ | 649 | 579 | 121 | 53 |

| | | | | | | |
|---|---|---|---|---|---|---|
| 13 | R | NH1 | 639 | 587 | 125 | 55 |
| 13 | R | NH2 | 660 | 584 | 116 | 54 |
| 13 | R | C | 665 | 550 | 166 | 34 |
| 13 | R | O | 663 | 560 | 171 | 34 |
| 14 | T | N | 661 | 538 | 172 | 33 |
| 14 | T | CA | 654 | 539 | 185 | 31 |
| 14 | T | CB | 650 | 525 | 189 | 32 |
| 14 | T | OG1 | 640 | 520 | 180 | 32 |
| 14 | T | CG2 | 645 | 524 | 204 | 31 |
| 14 | T | C | 664 | 545 | 195 | 30 |
| 14 | T | O | 660 | 553 | 203 | 30 |
| 15 | L | N | 676 | 540 | 195 | 30 |
| 15 | L | CA | 686 | 545 | 204 | 32 |
| 15 | L | CB | 699 | 537 | 205 | 32 |
| 15 | L | CG | 698 | 523 | 211 | 34 |
| 15 | L | CC1 | 710 | 515 | 207 | 35 |
| 15 | L | CC2 | 696 | 525 | 227 | 33 |
| 15 | L | C | 690 | 560 | 201 | 32 |
| 15 | L | O | 692 | 568 | 211 | 33 |
| 16 | M | N | 690 | 563 | 189 | 34 |
| 16 | M | CA | 693 | 578 | 185 | 35 |
| 16 | M | CB | 694 | 579 | 169 | 34 |
| 16 | M | CG | 697 | 593 | 164 | 38 |
| 16 | M | SD | 682 | 602 | 160 | 47 |
| 16 | M | CE | 676 | 594 | 146 | 43 |
| 16 | M | C | 682 | 587 | 190 | 35 |
| 16 | M | O | 685 | 598 | 196 | 34 |
| 17 | L | N | 670 | 583 | 189 | 36 |
| 17 | L | CA | 659 | 591 | 193 | 35 |
| 17 | L | CB | 646 | 585 | 188 | 35 |
| 17 | L | CG | 644 | 587 | 173 | 38 |
| 17 | L | CD1 | 634 | 577 | 167 | 34 |
| 17 | L | CD2 | 639 | 602 | 170 | 38 |
| 17 | L | C | 658 | 592 | 209 | 35 |
| 17 | L | O | 656 | 603 | 214 | 36 |
| 18 | L | N | 660 | 581 | 216 | 34 |
| 18 | L | CA | 662 | 582 | 231 | 34 |
| 18 | L | CB | 664 | 568 | 236 | 32 |
| 18 | L | CG | 652 | 559 | 238 | 34 |
| 18 | L | CD1 | 655 | 545 | 240 | 33 |
| 18 | L | CD2 | 643 | 565 | 250 | 32 |
| 18 | L | C | 673 | 592 | 235 | 32 |
| 18 | L | O | 672 | 599 | 244 | 32 |
| 19 | A | N | 684 | 591 | 228 | 32 |
| 19 | A | CA | 695 | 601 | 230 | 33 |
| 19 | A | CB | 708 | 597 | 222 | 31 |
| 19 | A | C | 691 | 615 | 229 | 34 |
| 19 | A | O | 694 | 624 | 237 | 35 |
| 20 | Q | N | 684 | 618 | 217 | 36 |
| 20 | Q | CA | 680 | 632 | 214 | 37 |
| 20 | Q | CB | 676 | 632 | 199 | 38 |
| 20 | Q | CG | 687 | 629 | 189 | 39 |
| 20 | Q | CD | 698 | 640 | 188 | 45 |
| 20 | Q | OE1 | 702 | 644 | 177 | 47 |
| 20 | Q | NE2 | 702 | 645 | 200 | 43 |
| 20 | Q | C | 668 | 636 | 222 | 39 |
| 20 | Q | O | 666 | 648 | 224 | 39 |
| 21 | M | N | 661 | 627 | 229 | 38 |
| 21 | M | CA | 651 | 631 | 239 | 39 |
| 21 | M | CB | 642 | 620 | 242 | 39 |
| 21 | M | CG | 632 | 616 | 232 | 41 |
| 21 | M | SD | 623 | 601 | 238 | 50 |
| 21 | M | CE | 623 | 594 | 225 | 35 |
| 21 | M | C | 657 | 637 | 252 | 41 |
| 21 | M | O | 649 | 643 | 259 | 39 |
| 22 | R | N | 669 | 633 | 256 | 42 |
| 22 | R | CA | 674 | 637 | 269 | 42 |
| 22 | R | CB | 689 | 633 | 270 | 42 |
| 22 | R | CG | 694 | 635 | 284 | 41 |
| 22 | R | CD | 706 | 628 | 288 | 43 |
| 22 | R | NE | 718 | 633 | 281 | 46 |
| 22 | R | CZ | 730 | 635 | 287 | 51 |
| 22 | R | NH1 | 740 | 640 | 280 | 47 |
| 22 | R | NH2 | 732 | 631 | 300 | 49 |
| 22 | R | C | 673 | 652 | 271 | 44 |
| 22 | R | O | 676 | 659 | 262 | 43 |
| 23 | R | N | 669 | 656 | 283 | 45 |
| 23 | R | CA | 668 | 670 | 286 | 48 |
| 23 | R | CB | 653 | 674 | 290 | 48 |
| 23 | R | CG | 643 | 673 | 279 | 51 |
| 23 | R | CD | 629 | 677 | 284 | 58 |
| 23 | R | NE | 621 | 680 | 272 | 65 |
| 23 | R | CZ | 608 | 684 | 274 | 70 |
| 23 | R | NH1 | 601 | 686 | 263 | 69 |
| 23 | R | NH2 | 603 | 687 | 286 | 70 |
| 23 | R | C | 677 | 675 | 298 | 49 |
| 23 | R | O | 681 | 686 | 298 | 50 |
| 24 | I | N | 679 | 665 | 307 | 49 |
| 24 | I | CA | 688 | 668 | 318 | 50 |
| 24 | I | CB | 680 | 671 | 331 | 49 |
| 24 | I | CG1 | 672 | 659 | 336 | 47 |
| 24 | I | CD1 | 665 | 661 | 349 | 49 |
| 24 | I | CG2 | 672 | 684 | 330 | 50 |
| 24 | I | C | 698 | 657 | 320 | 51 |
| 24 | I | O | 696 | 646 | 315 | 50 |
| 25 | S | N | 709 | 660 | 328 | 52 |
| 25 | S | CA | 719 | 651 | 331 | 55 |
| 25 | S | CB | 732 | 658 | 334 | 55 |
| 25 | S | OG | 741 | 649 | 340 | 59 |
| 25 | S | C | 715 | 642 | 343 | 56 |
| 25 | S | O | 708 | 646 | 353 | 55 |
| 26 | L | N | 720 | 629 | 343 | 59 |
| 26 | L | CA | 718 | 620 | 354 | 62 |
| 26 | L | CB | 723 | 606 | 350 | 62 |
| 26 | L | CG | 716 | 593 | 355 | 64 |
| 26 | L | CD1 | 701 | 595 | 358 | 64 |
| 26 | L | CD2 | 718 | 581 | 346 | 64 |
| 26 | L | C | 726 | 625 | 366 | 65 |
| 26 | L | O | 723 | 621 | 378 | 65 |
| 27 | F | N | 735 | 634 | 364 | 67 |
| 27 | F | CA | 744 | 638 | 375 | 69 |
| 27 | F | CB | 757 | 645 | 370 | 70 |
| 27 | F | CG | 767 | 636 | 365 | 75 |
| 27 | F | CD1 | 769 | 634 | 351 | 78 |
| 27 | F | CE1 | 779 | 625 | 346 | 80 |
| 27 | F | CZ | 787 | 617 | 355 | 82 |
| 27 | F | CE2 | 785 | 619 | 369 | 81 |
| 27 | F | CD2 | 775 | 628 | 374 | 79 |
| 27 | F | C | 736 | 648 | 385 | 69 |
| 27 | F | O | 740 | 648 | 396 | 68 |
| 28 | S | N | 726 | 654 | 380 | 68 |
| 28 | S | CA | 717 | 662 | 388 | 68 |
| 28 | S | CB | 708 | 672 | 380 | 68 |
| 28 | S | OG | 716 | 679 | 371 | 71 |
| 28 | S | C | 708 | 654 | 397 | 66 |
| 28 | S | O | 700 | 659 | 405 | 67 |
| 29 | C | N | 708 | 641 | 395 | 65 |
| 29 | C | CA | 697 | 632 | 400 | 62 |
| 29 | C | CB | 688 | 628 | 387 | 61 |
| 29 | C | SG | 682 | 642 | 378 | 59 |
| 29 | C | C | 701 | 620 | 408 | 61 |
| 29 | C | O | 694 | 610 | 408 | 60 |
| 30 | A | N | 711 | 622 | 416 | 61 |
| 30 | A | CA | 718 | 611 | 424 | 60 |
| 30 | A | CB | 730 | 616 | 431 | 61 |
| 30 | A | C | 708 | 604 | 433 | 59 |
| 30 | A | O | 709 | 592 | 435 | 59 |
| 31 | K | N | 700 | 612 | 440 | 58 |
| 31 | K | CA | 690 | 607 | 450 | 58 |
| 31 | K | CB | 683 | 619 | 456 | 59 |
| 31 | K | CG | 678 | 630 | 445 | 61 |
| 31 | K | CD | 671 | 642 | 451 | 65 |
| 31 | K | CE | 660 | 647 | 442 | 67 |
| 31 | K | NZ | 665 | 652 | 428 | 65 |
| 31 | K | C | 680 | 598 | 443 | 57 |
| 31 | K | O | 674 | 589 | 450 | 56 |
| 32 | D | N | 678 | 599 | 430 | 54 |
| 32 | D | CA | 668 | 591 | 423 | 52 |
| 32 | D | CB | 660 | 600 | 414 | 53 |
| 32 | D | CG | 654 | 612 | 421 | 54 |
| 32 | D | OD1 | 646 | 609 | 430 | 54 |
| 32 | D | OD2 | 657 | 623 | 417 | 55 |
| 32 | D | C | 673 | 579 | 415 | 51 |
| 32 | D | O | 665 | 572 | 409 | 50 |
| 33 | A | N | 686 | 577 | 415 | 49 |
| 33 | A | CA | 692 | 565 | 409 | 48 |
| 33 | A | CB | 708 | 565 | 412 | 48 |
| 33 | A | C | 685 | 552 | 413 | 47 |
| 33 | A | O | 681 | 551 | 425 | 47 |
| 34 | H | N | 684 | 542 | 405 | 46 |

| | | | | | |
|---|---|---|---|---|---|
| 34 | H | CA | 676 | 531 | 409 | 44 |
| 34 | H | CB | 661 | 534 | 407 | 45 |
| 34 | H | CG | 652 | 525 | 414 | 47 |
| 34 | H | ND1 | 646 | 514 | 408 | 47 |
| 34 | H | CE1 | 638 | 508 | 417 | 48 |
| 34 | H | NE2 | 639 | 514 | 428 | 53 |
| 34 | H | CD2 | 647 | 525 | 427 | 48 |
| 34 | H | C | 679 | 519 | 400 | 43 |
| 34 | H | O | 681 | 520 | 388 | 43 |
| 35 | D | N | 680 | 507 | 406 | 39 |
| 35 | D | CA | 682 | 494 | 400 | 38 |
| 35 | D | CB | 693 | 486 | 407 | 36 |
| 35 | D | CG | 697 | 474 | 399 | 36 |
| 35 | D | OD1 | 708 | 468 | 403 | 37 |
| 35 | D | OD2 | 691 | 469 | 390 | 34 |
| 35 | D | C | 669 | 487 | 398 | 37 |
| 35 | D | O | 662 | 483 | 408 | 35 |
| 36 | F | N | 664 | 486 | 385 | 36 |
| 36 | F | CA | 651 | 480 | 382 | 33 |
| 36 | F | CB | 645 | 486 | 370 | 33 |
| 36 | F | CG | 642 | 501 | 371 | 33 |
| 36 | F | CD1 | 652 | 510 | 368 | 36 |
| 36 | F | CE1 | 649 | 524 | 370 | 35 |
| 36 | F | CZ | 637 | 528 | 375 | 35 |
| 36 | F | CE2 | 628 | 519 | 379 | 35 |
| 36 | F | CD2 | 631 | 505 | 377 | 34 |
| 36 | F | C | 652 | 465 | 380 | 33 |
| 36 | F | O | 642 | 459 | 376 | 33 |
| 37 | G | N | 664 | 459 | 382 | 34 |
| 37 | G | CA | 665 | 445 | 380 | 34 |
| 37 | G | C | 661 | 440 | 366 | 34 |
| 37 | G | O | 654 | 430 | 365 | 34 |
| 38 | F | N | 667 | 446 | 356 | 34 |
| 38 | F | CA | 663 | 442 | 342 | 32 |
| 38 | F | CB | 671 | 451 | 332 | 32 |
| 38 | F | CG | 669 | 447 | 318 | 32 |
| 38 | F | CD1 | 656 | 447 | 312 | 29 |
| 38 | F | CE1 | 654 | 443 | 299 | 31 |
| 38 | F | CZ | 665 | 439 | 291 | 33 |
| 38 | F | CE2 | 677 | 438 | 296 | 33 |
| 38 | F | CD2 | 680 | 442 | 310 | 33 |
| 38 | F | C | 667 | 428 | 340 | 34 |
| 38 | F | O | 678 | 424 | 343 | 32 |
| 39 | P | N | 658 | 419 | 336 | 33 |
| 39 | P | CA | 661 | 405 | 334 | 34 |
| 39 | P | CB | 648 | 398 | 334 | 34 |
| 39 | P | CG | 639 | 409 | 327 | 34 |
| 39 | P | CD | 644 | 422 | 334 | 33 |
| 39 | P | C | 670 | 402 | 321 | 35 |
| 39 | P | O | 665 | 395 | 312 | 37 |
| 40 | Q | N | 682 | 406 | 321 | 37 |
| 40 | Q | CA | 690 | 405 | 309 | 38 |
| 40 | Q | CB | 703 | 412 | 311 | 38 |
| 40 | Q | CG | 712 | 407 | 323 | 40 |
| 40 | Q | CD | 725 | 415 | 323 | 46 |
| 40 | Q | OE1 | 725 | 426 | 327 | 44 |
| 40 | Q | NE2 | 736 | 409 | 317 | 48 |
| 40 | Q | C | 693 | 390 | 305 | 40 |
| 40 | Q | O | 695 | 387 | 293 | 40 |
| 41 | E | N | 693 | 381 | 315 | 40 |
| 41 | E | CA | 695 | 367 | 312 | 40 |
| 41 | E | CB | 695 | 359 | 326 | 41 |
| 41 | E | CG | 682 | 356 | 332 | 39 |
| 41 | E | CD | 677 | 368 | 340 | 35 |
| 41 | E | OE1 | 684 | 378 | 341 | 35 |
| 41 | E | OE2 | 665 | 367 | 345 | 35 |
| 41 | E | C | 684 | 361 | 302 | 41 |
| 41 | E | O | 687 | 351 | 296 | 41 |
| 42 | E | N | 673 | 367 | 301 | 42 |
| 42 | E | CA | 662 | 363 | 292 | 44 |
| 42 | E | CB | 649 | 369 | 295 | 45 |
| 42 | E | CG | 644 | 368 | 309 | 49 |
| 42 | E | CD | 643 | 354 | 315 | 53 |
| 42 | E | OE1 | 637 | 345 | 308 | 56 |
| 42 | E | OE2 | 649 | 351 | 325 | 62 |
| 42 | E | C | 666 | 365 | 277 | 45 |
| 42 | E | O | 659 | 360 | 268 | 46 |
| 43 | F | N | 677 | 372 | 275 | 48 |
| 43 | F | CA | 680 | 377 | 261 | 51 |
| 43 | F | CB | 681 | 392 | 261 | 50 |
| 43 | F | CG | 668 | 399 | 262 | 48 |
| 43 | F | CD1 | 664 | 403 | 275 | 47 |
| 43 | F | CE1 | 651 | 409 | 277 | 45 |
| 43 | F | CZ | 643 | 411 | 265 | 41 |
| 43 | F | CE2 | 648 | 407 | 252 | 43 |
| 43 | F | CD2 | 660 | 401 | 251 | 46 |
| 43 | F | C | 694 | 371 | 257 | 54 |
| 43 | F | O | 698 | 372 | 246 | 54 |
| 44 | G | N | 700 | 364 | 267 | 57 |
| 44 | G | CA | 714 | 359 | 265 | 60 |
| 44 | G | C | 716 | 345 | 260 | 63 |
| 44 | G | O | 706 | 339 | 255 | 63 |
| 45 | A | N | 728 | 340 | 262 | 65 |
| 45 | A | CA | 733 | 328 | 256 | 67 |
| 45 | A | CB | 749 | 329 | 256 | 67 |
| 45 | A | C | 729 | 315 | 261 | 69 |
| 45 | A | O | 733 | 304 | 256 | 69 |
| 46 | Q | N | 720 | 315 | 272 | 70 |
| 46 | Q | CA | 713 | 303 | 276 | 72 |
| 46 | Q | CB | 706 | 305 | 289 | 72 |
| 46 | Q | CG | 714 | 300 | 301 | 72 |
| 46 | Q | CD | 708 | 304 | 315 | 72 |
| 46 | Q | OE1 | 715 | 303 | 325 | 70 |
| 46 | Q | NE2 | 696 | 309 | 314 | 73 |
| 46 | Q | C | 703 | 299 | 265 | 73 |
| 46 | Q | O | 699 | 287 | 264 | 73 |
| 47 | F | N | 699 | 309 | 258 | 73 |
| 47 | F | CA | 688 | 308 | 248 | 74 |
| 47 | F | CB | 678 | 319 | 251 | 74 |
| 47 | F | CG | 672 | 318 | 265 | 74 |
| 47 | F | CD1 | 678 | 326 | 275 | 72 |
| 47 | F | CE1 | 673 | 325 | 288 | 73 |
| 47 | F | CZ | 663 | 316 | 291 | 73 |
| 47 | F | CE2 | 657 | 308 | 281 | 75 |
| 47 | F | CD2 | 662 | 309 | 268 | 75 |
| 47 | F | C | 693 | 309 | 233 | 74 |
| 47 | F | O | 704 | 315 | 230 | 74 |
| 48 | A | N | 685 | 303 | 224 | 74 |
| 48 | A | CA | 687 | 304 | 210 | 74 |
| 48 | A | CB | 682 | 291 | 203 | 74 |
| 48 | A | C | 681 | 317 | 205 | 74 |
| 48 | A | O | 671 | 322 | 211 | 74 |
| 49 | A | N | 686 | 322 | 193 | 74 |
| 49 | A | CA | 682 | 335 | 187 | 73 |
| 49 | A | CB | 691 | 338 | 175 | 74 |
| 49 | A | C | 667 | 336 | 184 | 72 |
| 49 | A | O | 662 | 347 | 185 | 73 |
| 50 | A | N | 661 | 325 | 180 | 70 |
| 50 | A | CA | 646 | 325 | 177 | 67 |
| 50 | A | CB | 643 | 314 | 167 | 68 |
| 50 | A | C | 638 | 322 | 190 | 66 |
| 50 | A | O | 626 | 324 | 189 | 65 |
| 51 | E | N | 644 | 319 | 201 | 63 |
| 51 | E | CA | 637 | 317 | 213 | 60 |
| 51 | E | CB | 644 | 307 | 222 | 61 |
| 51 | E | CG | 639 | 293 | 220 | 65 |
| 51 | E | CD | 646 | 283 | 230 | 71 |
| 51 | E | OE1 | 639 | 275 | 235 | 73 |
| 51 | E | OE2 | 659 | 285 | 232 | 72 |
| 51 | E | C | 635 | 330 | 220 | 57 |
| 51 | E | O | 626 | 332 | 229 | 57 |
| 52 | T | N | 643 | 340 | 217 | 53 |
| 52 | T | CA | 642 | 353 | 224 | 50 |
| 52 | T | CB | 656 | 359 | 226 | 50 |
| 52 | T | OG1 | 662 | 363 | 214 | 50 |
| 52 | T | CG2 | 666 | 349 | 232 | 51 |
| 52 | T | C | 634 | 363 | 216 | 47 |
| 52 | T | O | 631 | 374 | 221 | 46 |
| 53 | I | N | 629 | 359 | 204 | 43 |
| 53 | I | CA | 621 | 368 | 196 | 42 |
| 53 | I | CB | 617 | 362 | 182 | 42 |
| 53 | I | CG1 | 629 | 361 | 173 | 45 |
| 53 | I | CD1 | 640 | 371 | 173 | 50 |
| 53 | I | CG2 | 605 | 370 | 175 | 42 |
| 53 | I | C | 609 | 373 | 204 | 40 |
| 53 | I | O | 607 | 385 | 205 | 38 |
| 54 | P | N | 601 | 364 | 211 | 39 |
| 54 | P | CA | 589 | 369 | 219 | 39 |
| 54 | P | CB | 584 | 355 | 225 | 39 |
| 54 | P | CG | 588 | 345 | 215 | 40 |

| | | | | | | | | | | | | |
|---|---|---|---|---|---|---|---|---|---|---|---|---|
| 54 | P | CD | 602 | 350 | 210 | 40 | 64 | F | CA | 559 | 518 | 232 | 32 |
| 54 | P | C | 592 | 379 | 230 | 37 | 64 | F | CB | 553 | 511 | 220 | 30 |
| 54 | P | O | 584 | 387 | 233 | 35 | 64 | F | CG | 539 | 518 | 216 | 33 |
| 55 | V | N | 604 | 377 | 236 | 37 | 64 | F | CD1 | 539 | 529 | 208 | 35 |
| 55 | V | CA | 608 | 385 | 247 | 35 | 64 | F | CE1 | 527 | 535 | 205 | 38 |
| 55 | V | CB | 620 | 378 | 255 | 37 | 64 | F | CZ | 515 | 530 | 210 | 31 |
| 55 | V | CG1 | 621 | 383 | 268 | 38 | 64 | F | CE2 | 515 | 519 | 219 | 34 |
| 55 | V | CG2 | 616 | 363 | 257 | 36 | 64 | F | CD2 | 528 | 513 | 222 | 33 |
| 55 | V | C | 612 | 398 | 242 | 34 | 64 | F | C | 548 | 522 | 243 | 31 |
| 55 | V | O | 609 | 408 | 248 | 33 | 64 | F | O | 545 | 534 | 243 | 32 |
| 56 | L | N | 620 | 398 | 231 | 32 | 65 | N | N | 544 | 513 | 251 | 31 |
| 56 | L | CA | 624 | 411 | 225 | 32 | 65 | N | CA | 534 | 516 | 262 | 33 |
| 56 | L | CB | 634 | 410 | 214 | 32 | 65 | N | CB | 531 | 503 | 270 | 34 |
| 56 | L | CG | 638 | 423 | 207 | 37 | 65 | N | CG | 525 | 491 | 263 | 35 |
| 56 | L | CD1 | 646 | 433 | 216 | 37 | 65 | N | OD1 | 525 | 479 | 268 | 36 |
| 56 | L | CD2 | 646 | 420 | 194 | 37 | 65 | N | ND2 | 519 | 493 | 251 | 32 |
| 56 | L | C | 611 | 419 | 220 | 31 | 65 | N | C | 539 | 526 | 271 | 34 |
| 56 | L | O | 610 | 431 | 222 | 31 | 65 | N | O | 532 | 536 | 275 | 33 |
| 57 | H | N | 602 | 412 | 213 | 30 | 66 | L | N | 552 | 525 | 275 | 32 |
| 57 | H | CA | 590 | 417 | 209 | 30 | 66 | L | CA | 557 | 535 | 285 | 32 |
| 57 | H | CB | 581 | 407 | 201 | 30 | 66 | L | CB | 571 | 530 | 289 | 31 |
| 57 | H | CG | 568 | 412 | 196 | 29 | 66 | L | CG | 580 | 539 | 298 | 35 |
| 57 | H | ND1 | 557 | 411 | 204 | 31 | 66 | L | CD1 | 574 | 540 | 312 | 31 |
| 57 | H | CE1 | 546 | 416 | 197 | 32 | 66 | L | CD2 | 594 | 533 | 299 | 30 |
| 57 | H | NE2 | 550 | 418 | 185 | 32 | 66 | L | C | 558 | 549 | 279 | 32 |
| 57 | H | CD2 | 563 | 416 | 184 | 34 | 66 | L | O | 556 | 559 | 287 | 32 |
| 57 | H | C | 582 | 424 | 221 | 31 | 67 | F | N | 562 | 550 | 266 | 32 |
| 57 | H | O | 578 | 435 | 220 | 31 | 67 | F | CA | 564 | 563 | 260 | 33 |
| 58 | E | N | 581 | 416 | 232 | 30 | 67 | F | CB | 577 | 563 | 251 | 32 |
| 58 | E | CA | 575 | 422 | 244 | 31 | 67 | F | CG | 590 | 562 | 259 | 33 |
| 58 | E | CB | 574 | 412 | 255 | 31 | 67 | F | CD1 | 595 | 550 | 263 | 29 |
| 58 | E | CG | 566 | 417 | 267 | 30 | 67 | F | CE1 | 607 | 550 | 271 | 31 |
| 58 | E | CD | 551 | 417 | 264 | 36 | 67 | F | CZ | 613 | 562 | 275 | 37 |
| 58 | E | OE1 | 544 | 426 | 271 | 38 | 67 | F | CE2 | 608 | 574 | 271 | 37 |
| 58 | E | OE2 | 545 | 409 | 257 | 35 | 67 | F | CD2 | 596 | 574 | 263 | 34 |
| 58 | E | C | 582 | 434 | 249 | 31 | 67 | F | C | 552 | 569 | 253 | 34 |
| 58 | E | O | 575 | 444 | 252 | 28 | 67 | F | O | 553 | 580 | 248 | 35 |
| 59 | M | N | 595 | 434 | 249 | 31 | 68 | S | N | 541 | 562 | 253 | 35 |
| 59 | M | CA | 603 | 446 | 253 | 32 | 68 | S | CA | 529 | 567 | 246 | 37 |
| 59 | M | CB | 618 | 443 | 251 | 32 | 68 | S | CB | 524 | 556 | 237 | 35 |
| 59 | M | CG | 627 | 454 | 254 | 41 | 68 | S | OG | 518 | 545 | 244 | 36 |
| 59 | M | SD | 630 | 453 | 271 | 48 | 68 | S | C | 518 | 571 | 256 | 38 |
| 59 | M | CE | 643 | 467 | 273 | 38 | 68 | S | O | 506 | 573 | 251 | 39 |
| 59 | M | C | 599 | 459 | 244 | 30 | 69 | T | N | 521 | 572 | 269 | 40 |
| 59 | M | O | 597 | 469 | 250 | 27 | 69 | T | CA | 511 | 577 | 279 | 41 |
| 60 | I | N | 598 | 457 | 231 | 29 | 69 | T | CB | 515 | 573 | 293 | 41 |
| 60 | I | CA | 595 | 468 | 222 | 30 | 69 | T | OG1 | 527 | 580 | 297 | 41 |
| 60 | I | CB | 599 | 464 | 207 | 31 | 69 | T | CG2 | 517 | 558 | 295 | 41 |
| 60 | I | CG1 | 614 | 463 | 206 | 32 | 69 | T | C | 510 | 592 | 278 | 43 |
| 60 | I | CD1 | 619 | 456 | 194 | 35 | 69 | T | O | 519 | 599 | 272 | 43 |
| 60 | I | CG2 | 594 | 476 | 197 | 30 | 70 | A | N | 500 | 597 | 285 | 44 |
| 60 | I | C | 581 | 473 | 225 | 29 | 70 | A | CA | 499 | 612 | 286 | 44 |
| 60 | I | O | 578 | 485 | 226 | 30 | 70 | A | CB | 485 | 616 | 292 | 46 |
| 61 | Q | N | 571 | 464 | 225 | 28 | 70 | A | C | 510 | 617 | 295 | 43 |
| 61 | Q | CA | 558 | 468 | 228 | 29 | 70 | A | O | 516 | 628 | 292 | 44 |
| 61 | Q | CB | 548 | 456 | 229 | 27 | 71 | D | N | 515 | 610 | 305 | 43 |
| 61 | Q | CG | 533 | 459 | 234 | 31 | 71 | D | CA | 526 | 614 | 313 | 42 |
| 61 | Q | CD | 524 | 466 | 224 | 33 | 71 | D | CB | 528 | 604 | 324 | 42 |
| 61 | Q | OE1 | 517 | 476 | 227 | 38 | 71 | D | CG | 516 | 601 | 332 | 47 |
| 61 | Q | NE2 | 526 | 462 | 211 | 28 | 71 | D | OD1 | 514 | 610 | 341 | 49 |
| 61 | Q | C | 557 | 476 | 242 | 31 | 71 | D | OD2 | 508 | 592 | 330 | 50 |
| 61 | Q | O | 550 | 486 | 243 | 29 | 71 | D | C | 539 | 615 | 304 | 41 |
| 62 | Q | N | 564 | 470 | 252 | 30 | 71 | D | O | 546 | 625 | 305 | 41 |
| 62 | Q | CA | 565 | 478 | 265 | 29 | 72 | S | N | 541 | 606 | 295 | 40 |
| 62 | Q | CB | 571 | 469 | 276 | 29 | 72 | S | CA | 552 | 607 | 286 | 39 |
| 62 | Q | CG | 563 | 456 | 279 | 31 | 72 | S | CB | 554 | 594 | 278 | 37 |
| 62 | Q | CD | 549 | 459 | 284 | 33 | 72 | S | OG | 564 | 596 | 268 | 38 |
| 62 | Q | OE1 | 547 | 470 | 291 | 35 | 72 | S | C | 551 | 619 | 276 | 40 |
| 62 | Q | NE2 | 539 | 451 | 282 | 31 | 72 | S | O | 561 | 626 | 274 | 39 |
| 62 | Q | C | 571 | 491 | 264 | 28 | 73 | S | N | 539 | 621 | 271 | 42 |
| 62 | Q | O | 566 | 500 | 272 | 29 | 73 | S | CA | 537 | 633 | 263 | 44 |
| 63 | I | N | 581 | 493 | 256 | 28 | 73 | S | CB | 522 | 633 | 258 | 45 |
| 63 | I | CA | 587 | 506 | 255 | 28 | 73 | S | OG | 520 | 622 | 250 | 50 |
| 63 | I | CB | 600 | 504 | 246 | 29 | 73 | S | C | 540 | 646 | 270 | 44 |
| 63 | I | CG1 | 611 | 499 | 254 | 28 | 73 | S | O | 544 | 655 | 264 | 45 |
| 63 | I | CD1 | 624 | 494 | 245 | 29 | 74 | A | N | 538 | 646 | 284 | 46 |
| 63 | I | CG2 | 604 | 518 | 241 | 26 | 74 | A | CA | 542 | 658 | 291 | 46 |
| 63 | I | C | 577 | 515 | 249 | 30 | 74 | A | CB | 535 | 658 | 305 | 46 |
| 63 | I | O | 575 | 527 | 253 | 29 | 74 | A | C | 558 | 660 | 293 | 47 |
| 64 | F | N | 570 | 510 | 238 | 29 | 74 | A | O | 563 | 671 | 295 | 47 |

| | | | | | |
|---|---|---|---|---|---|
| 75 | A | N | 565 | 649 | 292 | 46 |
| 75 | A | CA | 579 | 648 | 296 | 44 |
| 75 | A | CB | 581 | 635 | 303 | 44 |
| 75 | A | C | 588 | 650 | 285 | 43 |
| 75 | A | O | 600 | 655 | 287 | 44 |
| 76 | W | N | 584 | 646 | 273 | 41 |
| 76 | W | CA | 593 | 645 | 261 | 40 |
| 76 | W | CB | 597 | 631 | 257 | 39 |
| 76 | W | CG | 600 | 622 | 268 | 34 |
| 76 | W | CD1 | 593 | 612 | 274 | 35 |
| 76 | W | NE1 | 599 | 607 | 285 | 34 |
| 76 | W | CE2 | 611 | 613 | 286 | 34 |
| 76 | W | CD2 | 612 | 623 | 275 | 33 |
| 76 | W | CE3 | 624 | 631 | 274 | 33 |
| 76 | W | CZ3 | 634 | 630 | 284 | 33 |
| 76 | W | CH2 | 633 | 620 | 294 | 33 |
| 76 | W | CZ2 | 622 | 612 | 295 | 30 |
| 76 | W | C | 588 | 653 | 249 | 42 |
| 76 | W | O | 576 | 653 | 247 | 43 |
| 77 | D | N | 597 | 657 | 241 | 43 |
| 77 | D | CA | 593 | 663 | 228 | 45 |
| 77 | D | CB | 607 | 666 | 221 | 46 |
| 77 | D | CG | 605 | 674 | 208 | 50 |
| 77 | D | OD1 | 604 | 668 | 197 | 56 |
| 77 | D | OD2 | 605 | 686 | 208 | 55 |
| 77 | D | C | 584 | 655 | 219 | 47 |
| 77 | D | O | 586 | 644 | 216 | 45 |
| 78 | E | N | 573 | 662 | 215 | 47 |
| 78 | E | CA | 563 | 656 | 206 | 49 |
| 78 | E | CB | 552 | 667 | 203 | 50 |
| 78 | E | CG | 539 | 663 | 197 | 56 |
| 78 | E | CD | 530 | 674 | 193 | 62 |
| 78 | E | OE1 | 521 | 672 | 184 | 66 |
| 78 | E | OE2 | 531 | 686 | 198 | 63 |
| 78 | E | C | 567 | 650 | 193 | 49 |
| 78 | E | O | 562 | 639 | 189 | 49 |
| 79 | T | N | 576 | 657 | 186 | 48 |
| 79 | T | CA | 581 | 652 | 173 | 48 |
| 79 | T | CB | 589 | 664 | 166 | 49 |
| 79 | T | OG1 | 580 | 675 | 166 | 53 |
| 79 | T | CG2 | 592 | 661 | 152 | 51 |
| 79 | T | C | 590 | 640 | 175 | 47 |
| 79 | T | O | 589 | 630 | 167 | 46 |
| 80 | L | N | 599 | 640 | 185 | 45 |
| 80 | L | CA | 608 | 629 | 187 | 43 |
| 80 | L | CB | 618 | 632 | 198 | 43 |
| 80 | L | CG | 628 | 642 | 194 | 42 |
| 80 | L | CD1 | 638 | 646 | 205 | 42 |
| 80 | L | CD2 | 636 | 638 | 181 | 45 |
| 80 | L | C | 599 | 617 | 191 | 41 |
| 80 | L | O | 601 | 606 | 185 | 40 |
| 81 | L | N | 589 | 619 | 200 | 39 |
| 81 | L | CA | 580 | 608 | 203 | 39 |
| 81 | L | CB | 570 | 612 | 214 | 39 |
| 81 | L | CG | 575 | 613 | 228 | 39 |
| 81 | L | CD1 | 564 | 619 | 237 | 39 |
| 81 | L | CD2 | 581 | 600 | 234 | 38 |
| 81 | L | C | 573 | 602 | 191 | 40 |
| 81 | L | O | 572 | 589 | 190 | 39 |
| 82 | D | N | 568 | 610 | 182 | 40 |
| 82 | D | CA | 561 | 605 | 171 | 40 |
| 82 | D | CB | 554 | 616 | 163 | 42 |
| 82 | D | CG | 548 | 612 | 150 | 45 |
| 82 | D | OD1 | 554 | 616 | 139 | 53 |
| 82 | D | OD2 | 539 | 604 | 149 | 49 |
| 82 | D | C | 571 | 597 | 162 | 39 |
| 82 | D | O | 568 | 586 | 157 | 39 |
| 83 | K | N | 583 | 602 | 160 | 37 |
| 83 | K | CA | 594 | 595 | 152 | 38 |
| 83 | K | CB | 606 | 604 | 152 | 38 |
| 83 | K | CG | 608 | 612 | 138 | 45 |
| 83 | K | CD | 619 | 622 | 139 | 44 |
| 83 | K | CE | 615 | 634 | 130 | 50 |
| 83 | K | NZ | 612 | 631 | 116 | 55 |
| 83 | K | C | 597 | 582 | 159 | 36 |
| 83 | K | O | 599 | 571 | 153 | 36 |
| 84 | F | N | 597 | 582 | 172 | 36 |
| 84 | F | CA | 601 | 570 | 181 | 34 |
| 84 | F | CB | 601 | 575 | 195 | 33 |
| 84 | F | CG | 607 | 565 | 205 | 34 |
| 84 | F | CD1 | 620 | 560 | 204 | 31 |
| 84 | F | CE1 | 625 | 551 | 214 | 31 |
| 84 | F | CZ | 617 | 548 | 225 | 29 |
| 84 | F | CE2 | 604 | 553 | 226 | 32 |
| 84 | F | CD2 | 599 | 562 | 216 | 34 |
| 84 | F | C | 590 | 560 | 179 | 35 |
| 84 | F | O | 593 | 548 | 175 | 35 |
| 85 | Y | N | 577 | 563 | 180 | 35 |
| 85 | Y | CA | 567 | 553 | 178 | 37 |
| 85 | Y | CB | 553 | 558 | 179 | 38 |
| 85 | Y | CG | 550 | 566 | 191 | 37 |
| 85 | Y | CD1 | 557 | 564 | 203 | 37 |
| 85 | Y | CE1 | 554 | 571 | 214 | 36 |
| 85 | Y | CZ | 545 | 582 | 214 | 37 |
| 85 | Y | OH | 542 | 589 | 225 | 36 |
| 85 | Y | CE2 | 538 | 585 | 202 | 41 |
| 85 | Y | CD2 | 541 | 577 | 190 | 39 |
| 85 | Y | C | 568 | 545 | 165 | 37 |
| 85 | Y | O | 566 | 533 | 164 | 37 |
| 86 | T | N | 572 | 552 | 154 | 38 |
| 86 | T | CA | 573 | 547 | 141 | 38 |
| 86 | T | CB | 576 | 558 | 131 | 40 |
| 86 | T | OG1 | 563 | 565 | 128 | 42 |
| 86 | T | CG2 | 580 | 553 | 117 | 41 |
| 86 | T | C | 583 | 536 | 141 | 37 |
| 86 | T | O | 581 | 525 | 135 | 36 |
| 87 | E | N | 595 | 539 | 147 | 35 |
| 87 | E | CA | 606 | 529 | 148 | 35 |
| 87 | E | CB | 618 | 535 | 154 | 34 |
| 87 | E | CG | 626 | 546 | 146 | 38 |
| 87 | E | CD | 627 | 542 | 131 | 42 |
| 87 | E | OE1 | 631 | 531 | 128 | 41 |
| 87 | E | OE2 | 625 | 551 | 123 | 43 |
| 87 | E | C | 601 | 517 | 156 | 34 |
| 87 | E | O | 604 | 506 | 152 | 34 |
| 88 | L | N | 593 | 519 | 166 | 34 |
| 88 | L | CA | 588 | 508 | 175 | 33 |
| 88 | L | CB | 582 | 513 | 188 | 32 |
| 88 | L | CG | 591 | 522 | 196 | 32 |
| 88 | L | CD1 | 584 | 527 | 208 | 29 |
| 88 | L | CD2 | 605 | 514 | 201 | 31 |
| 88 | L | C | 578 | 499 | 166 | 33 |
| 88 | L | O | 580 | 487 | 167 | 33 |
| 89 | Y | N | 569 | 506 | 159 | 34 |
| 89 | Y | CA | 559 | 498 | 151 | 34 |
| 89 | Y | CB | 549 | 506 | 143 | 35 |
| 89 | Y | CG | 541 | 516 | 151 | 32 |
| 89 | Y | CD1 | 536 | 513 | 164 | 37 |
| 89 | Y | CE1 | 529 | 523 | 171 | 38 |
| 89 | Y | CZ | 527 | 535 | 166 | 37 |
| 89 | Y | OH | 520 | 545 | 173 | 37 |
| 89 | Y | CE2 | 531 | 539 | 153 | 36 |
| 89 | Y | CD2 | 538 | 529 | 146 | 35 |
| 89 | Y | C | 566 | 489 | 141 | 34 |
| 89 | Y | O | 563 | 477 | 139 | 34 |
| 90 | Q | N | 576 | 495 | 134 | 34 |
| 90 | Q | CA | 584 | 488 | 124 | 36 |
| 90 | Q | CB | 593 | 497 | 116 | 38 |
| 90 | Q | CG | 602 | 490 | 106 | 44 |
| 90 | Q | CD | 593 | 486 | 93 | 50 |
| 90 | Q | OE1 | 587 | 495 | 87 | 54 |
| 90 | Q | NE2 | 592 | 473 | 90 | 53 |
| 90 | Q | C | 591 | 476 | 130 | 36 |
| 90 | Q | O | 591 | 465 | 124 | 36 |
| 91 | Q | N | 597 | 477 | 142 | 35 |
| 91 | Q | CA | 605 | 466 | 147 | 35 |
| 91 | Q | CB | 613 | 470 | 159 | 36 |
| 91 | Q | CG | 625 | 477 | 155 | 35 |
| 91 | Q | CD | 632 | 485 | 166 | 39 |
| 91 | Q | OE1 | 641 | 479 | 172 | 37 |
| 91 | Q | NE2 | 627 | 497 | 169 | 33 |
| 91 | Q | C | 595 | 455 | 152 | 34 |
| 91 | Q | O | 598 | 443 | 149 | 34 |
| 92 | L | N | 584 | 459 | 157 | 34 |
| 92 | L | CA | 574 | 449 | 161 | 34 |
| 92 | L | CB | 562 | 455 | 167 | 33 |
| 92 | L | CG | 565 | 461 | 181 | 36 |
| 92 | L | CD1 | 553 | 470 | 186 | 34 |
| 92 | L | CD2 | 568 | 450 | 192 | 34 |
| 92 | L | C | 569 | 441 | 148 | 36 |

| | | | | | |
|---|---|---|---|---|---|
| 92 | L | O | 567 | 428 | 149 | 35 |
| 93 | N | N | 565 | 448 | 138 | 37 |
| 93 | N | CA | 561 | 442 | 125 | 39 |
| 93 | N | CB | 559 | 453 | 115 | 40 |
| 93 | N | CG | 550 | 449 | 103 | 45 |
| 93 | N | OD1 | 553 | 440 | 96 | 47 |
| 93 | N | ND2 | 539 | 456 | 102 | 46 |
| 93 | N | C | 572 | 432 | 120 | 39 |
| 93 | N | O | 569 | 421 | 116 | 38 |
| 94 | D | N | 585 | 437 | 120 | 39 |
| 94 | D | CA | 595 | 428 | 115 | 42 |
| 94 | D | CB | 609 | 435 | 114 | 41 |
| 94 | D | CG | 608 | 445 | 103 | 46 |
| 94 | D | OD1 | 599 | 445 | 94 | 51 |
| 94 | D | OD2 | 617 | 454 | 102 | 48 |
| 94 | D | C | 597 | 415 | 124 | 42 |
| 94 | D | O | 599 | 404 | 118 | 42 |
| 95 | L | N | 596 | 417 | 137 | 42 |
| 95 | L | CA | 596 | 405 | 146 | 42 |
| 95 | L | CB | 598 | 409 | 161 | 41 |
| 95 | L | CG | 611 | 416 | 164 | 42 |
| 95 | L | CD1 | 610 | 422 | 178 | 41 |
| 95 | L | CD2 | 623 | 407 | 163 | 40 |
| 95 | L | C | 585 | 395 | 144 | 43 |
| 95 | L | O | 586 | 383 | 145 | 44 |
| 96 | E | N | 573 | 400 | 141 | 45 |
| 96 | E | CA | 561 | 392 | 138 | 47 |
| 96 | E | CB | 548 | 400 | 139 | 46 |
| 96 | E | CG | 545 | 405 | 152 | 45 |
| 96 | E | CD | 534 | 416 | 153 | 42 |
| 96 | E | OE1 | 525 | 416 | 144 | 39 |
| 96 | E | OE2 | 534 | 424 | 163 | 42 |
| 96 | E | C | 562 | 384 | 125 | 49 |
| 96 | E | O | 557 | 373 | 124 | 49 |
| 97 | A | N | 570 | 389 | 116 | 54 |
| 97 | A | CA | 572 | 383 | 102 | 58 |
| 97 | A | CB | 582 | 392 | 94 | 58 |
| 97 | A | C | 576 | 368 | 102 | 61 |
| 97 | A | O | 572 | 361 | 92 | 62 |
| 98 | A | N | 584 | 364 | 111 | 64 |
| 98 | A | CA | 588 | 349 | 111 | 66 |
| 98 | A | CB | 601 | 347 | 119 | 67 |
| 98 | A | C | 577 | 340 | 116 | 67 |
| 98 | A | O | 575 | 329 | 109 | 68 |
| 99 | A | N | 571 | 343 | 127 | 67 |
| 99 | A | CA | 559 | 335 | 132 | 68 |
| 99 | A | CB | 555 | 339 | 147 | 68 |
| 99 | A | C | 547 | 335 | 123 | 68 |
| 99 | A | O | 543 | 345 | 118 | 68 |
| 111 | M | N | 556 | 277 | 256 | 68 |
| 111 | M | CA | 569 | 282 | 251 | 68 |
| 111 | M | CB | 568 | 289 | 237 | 69 |
| 111 | M | CG | 557 | 299 | 235 | 72 |
| 111 | M | SD | 561 | 314 | 225 | 80 |
| 111 | M | CE | 560 | 327 | 237 | 76 |
| 111 | M | C | 576 | 291 | 261 | 67 |
| 111 | M | O | 584 | 286 | 270 | 68 |
| 112 | K | N | 574 | 304 | 261 | 64 |
| 112 | K | CA | 581 | 315 | 268 | 61 |
| 112 | K | CB | 590 | 323 | 258 | 62 |
| 112 | K | CG | 601 | 316 | 251 | 65 |
| 112 | K | CD | 612 | 312 | 261 | 68 |
| 112 | K | CE | 626 | 311 | 254 | 71 |
| 112 | K | NZ | 634 | 301 | 262 | 73 |
| 112 | K | C | 573 | 324 | 277 | 57 |
| 112 | K | O | 576 | 336 | 278 | 57 |
| 113 | A | N | 562 | 319 | 282 | 54 |
| 113 | A | CA | 552 | 328 | 289 | 50 |
| 113 | A | CB | 541 | 320 | 294 | 51 |
| 113 | A | C | 559 | 335 | 301 | 49 |
| 113 | A | O | 556 | 347 | 303 | 46 |
| 114 | D | N | 567 | 328 | 308 | 48 |
| 114 | D | CA | 573 | 333 | 321 | 47 |
| 114 | D | CB | 579 | 322 | 329 | 49 |
| 114 | D | CG | 569 | 313 | 336 | 52 |
| 114 | D | OD1 | 572 | 301 | 337 | 58 |
| 114 | D | OD2 | 558 | 317 | 340 | 56 |
| 114 | D | C | 583 | 343 | 317 | 44 |
| 114 | D | O | 584 | 353 | 324 | 44 |
| 115 | S | N | 590 | 342 | 306 | 42 |
| 115 | S | CA | 600 | 352 | 302 | 42 |
| 115 | S | CB | 610 | 347 | 292 | 42 |
| 115 | S | OG | 617 | 336 | 297 | 48 |
| 115 | S | C | 593 | 365 | 297 | 41 |
| 115 | S | O | 598 | 375 | 300 | 40 |
| 116 | I | N | 582 | 363 | 289 | 39 |
| 116 | I | CA | 574 | 375 | 285 | 39 |
| 116 | I | CB | 562 | 370 | 276 | 39 |
| 116 | I | CG1 | 568 | 366 | 262 | 40 |
| 116 | I | CD1 | 557 | 359 | 253 | 42 |
| 116 | I | CG2 | 551 | 381 | 275 | 40 |
| 116 | I | C | 569 | 383 | 297 | 38 |
| 116 | I | O | 570 | 395 | 298 | 38 |
| 117 | L | N | 564 | 375 | 307 | 38 |
| 117 | L | CA | 559 | 381 | 319 | 38 |
| 117 | L | CB | 554 | 369 | 328 | 41 |
| 117 | L | CG | 539 | 368 | 327 | 45 |
| 117 | L | CD1 | 534 | 353 | 326 | 52 |
| 117 | L | CD2 | 534 | 375 | 340 | 55 |
| 117 | L | C | 570 | 388 | 327 | 37 |
| 117 | L | O | 568 | 398 | 334 | 38 |
| 118 | A | N | 582 | 383 | 327 | 37 |
| 118 | A | CA | 593 | 390 | 335 | 36 |
| 118 | A | CB | 605 | 381 | 334 | 34 |
| 118 | A | C | 596 | 403 | 329 | 34 |
| 118 | A | O | 599 | 413 | 336 | 34 |
| 119 | V | N | 595 | 404 | 316 | 35 |
| 119 | V | CA | 597 | 417 | 308 | 34 |
| 119 | V | CB | 597 | 415 | 293 | 35 |
| 119 | V | CG1 | 596 | 429 | 286 | 35 |
| 119 | V | CG2 | 611 | 408 | 289 | 36 |
| 119 | V | C | 586 | 426 | 313 | 34 |
| 119 | V | O | 589 | 438 | 316 | 34 |
| 120 | R | N | 574 | 422 | 313 | 35 |
| 120 | R | CA | 563 | 430 | 317 | 37 |
| 120 | R | CB | 549 | 423 | 317 | 36 |
| 120 | R | CG | 544 | 422 | 304 | 41 |
| 120 | R | CD | 529 | 417 | 302 | 41 |
| 120 | R | NE | 527 | 412 | 289 | 40 |
| 120 | R | CZ | 521 | 401 | 285 | 43 |
| 120 | R | NH1 | 514 | 394 | 294 | 42 |
| 120 | R | NH2 | 521 | 398 | 272 | 41 |
| 120 | R | C | 565 | 436 | 331 | 36 |
| 120 | R | O | 562 | 447 | 334 | 38 |
| 121 | K | N | 570 | 427 | 340 | 36 |
| 121 | K | CA | 571 | 430 | 354 | 36 |
| 121 | K | CB | 574 | 418 | 362 | 36 |
| 121 | K | CG | 561 | 411 | 366 | 41 |
| 121 | K | CD | 564 | 398 | 375 | 50 |
| 121 | K | CE | 552 | 391 | 378 | 53 |
| 121 | K | NZ | 554 | 376 | 375 | 59 |
| 121 | K | C | 582 | 441 | 356 | 34 |
| 121 | K | O | 581 | 450 | 363 | 34 |
| 122 | Y | N | 593 | 440 | 348 | 33 |
| 122 | Y | CA | 603 | 450 | 348 | 32 |
| 122 | Y | CB | 614 | 446 | 337 | 31 |
| 122 | Y | CG | 623 | 457 | 332 | 30 |
| 122 | Y | CD1 | 622 | 462 | 319 | 31 |
| 122 | Y | CE1 | 632 | 472 | 315 | 30 |
| 122 | Y | CZ | 641 | 476 | 323 | 32 |
| 122 | Y | OH | 650 | 486 | 318 | 30 |
| 122 | Y | CE2 | 642 | 472 | 337 | 29 |
| 122 | Y | CD2 | 633 | 462 | 341 | 29 |
| 122 | Y | C | 597 | 464 | 344 | 31 |
| 122 | Y | O | 600 | 474 | 350 | 31 |
| 123 | F | N | 589 | 464 | 334 | 32 |
| 123 | F | CA | 582 | 477 | 330 | 31 |
| 123 | F | CB | 576 | 476 | 316 | 31 |
| 123 | F | CG | 586 | 478 | 305 | 31 |
| 123 | F | CD1 | 589 | 491 | 300 | 27 |
| 123 | F | CE1 | 599 | 492 | 290 | 28 |
| 123 | F | CZ | 606 | 481 | 285 | 30 |
| 123 | F | CE2 | 603 | 468 | 290 | 27 |
| 123 | F | CD2 | 593 | 467 | 300 | 28 |
| 123 | F | C | 572 | 481 | 341 | 32 |
| 123 | F | O | 570 | 493 | 343 | 31 |
| 124 | Q | N | 565 | 472 | 348 | 33 |
| 124 | Q | CA | 557 | 476 | 359 | 36 |
| 124 | Q | CB | 549 | 463 | 365 | 37 |
| 124 | Q | CG | 538 | 459 | 355 | 42 |

| | | | | | | | | | | | | |
|---|---|---|---|---|---|---|---|---|---|---|---|---|
| 124 | Q | CD | 532 | 445 | 358 | 48 | 133 | K | CG | 606 | 587 | 419 | 49 |
| 124 | Q | OE1 | 536 | 438 | 367 | 45 | 133 | K | CD | 617 | 593 | 427 | 55 |
| 124 | Q | NE2 | 524 | 440 | 348 | 49 | 133 | K | CE | 625 | 583 | 434 | 55 |
| 124 | Q | C | 565 | 482 | 371 | 36 | 133 | K | NZ | 634 | 590 | 444 | 56 |
| 124 | Q | O | 561 | 492 | 377 | 36 | 133 | K | C | 576 | 611 | 415 | 48 |
| 125 | R | N | 577 | 477 | 373 | 35 | 133 | K | O | 582 | 622 | 412 | 48 |
| 125 | R | CA | 586 | 483 | 382 | 35 | 134 | K | N | 563 | 609 | 413 | 48 |
| 125 | R | CB | 599 | 476 | 384 | 34 | 134 | K | CA | 554 | 618 | 406 | 49 |
| 125 | R | CG | 596 | 462 | 392 | 34 | 134 | K | CB | 550 | 630 | 416 | 51 |
| 125 | R | CD | 608 | 455 | 396 | 32 | 134 | K | CG | 544 | 624 | 430 | 56 |
| 125 | R | NE | 617 | 450 | 386 | 32 | 134 | K | CD | 541 | 635 | 440 | 64 |
| 125 | R | CZ | 616 | 438 | 379 | 32 | 134 | K | CE | 537 | 649 | 434 | 69 |
| 125 | R | NH1 | 605 | 431 | 381 | 32 | 134 | K | NZ | 529 | 657 | 443 | 74 |
| 125 | R | NH2 | 625 | 435 | 370 | 32 | 134 | K | C | 560 | 623 | 393 | 48 |
| 125 | R | C | 590 | 497 | 377 | 36 | 134 | K | O | 558 | 635 | 390 | 48 |
| 125 | R | O | 590 | 507 | 385 | 36 | 135 | Y | N | 566 | 615 | 385 | 47 |
| 126 | I | N | 593 | 499 | 364 | 34 | 135 | Y | CA | 570 | 619 | 372 | 46 |
| 126 | I | CA | 595 | 513 | 359 | 34 | 135 | Y | CB | 558 | 621 | 363 | 46 |
| 126 | I | CB | 600 | 513 | 345 | 33 | 135 | Y | CG | 549 | 609 | 362 | 47 |
| 126 | I | CG1 | 614 | 506 | 343 | 34 | 135 | Y | CD1 | 539 | 607 | 371 | 49 |
| 126 | I | CD1 | 617 | 502 | 330 | 31 | 135 | Y | CE1 | 530 | 596 | 371 | 50 |
| 126 | I | CG2 | 599 | 527 | 338 | 31 | 135 | Y | CZ | 533 | 586 | 361 | 50 |
| 126 | I | C | 583 | 522 | 362 | 36 | 135 | Y | OH | 525 | 575 | 361 | 54 |
| 126 | I | O | 585 | 533 | 366 | 37 | 135 | Y | CE2 | 543 | 588 | 352 | 48 |
| 127 | T | N | 572 | 517 | 358 | 38 | 135 | Y | CD2 | 551 | 599 | 352 | 45 |
| 127 | T | CA | 559 | 525 | 360 | 41 | 135 | Y | C | 579 | 631 | 372 | 44 |
| 127 | T | CB | 548 | 518 | 353 | 40 | 135 | Y | O | 578 | 639 | 363 | 44 |
| 127 | T | OG1 | 549 | 521 | 339 | 44 | 136 | S | N | 588 | 633 | 382 | 44 |
| 127 | T | CG2 | 534 | 523 | 357 | 43 | 136 | S | CA | 597 | 644 | 382 | 45 |
| 127 | T | C | 556 | 529 | 375 | 42 | 136 | S | CB | 606 | 643 | 395 | 45 |
| 127 | T | O | 553 | 540 | 378 | 43 | 136 | S | OG | 614 | 631 | 396 | 46 |
| 128 | L | N | 558 | 519 | 383 | 43 | 136 | S | C | 606 | 643 | 369 | 45 |
| 128 | L | CA | 556 | 521 | 398 | 45 | 136 | S | O | 608 | 632 | 364 | 46 |
| 128 | L | CB | 559 | 508 | 405 | 47 | 137 | P | N | 611 | 654 | 364 | 45 |
| 128 | L | CG | 551 | 504 | 417 | 53 | 137 | P | CA | 622 | 653 | 354 | 45 |
| 128 | L | CD1 | 539 | 513 | 422 | 56 | 137 | P | CB | 627 | 668 | 353 | 45 |
| 128 | L | CD2 | 546 | 489 | 415 | 57 | 137 | P | CG | 614 | 676 | 356 | 45 |
| 128 | L | C | 566 | 532 | 403 | 45 | 137 | P | CD | 607 | 668 | 367 | 45 |
| 128 | L | O | 562 | 541 | 410 | 45 | 137 | P | C | 633 | 644 | 357 | 45 |
| 129 | Y | N | 579 | 530 | 400 | 42 | 137 | P | O | 638 | 636 | 348 | 44 |
| 129 | Y | CA | 589 | 541 | 402 | 41 | 138 | C | N | 637 | 643 | 370 | 43 |
| 129 | Y | CB | 602 | 537 | 395 | 39 | 138 | C | CA | 648 | 634 | 374 | 44 |
| 129 | Y | CG | 613 | 548 | 395 | 37 | 138 | C | CB | 652 | 637 | 388 | 46 |
| 129 | Y | CD1 | 622 | 549 | 406 | 39 | 138 | C | SG | 665 | 650 | 388 | 51 |
| 129 | Y | CE1 | 631 | 558 | 407 | 38 | 138 | C | C | 644 | 620 | 372 | 42 |
| 129 | Y | CZ | 633 | 567 | 396 | 38 | 138 | C | O | 652 | 612 | 367 | 40 |
| 129 | Y | OH | 643 | 576 | 397 | 39 | 139 | A | N | 632 | 616 | 377 | 39 |
| 129 | Y | CE2 | 625 | 566 | 384 | 39 | 139 | A | CA | 627 | 602 | 376 | 39 |
| 129 | Y | CD2 | 615 | 557 | 384 | 37 | 139 | A | CB | 613 | 601 | 382 | 39 |
| 129 | Y | C | 585 | 555 | 398 | 41 | 139 | A | C | 627 | 599 | 361 | 37 |
| 129 | Y | O | 585 | 564 | 406 | 40 | 139 | A | O | 630 | 587 | 358 | 37 |
| 130 | L | N | 581 | 556 | 385 | 40 | 140 | W | N | 622 | 608 | 353 | 35 |
| 130 | L | CA | 576 | 569 | 380 | 41 | 140 | W | CA | 620 | 605 | 339 | 36 |
| 130 | L | CB | 572 | 569 | 365 | 38 | 140 | W | CB | 613 | 616 | 332 | 35 |
| 130 | L | CG | 583 | 569 | 355 | 39 | 140 | W | CG | 598 | 612 | 330 | 38 |
| 130 | L | CD1 | 579 | 565 | 341 | 33 | 140 | W | CD1 | 587 | 619 | 335 | 39 |
| 130 | L | CD2 | 591 | 583 | 353 | 36 | 140 | W | NE1 | 575 | 613 | 330 | 37 |
| 130 | L | C | 564 | 575 | 389 | 43 | 140 | W | CE2 | 578 | 602 | 322 | 38 |
| 130 | L | O | 563 | 588 | 391 | 44 | 140 | W | CD2 | 593 | 601 | 322 | 37 |
| 131 | K | N | 555 | 566 | 393 | 45 | 140 | W | CE3 | 599 | 591 | 315 | 32 |
| 131 | K | CA | 544 | 570 | 401 | 48 | 140 | W | CZ3 | 590 | 582 | 307 | 33 |
| 131 | K | CB | 534 | 559 | 403 | 48 | 140 | W | CH2 | 576 | 583 | 308 | 38 |
| 131 | K | CG | 524 | 557 | 392 | 50 | 140 | W | CZ2 | 570 | 593 | 315 | 38 |
| 131 | K | CD | 519 | 543 | 390 | 56 | 140 | W | C | 634 | 603 | 333 | 36 |
| 131 | K | CE | 508 | 541 | 380 | 58 | 140 | W | O | 636 | 596 | 323 | 35 |
| 131 | K | NZ | 502 | 527 | 380 | 59 | 141 | E | N | 644 | 611 | 337 | 36 |
| 131 | K | C | 549 | 575 | 415 | 48 | 141 | E | CA | 657 | 610 | 331 | 36 |
| 131 | K | O | 545 | 585 | 420 | 50 | 141 | E | CB | 667 | 622 | 334 | 37 |
| 132 | E | N | 558 | 567 | 421 | 50 | 141 | E | CG | 682 | 619 | 331 | 36 |
| 132 | E | CA | 563 | 571 | 434 | 51 | 141 | E | CD | 684 | 616 | 316 | 37 |
| 132 | E | CB | 573 | 560 | 440 | 53 | 141 | E | OE1 | 675 | 618 | 307 | 36 |
| 132 | E | CG | 565 | 548 | 446 | 58 | 141 | E | OE2 | 695 | 612 | 312 | 36 |
| 132 | E | CD | 575 | 536 | 449 | 67 | 141 | E | C | 664 | 596 | 335 | 35 |
| 132 | E | OE1 | 587 | 537 | 446 | 71 | 141 | E | O | 670 | 590 | 327 | 34 |
| 132 | E | OE2 | 570 | 526 | 455 | 71 | 142 | V | N | 661 | 592 | 348 | 35 |
| 132 | E | C | 570 | 584 | 434 | 51 | 142 | V | CA | 665 | 579 | 352 | 35 |
| 132 | E | O | 569 | 592 | 444 | 51 | 142 | V | CB | 662 | 576 | 367 | 35 |
| 133 | K | N | 576 | 587 | 423 | 50 | 142 | V | CG1 | 664 | 562 | 371 | 33 |
| 133 | K | CA | 584 | 600 | 421 | 49 | 142 | V | CG2 | 671 | 585 | 377 | 35 |
| 133 | K | CB | 597 | 597 | 413 | 48 | 142 | V | C | 660 | 568 | 343 | 34 |

| | | | | | | | | | | | | |
|---|---|---|---|---|---|---|---|---|---|---|---|---|
| 142 | V | O | 666 | 559 | 339 | 35 | 152 | S | OG | 730 | 494 | 236 | 48 |
| 143 | V | N | 647 | 569 | 341 | 32 | 152 | S | C | 714 | 469 | 243 | 37 |
| 143 | V | CA | 640 | 559 | 332 | 31 | 152 | S | O | 718 | 460 | 234 | 36 |
| 143 | V | CB | 625 | 561 | 333 | 30 | 153 | L | N | 714 | 465 | 256 | 37 |
| 143 | V | CG1 | 617 | 553 | 322 | 31 | 153 | L | CA | 717 | 451 | 260 | 40 |
| 143 | V | CG2 | 619 | 557 | 347 | 32 | 153 | L | CB | 715 | 449 | 275 | 40 |
| 143 | V | C | 645 | 559 | 318 | 31 | 153 | L | CG | 726 | 452 | 285 | 46 |
| 143 | V | O | 648 | 549 | 312 | 29 | 153 | L | CD1 | 720 | 448 | 299 | 48 |
| 144 | R | N | 647 | 571 | 313 | 31 | 153 | L | CD2 | 738 | 443 | 283 | 46 |
| 144 | R | CA | 651 | 572 | 299 | 32 | 153 | L | C | 709 | 441 | 254 | 39 |
| 144 | R | CB | 651 | 586 | 294 | 32 | 153 | L | O | 715 | 431 | 249 | 41 |
| 144 | R | CG | 655 | 588 | 278 | 32 | 154 | S | N | 696 | 443 | 253 | 39 |
| 144 | R | CD | 662 | 602 | 275 | 31 | 154 | S | CA | 688 | 432 | 248 | 41 |
| 144 | R | NE | 674 | 602 | 283 | 33 | 154 | S | CB | 674 | 433 | 252 | 42 |
| 144 | R | CZ | 686 | 596 | 280 | 35 | 154 | S | OG | 667 | 443 | 247 | 47 |
| 144 | R | NH1 | 686 | 589 | 268 | 33 | 154 | S | C | 690 | 431 | 232 | 43 |
| 144 | R | NH2 | 696 | 596 | 288 | 37 | 154 | S | O | 688 | 420 | 228 | 44 |
| 144 | R | C | 665 | 566 | 297 | 32 | 155 | T | N | 693 | 441 | 225 | 41 |
| 144 | R | O | 668 | 558 | 287 | 33 | 155 | T | CA | 695 | 440 | 211 | 43 |
| 145 | A | N | 675 | 569 | 306 | 31 | 155 | T | CB | 691 | 452 | 203 | 43 |
| 145 | A | CA | 688 | 563 | 306 | 31 | 155 | T | OG1 | 697 | 463 | 209 | 41 |
| 145 | A | CB | 697 | 569 | 317 | 30 | 155 | T | CG2 | 676 | 456 | 204 | 43 |
| 145 | A | C | 687 | 548 | 308 | 30 | 155 | T | C | 709 | 435 | 208 | 45 |
| 145 | A | O | 694 | 540 | 302 | 31 | 155 | T | O | 711 | 427 | 198 | 46 |
| 146 | E | N | 678 | 544 | 317 | 29 | 156 | N | N | 719 | 439 | 215 | 47 |
| 146 | E | CA | 676 | 530 | 320 | 29 | 156 | N | CA | 733 | 435 | 214 | 51 |
| 146 | E | CB | 666 | 528 | 331 | 29 | 156 | N | CB | 743 | 443 | 223 | 51 |
| 146 | E | CG | 660 | 513 | 333 | 31 | 156 | N | CG | 744 | 458 | 218 | 54 |
| 146 | E | CD | 671 | 503 | 336 | 34 | 156 | N | OD1 | 739 | 462 | 208 | 56 |
| 146 | E | OE1 | 670 | 490 | 333 | 28 | 156 | N | ND2 | 752 | 466 | 226 | 55 |
| 146 | E | OE2 | 681 | 507 | 343 | 33 | 156 | N | C | 735 | 420 | 217 | 54 |
| 146 | E | C | 672 | 522 | 307 | 29 | 156 | N | O | 741 | 413 | 209 | 53 |
| 146 | E | O | 677 | 512 | 304 | 29 | 157 | L | N | 729 | 416 | 228 | 57 |
| 147 | I | N | 662 | 527 | 299 | 27 | 157 | L | CA | 728 | 401 | 232 | 60 |
| 147 | I | CA | 657 | 520 | 287 | 28 | 157 | L | CB | 721 | 400 | 246 | 60 |
| 147 | I | CB | 644 | 528 | 282 | 29 | 157 | L | CG | 729 | 404 | 258 | 61 |
| 147 | I | CG1 | 633 | 526 | 293 | 29 | 157 | L | CD1 | 720 | 404 | 271 | 59 |
| 147 | I | CD1 | 629 | 512 | 296 | 28 | 157 | L | CD2 | 741 | 394 | 261 | 62 |
| 147 | I | CG2 | 640 | 522 | 268 | 28 | 157 | L | C | 720 | 393 | 221 | 63 |
| 147 | I | C | 667 | 520 | 277 | 29 | 157 | L | O | 724 | 382 | 218 | 63 |
| 147 | I | O | 670 | 510 | 270 | 30 | 158 | Q | N | 709 | 399 | 216 | 65 |
| 148 | M | N | 674 | 531 | 275 | 29 | 158 | Q | CA | 701 | 393 | 206 | 68 |
| 148 | M | CA | 685 | 531 | 266 | 33 | 158 | Q | CB | 689 | 401 | 203 | 69 |
| 148 | M | CB | 692 | 545 | 267 | 34 | 158 | Q | CG | 679 | 395 | 195 | 71 |
| 148 | M | CG | 703 | 547 | 259 | 42 | 158 | Q | CD | 677 | 401 | 181 | 75 |
| 148 | M | SD | 701 | 563 | 251 | 50 | 158 | Q | OE1 | 670 | 395 | 172 | 75 |
| 148 | M | CE | 710 | 560 | 237 | 42 | 158 | Q | NE2 | 682 | 414 | 179 | 74 |
| 148 | M | C | 696 | 520 | 269 | 33 | 158 | Q | C | 709 | 391 | 193 | 70 |
| 148 | M | O | 700 | 513 | 261 | 34 | 158 | Q | O | 708 | 380 | 187 | 70 |
| 149 | R | N | 699 | 519 | 282 | 31 | 159 | E | N | 718 | 400 | 189 | 71 |
| 149 | R | CA | 708 | 508 | 286 | 32 | 159 | E | CA | 726 | 399 | 177 | 73 |
| 149 | R | CB | 712 | 510 | 301 | 32 | 159 | E | CB | 733 | 412 | 174 | 73 |
| 149 | R | CG | 723 | 500 | 307 | 37 | 159 | E | CG | 735 | 415 | 159 | 75 |
| 149 | R | CD | 723 | 500 | 323 | 41 | 159 | E | CD | 748 | 423 | 157 | 76 |
| 149 | R | NE | 710 | 494 | 327 | 45 | 159 | E | OE1 | 749 | 428 | 145 | 78 |
| 149 | R | CZ | 707 | 481 | 329 | 49 | 159 | E | OE2 | 756 | 424 | 166 | 79 |
| 149 | R | NH1 | 695 | 478 | 333 | 47 | 159 | E | C | 737 | 388 | 179 | 74 |
| 149 | R | NH2 | 716 | 472 | 327 | 51 | 159 | E | O | 740 | 380 | 170 | 73 |
| 149 | R | C | 702 | 494 | 284 | 30 | 160 | S | N | 744 | 389 | 191 | 75 |
| 149 | R | O | 709 | 485 | 278 | 29 | 160 | S | CA | 752 | 379 | 197 | 75 |
| 150 | S | N | 690 | 492 | 288 | 28 | 160 | S | CB | 752 | 366 | 189 | 76 |
| 150 | S | CA | 684 | 478 | 287 | 29 | 160 | S | OG | 753 | 355 | 197 | 77 |
| 150 | S | CB | 672 | 476 | 296 | 31 | 160 | S | C | 766 | 384 | 201 | 76 |
| 150 | S | OG | 662 | 484 | 293 | 31 | 160 | S | O | 773 | 391 | 193 | 77 |
| 150 | S | C | 681 | 475 | 272 | 30 | 201 | X | N | 398 | 503 | 694 | 36 |
| 150 | S | O | 682 | 463 | 268 | 29 | 202 | X | N | 442 | 412 | −56 | 45 |
| 151 | F | N | 676 | 484 | 264 | 30 | 203 | X | N | 651 | 356 | 342 | 49 |
| 151 | F | CA | 673 | 481 | 250 | 30 | 204 | X | N | 491 | 73 | −151 | 54 |
| 151 | F | CB | 666 | 493 | 243 | 30 | 205 | X | N | 462 | 308 | −225 | 47 |
| 151 | F | CG | 662 | 491 | 229 | 32 | 206 | X | N | 480 | 684 | 807 | 59 |
| 151 | F | CD1 | 652 | 482 | 226 | 32 | 207 | X | N | 682 | 203 | 462 | 58 |
| 151 | F | CE1 | 648 | 479 | 213 | 35 | 1 | X | O | 292 | 497 | 910 | 30 |
| 151 | F | CZ | 655 | 485 | 202 | 34 | 2 | X | O | 248 | 627 | 824 | 27 |
| 151 | F | CE2 | 666 | 494 | 205 | 35 | 3 | X | O | 421 | 476 | 726 | 30 |
| 151 | F | CD2 | 669 | 497 | 219 | 33 | 4 | X | O | 364 | 474 | 749 | 31 |
| 151 | F | C | 686 | 478 | 243 | 30 | 5 | X | O | 299 | 521 | 839 | 27 |
| 151 | F | O | 686 | 468 | 235 | 31 | 6 | X | O | 285 | 484 | 827 | 34 |
| 152 | S | N | 696 | 486 | 245 | 30 | 7 | X | O | 252 | 644 | 928 | 31 |
| 152 | S | CA | 709 | 483 | 239 | 35 | 8 | X | O | 452 | 490 | 727 | 35 |
| 152 | S | CB | 719 | 494 | 244 | 34 | 9 | X | O | 468 | 443 | 771 | 32 |

| | | | | | | | | | | | | | |
|---|---|---|---|---|---|---|---|---|---|---|---|---|---|
| 10 | X | O | 251 | 677 | 805 | 29 | | 90 | X | O | 412 | 217 | 742 | 26 |
| 11 | X | O | 264 | 622 | 793 | 34 | | 91 | X | O | 436 | 215 | 731 | 35 |
| 12 | X | O | 382 | 575 | 691 | 41 | | 92 | X | O | 508 | 290 | 717 | 34 |
| 13 | X | O | 253 | 648 | 803 | 33 | | 93 | X | O | 338 | 185 | 768 | 33 |
| 14 | X | O | 436 | 463 | 825 | 37 | | 94 | X | O | 321 | 241 | 830 | 40 |
| 15 | X | O | 238 | 558 | 860 | 35 | | 95 | X | O | 538 | 396 | 571 | 45 |
| 16 | X | O | 289 | 499 | 805 | 35 | | 96 | X | O | 417 | 214 | 813 | 37 |
| 17 | X | O | 340 | 504 | 632 | 42 | | 97 | X | O | 379 | 410 | 813 | 49 |
| 18 | X | O | 408 | 504 | 983 | 37 | | 98 | X | O | 511 | 398 | 703 | 32 |
| 19 | X | O | 311 | 420 | 800 | 34 | | 99 | X | O | 499 | 231 | 749 | 36 |
| 20 | X | O | 464 | 528 | 890 | 32 | | 100 | X | O | 483 | 210 | 753 | 44 |
| 21 | X | O | 303 | 470 | 971 | 35 | | 101 | X | O | 452 | 206 | 751 | 46 |
| 22 | X | O | 327 | 482 | 697 | 36 | | 102 | X | O | 514 | 375 | 720 | 41 |
| 23 | X | O | 245 | 560 | 810 | 33 | | 103 | X | O | 324 | 323 | 645 | 43 |
| 24 | X | O | 266 | 685 | 826 | 38 | | 104 | X | O | 503 | 186 | 665 | 40 |
| 25 | X | O | 445 | 650 | 849 | 40 | | 105 | X | O | 357 | 191 | 664 | 32 |
| 26 | X | O | 380 | 380 | 825 | 43 | | 106 | X | O | 519 | 310 | 731 | 40 |
| 27 | X | O | 285 | 435 | 828 | 33 | | 107 | X | O | 523 | 231 | 762 | 41 |
| 28 | X | O | 436 | 461 | 863 | 45 | | 108 | X | O | 344 | 171 | 706 | 46 |
| 29 | X | O | 441 | 473 | 795 | 43 | | 109 | X | O | 419 | 190 | 747 | 41 |
| 30 | X | O | 273 | 658 | 937 | 46 | | 110 | X | O | 492 | 435 | 765 | 42 |
| 31 | X | O | 300 | 794 | 684 | 42 | | 111 | X | O | 371 | 171 | 640 | 42 |
| 32 | X | O | 459 | 560 | 966 | 49 | | 112 | X | O | 549 | 365 | 578 | 40 |
| 33 | X | O | 281 | 707 | 863 | 42 | | 113 | X | O | 360 | 403 | 734 | 41 |
| 34 | X | O | 279 | 445 | 746 | 46 | | 114 | X | O | 456 | 228 | 524 | 43 |
| 35 | X | O | 402 | 419 | 787 | 42 | | 115 | X | O | 442 | 245 | 539 | 40 |
| 36 | X | O | 274 | 424 | 849 | 46 | | 116 | X | O | 555 | 379 | 531 | 43 |
| 37 | X | O | 300 | 681 | 955 | 50 | | 117 | X | O | 494 | 411 | 783 | 41 |
| 38 | X | O | 311 | 432 | 774 | 38 | | 118 | X | O | 367 | 376 | 747 | 38 |
| 39 | X | O | 258 | 525 | 799 | 44 | | 119 | X | O | 533 | 378 | 741 | 43 |
| 40 | X | O | 454 | 502 | 780 | 39 | | 120 | X | O | 387 | 168 | 678 | 45 |
| 41 | X | O | 428 | 397 | 794 | 51 | | 121 | X | O | 539 | 399 | 678 | 45 |
| 42 | X | O | 343 | 682 | 938 | 38 | | 122 | X | O | 520 | 355 | 699 | 43 |
| 43 | X | O | 446 | 474 | 752 | 37 | | 123 | X | O | 426 | 253 | 832 | 38 |
| 44 | X | O | 251 | 504 | 742 | 43 | | 124 | X | O | 432 | 153 | 607 | 57 |
| 45 | X | O | 224 | 507 | 923 | 45 | | 125 | X | O | 484 | 153 | 659 | 45 |
| 46 | X | O | 461 | 458 | 828 | 45 | | 126 | X | O | 413 | 498 | 619 | 43 |
| 47 | X | O | 478 | 413 | 801 | 42 | | 127 | X | O | 411 | 172 | 767 | 47 |
| 48 | X | O | 440 | 473 | 888 | 40 | | 128 | X | O | 390 | 241 | 552 | 55 |
| 49 | X | O | 381 | 660 | 812 | 42 | | 129 | X | O | 519 | 380 | 765 | 38 |
| 50 | X | O | 256 | 476 | 907 | 46 | | 130 | X | O | 479 | 222 | 533 | 44 |
| 51 | X | O | 287 | 451 | 890 | 46 | | 131 | X | O | 357 | 447 | 731 | 38 |
| 52 | X | O | 478 | 462 | 813 | 57 | | 132 | X | O | 404 | 174 | 790 | 51 |
| 53 | X | O | 317 | 610 | 1045 | 49 | | 133 | X | O | 358 | 383 | 712 | 43 |
| 54 | X | O | 281 | 479 | 893 | 41 | | 134 | X | O | 462 | 472 | 772 | 47 |
| 55 | X | O | 460 | 556 | 939 | 51 | | 135 | X | O | 482 | 222 | 823 | 46 |
| 56 | X | O | 491 | 508 | 786 | 50 | | 160 | X | O | 535 | 528 | 568 | 40 |
| 57 | X | O | 248 | 734 | 681 | 50 | | 161 | X | O | 625 | 515 | 611 | 38 |
| 58 | X | O | 270 | 458 | 827 | 47 | | 162 | X | O | 542 | 474 | 632 | 36 |
| 59 | X | O | 261 | 517 | 827 | 51 | | 163 | X | O | 729 | 371 | 499 | 37 |
| 60 | X | O | 266 | 491 | 791 | 46 | | 164 | X | O | 627 | 378 | 655 | 40 |
| 61 | X | O | 401 | 664 | 797 | 44 | | 165 | X | O | 666 | 475 | 436 | 38 |
| 62 | X | O | 479 | 556 | 833 | 44 | | 166 | X | O | 626 | 482 | 412 | 42 |
| 63 | X | O | 419 | 654 | 779 | 46 | | 167 | X | O | 682 | 396 | 390 | 36 |
| 64 | X | O | 270 | 490 | 870 | 54 | | 168 | X | O | 645 | 457 | 410 | 45 |
| 65 | X | O | 378 | 391 | 961 | 52 | | 169 | X | O | 706 | 447 | 617 | 43 |
| 66 | X | O | 247 | 536 | 877 | 50 | | 170 | X | O | 749 | 400 | 480 | 47 |
| 67 | X | O | 292 | 590 | 657 | 62 | | 171 | X | O | 736 | 441 | 413 | 42 |
| 68 | X | O | 457 | 491 | 872 | 56 | | 172 | X | O | 732 | 190 | 457 | 46 |
| 69 | X | O | 328 | 697 | 951 | 46 | | 173 | X | O | 620 | 442 | 617 | 38 |
| 70 | X | O | 236 | 538 | 716 | 52 | | 174 | X | O | 709 | 334 | 292 | 52 |
| 71 | X | O | 475 | 551 | 881 | 49 | | 175 | X | O | 742 | 276 | 626 | 37 |
| 72 | X | O | 308 | 660 | 995 | 49 | | 176 | X | O | 719 | 269 | 639 | 43 |
| 73 | X | O | 490 | 512 | 815 | 48 | | 177 | X | O | 644 | 432 | 624 | 36 |
| 74 | X | O | 464 | 533 | 923 | 49 | | 178 | X | O | 724 | 198 | 522 | 47 |
| 75 | X | O | 262 | 430 | 870 | 58 | | 179 | X | O | 601 | 428 | 455 | 39 |
| 76 | X | O | 390 | 218 | 725 | 26 | | 180 | X | O | 639 | 528 | 572 | 41 |
| 77 | X | O | 335 | 427 | 763 | 27 | | 181 | X | O | 546 | 395 | 646 | 42 |
| 78 | X | O | 425 | 189 | 673 | 29 | | 182 | X | O | 585 | 432 | 512 | 38 |
| 79 | X | O | 499 | 358 | 686 | 30 | | 183 | X | O | 648 | 404 | 375 | 35 |
| 80 | X | O | 378 | 474 | 725 | 30 | | 184 | X | O | 648 | 238 | 624 | 44 |
| 81 | X | O | 435 | 454 | 725 | 28 | | 185 | X | O | 563 | 480 | 536 | 36 |
| 82 | X | O | 400 | 463 | 738 | 26 | | 186 | X | O | 620 | 452 | 646 | 49 |
| 83 | X | O | 328 | 398 | 798 | 31 | | 187 | X | O | 727 | 409 | 565 | 37 |
| 84 | X | O | 288 | 223 | 745 | 38 | | 188 | X | O | 746 | 382 | 459 | 44 |
| 85 | X | O | 423 | 375 | 829 | 33 | | 189 | X | O | 662 | 341 | 717 | 53 |
| 86 | X | O | 368 | 342 | 753 | 35 | | 190 | X | O | 581 | 461 | 497 | 42 |
| 87 | X | O | 360 | 315 | 745 | 29 | | 191 | X | O | 789 | 397 | 595 | 53 |
| 88 | X | O | 334 | 242 | 724 | 30 | | 192 | X | O | 596 | 378 | 368 | 42 |
| 89 | X | O | 346 | 468 | 713 | 32 | | 193 | X | O | 628 | 389 | 364 | 41 |

| | | | | | | | | | | | | | |
|---|---|---|---|---|---|---|---|---|---|---|---|---|---|
| 194 | X | O | 751 | 449 | 473 | 38 | | 274 | X | O | 272 | 146 | 2 | 34 |
| 195 | X | O | 576 | 438 | 453 | 46 | | 275 | X | O | 318 | 109 | 29 | 47 |
| 196 | X | O | 765 | 426 | 478 | 47 | | 276 | X | O | 415 | 122 | −16 | 40 |
| 197 | X | O | 759 | 463 | 492 | 49 | | 277 | X | O | 393 | 129 | −4 | 40 |
| 198 | X | O | 740 | 447 | 536 | 45 | | 278 | X | O | 362 | 235 | −2 | 37 |
| 199 | X | O | 624 | 536 | 499 | 47 | | 279 | X | O | 467 | 358 | −23 | 37 |
| 200 | X | O | 740 | 263 | 423 | 51 | | 280 | X | O | 384 | 386 | −38 | 41 |
| 201 | X | O | 604 | 410 | 432 | 56 | | 281 | X | O | 448 | 303 | 48 | 47 |
| 202 | X | O | 491 | 516 | 574 | 58 | | 282 | X | O | 322 | 103 | −51 | 44 |
| 203 | X | O | 675 | 277 | 688 | 48 | | 283 | X | O | 414 | 162 | 85 | 52 |
| 204 | X | O | 730 | 465 | 619 | 48 | | 284 | X | O | 361 | 249 | 30 | 33 |
| 205 | X | O | 763 | 225 | 475 | 57 | | 285 | X | O | 502 | 246 | −238 | 42 |
| 206 | X | O | 642 | 520 | 478 | 58 | | 286 | X | O | 384 | 295 | 2 | 33 |
| 207 | X | O | 723 | 378 | 346 | 56 | | 287 | X | O | 479 | 126 | 0 | 45 |
| 208 | X | O | 772 | 380 | 451 | 45 | | 288 | X | O | 561 | 265 | −108 | 45 |
| 209 | X | O | 560 | 541 | 565 | 48 | | 289 | X | O | 382 | 323 | −13 | 44 |
| 210 | X | O | 665 | 536 | 572 | 49 | | 290 | X | O | 358 | 294 | 11 | 46 |
| 211 | X | O | 741 | 423 | 546 | 45 | | 291 | X | O | 498 | 133 | −104 | 51 |
| 212 | X | O | 685 | 239 | 654 | 51 | | 292 | X | O | 374 | 299 | −35 | 48 |
| 213 | X | O | 770 | 312 | 459 | 49 | | 293 | X | O | 519 | 327 | 17 | 47 |
| 214 | X | O | 455 | 418 | 231 | 34 | | 294 | X | O | 394 | 99 | 0 | 49 |
| 215 | X | O | 511 | 411 | 204 | 40 | | 295 | X | O | 513 | 284 | −176 | 45 |
| 216 | X | O | 422 | 472 | 255 | 37 | | 296 | X | O | 512 | 132 | −172 | 44 |
| 217 | X | O | 507 | 374 | 266 | 40 | | 297 | X | O | 498 | 214 | −258 | 46 |
| 218 | X | O | 475 | 380 | 49 | 37 | | 298 | X | O | 388 | 368 | −19 | 46 |
| 219 | X | O | 401 | 391 | −3 | 35 | | 299 | X | O | 361 | 316 | −43 | 58 |
| 220 | X | O | 336 | 425 | 163 | 36 | | 300 | X | O | 513 | 403 | −44 | 53 |
| 221 | X | O | 554 | 395 | 227 | 40 | | 301 | X | O | 374 | 342 | −44 | 51 |
| 222 | X | O | 484 | 382 | 140 | 38 | | 302 | X | O | 527 | 285 | −47 | 46 |
| 223 | X | O | 408 | 415 | 236 | 43 | | 303 | X | O | 334 | 97 | −106 | 51 |
| 224 | X | O | 496 | 340 | 21 | 40 | | 304 | X | O | 494 | 130 | −214 | 57 |
| 225 | X | O | 345 | 446 | 92 | 35 | | 305 | X | O | 510 | 311 | −240 | 43 |
| 226 | X | O | 405 | 328 | 64 | 44 | | 306 | X | O | 378 | 262 | 7 | 45 |
| 227 | X | O | 471 | 371 | 75 | 34 | | 307 | X | O | 477 | 170 | −236 | 48 |
| 228 | X | O | 512 | 450 | 173 | 45 | | 308 | X | O | 469 | 277 | 51 | 55 |
| 229 | X | O | 484 | 349 | 126 | 37 | | 309 | X | O | 311 | 169 | 89 | 46 |
| 230 | X | O | 469 | 368 | 111 | 41 | | 310 | X | O | 336 | 238 | −58 | 46 |
| 231 | X | O | 291 | 433 | −5 | 43 | | 311 | X | O | 523 | 319 | −208 | 51 |
| 232 | X | O | 483 | 405 | 66 | 43 | | 312 | X | O | 554 | 279 | −74 | 51 |
| 233 | X | O | 517 | 303 | 219 | 45 | | 313 | X | O | 555 | 295 | −46 | 54 |
| 234 | X | O | 301 | 556 | 73 | 41 | | 314 | X | O | 530 | 263 | −31 | 45 |
| 235 | X | O | 433 | 401 | 236 | 41 | | 315 | X | O | 338 | 207 | 44 | 45 |
| 236 | X | O | 435 | 374 | −11 | 31 | | 316 | X | O | 614 | 411 | 358 | 35 |
| 237 | X | O | 457 | 383 | −24 | 36 | | 317 | X | O | 685 | 492 | 365 | 38 |
| 238 | X | O | 345 | 399 | 225 | 39 | | 318 | X | O | 555 | 496 | 297 | 30 |
| 239 | X | O | 499 | 307 | 53 | 42 | | 319 | X | O | 691 | 551 | 350 | 35 |
| 240 | X | O | 422 | 327 | 245 | 52 | | 320 | X | O | 713 | 443 | 401 | 34 |
| 241 | X | O | 489 | 479 | 250 | 42 | | 321 | X | O | 670 | 391 | 366 | 37 |
| 242 | X | O | 496 | 342 | 172 | 42 | | 322 | X | O | 719 | 551 | 294 | 37 |
| 243 | X | O | 367 | 403 | −54 | 52 | | 323 | X | O | 554 | 633 | 330 | 47 |
| 244 | X | O | 369 | 459 | 284 | 62 | | 324 | X | O | 526 | 630 | 346 | 50 |
| 245 | X | O | 339 | 360 | 23 | 45 | | 325 | X | O | 639 | 646 | 321 | 37 |
| 246 | X | O | 300 | 342 | −25 | 61 | | 326 | X | O | 615 | 644 | 309 | 42 |
| 247 | X | O | 314 | 376 | 2 | 53 | | 327 | X | O | 511 | 467 | 188 | 35 |
| 248 | X | O | 496 | 359 | 82 | 40 | | 328 | X | O | 499 | 514 | 256 | 43 |
| 249 | X | O | 295 | 468 | 133 | 45 | | 329 | X | O | 662 | 640 | 305 | 44 |
| 250 | X | O | 368 | 347 | −10 | 46 | | 330 | X | O | 520 | 432 | 182 | 42 |
| 251 | X | O | 477 | 504 | 268 | 45 | | 331 | X | O | 542 | 464 | 321 | 46 |
| 252 | X | O | 380 | 329 | 76 | 48 | | 332 | X | O | 720 | 578 | 286 | 43 |
| 253 | X | O | 534 | 488 | 117 | 57 | | 333 | X | O | 528 | 455 | 76 | 38 |
| 254 | X | O | 499 | 396 | 81 | 49 | | 334 | X | O | 580 | 433 | 395 | 44 |
| 255 | X | O | 414 | 308 | 209 | 54 | | 335 | X | O | 517 | 567 | 159 | 43 |
| 256 | X | O | 293 | 464 | −35 | 51 | | 336 | X | O | 720 | 615 | 317 | 40 |
| 257 | X | O | 424 | 293 | 118 | 62 | | 337 | X | O | 711 | 496 | 176 | 45 |
| 258 | X | O | 393 | 397 | 251 | 45 | | 338 | X | O | 510 | 436 | 145 | 39 |
| 259 | X | O | 312 | 550 | 43 | 49 | | 339 | X | O | 626 | 657 | 247 | 39 |
| 260 | X | O | 429 | 400 | 263 | 47 | | 340 | X | O | 721 | 594 | 264 | 45 |
| 261 | X | O | 325 | 414 | 78 | 46 | | 341 | X | O | 545 | 567 | 311 | 36 |
| 262 | X | O | 383 | 531 | 300 | 56 | | 342 | X | O | 716 | 476 | 426 | 38 |
| 263 | X | O | 361 | 394 | 248 | 51 | | 343 | X | O | 613 | 574 | 130 | 44 |
| 264 | X | O | 493 | 358 | 149 | 43 | | 344 | X | O | 536 | 487 | 330 | 45 |
| 265 | X | O | 396 | 99 | −74 | 39 | | 345 | X | O | 505 | 459 | 259 | 38 |
| 266 | X | O | 371 | 135 | −22 | 32 | | 346 | X | O | 686 | 527 | 362 | 42 |
| 267 | X | O | 318 | 164 | −19 | 34 | | 347 | X | O | 697 | 550 | 380 | 40 |
| 268 | X | O | 416 | 387 | −24 | 37 | | 348 | X | O | 717 | 619 | 253 | 42 |
| 269 | X | O | 399 | 126 | 67 | 43 | | 349 | X | O | 690 | 462 | 360 | 46 |
| 270 | X | O | 364 | 353 | 16 | 35 | | 350 | X | O | 500 | 404 | 320 | 48 |
| 271 | X | O | 483 | 250 | −258 | 41 | | 351 | X | O | 705 | 394 | 356 | 47 |
| 272 | X | O | 508 | 249 | −63 | 39 | | 352 | X | O | 600 | 499 | 412 | 47 |
| 273 | X | O | 500 | 180 | −33 | 40 | | 353 | X | O | 736 | 485 | 278 | 39 |

-continued

| | | | | | | |
|---|---|---|---|---|---|---|
| 354 | X | O | 504 | 534 | 270 | 45 |
| 355 | X | O | 648 | 453 | 165 | 47 |
| 356 | X | O | 580 | 358 | 353 | 50 |
| 357 | X | O | 633 | 665 | 390 | 51 |
| 358 | X | O | 699 | 672 | 202 | 56 |
| 359 | X | O | 539 | 472 | 143 | 47 |
| 360 | X | O | 519 | 491 | 352 | 50 |
| 361 | X | O | 633 | 673 | 319 | 48 |
| 362 | X | O | 515 | 599 | 170 | 59 |
| 363 | X | O | 526 | 457 | 128 | 57 |
| 364 | X | O | 748 | 526 | 233 | 51 |
| 365 | X | O | 733 | 537 | 271 | 51 |
| 366 | X | O | 760 | 633 | 316 | 54 |
| 367 | X | O | 708 | 445 | 332 | 46 |
| 368 | X | O | 480 | 582 | 293 | 56 |
| 369 | X | O | 711 | 499 | 375 | 45 |
| 370 | X | O | 532 | 505 | 307 | 51 |
| 371 | X | O | 511 | 455 | 294 | 49 |
| 372 | X | O | 368 | 556 | 1004 | 38 |
| 373 | X | O | 387 | 484 | 986 | 41 |
| 374 | X | O | 360 | 497 | 986 | 44 |
| 375 | X | O | 455 | 566 | 681 | 52 |

Example 10

Crystallographic Analysis of Ground Based Experiments (Form 2)

Prior to data collection, crystals were washed with the reservoir solution of the crystallization setup and transferred into the same solution with 20% glycerol added. The crystals were then flash-cooled in liquid nitrogen. X-ray diffraction was collected using a synchrotron radiation at the IMCA-CAT beam line ID17 equipped with an ADCS detector. Data were integrated and scaled using the HKL package.

| Data collection statistics: | |
|---|---|
| Resolution | 20.0 – 2.02 Å |
| No. of collected reflections | 273773 |
| No. of unique reflections (F >= 0) | 44617 |
| R-sym | 6.8% |
| Percent of theoretical (I/s >= 1) | 97.9% |
| Unit Cell | a = 114.7 Å, b = 98.4 Å, c = 62.4 Å, $\alpha = 90°, \beta = 93.9°, \gamma = 90°$ |
| Space Group | C2 |
| Asymmetric unit | 3 molecules |

Example 11

Structure Determination of Ground Based Derived Crystals (Form2)

The crystal structure was solved using molecular replacement using the search models 1RH2 from the PDB. Refinement was done using the program Refmac.

TABLE 4

Atomic Coordinates of $Zn^{2+}$ Complexed Interferon Alpha 2b Dimer-Crystal Form $C_2$

| | |
|---|---|
| Resolution Limits | 20.0 – 2.02 Å |
| Number of unobserved reflections | 1517 (2.3%) |
| Number of reflections in working set | 43731 (97.7%) |
| Number of reflections in test set | 886 (4.9%) |
| Number of protein residues | 437 |
| Number of solvent atoms | 183 |

TABLE 4-continued

Atomic Coordinates of $Zn^{2+}$ Complexed Interferon Alpha 2b Dimer-Crystal Form $C_2$

| | |
|---|---|
| Number of ions | 3 zinc ions |
| R-factor | 0.196 |
| R-free | 0.22.9 |
| RMSD bond length | 0.025 Å |
| RMSD bond angles | 1.86° |

The following table contains one line for each atom of the three alpha-interferon monomers, four zinc atoms and 186 water molecules in the asymmetric unit of the C-centered monoclinic space group. The three monomers are listed sequentially with the first monomer containing residues from 2 to 157 of SEQ ID NO:1, the second monomer from 6 to 160 of SEQ ID NO:1, and the third monomer from 7 to 156 of SEQ ID NO:1. The following 4 atom are the zinc atoms and at the end 186 water molecules are listed. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor.

| | | | | | | |
|---|---|---|---|---|---|---|
| 2 | A | N | 164 | −221 | 317 | 85 |
| 2 | A | CA | 167 | −207 | 313 | 85 |
| 2 | A | CB | 158 | −196 | 320 | 85 |
| 2 | A | C | 182 | −203 | 313 | 85 |
| 2 | A | O | 190 | −209 | 306 | 84 |
| 3 | L | N | 185 | −191 | 319 | 84 |
| 3 | L | CA | 196 | −182 | 315 | 84 |
| 3 | L | CB | 191 | −168 | 316 | 84 |
| 3 | L | CG | 178 | −165 | 309 | 82 |
| 3 | L | CD1 | 168 | −157 | 319 | 80 |
| 3 | L | CD2 | 180 | −157 | 296 | 80 |
| 3 | L | C | 210 | −184 | 319 | 84 |
| 3 | L | O | 213 | −191 | 329 | 84 |
| 4 | P | N | 220 | −177 | 313 | 85 |
| 4 | P | CA | 234 | −177 | 317 | 84 |
| 4 | P | CB | 240 | −166 | 307 | 85 |
| 4 | P | CG | 231 | −166 | 295 | 85 |
| 4 | P | CD | 217 | −168 | 301 | 85 |
| 4 | P | C | 237 | −173 | 331 | 84 |
| 4 | P | O | 228 | −166 | 337 | 84 |
| 5 | A | N | 248 | −177 | 336 | 84 |
| 5 | A | CA | 253 | −172 | 349 | 83 |
| 5 | A | CB | 267 | −178 | 353 | 84 |
| 5 | A | C | 253 | −157 | 350 | 83 |
| 5 | A | O | 249 | −151 | 360 | 83 |
| 6 | T | N | 258 | −151 | 339 | 82 |
| 6 | T | CA | 260 | −136 | 337 | 80 |
| 6 | T | CB | 271 | −134 | 326 | 80 |
| 6 | T | OG1 | 274 | −120 | 324 | 81 |
| 6 | T | CG2 | 267 | −140 | 313 | 81 |
| 6 | T | C | 248 | −127 | 335 | 78 |
| 6 | T | O | 250 | −114 | 334 | 78 |
| 7 | H | N | 236 | −132 | 335 | 75 |
| 7 | H | CA | 224 | −125 | 332 | 72 |
| 7 | H | CB | 212 | −133 | 327 | 72 |
| 7 | H | CG | 201 | −126 | 320 | 74 |
| 7 | H | ND1 | 202 | −121 | 307 | 74 |
| 7 | H | CE1 | 191 | −115 | 303 | 75 |
| 7 | H | NE2 | 183 | −115 | 314 | 76 |
| 7 | H | CD2 | 189 | −122 | 324 | 75 |
| 7 | H | C | 218 | −115 | 343 | 70 |
| 7 | H | O | 216 | −103 | 340 | 70 |
| 8 | S | N | 216 | −119 | 356 | 66 |
| 8 | S | CA | 211 | −109 | 365 | 62 |
| 8 | S | CB | 206 | −115 | 378 | 63 |
| 8 | S | OG | 197 | −105 | 384 | 63 |
| 8 | S | C | 221 | −98 | 368 | 59 |
| 8 | S | O | 217 | −86 | 371 | 57 |
| 9 | L | N | 234 | −101 | 366 | 56 |
| 9 | L | CA | 244 | −90 | 365 | 55 |
| 9 | L | CB | 258 | −96 | 364 | 57 |

| | | | | | | |
|---|---|---|---|---|---|---|
| 9 | L | CG | 270 | −86 | 364 | 61 |
| 9 | L | CD1 | 269 | −75 | 375 | 63 |
| 9 | L | CD2 | 283 | −94 | 365 | 64 |
| 9 | L | C | 241 | −80 | 354 | 53 |
| 9 | L | O | 243 | −68 | 355 | 51 |
| 10 | G | N | 236 | −85 | 342 | 50 |
| 10 | G | CA | 234 | −76 | 331 | 47 |
| 10 | G | C | 222 | −67 | 333 | 45 |
| 10 | G | O | 222 | −55 | 328 | 45 |
| 11 | S | N | 212 | −72 | 340 | 43 |
| 11 | S | CA | 201 | −65 | 344 | 43 |
| 11 | S | CB | 191 | −76 | 348 | 43 |
| 11 | S | OG | 184 | −72 | 360 | 50 |
| 11 | S | C | 205 | −54 | 355 | 41 |
| 11 | S | O | 201 | −43 | 354 | 40 |
| 12 | R | N | 214 | −58 | 364 | 40 |
| 12 | R | CA | 218 | −48 | 373 | 41 |
| 12 | R | CB | 225 | −54 | 385 | 42 |
| 12 | R | CG | 215 | −62 | 394 | 47 |
| 12 | R | CD | 220 | −65 | 408 | 56 |
| 12 | R | NE | 233 | −72 | 406 | 65 |
| 12 | R | CZ | 235 | −85 | 408 | 69 |
| 12 | R | NH1 | 225 | −93 | 412 | 74 |
| 12 | R | NH2 | 248 | −90 | 407 | 69 |
| 12 | R | C | 227 | −37 | 366 | 40 |
| 12 | R | O | 226 | −25 | 370 | 39 |
| 13 | R | N | 235 | −40 | 356 | 38 |
| 13 | R | CA | 243 | −30 | 349 | 39 |
| 13 | R | CB | 253 | −37 | 339 | 40 |
| 13 | R | CG | 265 | −43 | 346 | 48 |
| 13 | R | CD | 276 | −50 | 337 | 58 |
| 13 | R | NE | 271 | −58 | 325 | 62 |
| 13 | R | CZ | 271 | −71 | 325 | 66 |
| 13 | R | NH1 | 275 | −79 | 335 | 68 |
| 13 | R | NH2 | 266 | −77 | 314 | 65 |
| 13 | R | C | 234 | −21 | 341 | 37 |
| 13 | R | O | 236 | −9 | 339 | 37 |
| 14 | T | N | 223 | −27 | 336 | 35 |
| 14 | T | CA | 213 | −18 | 329 | 34 |
| 14 | T | CB | 202 | −28 | 323 | 34 |
| 14 | T | OG1 | 208 | −36 | 313 | 37 |
| 14 | T | CG2 | 192 | −20 | 315 | 35 |
| 14 | T | C | 206 | −7 | 338 | 32 |
| 14 | T | O | 205 | 4 | 334 | 31 |
| 15 | L | N | 202 | −11 | 350 | 31 |
| 15 | L | CA | 196 | −2 | 359 | 32 |
| 15 | L | CB | 191 | −9 | 372 | 31 |
| 15 | L | CG | 178 | −17 | 370 | 37 |
| 15 | L | CD1 | 176 | −25 | 383 | 39 |
| 15 | L | CD2 | 167 | −8 | 368 | 33 |
| 15 | L | C | 206 | 9 | 364 | 31 |
| 15 | L | O | 203 | 20 | 365 | 30 |
| 16 | M | N | 219 | 4 | 366 | 30 |
| 16 | M | CA | 230 | 14 | 369 | 33 |
| 16 | M | CB | 243 | 7 | 371 | 33 |
| 16 | M | CG | 254 | 17 | 377 | 39 |
| 16 | M | SD | 269 | 8 | 380 | 46 |
| 16 | M | CE | 280 | 20 | 387 | 45 |
| 16 | M | C | 231 | 25 | 358 | 32 |
| 16 | M | O | 233 | 37 | 361 | 32 |
| 17 | L | N | 231 | 21 | 346 | 32 |
| 17 | L | CA | 233 | 30 | 335 | 32 |
| 17 | L | CB | 235 | 23 | 321 | 32 |
| 17 | L | CG | 249 | 16 | 320 | 34 |
| 17 | L | CD1 | 249 | 6 | 308 | 34 |
| 17 | L | CD2 | 260 | 26 | 317 | 38 |
| 17 | L | C | 221 | 40 | 334 | 32 |
| 17 | L | O | 223 | 52 | 331 | 31 |
| 18 | L | N | 209 | 35 | 335 | 30 |
| 18 | L | CA | 197 | 44 | 336 | 32 |
| 18 | L | CB | 184 | 36 | 337 | 33 |
| 18 | L | CG | 178 | 31 | 324 | 36 |
| 18 | L | CD1 | 169 | 18 | 328 | 35 |
| 18 | L | CD2 | 171 | 42 | 317 | 33 |
| 18 | L | C | 198 | 54 | 348 | 31 |
| 18 | L | O | 194 | 65 | 346 | 30 |
| 19 | A | N | 203 | 49 | 359 | 31 |
| 19 | A | CA | 204 | 58 | 371 | 31 |
| 19 | A | CB | 208 | 49 | 383 | 30 |
| 19 | A | C | 215 | 69 | 369 | 31 |
| 19 | A | O | 213 | 80 | 373 | 33 |
| 20 | Q | N | 225 | 65 | 361 | 31 |
| 20 | Q | CA | 236 | 75 | 358 | 31 |
| 20 | Q | CB | 249 | 67 | 353 | 32 |
| 20 | Q | CG | 255 | 60 | 366 | 31 |
| 20 | Q | CD | 267 | 51 | 362 | 41 |
| 20 | Q | OE1 | 268 | 46 | 351 | 42 |
| 20 | Q | NE2 | 276 | 50 | 371 | 44 |
| 20 | Q | C | 232 | 84 | 346 | 31 |
| 20 | Q | O | 238 | 95 | 345 | 31 |
| 21 | M | N | 222 | 81 | 338 | 31 |
| 21 | M | CA | 217 | 90 | 327 | 32 |
| 21 | M | CB | 208 | 82 | 318 | 32 |
| 21 | M | CG | 216 | 74 | 307 | 32 |
| 21 | M | SD | 208 | 60 | 298 | 40 |
| 21 | M | CE | 194 | 70 | 294 | 34 |
| 21 | M | C | 209 | 101 | 333 | 32 |
| 21 | M | O | 208 | 111 | 326 | 33 |
| 22 | R | N | 203 | 99 | 344 | 32 |
| 22 | R | CA | 195 | 110 | 351 | 32 |
| 22 | R | CB | 192 | 106 | 365 | 34 |
| 22 | R | CG | 180 | 115 | 370 | 34 |
| 22 | R | CD | 177 | 117 | 385 | 43 |
| 22 | R | NE | 184 | 129 | 390 | 39 |
| 22 | R | CZ | 181 | 136 | 401 | 38 |
| 22 | R | NH1 | 171 | 135 | 410 | 38 |
| 22 | R | NH2 | 190 | 146 | 403 | 36 |
| 22 | R | C | 202 | 123 | 351 | 35 |
| 22 | R | O | 214 | 124 | 355 | 35 |
| 23 | R | N | 195 | 134 | 347 | 35 |
| 23 | R | CA | 200 | 147 | 346 | 37 |
| 23 | R | CB | 199 | 153 | 333 | 38 |
| 23 | R | CG | 208 | 146 | 323 | 40 |
| 23 | R | CD | 206 | 154 | 310 | 49 |
| 23 | R | NE | 216 | 149 | 300 | 55 |
| 23 | R | CZ | 217 | 155 | 288 | 62 |
| 23 | R | NH1 | 209 | 166 | 285 | 60 |
| 23 | R | NH2 | 226 | 150 | 279 | 59 |
| 23 | R | C | 193 | 156 | 356 | 37 |
| 23 | R | O | 199 | 165 | 362 | 38 |
| 24 | I | N | 180 | 155 | 356 | 35 |
| 24 | I | CA | 172 | 163 | 365 | 34 |
| 24 | I | CB | 163 | 174 | 357 | 33 |
| 24 | I | CG1 | 153 | 167 | 347 | 31 |
| 24 | I | CD1 | 144 | 177 | 340 | 37 |
| 24 | I | CG2 | 172 | 184 | 349 | 35 |
| 24 | I | C | 162 | 155 | 373 | 34 |
| 24 | I | O | 161 | 143 | 370 | 34 |
| 25 | S | N | 156 | 161 | 383 | 33 |
| 25 | S | CA | 148 | 155 | 392 | 33 |
| 25 | S | CB | 147 | 163 | 405 | 33 |
| 25 | S | OG | 138 | 156 | 415 | 33 |
| 25 | S | C | 134 | 153 | 387 | 32 |
| 25 | S | O | 128 | 162 | 382 | 31 |
| 26 | L | N | 128 | 141 | 389 | 32 |
| 26 | L | CA | 114 | 139 | 386 | 35 |
| 26 | L | CB | 111 | 124 | 390 | 34 |
| 26 | L | CG | 97 | 120 | 387 | 43 |
| 26 | L | CD1 | 97 | 120 | 372 | 44 |
| 26 | L | CD2 | 93 | 107 | 394 | 46 |
| 26 | L | C | 105 | 149 | 394 | 35 |
| 26 | L | O | 93 | 152 | 390 | 35 |
| 27 | F | N | 109 | 153 | 406 | 36 |
| 27 | F | CA | 102 | 162 | 415 | 36 |
| 27 | F | CB | 106 | 161 | 429 | 34 |
| 27 | F | CG | 101 | 149 | 436 | 36 |
| 27 | F | CD1 | 89 | 148 | 442 | 38 |
| 27 | F | CE1 | 84 | 137 | 447 | 39 |
| 27 | F | CZ | 92 | 125 | 446 | 37 |
| 27 | F | CE2 | 104 | 126 | 440 | 34 |
| 27 | F | CD2 | 109 | 137 | 435 | 33 |
| 27 | F | C | 103 | 177 | 409 | 35 |
| 27 | F | O | 95 | 185 | 414 | 38 |
| 28 | S | N | 112 | 180 | 400 | 36 |
| 28 | S | CA | 111 | 192 | 393 | 39 |
| 28 | S | CB | 125 | 196 | 388 | 39 |
| 28 | S | OG | 135 | 194 | 398 | 44 |
| 28 | S | C | 102 | 192 | 381 | 39 |
| 28 | S | O | 101 | 201 | 373 | 38 |
| 29 | C | N | 95 | 180 | 379 | 39 |

| | | | | | | | | | | | | | |
|---|---|---|---|---|---|---|---|---|---|---|---|---|---|
| 29 | C | CA | 87 | 178 | 367 | 38 | 38 | F | CZ | 67 | -40 | 327 | 31 |
| 29 | C | CB | 94 | 166 | 359 | 39 | 38 | F | CE2 | 62 | -37 | 340 | 30 |
| 29 | C | SG | 111 | 170 | 354 | 45 | 38 | F | CD2 | 53 | -27 | 343 | 29 |
| 29 | C | C | 73 | 173 | 371 | 38 | 38 | F | C | 19 | -21 | 330 | 29 |
| 29 | C | O | 67 | 166 | 363 | 36 | 38 | F | O | 15 | -23 | 342 | 29 |
| 30 | L | N | 68 | 177 | 382 | 37 | 39 | P | N | 19 | -31 | 321 | 29 |
| 30 | L | CA | 55 | 171 | 386 | 39 | 39 | P | CA | 12 | -44 | 324 | 29 |
| 30 | L | CB | 51 | 174 | 400 | 38 | 39 | P | CB | 9 | -49 | 310 | 30 |
| 30 | L | CG | 61 | 169 | 411 | 42 | 39 | P | CG | 20 | -43 | 301 | 31 |
| 30 | L | CD1 | 56 | 173 | 425 | 44 | 39 | P | CD | 23 | -29 | 307 | 28 |
| 30 | L | CD2 | 62 | 153 | 410 | 43 | 39 | P | C | 21 | -54 | 331 | 32 |
| 30 | L | C | 43 | 174 | 377 | 39 | 39 | P | O | 26 | -64 | 326 | 31 |
| 30 | L | O | 34 | 166 | 375 | 40 | 40 | Q | N | 24 | -50 | 344 | 33 |
| 31 | K | N | 44 | 186 | 370 | 41 | 40 | Q | CA | 33 | -58 | 353 | 34 |
| 31 | K | CA | 34 | 190 | 361 | 41 | 40 | Q | CB | 35 | -51 | 366 | 35 |
| 31 | K | CB | 36 | 204 | 355 | 42 | 40 | Q | CG | 22 | -50 | 374 | 40 |
| 31 | K | CG | 48 | 205 | 346 | 47 | 40 | Q | CD | 25 | -43 | 388 | 45 |
| 31 | K | CD | 52 | 220 | 343 | 51 | 40 | Q | OE1 | 25 | -31 | 388 | 48 |
| 31 | K | CE | 62 | 221 | 331 | 55 | 40 | Q | NE2 | 28 | -51 | 398 | 49 |
| 31 | K | NZ | 75 | 212 | 332 | 52 | 40 | Q | C | 28 | -72 | 355 | 35 |
| 31 | K | C | 33 | 180 | 349 | 40 | 40 | Q | O | 37 | -82 | 355 | 35 |
| 31 | K | O | 22 | 179 | 343 | 39 | 41 | E | N | 15 | -75 | 354 | 33 |
| 32 | D | N | 44 | 173 | 347 | 37 | 41 | E | CA | 10 | -88 | 354 | 34 |
| 32 | D | CA | 44 | 163 | 336 | 38 | 41 | E | CB | -6 | -88 | 355 | 35 |
| 32 | D | CB | 57 | 164 | 328 | 38 | 41 | E | CG | -13 | -85 | 342 | 35 |
| 32 | D | CG | 59 | 178 | 323 | 42 | 41 | E | CD | -13 | -70 | 338 | 34 |
| 32 | D | OD1 | 50 | 183 | 316 | 44 | 41 | E | OE1 | -7 | -62 | 345 | 34 |
| 32 | D | OD2 | 68 | 185 | 326 | 48 | 41 | E | OE2 | -19 | -67 | 327 | 31 |
| 32 | D | C | 42 | 149 | 340 | 37 | 41 | E | C | 14 | -98 | 343 | 36 |
| 32 | D | O | 43 | 139 | 332 | 37 | 41 | E | O | 15 | -110 | 346 | 36 |
| 33 | R | N | 38 | 146 | 352 | 37 | 42 | E | N | 19 | -93 | 332 | 36 |
| 33 | R | CA | 38 | 133 | 358 | 37 | 42 | E | CA | 25 | -102 | 322 | 37 |
| 33 | R | CB | 36 | 133 | 373 | 36 | 42 | E | CB | 28 | -95 | 309 | 39 |
| 33 | R | CG | 22 | 136 | 378 | 43 | 42 | E | CG | 18 | -87 | 301 | 40 |
| 33 | R | CD | 21 | 139 | 393 | 49 | 42 | E | CD | 4 | -91 | 302 | 44 |
| 33 | R | NE | 11 | 149 | 395 | 60 | 42 | E | OE1 | -1 | -101 | 296 | 45 |
| 33 | R | CZ | -2 | 146 | 397 | 65 | 42 | E | OE2 | -2 | -84 | 310 | 50 |
| 33 | R | NH1 | -5 | 133 | 398 | 67 | 42 | E | C | 38 | -108 | 327 | 40 |
| 33 | R | NH2 | -11 | 155 | 399 | 67 | 42 | E | O | 42 | -117 | 321 | 39 |
| 33 | R | C | 27 | 125 | 350 | 37 | 43 | F | N | 44 | -102 | 336 | 42 |
| 33 | R | O | 17 | 131 | 346 | 36 | 43 | F | CA | 57 | -106 | 342 | 47 |
| 34 | H | N | 29 | 112 | 349 | 35 | 43 | F | CB | 68 | -95 | 342 | 44 |
| 34 | H | CA | 20 | 104 | 340 | 35 | 43 | F | CG | 69 | -87 | 329 | 40 |
| 34 | H | CB | 23 | 107 | 326 | 36 | 43 | F | CD1 | 60 | -77 | 326 | 31 |
| 34 | H | CG | 13 | 101 | 316 | 40 | 43 | F | CE1 | 61 | -70 | 314 | 35 |
| 34 | H | ND1 | 3 | 108 | 310 | 45 | 43 | F | CZ | 72 | -72 | 306 | 34 |
| 34 | H | CE1 | -4 | 100 | 302 | 47 | 43 | F | CE2 | 80 | -82 | 309 | 34 |
| 34 | H | NE2 | 2 | 88 | 303 | 42 | 43 | F | CD2 | 79 | -90 | 320 | 38 |
| 34 | H | CD2 | 13 | 88 | 311 | 39 | 43 | F | C | 55 | -109 | 357 | 53 |
| 34 | H | C | 21 | 89 | 344 | 35 | 43 | F | O | 57 | -99 | 365 | 56 |
| 34 | H | O | 32 | 85 | 345 | 34 | 44 | G | N | 50 | -120 | 360 | 55 |
| 35 | D | N | 10 | 83 | 345 | 33 | 44 | G | CA | 47 | -123 | 374 | 60 |
| 35 | D | CA | 10 | 68 | 347 | 33 | 44 | G | C | 45 | -137 | 376 | 63 |
| 35 | D | CB | -2 | 65 | 357 | 34 | 44 | G | O | 46 | -145 | 366 | 63 |
| 35 | D | CG | -1 | 50 | 362 | 37 | 45 | N | N | 42 | -141 | 388 | 67 |
| 35 | D | OD1 | -6 | 47 | 373 | 38 | 45 | N | CA | 41 | -155 | 392 | 70 |
| 35 | D | OD2 | 4 | 40 | 355 | 36 | 45 | N | CB | 45 | -157 | 407 | 71 |
| 35 | D | C | 7 | 61 | 334 | 32 | 45 | N | CG | 60 | -155 | 409 | 74 |
| 35 | D | O | -4 | 63 | 329 | 29 | 45 | N | OD1 | 68 | -161 | 402 | 79 |
| 36 | F | N | 16 | 53 | 329 | 31 | 45 | N | ND2 | 63 | -146 | 419 | 78 |
| 36 | F | CA | 15 | 47 | 316 | 29 | 45 | N | C | 27 | -161 | 389 | 71 |
| 36 | F | CB | 29 | 46 | 310 | 29 | 45 | N | O | 23 | -171 | 396 | 72 |
| 36 | F | CG | 35 | 59 | 307 | 28 | 46 | Q | N | 21 | -156 | 379 | 72 |
| 36 | F | CD1 | 44 | 64 | 316 | 33 | 46 | Q | CA | 8 | -162 | 374 | 73 |
| 36 | F | CE1 | 51 | 76 | 314 | 28 | 46 | Q | CB | -2 | -151 | 372 | 73 |
| 36 | F | CZ | 48 | 84 | 302 | 33 | 46 | Q | CG | -15 | -154 | 365 | 74 |
| 36 | F | CE2 | 39 | 78 | 292 | 32 | 46 | Q | CD | -23 | -141 | 362 | 75 |
| 36 | F | CD2 | 32 | 66 | 295 | 31 | 46 | Q | OE1 | -28 | -134 | 370 | 73 |
| 36 | F | C | 8 | 34 | 316 | 31 | 46 | Q | NE2 | -25 | -139 | 349 | 76 |
| 36 | F | O | 7 | 27 | 305 | 30 | 46 | Q | C | 12 | -170 | 361 | 74 |
| 37 | G | N | 4 | 29 | 328 | 29 | 46 | Q | O | 3 | -178 | 356 | 74 |
| 37 | G | CA | -3 | 16 | 329 | 28 | 47 | F | N | 24 | -168 | 356 | 74 |
| 37 | G | C | 6 | 4 | 325 | 30 | 47 | F | CA | 29 | -176 | 345 | 74 |
| 37 | G | O | 2 | -4 | 316 | 28 | 47 | F | CB | 31 | -167 | 332 | 74 |
| 38 | F | N | 18 | 4 | 330 | 29 | 47 | F | CG | 19 | -157 | 329 | 74 |
| 38 | F | CA | 26 | -8 | 327 | 29 | 47 | F | CD1 | 8 | -162 | 323 | 75 |
| 38 | F | CB | 39 | -7 | 336 | 27 | 47 | F | CE1 | -3 | -153 | 320 | 77 |
| 38 | F | CG | 49 | -18 | 333 | 30 | 47 | F | CZ | -1 | -139 | 324 | 75 |
| 38 | F | CD1 | 54 | -20 | 320 | 31 | 47 | F | CE2 | 10 | -135 | 331 | 72 |
| 38 | F | CE1 | 63 | -31 | 317 | 31 | 47 | F | CD2 | 20 | -144 | 333 | 72 |

-continued

| | | | | | |
|---|---|---|---|---|---|
| 47 | F | C | 42 | −183 | 348 | 73 |
| 47 | F | O | 49 | −180 | 357 | 72 |
| 48 | G | N | 45 | −193 | 339 | 74 |
| 48 | G | CA | 54 | −204 | 341 | 74 |
| 48 | G | C | 69 | −202 | 345 | 75 |
| 48 | G | O | 75 | −210 | 353 | 76 |
| 49 | A | N | 75 | −192 | 338 | 74 |
| 49 | A | CA | 90 | −188 | 339 | 72 |
| 49 | A | CB | 99 | −198 | 347 | 72 |
| 49 | A | C | 95 | −186 | 324 | 70 |
| 49 | A | O | 99 | −175 | 320 | 70 |
| 50 | A | N | 94 | −197 | 317 | 68 |
| 50 | A | CA | 97 | −196 | 303 | 66 |
| 50 | A | CB | 102 | −210 | 297 | 66 |
| 50 | A | C | 85 | −191 | 295 | 64 |
| 50 | A | O | 86 | −188 | 283 | 64 |
| 51 | E | N | 74 | −189 | 302 | 61 |
| 51 | E | CA | 62 | −183 | 296 | 59 |
| 51 | E | CB | 50 | −185 | 304 | 61 |
| 51 | E | CG | 44 | −199 | 304 | 66 |
| 51 | E | CD | 30 | −200 | 311 | 71 |
| 51 | E | OE1 | 20 | −198 | 304 | 72 |
| 51 | E | OE2 | 30 | −203 | 323 | 72 |
| 51 | E | C | 64 | −168 | 295 | 55 |
| 51 | E | O | 58 | −161 | 286 | 55 |
| 52 | T | N | 72 | −162 | 303 | 50 |
| 52 | T | CA | 74 | −148 | 302 | 47 |
| 52 | T | CB | 73 | −141 | 316 | 48 |
| 52 | T | OG1 | 85 | −144 | 322 | 51 |
| 52 | T | CG2 | 62 | −148 | 324 | 50 |
| 52 | T | C | 87 | −143 | 294 | 43 |
| 52 | T | O | 89 | −131 | 293 | 41 |
| 53 | I | N | 95 | −152 | 290 | 39 |
| 53 | I | CA | 107 | −149 | 281 | 39 |
| 53 | I | CB | 115 | −162 | 277 | 39 |
| 53 | I | CG1 | 121 | −168 | 289 | 43 |
| 53 | I | CD1 | 128 | −158 | 299 | 48 |
| 53 | I | CG2 | 124 | −159 | 265 | 39 |
| 53 | I | C | 102 | −140 | 270 | 36 |
| 53 | I | O | 109 | −131 | 267 | 37 |
| 54 | P | N | 92 | −144 | 262 | 34 |
| 54 | P | CA | 89 | −136 | 250 | 34 |
| 54 | P | CB | 76 | −143 | 245 | 35 |
| 54 | P | CG | 77 | −157 | 250 | 35 |
| 54 | P | CD | 83 | −155 | 264 | 36 |
| 54 | P | C | 85 | −121 | 253 | 33 |
| 54 | P | O | 88 | −112 | 246 | 31 |
| 55 | V | N | 78 | −119 | 264 | 32 |
| 55 | V | CA | 73 | −106 | 268 | 32 |
| 55 | V | CB | 62 | −108 | 279 | 34 |
| 55 | V | CG1 | 68 | −112 | 292 | 36 |
| 55 | V | CG2 | 55 | −96 | 281 | 33 |
| 55 | V | C | 85 | −98 | 274 | 31 |
| 55 | V | O | 86 | −86 | 271 | 30 |
| 56 | L | N | 94 | −104 | 281 | 31 |
| 56 | L | CA | 106 | −98 | 286 | 34 |
| 56 | L | CB | 113 | −107 | 296 | 34 |
| 56 | L | CG | 126 | −100 | 301 | 43 |
| 56 | L | CD1 | 124 | −87 | 309 | 42 |
| 56 | L | CD2 | 134 | −110 | 310 | 46 |
| 56 | L | C | 115 | −94 | 274 | 33 |
| 56 | L | O | 121 | −83 | 274 | 32 |
| 57 | H | N | 116 | −103 | 264 | 32 |
| 57 | H | CA | 123 | −100 | 252 | 31 |
| 57 | H | CB | 124 | −113 | 243 | 30 |
| 57 | H | CG | 131 | −111 | 230 | 32 |
| 57 | H | ND1 | 124 | −106 | 219 | 33 |
| 57 | H | CE1 | 132 | −106 | 209 | 35 |
| 57 | H | NE2 | 144 | −109 | 213 | 35 |
| 57 | H | CD2 | 144 | −113 | 226 | 30 |
| 57 | H | C | 117 | −88 | 245 | 31 |
| 57 | H | O | 124 | −79 | 240 | 30 |
| 58 | E | N | 103 | −88 | 244 | 30 |
| 58 | E | CA | 97 | −76 | 238 | 30 |
| 58 | E | CB | 82 | −78 | 237 | 31 |
| 58 | E | CG | 75 | −66 | 230 | 31 |
| 58 | E | CD | 78 | −65 | 215 | 36 |
| 58 | E | OE1 | 77 | −55 | 209 | 37 |
| 58 | E | OE2 | 79 | −76 | 209 | 38 |
| 58 | E | C | 100 | −63 | 246 | 32 |
| 58 | E | O | 103 | −52 | 239 | 33 |
| 59 | M | N | 100 | −64 | 259 | 29 |
| 59 | M | CA | 103 | −52 | 267 | 31 |
| 59 | M | CB | 103 | −57 | 282 | 31 |
| 59 | M | CG | 106 | −48 | 294 | 39 |
| 59 | M | SD | 92 | −36 | 295 | 46 |
| 59 | M | CE | 100 | −25 | 309 | 38 |
| 59 | M | C | 118 | −46 | 264 | 30 |
| 59 | M | O | 120 | −34 | 262 | 31 |
| 60 | I | N | 127 | −55 | 263 | 30 |
| 60 | I | CA | 141 | −52 | 260 | 32 |
| 60 | I | CB | 150 | −63 | 264 | 32 |
| 60 | I | CG1 | 150 | −65 | 279 | 36 |
| 60 | I | CD1 | 156 | −77 | 284 | 43 |
| 60 | I | CG2 | 165 | −59 | 259 | 34 |
| 60 | I | C | 143 | −46 | 247 | 31 |
| 60 | I | O | 149 | −35 | 245 | 31 |
| 61 | Q | N | 137 | −52 | 237 | 31 |
| 61 | Q | CA | 138 | −47 | 224 | 32 |
| 61 | Q | CB | 131 | −57 | 214 | 32 |
| 61 | Q | CG | 129 | −50 | 200 | 30 |
| 61 | Q | CD | 142 | −51 | 192 | 35 |
| 61 | Q | OE1 | 148 | −61 | 192 | 35 |
| 61 | Q | NE2 | 145 | −40 | 185 | 36 |
| 61 | Q | C | 131 | −33 | 223 | 32 |
| 61 | Q | O | 136 | −24 | 216 | 33 |
| 62 | Q | N | 120 | −31 | 229 | 30 |
| 62 | Q | CA | 113 | −18 | 229 | 29 |
| 62 | Q | CB | 99 | −19 | 236 | 30 |
| 62 | Q | CG | 88 | −27 | 227 | 32 |
| 62 | Q | CD | 86 | −21 | 214 | 36 |
| 62 | Q | OE1 | 87 | −9 | 212 | 40 |
| 62 | Q | NE2 | 83 | −29 | 204 | 38 |
| 62 | Q | C | 121 | −7 | 237 | 29 |
| 62 | Q | O | 121 | 5 | 233 | 28 |
| 63 | I | N | 128 | −11 | 248 | 27 |
| 63 | I | CA | 136 | −1 | 255 | 29 |
| 63 | I | CB | 142 | −7 | 268 | 28 |
| 63 | I | CG1 | 131 | −8 | 279 | 29 |
| 63 | I | CD1 | 135 | −18 | 290 | 30 |
| 63 | I | CG2 | 154 | 1 | 274 | 28 |
| 63 | I | C | 148 | 3 | 245 | 29 |
| 63 | I | O | 151 | 14 | 244 | 29 |
| 64 | F | N | 154 | −7 | 238 | 31 |
| 64 | F | CA | 163 | −4 | 228 | 32 |
| 64 | F | CB | 169 | −17 | 222 | 32 |
| 64 | F | CG | 179 | −13 | 211 | 35 |
| 64 | F | CD1 | 193 | −12 | 213 | 39 |
| 64 | F | CE1 | 202 | −9 | 203 | 45 |
| 64 | F | CZ | 197 | −6 | 190 | 38 |
| 64 | F | CE2 | 184 | −7 | 187 | 40 |
| 64 | F | CD2 | 175 | −10 | 198 | 36 |
| 64 | F | C | 157 | 6 | 217 | 33 |
| 64 | F | O | 163 | 16 | 214 | 34 |
| 65 | N | N | 145 | 3 | 213 | 35 |
| 65 | N | CA | 140 | 11 | 202 | 35 |
| 65 | N | CB | 126 | 7 | 197 | 35 |
| 65 | N | CG | 126 | −7 | 190 | 40 |
| 65 | N | OD1 | 137 | −12 | 186 | 41 |
| 65 | N | ND2 | 114 | −13 | 188 | 40 |
| 65 | N | C | 138 | 26 | 207 | 36 |
| 65 | N | O | 141 | 35 | 200 | 37 |
| 66 | L | N | 133 | 27 | 220 | 32 |
| 66 | L | CA | 131 | 40 | 226 | 33 |
| 66 | L | CB | 124 | 38 | 239 | 32 |
| 66 | L | CG | 121 | 51 | 248 | 33 |
| 66 | L | CD1 | 110 | 60 | 242 | 33 |
| 66 | L | CD2 | 115 | 45 | 262 | 35 |
| 66 | L | C | 143 | 48 | 228 | 32 |
| 66 | L | O | 143 | 60 | 226 | 33 |
| 67 | F | N | 154 | 2 | 232 | 31 |
| 67 | F | CA | 166 | 50 | 236 | 30 |
| 67 | F | CB | 173 | 44 | 248 | 29 |
| 67 | F | CG | 165 | 48 | 261 | 31 |
| 67 | F | CD1 | 156 | 40 | 266 | 32 |
| 67 | F | CE1 | 149 | 43 | 278 | 34 |
| 67 | F | CZ | 151 | 55 | 285 | 32 |
| 67 | F | CE2 | 161 | 64 | 279 | 34 |
| 67 | F | CD2 | 168 | 60 | 267 | 32 |
| 67 | F | C | 176 | 51 | 224 | 33 |

| 67 | F | O | 187 | 57 | 227 | 34 |
| 68 | S | N | 173 | 46 | 213 | 34 |
| 68 | S | CA | 182 | 46 | 201 | 37 |
| 68 | S | CB | 185 | 32 | 196 | 35 |
| 68 | S | OG | 174 | 27 | 189 | 35 |
| 68 | S | C | 178 | 56 | 190 | 39 |
| 68 | S | O | 184 | 56 | 180 | 42 |
| 69 | T | N | 167 | 64 | 193 | 39 |
| 69 | T | CA | 163 | 74 | 184 | 41 |
| 69 | T | CB | 149 | 80 | 187 | 40 |
| 69 | T | OG1 | 149 | 85 | 200 | 38 |
| 69 | T | CG2 | 137 | 69 | 186 | 39 |
| 69 | T | C | 172 | 86 | 184 | 42 |
| 69 | T | O | 181 | 87 | 193 | 42 |
| 70 | A | N | 171 | 95 | 174 | 43 |
| 70 | A | CA | 178 | 107 | 174 | 43 |
| 70 | A | CB | 176 | 114 | 160 | 44 |
| 70 | A | C | 174 | 116 | 185 | 42 |
| 70 | A | O | 181 | 124 | 190 | 42 |
| 71 | D | N | 161 | 116 | 189 | 42 |
| 71 | D | CA | 156 | 123 | 200 | 41 |
| 71 | D | CB | 141 | 121 | 202 | 42 |
| 71 | D | CG | 134 | 125 | 189 | 48 |
| 71 | D | OD1 | 131 | 137 | 187 | 50 |
| 71 | D | OD2 | 131 | 117 | 180 | 49 |
| 71 | D | C | 163 | 119 | 214 | 40 |
| 71 | D | O | 166 | 127 | 222 | 39 |
| 72 | S | N | 165 | 106 | 215 | 38 |
| 72 | S | CA | 172 | 101 | 227 | 38 |
| 72 | S | CB | 171 | 86 | 228 | 36 |
| 72 | S | OG | 179 | 80 | 239 | 37 |
| 72 | S | C | 187 | 105 | 227 | 40 |
| 72 | S | O | 193 | 109 | 237 | 38 |
| 73 | S | N | 193 | 104 | 215 | 40 |
| 73 | S | CA | 207 | 109 | 213 | 43 |
| 73 | S | CB | 212 | 107 | 199 | 44 |
| 73 | S | OG | 216 | 93 | 198 | 46 |
| 73 | S | C | 209 | 124 | 218 | 42 |
| 73 | S | O | 219 | 127 | 223 | 43 |
| 74 | A | N | 199 | 132 | 215 | 42 |
| 74 | A | CA | 199 | 146 | 220 | 43 |
| 74 | A | CB | 189 | 154 | 211 | 43 |
| 74 | A | C | 196 | 148 | 235 | 42 |
| 74 | A | O | 199 | 159 | 241 | 42 |
| 75 | A | N | 190 | 138 | 241 | 39 |
| 75 | A | CA | 185 | 139 | 255 | 36 |
| 75 | A | CB | 171 | 132 | 256 | 34 |
| 75 | A | C | 195 | 134 | 265 | 35 |
| 75 | A | O | 195 | 138 | 277 | 36 |
| 76 | W | N | 204 | 124 | 262 | 35 |
| 76 | W | CA | 211 | 117 | 272 | 36 |
| 76 | W | CB | 206 | 102 | 273 | 34 |
| 76 | W | CG | 191 | 102 | 276 | 35 |
| 76 | W | CD1 | 181 | 97 | 267 | 32 |
| 76 | W | NE1 | 169 | 98 | 273 | 32 |
| 76 | W | CE2 | 171 | 104 | 286 | 32 |
| 76 | W | CD2 | 185 | 106 | 288 | 29 |
| 76 | W | CE3 | 189 | 112 | 300 | 31 |
| 76 | W | CZ3 | 180 | 115 | 309 | 27 |
| 76 | W | CH2 | 166 | 113 | 308 | 28 |
| 76 | W | CZ2 | 161 | 107 | 296 | 29 |
| 76 | W | C | 226 | 116 | 268 | 39 |
| 76 | W | O | 229 | 117 | 256 | 40 |
| 77 | D | N | 234 | 114 | 278 | 40 |
| 77 | D | CA | 248 | 112 | 275 | 42 |
| 77 | D | CB | 256 | 110 | 288 | 41 |
| 77 | D | CG | 271 | 109 | 286 | 45 |
| 77 | D | OD1 | 278 | 98 | 286 | 50 |
| 77 | D | OD2 | 278 | 119 | 282 | 52 |
| 77 | D | C | 252 | 101 | 265 | 42 |
| 77 | D | O | 249 | 89 | 267 | 40 |
| 78 | E | N | 260 | 105 | 255 | 42 |
| 78 | E | CA | 264 | 96 | 244 | 44 |
| 78 | E | CB | 270 | 103 | 232 | 45 |
| 78 | E | CG | 275 | 94 | 220 | 52 |
| 78 | E | CD | 285 | 101 | 210 | 61 |
| 78 | E | OE1 | 288 | 95 | 200 | 65 |
| 78 | E | OE2 | 290 | 113 | 213 | 62 |
| 78 | E | C | 272 | 84 | 249 | 43 |
| 78 | E | O | 270 | 73 | 245 | 44 |
| 79 | T | N | 282 | 85 | 258 | 42 |
| 79 | T | CA | 289 | 74 | 264 | 43 |
| 79 | T | CB | 301 | 79 | 273 | 44 |
| 79 | T | OG1 | 309 | 88 | 266 | 51 |
| 79 | T | CG2 | 310 | 68 | 278 | 45 |
| 79 | T | C | 280 | 64 | 271 | 42 |
| 79 | T | O | 282 | 52 | 270 | 40 |
| 80 | L | N | 271 | 70 | 279 | 39 |
| 80 | L | CA | 262 | 61 | 287 | 36 |
| 80 | L | CB | 254 | 70 | 297 | 35 |
| 80 | L | CG | 262 | 76 | 309 | 38 |
| 80 | L | CD1 | 253 | 83 | 319 | 38 |
| 80 | L | CD2 | 270 | 65 | 316 | 40 |
| 80 | L | C | 252 | 53 | 278 | 35 |
| 80 | L | O | 250 | 41 | 280 | 34 |
| 81 | L | N | 247 | 60 | 268 | 35 |
| 81 | L | CA | 238 | 54 | 258 | 37 |
| 81 | L | CB | 233 | 64 | 248 | 34 |
| 81 | L | CG | 221 | 73 | 253 | 37 |
| 81 | L | CD1 | 217 | 82 | 241 | 34 |
| 81 | L | CD2 | 209 | 63 | 256 | 33 |
| 81 | L | C | 245 | 42 | 251 | 38 |
| 81 | L | O | 239 | 31 | 249 | 38 |
| 82 | D | N | 258 | 44 | 247 | 39 |
| 82 | D | CA | 265 | 33 | 241 | 39 |
| 82 | D | CB | 279 | 39 | 237 | 42 |
| 82 | D | CG | 283 | 34 | 224 | 50 |
| 82 | D | OD1 | 276 | 38 | 213 | 58 |
| 82 | D | OD2 | 292 | 25 | 223 | 57 |
| 82 | D | C | 267 | 21 | 250 | 38 |
| 82 | D | O | 266 | 10 | 245 | 36 |
| 83 | K | N | 271 | 23 | 262 | 37 |
| 83 | K | CA | 272 | 12 | 271 | 38 |
| 83 | K | CB | 277 | 16 | 285 | 37 |
| 83 | K | CG | 291 | 23 | 284 | 44 |
| 83 | K | CD | 297 | 24 | 298 | 48 |
| 83 | K | CE | 313 | 26 | 297 | 60 |
| 83 | K | NZ | 319 | 33 | 309 | 64 |
| 83 | K | C | 258 | 5 | 274 | 36 |
| 83 | K | O | 258 | −7 | 276 | 36 |
| 84 | F | N | 248 | 13 | 274 | 36 |
| 84 | F | CA | 234 | 9 | 275 | 35 |
| 84 | F | CB | 225 | 21 | 276 | 35 |
| 84 | F | CG | 210 | 19 | 280 | 33 |
| 84 | F | CD1 | 207 | 13 | 292 | 34 |
| 84 | F | CE1 | 193 | 12 | 296 | 35 |
| 84 | F | CZ | 183 | 17 | 288 | 31 |
| 84 | F | CE2 | 186 | 23 | 276 | 35 |
| 84 | F | CD2 | 200 | 25 | 272 | 34 |
| 84 | F | C | 229 | 0 | 263 | 36 |
| 84 | F | O | 224 | −11 | 265 | 36 |
| 85 | Y | N | 232 | 4 | 251 | 37 |
| 85 | Y | CA | 230 | −5 | 239 | 38 |
| 85 | Y | CB | 235 | 2 | 226 | 37 |
| 85 | Y | CG | 229 | 15 | 223 | 36 |
| 85 | Y | CD1 | 216 | 18 | 228 | 36 |
| 85 | Y | CE1 | 210 | 30 | 226 | 35 |
| 85 | Y | CZ | 217 | 41 | 219 | 35 |
| 85 | Y | OH | 212 | 53 | 217 | 35 |
| 85 | Y | CE2 | 230 | 38 | 215 | 39 |
| 85 | Y | CD2 | 236 | 26 | 217 | 36 |
| 85 | Y | C | 237 | −18 | 240 | 38 |
| 85 | Y | O | 231 | −29 | 239 | 39 |
| 86 | T | N | 249 | −18 | 245 | 39 |
| 86 | T | CA | 256 | −30 | 247 | 40 |
| 86 | T | CB | 271 | −27 | 252 | 41 |
| 86 | T | OG1 | 279 | −22 | 241 | 44 |
| 86 | T | CG2 | 278 | −41 | 255 | 43 |
| 86 | T | C | 249 | −39 | 257 | 39 |
| 86 | T | O | 248 | −51 | 254 | 39 |
| 87 | E | N | 245 | −34 | 268 | 37 |
| 87 | E | CA | 238 | −43 | 278 | 37 |
| 87 | E | CB | 235 | −36 | 291 | 39 |
| 87 | E | CG | 247 | −30 | 298 | 40 |
| 87 | E | CD | 257 | −42 | 301 | 48 |
| 87 | E | OE1 | 252 | −53 | 305 | 51 |
| 87 | E | OE2 | 269 | −40 | 299 | 49 |
| 87 | E | C | 225 | −48 | 272 | 36 |
| 87 | E | O | 222 | −60 | 273 | 38 |
| 88 | L | N | 218 | −40 | 265 | 35 |

| | | | | | | |
|---|---|---|---|---|---|---|
| 88 | L | CA | 206 | −44 | 259 | 36 |
| 88 | L | CB | 199 | −31 | 253 | 34 |
| 88 | L | CG | 194 | −21 | 264 | 35 |
| 88 | L | CD1 | 188 | −10 | 256 | 35 |
| 88 | L | CD2 | 183 | −27 | 273 | 35 |
| 88 | L | C | 208 | −55 | 248 | 38 |
| 88 | L | O | 201 | −65 | 249 | 37 |
| 89 | Y | N | 217 | −54 | 239 | 38 |
| 89 | Y | CA | 220 | −65 | 230 | 39 |
| 89 | Y | CB | 233 | −62 | 221 | 39 |
| 89 | Y | CG | 232 | −51 | 212 | 42 |
| 89 | Y | CD1 | 220 | −49 | 204 | 44 |
| 89 | Y | CE1 | 219 | −38 | 195 | 50 |
| 89 | Y | CZ | 230 | −29 | 194 | 51 |
| 89 | Y | OH | 230 | −18 | 185 | 55 |
| 89 | Y | CE2 | 242 | −31 | 201 | 47 |
| 89 | Y | CD2 | 243 | −42 | 210 | 45 |
| 89 | Y | C | 223 | −78 | 236 | 39 |
| 89 | Y | O | 219 | −88 | 232 | 38 |
| 90 | Q | N | 231 | −78 | 247 | 38 |
| 90 | Q | CA | 235 | −90 | 254 | 40 |
| 90 | Q | CB | 246 | −87 | 264 | 41 |
| 90 | Q | CG | 252 | −99 | 271 | 49 |
| 90 | Q | CD | 257 | −111 | 261 | 59 |
| 90 | Q | OE1 | 263 | −108 | 250 | 63 |
| 90 | Q | NE2 | 254 | −123 | 264 | 59 |
| 90 | Q | C | 223 | −97 | 260 | 40 |
| 90 | Q | O | 220 | −109 | 259 | 37 |
| 91 | Q | N | 214 | −89 | 267 | 38 |
| 91 | Q | CA | 202 | −94 | 272 | 38 |
| 91 | Q | CB | 194 | −84 | 280 | 38 |
| 91 | Q | CG | 202 | −81 | 293 | 41 |
| 91 | Q | CD | 194 | −70 | 301 | 48 |
| 91 | Q | OE1 | 186 | −74 | 309 | 50 |
| 91 | Q | NE2 | 198 | −58 | 298 | 45 |
| 91 | Q | C | 193 | −100 | 261 | 37 |
| 91 | Q | O | 187 | −111 | 263 | 36 |
| 92 | L | N | 191 | −93 | 250 | 37 |
| 92 | L | CA | 183 | −98 | 239 | 38 |
| 92 | L | CB | 183 | −88 | 228 | 37 |
| 92 | L | CG | 174 | −76 | 229 | 43 |
| 92 | L | CD1 | 176 | −66 | 217 | 42 |
| 92 | L | CD2 | 158 | −80 | 229 | 37 |
| 92 | L | C | 189 | −112 | 234 | 39 |
| 92 | L | O | 182 | −121 | 232 | 38 |
| 93 | N | N | 202 | −113 | 232 | 41 |
| 93 | N | CA | 208 | −125 | 228 | 42 |
| 93 | N | CB | 223 | −124 | 226 | 44 |
| 93 | N | CG | 226 | −123 | 212 | 51 |
| 93 | N | OD1 | 226 | −133 | 205 | 58 |
| 93 | N | ND2 | 230 | −111 | 208 | 58 |
| 93 | N | C | 206 | −136 | 238 | 41 |
| 93 | N | O | 203 | −148 | 234 | 42 |
| 94 | D | N | 208 | −134 | 251 | 40 |
| 94 | D | CA | 205 | −144 | 261 | 41 |
| 94 | D | CB | 208 | −139 | 275 | 42 |
| 94 | D | CG | 223 | −136 | 277 | 48 |
| 94 | D | OD1 | 231 | −137 | 268 | 53 |
| 94 | D | OD2 | 227 | −132 | 289 | 54 |
| 94 | D | C | 191 | −149 | 261 | 40 |
| 94 | D | O | 189 | −161 | 262 | 40 |
| 95 | L | N | 182 | −140 | 258 | 38 |
| 95 | L | CA | 168 | −144 | 258 | 39 |
| 95 | L | CB | 158 | −132 | 259 | 37 |
| 95 | L | CG | 159 | −125 | 272 | 37 |
| 95 | L | CD1 | 152 | −112 | 272 | 35 |
| 95 | L | CD2 | 153 | −133 | 284 | 37 |
| 95 | L | C | 164 | −152 | 246 | 40 |
| 95 | L | O | 157 | −162 | 246 | 40 |
| 96 | E | N | 170 | −148 | 234 | 40 |
| 96 | E | CA | 169 | −155 | 222 | 43 |
| 96 | E | CB | 176 | −146 | 211 | 43 |
| 96 | E | CG | 167 | −134 | 208 | 46 |
| 96 | E | CD | 173 | −124 | 198 | 49 |
| 96 | E | OE1 | 181 | −129 | 189 | 51 |
| 96 | E | OE2 | 169 | −112 | 198 | 44 |
| 96 | E | C | 175 | −169 | 222 | 45 |
| 96 | E | O | 170 | −178 | 215 | 45 |
| 97 | A | N | 186 | −171 | 230 | 45 |
| 97 | A | CA | 191 | −185 | 231 | 48 |
| 97 | A | CB | 204 | −184 | 240 | 47 |
| 97 | A | C | 182 | −195 | 237 | 49 |
| 97 | A | O | 183 | −207 | 236 | 49 |
| 98 | C | N | 171 | −190 | 244 | 51 |
| 98 | C | CA | 161 | −199 | 251 | 53 |
| 98 | C | CB | 152 | −191 | 260 | 53 |
| 98 | C | SG | 160 | −184 | 274 | 56 |
| 98 | C | C | 153 | −206 | 240 | 53 |
| 98 | C | O | 147 | −217 | 243 | 53 |
| 99 | V | N | 152 | −200 | 228 | 54 |
| 99 | V | CA | 145 | −207 | 217 | 56 |
| 99 | V | CB | 146 | −198 | 204 | 56 |
| 99 | V | CG1 | 141 | −206 | 193 | 56 |
| 99 | V | CG2 | 137 | −185 | 206 | 56 |
| 99 | V | C | 151 | −221 | 214 | 57 |
| 99 | V | O | 144 | −231 | 214 | 56 |
| 100 | I | N | 164 | −222 | 212 | 58 |
| 100 | I | CA | 171 | −235 | 209 | 61 |
| 100 | I | CB | 187 | −233 | 208 | 60 |
| 100 | I | CG1 | 190 | −225 | 196 | 63 |
| 100 | I | CD1 | 182 | −229 | 183 | 65 |
| 100 | I | CG2 | 194 | −247 | 208 | 63 |
| 100 | I | C | 168 | −245 | 220 | 61 |
| 100 | I | O | 163 | −256 | 217 | 61 |
| 101 | Q | N | 170 | −241 | 233 | 62 |
| 101 | Q | CA | 166 | −249 | 245 | 63 |
| 101 | Q | CB | 169 | −241 | 258 | 63 |
| 101 | Q | CG | 183 | −238 | 261 | 66 |
| 101 | Q | CD | 184 | −229 | 274 | 70 |
| 101 | Q | OE1 | 174 | −229 | 282 | 70 |
| 101 | Q | NE2 | 195 | −223 | 276 | 71 |
| 101 | Q | C | 152 | −254 | 245 | 62 |
| 101 | Q | O | 149 | −263 | 253 | 63 |
| 102 | G | N | 143 | −248 | 238 | 62 |
| 102 | G | CA | 129 | −252 | 238 | 61 |
| 102 | G | C | 125 | −262 | 227 | 62 |
| 102 | G | O | 113 | −267 | 227 | 61 |
| 103 | V | N | 134 | −266 | 218 | 62 |
| 103 | V | CA | 130 | −274 | 206 | 62 |
| 103 | V | CB | 141 | −275 | 196 | 62 |
| 103 | V | CG1 | 137 | −284 | 184 | 61 |
| 103 | V | CG2 | 144 | −261 | 191 | 62 |
| 103 | V | C | 124 | −288 | 210 | 62 |
| 103 | V | O | 130 | −296 | 217 | 62 |
| 110 | A | N | 19 | −211 | 261 | 74 |
| 110 | A | CA | 24 | −211 | 247 | 74 |
| 110 | A | CB | 21 | −224 | 240 | 74 |
| 110 | A | C | 21 | −199 | 238 | 73 |
| 110 | A | O | 30 | −193 | 232 | 73 |
| 111 | A | N | 8 | −194 | 238 | 71 |
| 111 | A | CA | 4 | −182 | 230 | 69 |
| 111 | A | CB | −11 | −184 | 225 | 70 |
| 111 | A | C | 5 | −169 | 238 | 66 |
| 111 | A | O | −3 | −166 | 247 | 67 |
| 112 | K | N | 16 | −162 | 236 | 62 |
| 112 | K | CA | 17 | −149 | 242 | 57 |
| 112 | K | CB | 32 | −147 | 248 | 58 |
| 112 | K | CG | 34 | −156 | 261 | 59 |
| 112 | K | CD | 22 | −155 | 270 | 61 |
| 112 | K | CE | 25 | −162 | 284 | 61 |
| 112 | K | NZ | 17 | −156 | 295 | 64 |
| 112 | K | C | 15 | −137 | 233 | 52 |
| 112 | K | O | 20 | −126 | 237 | 50 |
| 113 | A | N | 8 | −139 | 222 | 46 |
| 113 | A | CA | 7 | −128 | 212 | 43 |
| 113 | A | CB | −1 | −131 | 200 | 42 |
| 113 | A | C | 1 | −115 | 218 | 42 |
| 113 | A | O | 5 | −104 | 214 | 41 |
| 114 | D | N | −10 | −116 | 226 | 40 |
| 114 | D | CA | −17 | −104 | 231 | 39 |
| 114 | D | CB | −30 | −108 | 236 | 40 |
| 114 | D | CG | −40 | −111 | 225 | 46 |
| 114 | D | OD1 | −47 | −122 | 226 | 54 |
| 114 | D | OD2 | −41 | −105 | 214 | 51 |
| 114 | D | C | −8 | −98 | 242 | 35 |
| 114 | D | O | −9 | −86 | 243 | 36 |
| 115 | S | N | −1 | −106 | 250 | 33 |
| 115 | S | CA | 8 | −101 | 260 | 34 |
| 115 | S | CB | 14 | −112 | 269 | 34 |
| 115 | S | OG | 3 | −118 | 276 | 39 |

-continued

| | | | | | | |
|---|---|---|---|---|---|---|
| 115 | S | C | 20 | −93 | 254 | 34 |
| 115 | S | O | 24 | −83 | 259 | 32 |
| 116 | I | N | 26 | −99 | 243 | 33 |
| 116 | I | CA | 35 | −91 | 235 | 33 |
| 116 | I | CB | 40 | −100 | 223 | 34 |
| 116 | I | CG1 | 49 | −111 | 229 | 33 |
| 116 | I | CD1 | 54 | −122 | 219 | 41 |
| 116 | I | CG2 | 49 | −91 | 214 | 36 |
| 116 | I | C | 30 | −78 | 231 | 32 |
| 116 | I | O | 36 | −68 | 232 | 30 |
| 117 | L | N | 18 | −78 | 225 | 32 |
| 117 | L | CA | 12 | −66 | 220 | 33 |
| 117 | L | CB | −2 | −68 | 213 | 34 |
| 117 | L | CG | 0 | −75 | 199 | 42 |
| 117 | L | CD1 | −13 | −78 | 192 | 47 |
| 117 | L | CD2 | 10 | −69 | 190 | 46 |
| 117 | L | C | 9 | −56 | 232 | 32 |
| 117 | L | O | 10 | −44 | 230 | 31 |
| 118 | A | N | 6 | −61 | 244 | 30 |
| 118 | A | CA | 3 | −52 | 255 | 29 |
| 118 | A | CB | −1 | −60 | 267 | 28 |
| 118 | A | C | 16 | −44 | 259 | 29 |
| 118 | A | O | 15 | −33 | 262 | 27 |
| 119 | V | N | 28 | −51 | 259 | 29 |
| 119 | V | CA | 41 | −44 | 260 | 30 |
| 119 | V | CB | 52 | −55 | 262 | 31 |
| 119 | V | CG1 | 66 | −47 | 263 | 32 |
| 119 | V | CG2 | 50 | −63 | 274 | 29 |
| 119 | V | C | 43 | −34 | 250 | 31 |
| 119 | V | O | 47 | −23 | 252 | 31 |
| 120 | R | N | 41 | −37 | 237 | 31 |
| 120 | R | CA | 42 | −27 | 226 | 32 |
| 120 | R | CB | 38 | −33 | 213 | 33 |
| 120 | R | CG | 48 | −40 | 206 | 35 |
| 120 | R | CD | 46 | −44 | 191 | 37 |
| 120 | R | NE | 55 | −56 | 190 | 36 |
| 120 | R | CZ | 53 | −67 | 184 | 39 |
| 120 | R | NH1 | 42 | −68 | 176 | 39 |
| 120 | R | NH2 | 62 | −77 | 186 | 36 |
| 120 | R | C | 33 | −16 | 228 | 31 |
| 120 | R | O | 37 | −5 | 225 | 33 |
| 121 | K | N | 20 | −18 | 232 | 29 |
| 121 | K | CA | 11 | −6 | 234 | 29 |
| 121 | K | CB | −3 | −10 | 237 | 29 |
| 121 | K | CG | −10 | −17 | 225 | 34 |
| 121 | K | CD | −24 | −20 | 229 | 41 |
| 121 | K | CE | −31 | −28 | 217 | 49 |
| 121 | K | NZ | −39 | −19 | 208 | 55 |
| 121 | K | C | 16 | 3 | 246 | 28 |
| 121 | K | O | 14 | 15 | 246 | 28 |
| 122 | Y | N | 22 | −3 | 256 | 27 |
| 122 | Y | CA | 27 | 5 | 267 | 28 |
| 122 | Y | CB | 33 | −5 | 278 | 27 |
| 122 | Y | CG | 43 | 1 | 287 | 27 |
| 122 | Y | CD1 | 39 | 9 | 298 | 25 |
| 122 | Y | CE1 | 48 | 14 | 307 | 29 |
| 122 | Y | CZ | 62 | 11 | 306 | 29 |
| 122 | Y | OH | 71 | 15 | 315 | 29 |
| 122 | Y | CE2 | 66 | 3 | 296 | 29 |
| 122 | Y | CD2 | 57 | −2 | 287 | 24 |
| 122 | Y | C | 38 | 14 | 262 | 28 |
| 122 | Y | O | 38 | 26 | 264 | 27 |
| 123 | F | N | 48 | 9 | 254 | 29 |
| 123 | F | CA | 58 | 18 | 247 | 30 |
| 123 | F | CB | 69 | 9 | 241 | 29 |
| 123 | F | CG | 79 | 4 | 251 | 31 |
| 123 | F | CD1 | 89 | 12 | 256 | 30 |
| 123 | F | CE1 | 98 | 8 | 265 | 26 |
| 123 | F | CZ | 96 | −5 | 272 | 29 |
| 123 | F | CE2 | 85 | −13 | 268 | 29 |
| 123 | F | CD2 | 77 | −8 | 257 | 29 |
| 123 | F | C | 52 | 27 | 237 | 31 |
| 123 | F | O | 57 | 38 | 235 | 31 |
| 124 | Q | N | 40 | 24 | 230 | 29 |
| 124 | Q | CA | 34 | 34 | 222 | 28 |
| 124 | Q | CB | 22 | 28 | 214 | 28 |
| 124 | Q | CG | 27 | 19 | 203 | 33 |
| 124 | Q | CD | 15 | 10 | 198 | 42 |
| 124 | Q | OE1 | 3 | 11 | 202 | 41 |
| 124 | Q | NE2 | 18 | 1 | 188 | 45 |
| 124 | Q | C | 29 | 46 | 230 | 30 |
| 124 | Q | O | 29 | 57 | 225 | 29 |
| 125 | R | N | 23 | 43 | 242 | 28 |
| 125 | R | CA | 19 | 53 | 251 | 28 |
| 125 | R | CB | 12 | 48 | 263 | 29 |
| 125 | R | CG | −2 | 41 | 260 | 30 |
| 125 | R | CD | −11 | 39 | 272 | 26 |
| 125 | R | NE | −5 | 28 | 281 | 29 |
| 125 | R | CZ | −7 | 15 | 279 | 29 |
| 125 | R | NH1 | −14 | 11 | 268 | 28 |
| 125 | R | NH2 | −2 | 6 | 287 | 29 |
| 125 | R | C | 31 | 62 | 255 | 28 |
| 125 | R | O | 30 | 74 | 255 | 29 |
| 126 | I | N | 42 | 56 | 258 | 28 |
| 126 | I | CA | 54 | 64 | 261 | 28 |
| 126 | I | CB | 66 | 54 | 266 | 27 |
| 126 | I | CG1 | 63 | 49 | 281 | 27 |
| 126 | I | CD1 | 73 | 37 | 285 | 27 |
| 126 | I | CG2 | 80 | 61 | 266 | 26 |
| 126 | I | C | 59 | 73 | 250 | 30 |
| 126 | I | O | 61 | 85 | 252 | 31 |
| 127 | T | N | 60 | 67 | 238 | 30 |
| 127 | T | CA | 63 | 75 | 225 | 35 |
| 127 | T | CB | 64 | 65 | 213 | 35 |
| 127 | T | OG1 | 75 | 57 | 215 | 43 |
| 127 | T | CG2 | 66 | 72 | 200 | 41 |
| 127 | T | C | 54 | 86 | 222 | 34 |
| 127 | T | O | 58 | 98 | 219 | 36 |
| 128 | L | N | 41 | 84 | 222 | 35 |
| 128 | L | CA | 31 | 94 | 221 | 35 |
| 128 | L | CB | 17 | 89 | 221 | 35 |
| 128 | L | CG | 6 | 99 | 220 | 37 |
| 128 | L | CD1 | 7 | 107 | 206 | 34 |
| 128 | L | CD2 | −7 | 92 | 220 | 40 |
| 128 | L | C | 33 | 105 | 231 | 36 |
| 128 | L | O | 31 | 117 | 228 | 35 |
| 129 | Y | N | 34 | 102 | 244 | 34 |
| 129 | Y | CA | 36 | 111 | 254 | 32 |
| 129 | Y | CB | 38 | 104 | 268 | 31 |
| 129 | Y | CG | 44 | 112 | 279 | 34 |
| 129 | Y | CD1 | 35 | 118 | 288 | 31 |
| 129 | Y | CE1 | 41 | 126 | 299 | 32 |
| 129 | Y | CZ | 54 | 127 | 300 | 30 |
| 129 | Y | OH | 59 | 135 | 311 | 29 |
| 129 | Y | CE2 | 63 | 121 | 291 | 31 |
| 129 | Y | CD2 | 58 | 113 | 281 | 28 |
| 129 | Y | C | 49 | 121 | 251 | 32 |
| 129 | Y | O | 48 | 133 | 252 | 33 |
| 130 | L | N | 60 | 115 | 247 | 32 |
| 130 | L | CA | 72 | 123 | 244 | 33 |
| 130 | L | CB | 83 | 114 | 241 | 31 |
| 130 | L | CG | 91 | 107 | 253 | 34 |
| 130 | L | CD1 | 100 | 96 | 248 | 27 |
| 130 | L | CD2 | 98 | 118 | 262 | 29 |
| 130 | L | C | 70 | 133 | 232 | 36 |
| 130 | L | O | 74 | 145 | 233 | 33 |
| 131 | K | N | 64 | 127 | 222 | 36 |
| 131 | K | CA | 60 | 135 | 210 | 39 |
| 131 | K | CB | 53 | 126 | 200 | 40 |
| 131 | K | CG | 50 | 131 | 186 | 49 |
| 131 | K | CD | 44 | 120 | 178 | 55 |
| 131 | K | CE | 48 | 121 | 163 | 63 |
| 131 | K | NZ | 41 | 133 | 156 | 67 |
| 131 | K | C | 51 | 147 | 214 | 38 |
| 131 | K | O | 54 | 158 | 211 | 40 |
| 132 | E | N | 40 | 144 | 221 | 38 |
| 132 | E | CA | 32 | 155 | 225 | 39 |
| 132 | E | CB | 19 | 150 | 232 | 41 |
| 132 | E | CG | 11 | 141 | 222 | 47 |
| 132 | E | CD | −3 | 137 | 225 | 55 |
| 132 | E | OE1 | −6 | 135 | 237 | 56 |
| 132 | E | OE2 | −12 | 136 | 215 | 63 |
| 132 | E | C | 38 | 166 | 235 | 40 |
| 132 | E | O | 32 | 177 | 235 | 39 |
| 133 | K | N | 48 | 162 | 243 | 38 |
| 133 | K | CA | 55 | 171 | 251 | 39 |
| 133 | K | CB | 60 | 164 | 265 | 39 |
| 133 | K | CG | 49 | 159 | 273 | 38 |
| 133 | K | CD | 43 | 168 | 283 | 44 |
| 133 | K | CE | 32 | 161 | 292 | 44 |

| | | | | | |
|---|---|---|---|---|---|
| 133 | K | NZ | 28 | 172 | 302 | 48 |
| 133 | K | C | 68 | 177 | 244 | 39 |
| 133 | K | O | 76 | 183 | 251 | 40 |
| 134 | K | N | 69 | 172 | 232 | 40 |
| 134 | K | CA | 80 | 177 | 223 | 41 |
| 134 | K | CB | 78 | 192 | 219 | 42 |
| 134 | K | CG | 66 | 195 | 211 | 46 |
| 134 | K | CD | 64 | 210 | 208 | 57 |
| 134 | K | CE | 60 | 218 | 220 | 60 |
| 134 | K | NZ | 53 | 232 | 217 | 65 |
| 134 | K | C | 93 | 174 | 230 | 41 |
| 134 | K | O | 102 | 183 | 229 | 40 |
| 135 | Y | N | 95 | 163 | 236 | 38 |
| 135 | Y | CA | 107 | 158 | 240 | 37 |
| 135 | Y | CB | 116 | 156 | 228 | 38 |
| 135 | Y | CG | 110 | 145 | 218 | 42 |
| 135 | Y | CD1 | 102 | 150 | 207 | 47 |
| 135 | Y | CE1 | 97 | 140 | 199 | 48 |
| 135 | Y | CZ | 98 | 127 | 201 | 46 |
| 135 | Y | OH | 93 | 117 | 193 | 51 |
| 135 | Y | CE2 | 106 | 122 | 212 | 47 |
| 135 | Y | CD2 | 112 | 132 | 221 | 41 |
| 135 | Y | C | 115 | 167 | 250 | 35 |
| 135 | Y | O | 127 | 168 | 249 | 37 |
| 136 | S | N | 107 | 174 | 258 | 35 |
| 136 | S | CA | 113 | 184 | 268 | 37 |
| 136 | S | CB | 101 | 191 | 275 | 34 |
| 136 | S | OG | 94 | 182 | 284 | 38 |
| 136 | S | C | 121 | 176 | 278 | 37 |
| 136 | S | O | 119 | 164 | 280 | 38 |
| 137 | P | N | 131 | 182 | 285 | 37 |
| 137 | P | CA | 138 | 176 | 296 | 34 |
| 137 | P | CB | 145 | 188 | 303 | 36 |
| 137 | P | CG | 149 | 197 | 290 | 39 |
| 137 | P | CD | 136 | 196 | 281 | 36 |
| 137 | P | C | 129 | 169 | 306 | 33 |
| 137 | P | O | 133 | 159 | 310 | 32 |
| 138 | C | N | 118 | 176 | 311 | 32 |
| 138 | C | CA | 110 | 170 | 320 | 34 |
| 138 | C | CB | 99 | 180 | 325 | 35 |
| 138 | C | SG | 106 | 191 | 337 | 43 |
| 138 | C | C | 102 | 157 | 315 | 34 |
| 138 | C | O | 101 | 148 | 323 | 33 |
| 139 | A | N | 98 | 157 | 302 | 32 |
| 139 | A | CA | 91 | 145 | 297 | 30 |
| 139 | A | CB | 85 | 147 | 283 | 28 |
| 139 | A | C | 101 | 133 | 296 | 29 |
| 139 | A | O | 97 | 122 | 300 | 30 |
| 140 | W | N | 113 | 136 | 292 | 29 |
| 140 | W | CA | 123 | 126 | 291 | 31 |
| 140 | W | CB | 136 | 131 | 285 | 30 |
| 140 | W | CG | 137 | 128 | 270 | 34 |
| 140 | W | CD1 | 138 | 138 | 260 | 30 |
| 140 | W | NE1 | 138 | 131 | 248 | 33 |
| 140 | W | CE2 | 138 | 117 | 250 | 34 |
| 140 | W | CD2 | 136 | 115 | 264 | 33 |
| 140 | W | CE3 | 136 | 102 | 269 | 31 |
| 140 | W | CZ3 | 136 | 91 | 260 | 31 |
| 140 | W | CH2 | 138 | 93 | 246 | 36 |
| 140 | W | CZ2 | 138 | 106 | 241 | 34 |
| 140 | W | C | 127 | 120 | 305 | 31 |
| 140 | W | O | 129 | 108 | 306 | 31 |
| 141 | E | N | 127 | 129 | 316 | 30 |
| 141 | E | CA | 130 | 124 | 329 | 30 |
| 141 | E | CB | 132 | 136 | 339 | 28 |
| 141 | E | CG | 133 | 132 | 354 | 29 |
| 141 | E | CD | 143 | 120 | 356 | 31 |
| 141 | E | OE1 | 152 | 117 | 348 | 28 |
| 141 | E | OE2 | 141 | 113 | 366 | 32 |
| 141 | E | C | 118 | 115 | 334 | 30 |
| 141 | E | O | 120 | 105 | 340 | 30 |
| 142 | V | N | 106 | 120 | 333 | 28 |
| 142 | V | CA | 94 | 112 | 336 | 28 |
| 142 | V | CB | 81 | 118 | 332 | 27 |
| 142 | V | CG1 | 69 | 108 | 333 | 27 |
| 142 | V | CG2 | 78 | 131 | 341 | 27 |
| 142 | V | C | 96 | 97 | 329 | 28 |
| 142 | V | O | 93 | 87 | 336 | 28 |
| 143 | V | N | 100 | 97 | 317 | 29 |
| 143 | V | CA | 101 | 84 | 309 | 28 |
| 143 | V | CB | 102 | 87 | 293 | 27 |
| 143 | V | CG1 | 107 | 74 | 286 | 25 |
| 143 | V | CG2 | 89 | 92 | 288 | 25 |
| 143 | V | C | 113 | 76 | 314 | 29 |
| 143 | V | O | 111 | 63 | 316 | 27 |
| 144 | R | N | 124 | 82 | 317 | 28 |
| 144 | R | CA | 136 | 75 | 322 | 29 |
| 144 | R | CB | 148 | 85 | 322 | 29 |
| 144 | R | CG | 161 | 78 | 328 | 31 |
| 144 | R | CD | 170 | 89 | 336 | 34 |
| 144 | R | NE | 163 | 93 | 348 | 31 |
| 144 | R | CZ | 163 | 85 | 359 | 29 |
| 144 | R | NH1 | 171 | 74 | 360 | 32 |
| 144 | R | NH2 | 156 | 89 | 369 | 34 |
| 144 | R | C | 133 | 69 | 335 | 28 |
| 144 | R | O | 136 | 57 | 337 | 27 |
| 145 | A | N | 126 | 77 | 344 | 28 |
| 145 | A | CA | 122 | 71 | 357 | 28 |
| 145 | A | CB | 117 | 82 | 366 | 27 |
| 145 | A | C | 112 | 60 | 356 | 28 |
| 145 | A | O | 113 | 50 | 364 | 29 |
| 146 | E | N | 103 | 61 | 348 | 29 |
| 146 | E | CA | 93 | 51 | 345 | 28 |
| 146 | E | CB | 83 | 56 | 334 | 29 |
| 146 | E | CG | 75 | 46 | 327 | 30 |
| 146 | E | CD | 64 | 39 | 336 | 33 |
| 146 | E | OE1 | 60 | 28 | 334 | 31 |
| 146 | E | OE2 | 60 | 46 | 346 | 36 |
| 146 | E | C | 99 | 38 | 340 | 27 |
| 146 | E | O | 96 | 27 | 345 | 26 |
| 147 | I | N | 109 | 39 | 331 | 25 |
| 147 | I | CA | 115 | 27 | 326 | 26 |
| 147 | I | CB | 124 | 31 | 313 | 27 |
| 147 | I | CG1 | 115 | 35 | 301 | 31 |
| 147 | I | CD1 | 104 | 24 | 297 | 36 |
| 147 | I | CG2 | 132 | 18 | 309 | 29 |
| 147 | I | C | 124 | 20 | 336 | 28 |
| 147 | I | O | 125 | 8 | 337 | 29 |
| 148 | M | N | 131 | 28 | 344 | 29 |
| 148 | M | CA | 138 | 23 | 355 | 31 |
| 148 | M | CB | 146 | 34 | 363 | 33 |
| 148 | M | CG | 160 | 31 | 366 | 41 |
| 148 | M | SD | 168 | 43 | 375 | 45 |
| 148 | M | CE | 173 | 32 | 389 | 44 |
| 148 | M | C | 129 | 14 | 365 | 30 |
| 148 | M | O | 133 | 3 | 368 | 30 |
| 149 | R | N | 117 | 20 | 368 | 29 |
| 149 | R | CA | 108 | 12 | 376 | 30 |
| 149 | R | CB | 97 | 21 | 381 | 30 |
| 149 | R | CG | 102 | 34 | 389 | 34 |
| 149 | R | CD | 91 | 42 | 397 | 33 |
| 149 | R | NE | 80 | 46 | 388 | 37 |
| 149 | R | CZ | 80 | 57 | 381 | 38 |
| 149 | R | NH1 | 89 | 66 | 382 | 38 |
| 149 | R | NH2 | 69 | 59 | 374 | 39 |
| 149 | R | C | 102 | 0 | 369 | 30 |
| 149 | R | O | 101 | −11 | 375 | 30 |
| 150 | S | N | 98 | 1 | 356 | 28 |
| 150 | S | CA | 92 | −10 | 350 | 30 |
| 150 | S | CB | 83 | −6 | 338 | 27 |
| 150 | S | OG | 91 | 0 | 328 | 31 |
| 150 | S | C | 102 | −21 | 346 | 30 |
| 150 | S | O | 99 | −33 | 347 | 31 |
| 151 | F | N | 114 | −17 | 342 | 30 |
| 151 | F | CA | 124 | −27 | 339 | 31 |
| 151 | F | CB | 136 | −20 | 333 | 31 |
| 151 | F | CG | 147 | −30 | 330 | 33 |
| 151 | F | CD1 | 147 | −38 | 319 | 37 |
| 151 | F | CE1 | 158 | −47 | 317 | 39 |
| 151 | F | CZ | 168 | −48 | 326 | 36 |
| 151 | F | CE2 | 168 | −39 | 337 | 37 |
| 151 | F | CD2 | 158 | −31 | 339 | 36 |
| 151 | F | C | 128 | −34 | 352 | 32 |
| 151 | F | O | 130 | −46 | 352 | 31 |
| 152 | S | N | 130 | −27 | 363 | 33 |
| 152 | S | CA | 133 | −33 | 375 | 37 |
| 152 | S | CB | 136 | −23 | 387 | 36 |
| 152 | S | OG | 139 | −30 | 398 | 47 |
| 152 | S | C | 122 | −43 | 380 | 38 |
| 152 | S | O | 125 | −55 | 384 | 38 |

-continued

| | | | | | | | | | | | | | |
|---|---|---|---|---|---|---|---|---|---|---|---|---|---|
| 153 | L | N | 110 | −39 | 378 | 39 | 12 | R | NH1 | 160 | 19 | 614 | 69 |
| 153 | L | CA | 99 | −48 | 381 | 43 | 12 | R | NH2 | 140 | 17 | 626 | 73 |
| 153 | L | CB | 86 | −41 | 379 | 43 | 12 | R | C | 191 | 1 | 568 | 37 |
| 153 | L | CG | 72 | −45 | 386 | 49 | 12 | R | O | 202 | 1 | 573 | 37 |
| 153 | L | CD1 | 74 | −49 | 400 | 51 | 13 | R | N | 188 | −6 | 557 | 36 |
| 153 | L | CD2 | 62 | −33 | 385 | 51 | 13 | R | CA | 198 | −14 | 550 | 38 |
| 153 | L | C | 99 | −61 | 372 | 43 | 13 | R | CB | 192 | −24 | 540 | 39 |
| 153 | L | O | 97 | −72 | 376 | 44 | 13 | R | CG | 183 | −34 | 545 | 46 |
| 154 | S | N | 101 | −59 | 359 | 43 | 13 | R | CD | 177 | −44 | 534 | 58 |
| 154 | S | CA | 99 | −70 | 350 | 44 | 13 | R | NE | 164 | −40 | 529 | 62 |
| 154 | S | CB | 97 | −64 | 336 | 41 | 13 | R | CZ | 152 | −41 | 537 | 64 |
| 154 | S | OG | 109 | −60 | 331 | 46 | 13 | R | NH1 | 152 | −44 | 550 | 60 |
| 154 | S | C | 111 | −79 | 350 | 46 | 13 | R | NH2 | 141 | −37 | 531 | 61 |
| 154 | S | O | 110 | −91 | 346 | 46 | 13 | R | C | 209 | −6 | 544 | 38 |
| 155 | T | N | 122 | −75 | 355 | 47 | 13 | R | O | 221 | −10 | 543 | 38 |
| 155 | T | CA | 134 | −84 | 357 | 51 | 14 | T | N | 206 | 6 | 539 | 36 |
| 155 | T | CB | 147 | −78 | 352 | 50 | 14 | T | CA | 215 | 16 | 535 | 35 |
| 155 | T | OG1 | 150 | −66 | 359 | 46 | 14 | T | CB | 208 | 29 | 529 | 34 |
| 155 | T | CG2 | 146 | −73 | 337 | 48 | 14 | T | OG1 | 199 | 25 | 518 | 33 |
| 155 | T | C | 135 | −90 | 371 | 55 | 14 | T | CG2 | 217 | 38 | 523 | 34 |
| 155 | T | O | 142 | −100 | 372 | 56 | 14 | T | C | 226 | 20 | 546 | 35 |
| 156 | N | N | 129 | −84 | 381 | 59 | 14 | T | O | 237 | 20 | 543 | 36 |
| 156 | N | CA | 129 | −91 | 394 | 64 | 15 | L | N | 221 | 23 | 558 | 35 |
| 156 | N | CB | 131 | −81 | 406 | 65 | 15 | L | CA | 230 | 28 | 568 | 35 |
| 156 | N | CG | 143 | −71 | 404 | 71 | 15 | L | CB | 222 | 33 | 580 | 35 |
| 156 | N | OD1 | 143 | −60 | 410 | 75 | 15 | L | CG | 216 | 48 | 577 | 36 |
| 156 | N | ND2 | 154 | −75 | 396 | 75 | 15 | L | CD1 | 206 | 51 | 587 | 35 |
| 156 | N | C | 117 | −100 | 396 | 67 | 15 | L | CD2 | 228 | 58 | 577 | 35 |
| 156 | N | O | 118 | −110 | 403 | 68 | 15 | L | C | 239 | 15 | 572 | 36 |
| 157 | A | N | 106 | −97 | 389 | 69 | 15 | L | O | 250 | 17 | 576 | 36 |
| 157 | A | CA | 95 | −107 | 387 | 70 | 16 | M | N | 233 | 3 | 572 | 36 |
| 157 | A | CB | 82 | −100 | 385 | 70 | 16 | M | CA | 240 | −9 | 576 | 38 |
| 157 | A | C | 98 | −117 | 376 | 72 | 16 | M | CB | 231 | −21 | 577 | 37 |
| 157 | A | O | 106 | −127 | 378 | 73 | 16 | M | CG | 238 | −34 | 581 | 43 |
| 6 | A | N | 53 | 30 | 586 | 73 | 16 | M | SD | 243 | −44 | 566 | 59 |
| 6 | A | CA | 65 | 30 | 594 | 72 | 16 | M | CE | 227 | −51 | 559 | 55 |
| 6 | A | CB | 66 | 16 | 602 | 73 | 16 | M | C | 251 | −12 | 566 | 38 |
| 6 | A | C | 78 | 32 | 585 | 71 | 16 | M | O | 262 | −15 | 571 | 38 |
| 6 | A | O | 78 | 37 | 574 | 72 | 17 | L | N | 249 | −11 | 553 | 37 |
| 7 | H | N | 90 | 27 | 591 | 70 | 17 | L | CA | 259 | −13 | 543 | 38 |
| 7 | H | CA | 103 | 31 | 587 | 67 | 17 | L | CB | 253 | −13 | 529 | 36 |
| 7 | H | CB | 114 | 28 | 598 | 68 | 17 | L | CG | 245 | −26 | 527 | 39 |
| 7 | H | CG | 126 | 35 | 596 | 69 | 17 | L | CD1 | 236 | −23 | 515 | 39 |
| 7 | H | ND1 | 130 | 46 | 604 | 71 | 17 | L | CD2 | 253 | −39 | 525 | 36 |
| 7 | H | CE1 | 142 | 50 | 601 | 70 | 17 | L | C | 270 | −2 | 544 | 39 |
| 7 | H | NE2 | 147 | 43 | 592 | 72 | 17 | L | O | 281 | −6 | 542 | 40 |
| 7 | H | CD2 | 137 | 33 | 589 | 69 | 18 | L | N | 266 | 10 | 547 | 39 |
| 7 | H | C | 107 | 25 | 574 | 65 | 18 | L | CA | 276 | 20 | 548 | 41 |
| 7 | H | O | 105 | 13 | 571 | 65 | 18 | L | CB | 271 | 34 | 551 | 39 |
| 8 | S | N | 113 | 33 | 565 | 61 | 18 | L | CG | 267 | 42 | 538 | 41 |
| 8 | S | CA | 118 | 27 | 553 | 57 | 18 | L | CD1 | 259 | 54 | 541 | 39 |
| 8 | S | CB | 123 | 39 | 543 | 57 | 18 | L | CD2 | 279 | 45 | 530 | 32 |
| 8 | S | OG | 133 | 34 | 535 | 52 | 18 | L | C | 285 | 18 | 560 | 41 |
| 8 | S | C | 129 | 17 | 556 | 55 | 18 | L | O | 297 | 20 | 560 | 41 |
| 8 | S | O | 139 | 20 | 563 | 54 | 19 | A | N | 279 | 13 | 571 | 41 |
| 9 | L | N | 128 | 5 | 551 | 52 | 19 | A | CA | 286 | 9 | 583 | 43 |
| 9 | L | CA | 137 | −5 | 554 | 51 | 19 | A | CB | 276 | 4 | 594 | 43 |
| 9 | L | CB | 130 | −19 | 554 | 52 | 19 | A | C | 296 | −3 | 580 | 43 |
| 9 | L | CG | 119 | −20 | 565 | 57 | 19 | A | O | 307 | −2 | 585 | 44 |
| 9 | L | CD1 | 112 | −34 | 564 | 58 | 20 | Q | N | 292 | −12 | 571 | 44 |
| 9 | L | CD2 | 124 | −18 | 580 | 59 | 20 | Q | CA | 300 | −24 | 568 | 45 |
| 9 | L | C | 149 | −5 | 544 | 48 | 20 | Q | CB | 291 | −34 | 561 | 45 |
| 9 | L | O | 160 | −10 | 547 | 47 | 20 | Q | CG | 282 | −43 | 569 | 50 |
| 10 | G | N | 147 | 0 | 532 | 44 | 20 | Q | CD | 276 | −54 | 561 | 62 |
| 10 | G | CA | 158 | 3 | 523 | 42 | 20 | Q | OE1 | 265 | −55 | 558 | 67 |
| 10 | G | C | 167 | 12 | 531 | 39 | 20 | Q | NE2 | 285 | −64 | 556 | 68 |
| 10 | G | O | 179 | 10 | 530 | 38 | 20 | Q | C | 311 | −21 | 558 | 45 |
| 11 | S | N | 162 | 21 | 538 | 36 | 20 | Q | O | 320 | −29 | 557 | 44 |
| 11 | S | CA | 169 | 31 | 545 | 38 | 21 | M | N | 309 | −10 | 550 | 44 |
| 11 | S | CB | 158 | 40 | 551 | 39 | 21 | M | CA | 319 | −6 | 541 | 43 |
| 11 | S | OG | 165 | 51 | 556 | 46 | 21 | M | CB | 313 | 4 | 531 | 42 |
| 11 | S | C | 178 | 25 | 556 | 39 | 21 | M | CG | 304 | −2 | 520 | 46 |
| 11 | S | O | 189 | 30 | 558 | 38 | 21 | M | SD | 293 | 10 | 511 | 50 |
| 12 | R | N | 172 | 15 | 564 | 38 | 21 | M | CE | 304 | 22 | 511 | 41 |
| 12 | R | CA | 180 | 9 | 574 | 39 | 21 | M | C | 332 | −1 | 547 | 41 |
| 12 | R | CB | 172 | −2 | 583 | 39 | 21 | M | O | 342 | 0 | 541 | 39 |
| 12 | R | CG | 160 | 4 | 589 | 45 | 22 | R | N | 330 | 4 | 560 | 42 |
| 12 | R | CD | 153 | −5 | 600 | 55 | 22 | R | CA | 341 | 11 | 566 | 43 |
| 12 | R | NE | 145 | 1 | 611 | 60 | 22 | R | CB | 338 | 13 | 580 | 43 |
| 12 | R | CZ | 149 | 12 | 617 | 64 | 22 | R | CG | 347 | 23 | 587 | 43 |

| | | | | | | |
|---|---|---|---|---|---|---|
| 22 | R | CD | 343 | 24 | 601 | 51 |
| 22 | R | NE | 350 | 34 | 608 | 58 |
| 22 | R | CZ | 351 | 35 | 622 | 63 |
| 22 | R | NH1 | 346 | 25 | 629 | 62 |
| 22 | R | NH2 | 357 | 45 | 627 | 59 |
| 22 | R | C | 354 | 3 | 567 | 46 |
| 22 | R | O | 354 | −9 | 570 | 45 |
| 23 | R | N | 366 | 9 | 563 | 47 |
| 23 | R | CA | 378 | 2 | 562 | 49 |
| 23 | R | CB | 385 | 3 | 548 | 48 |
| 23 | R | CG | 378 | −5 | 538 | 52 |
| 23 | R | CD | 380 | −1 | 524 | 57 |
| 23 | R | NE | 390 | −10 | 517 | 64 |
| 23 | R | CZ | 400 | −6 | 510 | 70 |
| 23 | R | NH1 | 403 | 7 | 508 | 71 |
| 23 | R | NH2 | 408 | −15 | 504 | 73 |
| 23 | R | C | 388 | 7 | 573 | 50 |
| 23 | R | O | 396 | 0 | 578 | 51 |
| 24 | I | N | 389 | 20 | 575 | 51 |
| 24 | I | CA | 398 | 25 | 585 | 53 |
| 24 | I | CB | 409 | 33 | 578 | 53 |
| 24 | I | CG1 | 404 | 45 | 570 | 50 |
| 24 | I | CD1 | 414 | 55 | 566 | 50 |
| 24 | I | CG2 | 417 | 24 | 569 | 54 |
| 24 | I | C | 390 | 34 | 594 | 55 |
| 24 | I | O | 378 | 37 | 592 | 55 |
| 25 | S | N | 396 | 38 | 605 | 58 |
| 25 | S | CA | 390 | 46 | 615 | 60 |
| 25 | S | CB | 395 | 42 | 629 | 61 |
| 25 | S | OG | 388 | 49 | 639 | 62 |
| 25 | S | C | 394 | 61 | 612 | 63 |
| 25 | S | O | 405 | 63 | 606 | 61 |
| 26 | L | N | 387 | 70 | 618 | 66 |
| 26 | L | CA | 390 | 84 | 617 | 70 |
| 26 | L | CB | 377 | 93 | 619 | 70 |
| 26 | L | CG | 373 | 103 | 609 | 72 |
| 26 | L | CD1 | 378 | 102 | 595 | 70 |
| 26 | L | CD2 | 357 | 104 | 610 | 72 |
| 26 | L | C | 401 | 88 | 627 | 72 |
| 26 | L | O | 405 | 100 | 627 | 73 |
| 27 | F | N | 405 | 79 | 635 | 74 |
| 27 | F | CA | 418 | 79 | 643 | 76 |
| 27 | F | CB | 420 | 64 | 649 | 77 |
| 27 | F | CG | 433 | 63 | 656 | 82 |
| 27 | F | CD1 | 433 | 64 | 670 | 86 |
| 27 | F | CE1 | 445 | 62 | 677 | 88 |
| 27 | F | CZ | 457 | 59 | 670 | 89 |
| 27 | F | CE2 | 457 | 58 | 656 | 88 |
| 27 | F | CD2 | 445 | 59 | 649 | 85 |
| 27 | F | C | 430 | 84 | 635 | 76 |
| 27 | F | O | 437 | 93 | 640 | 76 |
| 28 | S | N | 431 | 79 | 623 | 75 |
| 28 | S | CA | 443 | 82 | 614 | 74 |
| 28 | S | CB | 445 | 71 | 604 | 75 |
| 28 | S | OG | 434 | 61 | 606 | 73 |
| 28 | S | C | 442 | 96 | 607 | 73 |
| 28 | S | O | 452 | 101 | 602 | 72 |
| 29 | C | N | 430 | 101 | 607 | 71 |
| 29 | C | CA | 426 | 112 | 597 | 70 |
| 29 | C | CB | 414 | 107 | 589 | 70 |
| 29 | C | SG | 413 | 89 | 586 | 71 |
| 29 | C | C | 422 | 126 | 602 | 70 |
| 29 | C | O | 416 | 134 | 595 | 69 |
| 30 | L | N | 427 | 129 | 615 | 68 |
| 30 | L | CA | 424 | 142 | 621 | 68 |
| 30 | L | CB | 432 | 144 | 634 | 69 |
| 30 | L | CG | 431 | 135 | 646 | 73 |
| 30 | L | CD1 | 440 | 140 | 658 | 75 |
| 30 | L | CD2 | 416 | 133 | 650 | 77 |
| 30 | L | C | 426 | 154 | 612 | 66 |
| 30 | L | O | 418 | 164 | 611 | 65 |
| 31 | A | N | 437 | 153 | 605 | 64 |
| 31 | A | CA | 441 | 163 | 595 | 62 |
| 31 | A | CB | 455 | 159 | 589 | 63 |
| 31 | A | C | 431 | 165 | 583 | 60 |
| 31 | A | O | 430 | 175 | 577 | 59 |
| 32 | D | N | 422 | 155 | 581 | 57 |
| 32 | D | CA | 413 | 156 | 570 | 56 |
| 32 | D | CB | 413 | 143 | 561 | 56 |
| 32 | D | CG | 427 | 139 | 556 | 59 |
| 32 | D | OD1 | 432 | 147 | 547 | 59 |
| 32 | D | OD2 | 434 | 130 | 561 | 61 |
| 32 | D | C | 398 | 159 | 573 | 54 |
| 32 | D | O | 390 | 161 | 565 | 54 |
| 33 | R | N | 395 | 159 | 587 | 51 |
| 33 | R | CA | 382 | 162 | 592 | 50 |
| 33 | R | CB | 382 | 164 | 607 | 52 |
| 33 | R | CG | 386 | 152 | 616 | 58 |
| 33 | R | CD | 378 | 139 | 613 | 67 |
| 33 | R | NE | 364 | 141 | 618 | 73 |
| 33 | R | CZ | 359 | 137 | 630 | 77 |
| 33 | R | NH1 | 366 | 130 | 638 | 77 |
| 33 | R | NH2 | 346 | 139 | 633 | 76 |
| 33 | R | C | 376 | 174 | 585 | 48 |
| 33 | R | O | 383 | 184 | 583 | 45 |
| 34 | H | N | 363 | 174 | 582 | 44 |
| 34 | H | CA | 358 | 186 | 574 | 42 |
| 34 | H | CB | 361 | 183 | 559 | 41 |
| 34 | H | CG | 358 | 195 | 550 | 44 |
| 34 | H | ND1 | 368 | 203 | 546 | 46 |
| 34 | H | CE1 | 362 | 212 | 537 | 49 |
| 34 | H | NE2 | 350 | 209 | 537 | 44 |
| 34 | H | CD2 | 347 | 198 | 544 | 45 |
| 34 | H | C | 344 | 187 | 576 | 39 |
| 34 | H | O | 336 | 177 | 577 | 36 |
| 35 | D | N | 340 | 200 | 577 | 36 |
| 35 | D | CA | 325 | 203 | 578 | 37 |
| 35 | D | CB | 323 | 215 | 589 | 37 |
| 35 | D | CG | 308 | 217 | 591 | 38 |
| 35 | D | OD1 | 306 | 225 | 601 | 38 |
| 35 | D | OD2 | 299 | 213 | 584 | 35 |
| 35 | D | C | 320 | 207 | 564 | 36 |
| 35 | D | O | 324 | 218 | 559 | 34 |
| 36 | F | N | 310 | 200 | 559 | 36 |
| 36 | F | CA | 305 | 202 | 545 | 35 |
| 36 | F | CB | 302 | 188 | 539 | 34 |
| 36 | F | CG | 314 | 179 | 537 | 36 |
| 36 | F | CD1 | 318 | 170 | 546 | 36 |
| 36 | F | CE1 | 329 | 161 | 544 | 34 |
| 36 | F | CZ | 337 | 163 | 532 | 30 |
| 36 | F | CE2 | 333 | 173 | 523 | 32 |
| 36 | F | CD2 | 322 | 181 | 525 | 34 |
| 36 | F | C | 292 | 210 | 545 | 35 |
| 36 | F | O | 286 | 212 | 534 | 33 |
| 37 | G | N | 288 | 215 | 557 | 34 |
| 37 | G | CA | 277 | 224 | 558 | 34 |
| 37 | G | C | 264 | 217 | 552 | 34 |
| 37 | G | O | 257 | 223 | 544 | 37 |
| 38 | F | N | 261 | 206 | 557 | 34 |
| 38 | F | CA | 249 | 198 | 552 | 34 |
| 38 | F | CB | 248 | 185 | 559 | 33 |
| 38 | F | CG | 236 | 177 | 556 | 35 |
| 38 | F | CD1 | 233 | 173 | 543 | 32 |
| 38 | F | CE1 | 222 | 166 | 539 | 32 |
| 38 | F | CZ | 212 | 163 | 549 | 33 |
| 38 | F | CE2 | 215 | 166 | 562 | 32 |
| 38 | F | CD2 | 226 | 174 | 566 | 34 |
| 38 | F | C | 236 | 207 | 555 | 34 |
| 38 | F | O | 235 | 211 | 566 | 32 |
| 39 | P | N | 228 | 209 | 545 | 35 |
| 39 | P | CA | 216 | 217 | 548 | 37 |
| 39 | P | CB | 212 | 223 | 535 | 35 |
| 39 | P | CG | 216 | 212 | 525 | 35 |
| 39 | P | CD | 229 | 206 | 531 | 36 |
| 39 | P | C | 204 | 209 | 556 | 38 |
| 39 | P | O | 194 | 206 | 549 | 37 |
| 40 | Q | N | 206 | 206 | 568 | 38 |
| 40 | Q | CA | 197 | 198 | 576 | 40 |
| 40 | Q | CB | 203 | 193 | 589 | 42 |
| 40 | Q | CG | 204 | 204 | 600 | 48 |
| 40 | Q | CD | 209 | 198 | 613 | 54 |
| 40 | Q | OE1 | 221 | 197 | 615 | 54 |
| 40 | Q | NE2 | 200 | 194 | 622 | 55 |
| 40 | Q | C | 184 | 205 | 578 | 40 |
| 40 | Q | O | 173 | 199 | 579 | 39 |
| 41 | E | N | 184 | 218 | 578 | 41 |
| 41 | E | CA | 171 | 226 | 579 | 42 |
| 41 | E | CB | 174 | 241 | 579 | 42 |
| 41 | E | CG | 178 | 248 | 566 | 41 |
| 41 | E | CD | 192 | 245 | 562 | 40 |

| 41 | E | OE1 | 200 | 239 | 570 | 40 |
| 41 | E | OE2 | 196 | 250 | 552 | 43 |
| 41 | E | C | 162 | 223 | 568 | 44 |
| 41 | E | O | 150 | 225 | 569 | 44 |
| 42 | E | N | 167 | 218 | 556 | 43 |
| 42 | E | CA | 158 | 214 | 545 | 45 |
| 42 | E | CB | 167 | 209 | 534 | 45 |
| 42 | E | CG | 164 | 217 | 522 | 49 |
| 42 | E | CD | 169 | 232 | 524 | 55 |
| 42 | E | OE1 | 161 | 241 | 520 | 54 |
| 42 | E | OE2 | 179 | 233 | 530 | 55 |
| 42 | E | C | 149 | 202 | 548 | 46 |
| 42 | E | O | 139 | 199 | 541 | 46 |
| 43 | F | N | 152 | 194 | 559 | 47 |
| 43 | F | CA | 145 | 182 | 562 | 51 |
| 43 | F | CB | 154 | 170 | 564 | 47 |
| 43 | F | CG | 162 | 166 | 551 | 43 |
| 43 | F | CD1 | 174 | 173 | 548 | 33 |
| 43 | F | CE1 | 180 | 170 | 536 | 39 |
| 43 | F | CZ | 175 | 160 | 528 | 36 |
| 43 | F | CE2 | 163 | 154 | 531 | 38 |
| 43 | F | CD2 | 157 | 157 | 542 | 36 |
| 43 | F | C | 136 | 184 | 575 | 56 |
| 43 | F | O | 128 | 175 | 579 | 57 |
| 44 | G | N | 137 | 197 | 581 | 60 |
| 44 | G | CA | 132 | 200 | 594 | 66 |
| 44 | G | C | 118 | 204 | 597 | 70 |
| 44 | G | O | 110 | 204 | 588 | 71 |
| 45 | N | N | 115 | 208 | 610 | 73 |
| 45 | N | CA | 102 | 211 | 615 | 76 |
| 45 | N | CB | 101 | 209 | 630 | 77 |
| 45 | N | CG | 97 | 195 | 634 | 80 |
| 45 | N | OD1 | 86 | 190 | 633 | 82 |
| 45 | N | ND2 | 107 | 188 | 640 | 81 |
| 45 | N | C | 96 | 224 | 610 | 77 |
| 45 | N | O | 85 | 228 | 615 | 78 |
| 46 | Q | N | 103 | 231 | 601 | 78 |
| 46 | Q | CA | 98 | 242 | 594 | 79 |
| 46 | Q | CB | 109 | 251 | 589 | 80 |
| 46 | Q | CG | 105 | 262 | 579 | 82 |
| 46 | Q | CD | 117 | 271 | 574 | 85 |
| 46 | Q | OE1 | 129 | 267 | 576 | 87 |
| 46 | Q | NE2 | 114 | 283 | 569 | 86 |
| 46 | Q | C | 89 | 236 | 582 | 79 |
| 46 | Q | O | 81 | 244 | 576 | 79 |
| 47 | F | N | 91 | 224 | 578 | 79 |
| 47 | F | CA | 83 | 216 | 568 | 79 |
| 47 | F | CB | 93 | 212 | 556 | 79 |
| 47 | F | CG | 103 | 223 | 552 | 81 |
| 47 | F | CD1 | 116 | 223 | 557 | 80 |
| 47 | F | CE1 | 125 | 233 | 553 | 81 |
| 47 | F | CZ | 121 | 243 | 544 | 82 |
| 47 | F | CE2 | 108 | 243 | 539 | 83 |
| 47 | F | CD2 | 99 | 233 | 543 | 83 |
| 47 | F | C | 75 | 204 | 572 | 78 |
| 47 | F | O | 79 | 198 | 583 | 78 |
| 48 | G | N | 66 | 200 | 564 | 78 |
| 48 | G | CA | 58 | 187 | 567 | 77 |
| 48 | G | C | 60 | 175 | 558 | 76 |
| 48 | G | O | 58 | 176 | 545 | 77 |
| 49 | A | N | 62 | 163 | 564 | 74 |
| 49 | A | CA | 66 | 151 | 557 | 72 |
| 49 | A | CB | 58 | 139 | 562 | 72 |
| 49 | A | C | 68 | 151 | 542 | 69 |
| 49 | A | O | 79 | 151 | 536 | 69 |
| 50 | A | N | 56 | 150 | 535 | 67 |
| 50 | A | CA | 55 | 150 | 521 | 63 |
| 50 | A | CB | 40 | 150 | 517 | 64 |
| 50 | A | C | 62 | 162 | 515 | 60 |
| 50 | A | O | 66 | 161 | 503 | 61 |
| 51 | A | N | 63 | 172 | 522 | 56 |
| 51 | A | CA | 70 | 184 | 517 | 52 |
| 51 | A | CB | 69 | 196 | 527 | 53 |
| 51 | A | C | 85 | 182 | 514 | 49 |
| 51 | A | O | 91 | 188 | 506 | 49 |
| 52 | T | N | 91 | 173 | 522 | 44 |
| 52 | T | CA | 106 | 171 | 521 | 44 |
| 52 | T | CB | 112 | 169 | 535 | 42 |
| 52 | T | OG1 | 107 | 158 | 542 | 43 |
| 52 | T | CG2 | 108 | 181 | 544 | 44 |
| 52 | T | C | 109 | 158 | 513 | 42 |
| 52 | T | O | 121 | 156 | 510 | 41 |
| 53 | I | N | 99 | 151 | 507 | 40 |
| 53 | I | CA | 102 | 140 | 499 | 38 |
| 53 | I | CB | 88 | 134 | 493 | 39 |
| 53 | I | CG1 | 80 | 126 | 504 | 42 |
| 53 | I | CD1 | 87 | 116 | 511 | 49 |
| 53 | I | CG2 | 91 | 124 | 481 | 39 |
| 53 | I | C | 111 | 144 | 487 | 36 |
| 53 | I | O | 120 | 136 | 485 | 37 |
| 54 | P | N | 109 | 155 | 480 | 35 |
| 54 | P | CA | 117 | 158 | 469 | 34 |
| 54 | P | CB | 112 | 172 | 464 | 33 |
| 54 | P | CG | 98 | 172 | 469 | 35 |
| 54 | P | CD | 98 | 165 | 482 | 34 |
| 54 | P | C | 132 | 159 | 473 | 33 |
| 54 | P | O | 141 | 156 | 465 | 32 |
| 55 | V | N | 135 | 164 | 485 | 33 |
| 55 | V | CA | 149 | 166 | 489 | 32 |
| 55 | V | CB | 149 | 178 | 499 | 35 |
| 55 | V | CG1 | 142 | 175 | 511 | 37 |
| 55 | V | CG2 | 162 | 180 | 504 | 39 |
| 55 | V | C | 155 | 153 | 494 | 31 |
| 55 | V | O | 166 | 150 | 492 | 29 |
| 56 | L | N | 147 | 145 | 501 | 30 |
| 56 | L | CA | 151 | 131 | 504 | 30 |
| 56 | L | CB | 141 | 124 | 513 | 31 |
| 56 | L | CG | 144 | 109 | 515 | 35 |
| 56 | L | CD1 | 159 | 109 | 523 | 38 |
| 56 | L | CD2 | 133 | 103 | 524 | 39 |
| 56 | L | C | 155 | 123 | 491 | 30 |
| 56 | L | O | 165 | 116 | 491 | 29 |
| 57 | H | N | 146 | 124 | 481 | 29 |
| 57 | H | CA | 148 | 117 | 468 | 29 |
| 57 | H | CB | 135 | 120 | 459 | 29 |
| 57 | H | CG | 136 | 114 | 445 | 28 |
| 57 | H | ND1 | 142 | 121 | 435 | 34 |
| 57 | H | CE1 | 141 | 114 | 424 | 29 |
| 57 | H | NE2 | 135 | 102 | 427 | 29 |
| 57 | H | CD2 | 132 | 102 | 440 | 30 |
| 57 | H | C | 161 | 122 | 462 | 29 |
| 57 | H | O | 169 | 114 | 457 | 28 |
| 58 | E | N | 163 | 135 | 462 | 29 |
| 58 | E | CA | 176 | 140 | 456 | 29 |
| 58 | E | CB | 177 | 156 | 456 | 29 |
| 58 | E | CG | 189 | 162 | 449 | 30 |
| 58 | E | CD | 188 | 159 | 434 | 36 |
| 58 | E | OE1 | 198 | 157 | 427 | 34 |
| 58 | E | OE2 | 177 | 159 | 428 | 34 |
| 58 | E | C | 188 | 135 | 464 | 29 |
| 58 | E | O | 198 | 131 | 458 | 27 |
| 59 | M | N | 187 | 134 | 477 | 29 |
| 59 | M | CA | 198 | 129 | 485 | 32 |
| 59 | M | CB | 193 | 129 | 500 | 31 |
| 59 | M | CG | 204 | 125 | 508 | 41 |
| 59 | M | SD | 212 | 140 | 514 | 47 |
| 59 | M | CE | 221 | 131 | 528 | 43 |
| 59 | M | C | 201 | 114 | 481 | 29 |
| 59 | M | O | 213 | 110 | 480 | 27 |
| 60 | I | N | 191 | 106 | 480 | 27 |
| 60 | I | CA | 193 | 92 | 475 | 27 |
| 60 | I | CB | 180 | 84 | 476 | 29 |
| 60 | I | CG1 | 176 | 83 | 490 | 31 |
| 60 | I | CD1 | 161 | 80 | 492 | 34 |
| 60 | I | CG2 | 182 | 70 | 470 | 28 |
| 60 | I | C | 200 | 91 | 462 | 27 |
| 60 | I | O | 209 | 83 | 460 | 26 |
| 61 | Q | N | 195 | 99 | 452 | 25 |
| 61 | Q | CA | 201 | 98 | 439 | 26 |
| 61 | Q | CB | 193 | 108 | 430 | 26 |
| 61 | Q | CG | 200 | 110 | 415 | 29 |
| 61 | Q | CD | 199 | 97 | 406 | 35 |
| 61 | Q | OE1 | 188 | 91 | 405 | 31 |
| 61 | Q | NE2 | 210 | 93 | 400 | 28 |
| 61 | Q | C | 215 | 103 | 440 | 28 |
| 61 | Q | O | 224 | 97 | 433 | 28 |
| 62 | Q | N | 218 | 114 | 448 | 26 |
| 62 | Q | CA | 232 | 119 | 448 | 26 |
| 62 | Q | CB | 233 | 133 | 455 | 28 |
| 62 | Q | CG | 226 | 144 | 448 | 29 |

| 62 | Q | CD | 232 | 147 | 435 | 34 | 72 | S | OG | 321 | 42 | 454 | 38 |
| --- | --- | --- | --- | --- | --- | --- | --- | --- | --- | --- | --- | --- | --- |
| 62 | Q | OE1 | 244 | 145 | 433 | 34 | 72 | S | C | 345 | 32 | 444 | 39 |
| 62 | Q | NE2 | 224 | 150 | 425 | 30 | 72 | S | O | 347 | 25 | 455 | 37 |
| 62 | Q | C | 241 | 109 | 456 | 26 | 73 | S | N | 345 | 27 | 432 | 39 |
| 62 | Q | O | 253 | 108 | 452 | 26 | 73 | S | CA | 348 | 13 | 429 | 44 |
| 63 | I | N | 235 | 102 | 466 | 26 | 73 | S | CB | 347 | 10 | 414 | 44 |
| 63 | I | CA | 243 | 91 | 472 | 26 | 73 | S | OG | 333 | 9 | 411 | 50 |
| 63 | I | CB | 236 | 86 | 485 | 26 | 73 | S | C | 362 | 9 | 434 | 43 |
| 63 | I | CG1 | 236 | 96 | 496 | 27 | 73 | S | O | 364 | −3 | 439 | 42 |
| 63 | I | CD1 | 227 | 93 | 508 | 27 | 74 | A | N | 372 | 18 | 434 | 44 |
| 63 | I | CG2 | 243 | 73 | 490 | 27 | 74 | A | CA | 386 | 15 | 438 | 45 |
| 63 | I | C | 247 | 80 | 462 | 28 | 74 | A | CB | 395 | 25 | 431 | 45 |
| 63 | I | O | 259 | 76 | 461 | 28 | 74 | A | C | 387 | 17 | 453 | 46 |
| 64 | F | N | 237 | 77 | 454 | 28 | 74 | A | O | 397 | 15 | 459 | 47 |
| 64 | F | CA | 241 | 67 | 443 | 29 | 75 | A | N | 376 | 21 | 459 | 44 |
| 64 | F | CB | 228 | 64 | 434 | 28 | 75 | A | CA | 377 | 25 | 473 | 42 |
| 64 | F | CG | 232 | 57 | 421 | 30 | 75 | A | CB | 372 | 39 | 475 | 42 |
| 64 | F | CD1 | 233 | 43 | 421 | 32 | 75 | A | C | 370 | 16 | 483 | 41 |
| 64 | F | CE1 | 237 | 37 | 409 | 27 | 75 | A | O | 374 | 15 | 494 | 41 |
| 64 | F | CZ | 239 | 44 | 397 | 28 | 76 | W | N | 360 | 9 | 478 | 41 |
| 64 | F | CE2 | 238 | 58 | 397 | 35 | 76 | W | CA | 351 | 1 | 487 | 41 |
| 64 | F | CD2 | 234 | 65 | 409 | 33 | 76 | W | CB | 337 | 8 | 489 | 40 |
| 64 | F | C | 251 | 73 | 433 | 31 | 76 | W | CG | 338 | 23 | 492 | 36 |
| 64 | F | O | 260 | 66 | 429 | 31 | 76 | W | CD1 | 335 | 34 | 484 | 33 |
| 65 | N | N | 250 | 86 | 430 | 29 | 76 | W | NE1 | 337 | 45 | 491 | 32 |
| 65 | N | CA | 260 | 92 | 420 | 30 | 76 | W | CE2 | 342 | 42 | 504 | 36 |
| 65 | N | CB | 257 | 107 | 417 | 28 | 76 | W | CD2 | 342 | 28 | 505 | 35 |
| 65 | N | CG | 244 | 109 | 409 | 34 | 76 | W | CE3 | 347 | 22 | 517 | 36 |
| 65 | N | OD1 | 239 | 99 | 403 | 33 | 76 | W | CZ3 | 350 | 30 | 528 | 34 |
| 65 | N | ND2 | 238 | 121 | 408 | 31 | 76 | W | CH2 | 349 | 44 | 527 | 38 |
| 65 | N | C | 274 | 92 | 426 | 30 | 76 | W | CZ2 | 345 | 50 | 515 | 34 |
| 65 | N | O | 284 | 88 | 420 | 30 | 76 | W | C | 348 | −12 | 481 | 42 |
| 66 | L | N | 275 | 95 | 439 | 30 | 76 | W | O | 349 | −15 | 469 | 41 |
| 66 | L | CA | 288 | 96 | 446 | 29 | 77 | D | N | 345 | −21 | 490 | 43 |
| 66 | L | CB | 285 | 102 | 461 | 28 | 77 | D | CA | 341 | −35 | 486 | 45 |
| 66 | L | CG | 298 | 103 | 470 | 31 | 77 | D | CB | 336 | −43 | 497 | 45 |
| 66 | L | CD1 | 309 | 111 | 464 | 32 | 77 | D | CG | 334 | −57 | 493 | 51 |
| 66 | L | CD2 | 293 | 107 | 484 | 29 | 77 | D | OD1 | 323 | −61 | 491 | 52 |
| 66 | L | C | 294 | 82 | 447 | 31 | 77 | D | OD2 | 344 | −66 | 492 | 54 |
| 66 | L | O | 306 | 80 | 445 | 31 | 77 | D | C | 330 | −36 | 475 | 47 |
| 67 | F | N | 286 | 71 | 450 | 30 | 77 | D | O | 319 | −30 | 476 | 46 |
| 67 | F | CA | 292 | 58 | 452 | 30 | 78 | E | N | 334 | −43 | 464 | 48 |
| 67 | F | CB | 285 | 51 | 464 | 28 | 78 | E | CA | 325 | −44 | 452 | 50 |
| 67 | F | CG | 289 | 56 | 477 | 31 | 78 | E | CB | 333 | −52 | 441 | 50 |
| 67 | F | CD1 | 282 | 67 | 483 | 30 | 78 | E | CG | 324 | −60 | 432 | 59 |
| 67 | F | CE1 | 285 | 73 | 495 | 28 | 78 | E | CD | 332 | −67 | 420 | 68 |
| 67 | F | CZ | 297 | 68 | 502 | 33 | 78 | E | OE1 | 328 | −64 | 409 | 70 |
| 67 | F | CE2 | 304 | 57 | 496 | 34 | 78 | E | OE2 | 341 | −75 | 423 | 70 |
| 67 | F | CD2 | 301 | 52 | 484 | 32 | 78 | E | C | 312 | −51 | 455 | 48 |
| 67 | F | C | 292 | 49 | 440 | 31 | 78 | E | O | 302 | −47 | 450 | 48 |
| 67 | F | O | 296 | 38 | 441 | 32 | 79 | T | N | 312 | −60 | 465 | 47 |
| 68 | S | N | 288 | 54 | 428 | 32 | 79 | T | CA | 300 | −67 | 468 | 46 |
| 68 | S | CA | 289 | 46 | 416 | 34 | 79 | T | CB | 303 | −81 | 475 | 47 |
| 68 | S | CB | 275 | 46 | 409 | 33 | 79 | T | OG1 | 311 | −89 | 466 | 50 |
| 68 | S | OG | 272 | 59 | 405 | 33 | 79 | T | CG2 | 290 | −89 | 475 | 46 |
| 68 | S | C | 299 | 50 | 406 | 37 | 79 | T | C | 290 | −58 | 476 | 45 |
| 68 | S | O | 299 | 46 | 395 | 38 | 79 | T | O | 278 | −59 | 473 | 42 |
| 69 | T | N | 308 | 59 | 410 | 39 | 80 | L | N | 296 | −51 | 485 | 42 |
| 69 | T | CA | 319 | 63 | 401 | 40 | 80 | L | CA | 288 | −42 | 493 | 43 |
| 69 | T | CB | 326 | 76 | 405 | 38 | 80 | L | CB | 296 | −37 | 506 | 42 |
| 69 | T | OG1 | 332 | 74 | 418 | 39 | 80 | L | CG | 301 | −47 | 517 | 45 |
| 69 | T | CG2 | 317 | 88 | 407 | 39 | 80 | L | CD1 | 311 | −40 | 527 | 43 |
| 69 | T | C | 330 | 52 | 401 | 42 | 80 | L | CD2 | 290 | −54 | 524 | 46 |
| 69 | T | O | 330 | 43 | 410 | 42 | 80 | L | C | 282 | −31 | 485 | 41 |
| 70 | A | N | 339 | 53 | 392 | 43 | 80 | L | O | 270 | −28 | 486 | 42 |
| 70 | A | CA | 351 | 44 | 392 | 43 | 81 | L | N | 290 | −25 | 476 | 40 |
| 70 | A | CB | 359 | 46 | 378 | 45 | 81 | L | CA | 285 | −15 | 466 | 41 |
| 70 | A | C | 359 | 47 | 404 | 42 | 81 | L | CB | 297 | −10 | 457 | 39 |
| 70 | A | O | 365 | 38 | 410 | 42 | 81 | L | CG | 307 | −1 | 464 | 39 |
| 71 | D | N | 360 | 60 | 408 | 41 | 81 | L | CD1 | 318 | 2 | 453 | 38 |
| 71 | D | CA | 367 | 62 | 421 | 41 | 81 | L | CD2 | 301 | 12 | 469 | 33 |
| 71 | D | CB | 367 | 77 | 424 | 42 | 81 | L | C | 273 | −20 | 458 | 41 |
| 71 | D | CG | 373 | 85 | 413 | 46 | 81 | L | O | 263 | −13 | 457 | 40 |
| 71 | D | OD1 | 386 | 83 | 411 | 50 | 82 | D | N | 275 | −32 | 452 | 42 |
| 71 | D | OD2 | 367 | 93 | 405 | 48 | 82 | D | CA | 264 | −37 | 444 | 42 |
| 71 | D | C | 362 | 55 | 433 | 41 | 82 | D | CB | 268 | −51 | 438 | 44 |
| 71 | D | O | 370 | 50 | 441 | 39 | 82 | D | CG | 256 | −57 | 431 | 47 |
| 72 | S | N | 348 | 55 | 434 | 40 | 82 | D | OD1 | 253 | −52 | 421 | 52 |
| 72 | S | CA | 342 | 47 | 445 | 38 | 82 | D | OD2 | 249 | −67 | 436 | 53 |
| 72 | S | CB | 327 | 49 | 444 | 36 | 82 | D | C | 251 | −38 | 452 | 42 |

| 82 | D | O | 241 | −34 | 447 | 43 | | 91 | Q | CB | 151 | 44 | 486 | 35 |
|---|---|---|---|---|---|---|---|---|---|---|---|---|---|---|
| 83 | K | N | 252 | −44 | 464 | 41 | | 91 | Q | CG | 154 | 35 | 498 | 33 |
| 83 | K | CA | 241 | −44 | 473 | 41 | | 91 | Q | CD | 165 | 40 | 507 | 35 |
| 83 | K | CB | 245 | −50 | 486 | 41 | | 91 | Q | OE1 | 163 | 48 | 516 | 33 |
| 83 | K | CG | 247 | −65 | 485 | 48 | | 91 | Q | NE2 | 177 | 35 | 504 | 34 |
| 83 | K | CD | 249 | −72 | 499 | 54 | | 91 | Q | C | 136 | 49 | 467 | 34 |
| 83 | K | CE | 255 | −86 | 498 | 60 | | 91 | Q | O | 126 | 55 | 469 | 35 |
| 83 | K | NZ | 265 | −88 | 510 | 65 | | 92 | L | N | 143 | 50 | 456 | 32 |
| 83 | K | C | 235 | −29 | 477 | 39 | | 92 | L | CA | 139 | 60 | 446 | 33 |
| 83 | K | O | 223 | −28 | 480 | 38 | | 92 | L | CB | 149 | 61 | 435 | 32 |
| 84 | F | N | 245 | −20 | 478 | 36 | | 92 | L | CG | 163 | 67 | 439 | 34 |
| 84 | F | CA | 242 | −6 | 482 | 35 | | 92 | L | CD1 | 172 | 66 | 427 | 34 |
| 84 | F | CB | 255 | 1 | 484 | 33 | | 92 | L | CD2 | 163 | 82 | 443 | 28 |
| 84 | F | CG | 254 | 15 | 490 | 33 | | 92 | L | C | 125 | 56 | 440 | 36 |
| 84 | F | CD1 | 249 | 16 | 503 | 29 | | 92 | L | O | 116 | 64 | 438 | 34 |
| 84 | F | CE1 | 248 | 9 | 508 | 33 | | 93 | N | N | 125 | 43 | 436 | 38 |
| 84 | F | CZ | 253 | 40 | 502 | 27 | | 93 | N | CA | 114 | 36 | 431 | 41 |
| 84 | F | CE2 | 258 | 39 | 489 | 26 | | 93 | N | CB | 117 | 21 | 430 | 41 |
| 84 | F | CD2 | 259 | 27 | 483 | 31 | | 93 | N | CG | 107 | 14 | 422 | 50 |
| 84 | F | C | 233 | 0 | 470 | 34 | | 93 | N | OD1 | 96 | 13 | 425 | 53 |
| 84 | F | O | 223 | 6 | 473 | 35 | | 93 | N | ND2 | 112 | 9 | 411 | 57 |
| 85 | Y | N | 238 | −2 | 458 | 34 | | 93 | N | C | 101 | 39 | 440 | 42 |
| 85 | Y | CA | 230 | 4 | 446 | 35 | | 93 | N | O | 91 | 44 | 435 | 42 |
| 85 | Y | CB | 236 | 0 | 433 | 34 | | 94 | D | N | 102 | 36 | 453 | 42 |
| 85 | Y | CG | 250 | 4 | 432 | 36 | | 94 | D | CA | 92 | 38 | 462 | 43 |
| 85 | Y | CD1 | 255 | 15 | 439 | 31 | | 94 | D | CB | 96 | 33 | 476 | 44 |
| 85 | Y | CE1 | 268 | 19 | 438 | 33 | | 94 | D | CG | 97 | 18 | 478 | 49 |
| 85 | Y | CZ | 277 | 114 | 29 | 38 | | 94 | D | OD1 | 94 | 10 | 468 | 51 |
| 85 | Y | OH | 290 | 15 | 429 | 38 | | 94 | D | OD2 | 101 | 13 | 488 | 53 |
| 85 | Y | CE2 | 272 | 0 | 422 | 40 | | 94 | D | C | 87 | 52 | 463 | 44 |
| 85 | Y | CD2 | 259 | −3 | 423 | 37 | | 94 | D | O | 75 | 55 | 462 | 45 |
| 85 | Y | C | 216 | −2 | 446 | 37 | | 95 | L | N | 96 | 62 | 464 | 44 |
| 85 | Y | O | 206 | 6 | 444 | 36 | | 95 | L | CA | 93 | 76 | 464 | 43 |
| 86 | T | N | 215 | −15 | 448 | 37 | | 95 | L | CB | 105 | 85 | 467 | 43 |
| 86 | T | CA | 201 | −21 | 450 | 40 | | 95 | L | CG | 111 | 82 | 481 | 43 |
| 86 | T | CB | 203 | −36 | 452 | 39 | | 95 | L | CD1 | 124 | 89 | 484 | 41 |
| 86 | T | OG1 | 207 | −42 | 440 | 43 | | 95 | L | CD2 | 101 | 85 | 492 | 45 |
| 86 | T | CG2 | 189 | −43 | 455 | 43 | | 95 | L | C | 86 | 81 | 451 | 43 |
| 86 | T | C | 192 | −14 | 459 | 38 | | 95 | L | O | 76 | 88 | 452 | 45 |
| 86 | T | O | 180 | −11 | 456 | 38 | | 96 | E | N | 91 | 77 | 440 | 43 |
| 87 | E | N | 196 | −12 | 471 | 36 | | 96 | E | CA | 84 | 80 | 427 | 43 |
| 87 | E | CA | 188 | −4 | 481 | 36 | | 96 | E | CB | 93 | 76 | 416 | 42 |
| 87 | E | CB | 194 | −4 | 495 | 37 | | 96 | E | CG | 106 | 84 | 416 | 40 |
| 87 | E | CG | 198 | −18 | 500 | 40 | | 96 | E | CD | 117 | 78 | 407 | 38 |
| 87 | E | CD | 186 | −26 | 503 | 46 | | 96 | E | OE1 | 113 | 68 | 400 | 38 |
| 87 | E | OE1 | 175 | −20 | 504 | 44 | | 96 | E | OE2 | 128 | 82 | 408 | 38 |
| 87 | E | OE2 | 187 | −38 | 504 | 48 | | 96 | E | C | 70 | 73 | 425 | 46 |
| 87 | E | C | 185 | 10 | 477 | 34 | | 96 | E | O | 61 | 80 | 421 | 44 |
| 87 | E | O | 174 | 15 | 480 | 33 | | 97 | A | N | 70 | 60 | 427 | 48 |
| 88 | L | N | 194 | 17 | 470 | 33 | | 97 | A | CA | 57 | 53 | 426 | 50 |
| 88 | L | CA | 191 | 31 | 466 | 32 | | 97 | A | CB | 58 | 38 | 429 | 49 |
| 88 | L | CB | 204 | 38 | 461 | 30 | | 97 | A | C | 46 | 60 | 434 | 51 |
| 88 | L | CG | 215 | 38 | 473 | 27 | | 97 | A | O | 35 | 61 | 428 | 51 |
| 88 | L | CD1 | 228 | 43 | 466 | 25 | | 98 | C | N | 48 | 64 | 446 | 53 |
| 88 | L | CD2 | 211 | 48 | 484 | 28 | | 98 | C | CA | 38 | 72 | 453 | 56 |
| 88 | L | C | 181 | 31 | 455 | 33 | | 98 | C | CB | 42 | 76 | 467 | 56 |
| 88 | L | O | 171 | 39 | 456 | 32 | | 98 | C | SG | 42 | 61 | 477 | 64 |
| 89 | Y | N | 182 | 22 | 445 | 33 | | 98 | C | C | 32 | 84 | 446 | 56 |
| 89 | Y | CA | 171 | 21 | 434 | 35 | | 98 | C | O | 20 | 87 | 447 | 56 |
| 89 | Y | CB | 173 | 9 | 424 | 34 | | 99 | V | N | 41 | 93 | 441 | 57 |
| 89 | Y | CG | 187 | 9 | 417 | 33 | | 99 | V | CA | 37 | 105 | 434 | 59 |
| 89 | Y | CD1 | 194 | 20 | 414 | 35 | | 99 | V | CB | 50 | 114 | 432 | 59 |
| 89 | Y | CE1 | 207 | 19 | 408 | 36 | | 99 | V | CG1 | 45 | 127 | 427 | 62 |
| 89 | Y | CZ | 213 | 7 | 405 | 33 | | 99 | V | CG2 | 58 | 115 | 445 | 63 |
| 89 | Y | OH | 225 | 6 | 400 | 33 | | 99 | V | C | 30 | 103 | 421 | 59 |
| 89 | Y | CE2 | 206 | −5 | 409 | 35 | | 99 | V | O | 21 | 110 | 418 | 58 |
| 89 | Y | CD2 | 193 | −4 | 415 | 34 | | 100 | I | N | 34 | 92 | 414 | 59 |
| 89 | Y | C | 157 | 18 | 440 | 36 | | 100 | I | CA | 27 | 89 | 401 | 60 |
| 89 | Y | O | 147 | 24 | 435 | 37 | | 100 | I | CB | 35 | 80 | 392 | 61 |
| 90 | Q | N | 157 | 9 | 450 | 36 | | 100 | I | CG1 | 49 | 87 | 388 | 60 |
| 90 | Q | CA | 144 | 6 | 456 | 39 | | 100 | I | CD1 | 48 | 97 | 376 | 64 |
| 90 | Q | CB | 145 | −6 | 465 | 39 | | 100 | I | CG2 | 28 | 74 | 380 | 59 |
| 90 | Q | CG | 132 | −15 | 468 | 48 | | 100 | I | C | 12 | 84 | 404 | 61 |
| 90 | Q | CD | 121 | −15 | 456 | 56 | | 100 | I | O | 3 | 85 | 396 | 62 |
| 90 | Q | OE1 | 124 | −19 | 445 | 59 | | 101 | Q | N | 11 | 77 | 416 | 63 |
| 90 | Q | NE2 | 110 | −9 | 459 | 55 | | 101 | Q | CA | −2 | 73 | 421 | 64 |
| 90 | Q | C | 138 | 18 | 463 | 36 | | 101 | Q | CB | 0 | 62 | 432 | 64 |
| 90 | Q | O | 125 | 20 | 462 | 36 | | 101 | Q | CG | 2 | 48 | 426 | 69 |
| 91 | Q | N | 146 | 26 | 471 | 35 | | 101 | Q | CD | 10 | 39 | 435 | 76 |
| 91 | Q | CA | 141 | 38 | 477 | 34 | | 101 | Q | OE1 | 9 | 41 | 448 | 78 |

| | | | | | | | | | | | | |
|---|---|---|---|---|---|---|---|---|---|---|---|---|
| 101 | Q | NE2 | 18 | 29 | 430 | 76 | 120 | R | CA | 231 | 190 | 450 | 34 |
| 101 | Q | C | -10 | 84 | 428 | 64 | 120 | R | CB | 227 | 195 | 436 | 34 |
| 101 | Q | O | -21 | 82 | 433 | 64 | 120 | R | CG | 218 | 185 | 429 | 37 |
| 102 | G | N | -5 | 96 | 428 | 66 | 120 | R | CD | 215 | 188 | 414 | 35 |
| 102 | G | CA | -12 | 108 | 434 | 67 | 120 | R | NE | 202 | 181 | 412 | 39 |
| 102 | G | C | -9 | 109 | 449 | 69 | 120 | R | CZ | 192 | 185 | 405 | 40 |
| 102 | G | O | -14 | 119 | 456 | 69 | 120 | R | NH1 | 193 | 196 | 398 | 39 |
| 103 | V | N | -1 | 100 | 455 | 70 | 120 | R | NH2 | 181 | 178 | 404 | 40 |
| 103 | V | CA | 2 | 100 | 470 | 71 | 120 | R | C | 244 | 197 | 453 | 34 |
| 103 | V | CB | 5 | 85 | 475 | 71 | 120 | R | O | 255 | 191 | 450 | 35 |
| 103 | V | CG1 | 8 | 85 | 490 | 72 | 121 | K | N | 244 | 209 | 457 | 33 |
| 103 | V | CG2 | -7 | 76 | 471 | 72 | 121 | K | CA | 256 | 217 | 461 | 34 |
| 103 | V | C | 14 | 109 | 473 | 71 | 121 | K | CB | 252 | 231 | 464 | 34 |
| 103 | V | O | 13 | 120 | 475 | 71 | 121 | K | CG | 249 | 239 | 451 | 39 |
| 111 | A | N | 68 | 236 | 456 | 64 | 121 | K | CD | 247 | 253 | 455 | 46 |
| 111 | A | CA | 80 | 241 | 448 | 63 | 121 | K | CE | 239 | 262 | 444 | 51 |
| 111 | A | CB | 77 | 256 | 442 | 64 | 121 | K | NZ | 249 | 267 | 435 | 54 |
| 111 | A | C | 92 | 242 | 457 | 62 | 121 | K | C | 264 | 211 | 472 | 32 |
| 111 | A | O | 94 | 251 | 465 | 63 | 121 | K | O | 276 | 211 | 472 | 33 |
| 112 | K | N | 101 | 232 | 455 | 59 | 122 | Y | N | 257 | 205 | 482 | 32 |
| 112 | K | CA | 113 | 229 | 462 | 55 | 122 | Y | CA | 264 | 197 | 493 | 30 |
| 112 | K | CB | 112 | 215 | 469 | 55 | 122 | Y | CB | 253 | 192 | 502 | 29 |
| 112 | K | CG | 101 | 214 | 479 | 58 | 122 | Y | CG | 257 | 181 | 512 | 29 |
| 112 | K | CD | 104 | 222 | 492 | 65 | 122 | Y | CD1 | 252 | 169 | 510 | 29 |
| 112 | K | CE | 91 | 225 | 499 | 71 | 122 | Y | CE1 | 255 | 158 | 519 | 32 |
| 112 | K | NZ | 93 | 237 | 509 | 78 | 122 | Y | CZ | 264 | 161 | 530 | 27 |
| 112 | K | C | 126 | 229 | 454 | 51 | 122 | Y | OH | 266 | 150 | 538 | 28 |
| 112 | K | O | 135 | 223 | 458 | 50 | 122 | Y | CE2 | 269 | 174 | 532 | 27 |
| 113 | E | N | 126 | 237 | 443 | 46 | 122 | Y | CD2 | 266 | 184 | 523 | 28 |
| 113 | E | CA | 137 | 237 | 434 | 46 | 122 | Y | C | 272 | 186 | 487 | 28 |
| 113 | E | CB | 135 | 247 | 423 | 46 | 122 | Y | O | 283 | 184 | 491 | 27 |
| 113 | E | CG | 128 | 242 | 410 | 56 | 123 | F | N | 266 | 179 | 478 | 29 |
| 113 | E | CD | 132 | 228 | 406 | 60 | 123 | F | CA | 274 | 168 | 471 | 29 |
| 113 | E | OE1 | 143 | 226 | 400 | 64 | 123 | F | CB | 265 | 157 | 464 | 28 |
| 113 | E | OE2 | 125 | 218 | 410 | 65 | 123 | F | CG | 258 | 148 | 473 | 28 |
| 113 | E | C | 150 | 241 | 441 | 45 | 123 | F | CD1 | 264 | 136 | 477 | 25 |
| 113 | E | O | 161 | 235 | 438 | 41 | 123 | F | CE1 | 258 | 128 | 486 | 29 |
| 114 | D | N | 150 | 251 | 450 | 42 | 123 | F | CZ | 246 | 131 | 492 | 29 |
| 114 | D | CA | 162 | 256 | 456 | 42 | 123 | F | CE2 | 240 | 143 | 489 | 26 |
| 114 | D | CB | 159 | 270 | 463 | 42 | 123 | F | CD2 | 246 | 152 | 480 | 26 |
| 114 | D | CG | 157 | 281 | 452 | 49 | 123 | F | C | 285 | 173 | 462 | 29 |
| 114 | D | OD1 | 149 | 291 | 455 | 53 | 123 | F | O | 295 | 166 | 461 | 29 |
| 114 | D | OD2 | 162 | 281 | 440 | 54 | 124 | Q | N | 283 | 184 | 456 | 30 |
| 114 | D | C | 167 | 247 | 467 | 39 | 124 | Q | CA | 294 | 191 | 449 | 30 |
| 114 | D | O | 178 | 246 | 469 | 39 | 124 | Q | CB | 289 | 204 | 442 | 30 |
| 115 | S | N | 158 | 240 | 474 | 37 | 124 | Q | CG | 281 | 201 | 429 | 38 |
| 115 | S | CA | 161 | 230 | 483 | 38 | 124 | Q | CD | 274 | 213 | 424 | 47 |
| 115 | S | CB | 149 | 225 | 491 | 36 | 124 | Q | OE1 | 273 | 223 | 430 | 50 |
| 115 | S | OG | 146 | 235 | 500 | 46 | 124 | Q | NE2 | 268 | 211 | 412 | 51 |
| 115 | S | C | 168 | 218 | 476 | 37 | 124 | Q | C | 306 | 194 | 458 | 31 |
| 115 | S | O | 177 | 213 | 481 | 33 | 124 | Q | O | 317 | 191 | 455 | 30 |
| 116 | I | N | 162 | 214 | 464 | 35 | 125 | R | N | 302 | 199 | 470 | 31 |
| 116 | I | CA | 168 | 204 | 456 | 35 | 125 | R | CA | 313 | 201 | 480 | 32 |
| 116 | I | CB | 160 | 200 | 444 | 35 | 125 | R | CB | 308 | 208 | 493 | 31 |
| 116 | I | CG1 | 148 | 191 | 449 | 37 | 125 | R | CG | 303 | 222 | 489 | 34 |
| 116 | I | CD1 | 137 | 190 | 438 | 38 | 125 | R | CD | 300 | 231 | 502 | 31 |
| 116 | I | CG2 | 168 | 193 | 433 | 33 | 125 | R | NE | 288 | 226 | 510 | 33 |
| 116 | I | C | 182 | 208 | 452 | 35 | 125 | R | CZ | 276 | 229 | 507 | 28 |
| 116 | I | O | 192 | 200 | 454 | 34 | 125 | R | NH1 | 272 | 236 | 497 | 34 |
| 117 | L | N | 184 | 220 | 447 | 35 | 125 | R | NH2 | 266 | 225 | 516 | 30 |
| 117 | L | CA | 197 | 225 | 444 | 36 | 125 | R | C | 320 | 188 | 484 | 32 |
| 117 | L | CB | 197 | 239 | 438 | 38 | 125 | R | O | 332 | 188 | 486 | 32 |
| 117 | L | CG | 190 | 240 | 424 | 48 | 126 | I | N | 312 | 177 | 485 | 33 |
| 117 | L | CD1 | 193 | 253 | 417 | 52 | 126 | I | CA | 319 | 164 | 489 | 32 |
| 117 | L | CD2 | 194 | 228 | 414 | 52 | 126 | I | CB | 308 | 153 | 491 | 32 |
| 117 | L | C | 207 | 225 | 456 | 34 | 126 | I | CG1 | 300 | 156 | 505 | 31 |
| 117 | L | O | 219 | 223 | 454 | 33 | 126 | I | CD1 | 290 | 146 | 508 | 29 |
| 118 | A | N | 202 | 229 | 468 | 34 | 126 | I | CG2 | 314 | 139 | 490 | 31 |
| 118 | A | CA | 210 | 229 | 480 | 32 | 126 | I | C | 328 | 160 | 477 | 34 |
| 118 | A | CB | 202 | 234 | 492 | 33 | 126 | I | O | 339 | 155 | 480 | 32 |
| 118 | A | C | 216 | 215 | 483 | 33 | 127 | T | N | 324 | 161 | 465 | 36 |
| 118 | A | O | 228 | 214 | 486 | 30 | 127 | T | CA | 332 | 157 | 453 | 38 |
| 119 | V | N | 208 | 205 | 481 | 32 | 127 | T | CB | 323 | 157 | 441 | 38 |
| 119 | V | CA | 213 | 191 | 483 | 32 | 127 | T | OG1 | 315 | 145 | 441 | 43 |
| 119 | V | CB | 201 | 181 | 482 | 34 | 127 | T | CG2 | 332 | 154 | 428 | 42 |
| 119 | V | CG1 | 207 | 167 | 482 | 35 | 127 | T | C | 344 | 166 | 451 | 38 |
| 119 | V | CG2 | 193 | 182 | 494 | 34 | 127 | T | O | 355 | 161 | 448 | 38 |
| 119 | V | C | 224 | 188 | 473 | 32 | 128 | L | N | 343 | 179 | 454 | 39 |
| 119 | V | O | 235 | 182 | 476 | 29 | 128 | L | CA | 355 | 188 | 454 | 41 |
| 120 | R | N | 222 | 192 | 460 | 31 | 128 | L | CB | 351 | 203 | 456 | 40 |

| | | | | | | |
|---|---|---|---|---|---|---|
| 128 | L | CG | 344 | 210 | 444 | 47 |
| 128 | L | CD1 | 337 | 223 | 449 | 49 |
| 128 | L | CD2 | 355 | 213 | 433 | 45 |
| 128 | L | C | 365 | 184 | 464 | 39 |
| 128 | L | O | 377 | 185 | 462 | 40 |
| 129 | Y | N | 359 | 181 | 476 | 39 |
| 129 | Y | CA | 368 | 176 | 487 | 38 |
| 129 | Y | CB | 360 | 175 | 500 | 35 |
| 129 | Y | CG | 367 | 167 | 511 | 37 |
| 129 | Y | CD1 | 374 | 174 | 521 | 36 |
| 129 | Y | CE1 | 380 | 167 | 532 | 36 |
| 129 | Y | CZ | 380 | 153 | 532 | 34 |
| 129 | Y | OH | 386 | 146 | 542 | 35 |
| 129 | Y | CE2 | 373 | 146 | 522 | 34 |
| 129 | Y | CD2 | 367 | 153 | 511 | 28 |
| 129 | Y | C | 375 | 164 | 484 | 38 |
| 129 | Y | O | 387 | 163 | 486 | 40 |
| 130 | L | N | 369 | 154 | 478 | 38 |
| 130 | L | CA | 376 | 142 | 474 | 39 |
| 130 | L | CB | 366 | 131 | 469 | 38 |
| 130 | L | CG | 357 | 124 | 479 | 39 |
| 130 | L | CD1 | 346 | 116 | 471 | 31 |
| 130 | L | CD2 | 365 | 114 | 488 | 32 |
| 130 | L | C | 387 | 145 | 463 | 40 |
| 130 | L | O | 398 | 139 | 463 | 41 |
| 131 | K | N | 383 | 153 | 453 | 42 |
| 131 | K | CA | 393 | 157 | 443 | 46 |
| 131 | K | CB | 386 | 166 | 432 | 46 |
| 131 | K | CG | 378 | 158 | 423 | 47 |
| 131 | K | CD | 368 | 168 | 415 | 52 |
| 131 | K | CE | 361 | 160 | 404 | 54 |
| 131 | K | NZ | 352 | 170 | 395 | 54 |
| 131 | K | C | 405 | 164 | 449 | 46 |
| 131 | K | O | 417 | 160 | 446 | 47 |
| 132 | E | N | 403 | 174 | 457 | 48 |
| 132 | E | CA | 414 | 181 | 464 | 50 |
| 132 | E | CB | 409 | 191 | 474 | 51 |
| 132 | E | CG | 404 | 204 | 469 | 56 |
| 132 | E | CD | 396 | 212 | 479 | 64 |
| 132 | E | OE1 | 403 | 217 | 489 | 67 |
| 132 | E | OE2 | 383 | 213 | 478 | 66 |
| 132 | E | C | 423 | 171 | 472 | 49 |
| 132 | E | O | 435 | 172 | 471 | 50 |
| 133 | K | N | 417 | 161 | 479 | 47 |
| 133 | K | CA | 424 | 152 | 486 | 45 |
| 133 | K | CB | 416 | 147 | 498 | 46 |
| 133 | K | CG | 410 | 157 | 507 | 47 |
| 133 | K | CD | 421 | 164 | 515 | 52 |
| 133 | K | CE | 416 | 172 | 526 | 52 |
| 133 | K | NZ | 427 | 174 | 537 | 55 |
| 133 | K | C | 429 | 140 | 478 | 45 |
| 133 | K | O | 435 | 131 | 484 | 44 |
| 134 | K | N | 427 | 140 | 465 | 45 |
| 134 | K | CA | 430 | 129 | 456 | 47 |
| 134 | K | CB | 446 | 129 | 454 | 49 |
| 134 | K | CG | 451 | 142 | 447 | 51 |
| 134 | K | CD | 466 | 142 | 446 | 61 |
| 134 | K | CE | 471 | 134 | 433 | 66 |
| 134 | K | NZ | 486 | 133 | 432 | 70 |
| 134 | K | C | 425 | 116 | 461 | 46 |
| 134 | K | O | 433 | 106 | 460 | 45 |
| 135 | Y | N | 413 | 115 | 466 | 45 |
| 135 | Y | CA | 406 | 103 | 469 | 44 |
| 135 | Y | CB | 403 | 95 | 456 | 43 |
| 135 | Y | CG | 393 | 103 | 447 | 43 |
| 135 | Y | CD1 | 379 | 103 | 449 | 40 |
| 135 | Y | CE1 | 371 | 111 | 440 | 42 |
| 135 | Y | CZ | 377 | 118 | 430 | 46 |
| 135 | Y | OH | 369 | 126 | 421 | 48 |
| 135 | Y | CE2 | 391 | 118 | 428 | 43 |
| 135 | Y | CD2 | 399 | 111 | 436 | 45 |
| 135 | Y | C | 414 | 94 | 478 | 44 |
| 135 | Y | O | 413 | 82 | 477 | 43 |
| 136 | S | N | 421 | 99 | 487 | 44 |
| 136 | S | CA | 428 | 92 | 498 | 45 |
| 136 | S | CB | 437 | 101 | 506 | 44 |
| 136 | S | OG | 429 | 109 | 515 | 47 |
| 136 | S | C | 419 | 83 | 507 | 46 |
| 136 | S | O | 408 | 87 | 509 | 46 |
| 137 | P | N | 424 | 72 | 512 | 47 |
| 137 | P | CA | 417 | 64 | 521 | 45 |
| 137 | P | CB | 428 | 54 | 527 | 45 |
| 137 | P | CG | 437 | 51 | 514 | 45 |
| 137 | P | CD | 438 | 66 | 509 | 47 |
| 137 | P | C | 411 | 72 | 533 | 45 |
| 137 | P | O | 399 | 69 | 536 | 44 |
| 138 | C | N | 418 | 81 | 538 | 43 |
| 138 | C | CA | 413 | 91 | 548 | 43 |
| 138 | C | CB | 424 | 100 | 553 | 44 |
| 138 | C | SG | 434 | 90 | 565 | 55 |
| 138 | C | C | 401 | 100 | 543 | 41 |
| 138 | C | O | 392 | 102 | 550 | 41 |
| 139 | A | N | 403 | 105 | 531 | 37 |
| 139 | A | CA | 393 | 114 | 525 | 37 |
| 139 | A | CB | 397 | 120 | 512 | 36 |
| 139 | A | C | 380 | 106 | 524 | 36 |
| 139 | A | O | 369 | 111 | 527 | 36 |
| 140 | W | N | 381 | 94 | 519 | 35 |
| 140 | W | CA | 370 | 85 | 517 | 36 |
| 140 | W | CB | 374 | 72 | 509 | 34 |
| 140 | W | CG | 371 | 74 | 494 | 36 |
| 140 | W | CD1 | 380 | 73 | 483 | 36 |
| 140 | W | NE1 | 374 | 75 | 471 | 38 |
| 140 | W | CE2 | 361 | 77 | 473 | 37 |
| 140 | W | CD2 | 359 | 76 | 487 | 37 |
| 140 | W | CE3 | 346 | 78 | 492 | 35 |
| 140 | W | CZ3 | 335 | 80 | 483 | 33 |
| 140 | W | CH2 | 337 | 81 | 470 | 38 |
| 140 | W | CZ2 | 350 | 79 | 464 | 39 |
| 140 | W | C | 363 | 81 | 530 | 36 |
| 140 | W | O | 351 | 80 | 531 | 35 |
| 141 | E | N | 371 | 81 | 541 | 34 |
| 141 | E | CA | 365 | 77 | 553 | 35 |
| 141 | E | CB | 376 | 71 | 564 | 35 |
| 141 | E | CG | 370 | 69 | 577 | 37 |
| 141 | E | CD | 357 | 60 | 578 | 41 |
| 141 | E | OE1 | 355 | 52 | 569 | 41 |
| 141 | E | OE2 | 350 | 61 | 588 | 42 |
| 141 | E | C | 358 | 89 | 559 | 35 |
| 141 | E | O | 347 | 87 | 565 | 34 |
| 142 | V | N | 364 | 101 | 558 | 34 |
| 142 | V | CA | 357 | 113 | 562 | 35 |
| 142 | V | CB | 365 | 125 | 560 | 35 |
| 142 | V | CG1 | 357 | 138 | 561 | 36 |
| 142 | V | CG2 | 378 | 126 | 569 | 37 |
| 142 | V | C | 343 | 113 | 555 | 35 |
| 142 | V | O | 333 | 116 | 561 | 34 |
| 143 | V | N | 344 | 110 | 542 | 33 |
| 143 | V | CA | 332 | 111 | 533 | 31 |
| 143 | V | CB | 335 | 111 | 518 | 30 |
| 143 | V | CG1 | 321 | 110 | 510 | 26 |
| 143 | V | CG2 | 341 | 124 | 513 | 28 |
| 143 | V | C | 321 | 100 | 537 | 33 |
| 143 | V | O | 310 | 103 | 539 | 32 |
| 144 | R | N | 326 | 88 | 539 | 32 |
| 144 | R | CA | 317 | 77 | 543 | 34 |
| 144 | R | CB | 324 | 64 | 545 | 34 |
| 144 | R | CG | 315 | 51 | 547 | 34 |
| 144 | R | CD | 323 | 40 | 555 | 33 |
| 144 | R | NE | 327 | 45 | 567 | 35 |
| 144 | R | CZ | 319 | 46 | 578 | 42 |
| 144 | R | NH1 | 306 | 42 | 576 | 35 |
| 144 | R | NH2 | 323 | 52 | 589 | 44 |
| 144 | R | C | 309 | 80 | 556 | 36 |
| 144 | R | O | 297 | 78 | 558 | 34 |
| 145 | A | N | 317 | 85 | 566 | 35 |
| 145 | A | CA | 312 | 89 | 579 | 34 |
| 145 | A | CB | 323 | 93 | 589 | 34 |
| 145 | A | C | 302 | 101 | 577 | 33 |
| 145 | A | O | 292 | 102 | 584 | 33 |
| 146 | E | N | 306 | 110 | 569 | 32 |
| 146 | E | CA | 297 | 122 | 567 | 32 |
| 146 | E | CB | 304 | 132 | 558 | 33 |
| 146 | E | CG | 295 | 143 | 552 | 33 |
| 146 | E | CD | 289 | 153 | 563 | 36 |
| 146 | E | OE1 | 278 | 159 | 561 | 34 |
| 146 | E | OE2 | 295 | 154 | 574 | 40 |
| 146 | E | C | 283 | 117 | 561 | 31 |
| 146 | E | O | 273 | 122 | 566 | 31 |
| 147 | I | N | 283 | 109 | 551 | 30 |

| | | | | | | |
|---|---|---|---|---|---|---|
| 147 | I | CA | 271 | 104 | 545 | 30 |
| 147 | I | CB | 274 | 96 | 532 | 30 |
| 147 | I | CG1 | 281 | 105 | 522 | 31 |
| 147 | I | CD1 | 272 | 119 | 519 | 33 |
| 147 | I | CG2 | 260 | 88 | 527 | 28 |
| 147 | I | C | 262 | 96 | 555 | 30 |
| 147 | I | O | 250 | 97 | 555 | 30 |
| 148 | M | N | 269 | 87 | 563 | 31 |
| 148 | M | CA | 261 | 80 | 573 | 33 |
| 148 | M | CB | 270 | 71 | 581 | 37 |
| 148 | M | CG | 267 | 56 | 577 | 45 |
| 148 | M | SD | 273 | 46 | 589 | 60 |
| 148 | M | CE | 258 | 41 | 598 | 56 |
| 148 | M | C | 254 | 90 | 582 | 34 |
| 148 | M | O | 242 | 88 | 585 | 33 |
| 149 | R | N | 261 | 100 | 586 | 33 |
| 149 | R | CA | 256 | 110 | 595 | 35 |
| 149 | R | CB | 267 | 120 | 600 | 36 |
| 149 | R | CG | 262 | 131 | 610 | 41 |
| 149 | R | CD | 273 | 143 | 611 | 49 |
| 149 | R | NE | 273 | 150 | 598 | 51 |
| 149 | R | CZ | 265 | 160 | 595 | 54 |
| 149 | R | NH1 | 256 | 164 | 603 | 56 |
| 149 | R | NH2 | 266 | 165 | 582 | 48 |
| 149 | R | C | 245 | 119 | 588 | 34 |
| 149 | R | O | 234 | 120 | 594 | 34 |
| 150 | S | N | 247 | 124 | 577 | 31 |
| 150 | S | CA | 237 | 132 | 571 | 31 |
| 150 | S | CB | 243 | 141 | 559 | 31 |
| 150 | S | OG | 247 | 133 | 548 | 29 |
| 150 | S | C | 225 | 124 | 566 | 32 |
| 150 | S | O | 214 | 129 | 566 | 31 |
| 151 | F | N | 227 | 112 | 560 | 31 |
| 151 | F | CA | 216 | 104 | 555 | 33 |
| 151 | F | CB | 221 | 92 | 547 | 31 |
| 151 | F | CG | 210 | 83 | 542 | 34 |
| 151 | F | CD1 | 201 | 88 | 532 | 33 |
| 151 | F | CE1 | 191 | 81 | 527 | 35 |
| 151 | F | CZ | 188 | 68 | 532 | 33 |
| 151 | F | CE2 | 196 | 63 | 542 | 36 |
| 151 | F | CD2 | 207 | 71 | 547 | 34 |
| 151 | F | C | 207 | 100 | 567 | 35 |
| 151 | F | O | 195 | 100 | 566 | 35 |
| 152 | S | N | 214 | 96 | 578 | 36 |
| 152 | S | CA | 207 | 93 | 590 | 40 |
| 152 | S | CB | 217 | 88 | 600 | 41 |
| 152 | S | OG | 210 | 83 | 611 | 48 |
| 152 | S | C | 198 | 105 | 595 | 42 |
| 152 | S | O | 186 | 104 | 597 | 42 |
| 153 | L | N | 205 | 116 | 595 | 42 |
| 153 | L | CA | 198 | 129 | 598 | 46 |
| 153 | L | CB | 207 | 141 | 597 | 46 |
| 153 | L | CG | 207 | 153 | 606 | 48 |
| 153 | L | CD1 | 204 | 149 | 621 | 48 |
| 153 | L | CD2 | 220 | 160 | 605 | 48 |
| 153 | L | C | 186 | 132 | 589 | 46 |
| 153 | L | O | 176 | 135 | 594 | 48 |
| 154 | S | N | 188 | 131 | 576 | 46 |
| 154 | S | CA | 177 | 133 | 566 | 47 |
| 154 | S | CB | 183 | 130 | 552 | 46 |
| 154 | S | OG | 192 | 139 | 550 | 53 |
| 154 | S | C | 166 | 123 | 568 | 47 |
| 154 | S | O | 155 | 126 | 563 | 46 |
| 155 | T | N | 168 | 111 | 572 | 45 |
| 155 | T | CA | 157 | 101 | 572 | 49 |
| 155 | T | CB | 162 | 87 | 570 | 49 |
| 155 | T | OG1 | 174 | 85 | 578 | 51 |
| 155 | T | CG2 | 166 | 84 | 556 | 48 |
| 155 | T | C | 150 | 102 | 585 | 51 |
| 155 | T | O | 138 | 101 | 585 | 51 |
| 156 | N | N | 156 | 105 | 596 | 53 |
| 156 | N | CA | 150 | 107 | 609 | 57 |
| 156 | N | CB | 161 | 107 | 620 | 56 |
| 156 | N | CG | 167 | 93 | 622 | 61 |
| 156 | N | OD1 | 176 | 91 | 629 | 68 |
| 156 | N | ND2 | 161 | 83 | 615 | 63 |
| 156 | N | C | 142 | 119 | 610 | 60 |
| 156 | N | O | 131 | 118 | 614 | 59 |
| 157 | L | N | 147 | 130 | 604 | 62 |
| 157 | L | CA | 139 | 143 | 603 | 64 |
| 157 | L | CB | 148 | 155 | 600 | 63 |
| 157 | L | CG | 158 | 160 | 610 | 61 |
| 157 | L | CD1 | 169 | 168 | 603 | 57 |
| 157 | L | CD2 | 151 | 168 | 621 | 62 |
| 157 | L | C | 127 | 141 | 593 | 65 |
| 157 | L | O | 116 | 146 | 596 | 66 |
| 158 | Q | N | 130 | 135 | 581 | 67 |
| 158 | Q | CA | 119 | 134 | 571 | 69 |
| 158 | Q | CB | 124 | 128 | 558 | 69 |
| 158 | Q | CG | 114 | 127 | 545 | 69 |
| 158 | Q | CD | 103 | 116 | 546 | 70 |
| 158 | Q | OE1 | 92 | 118 | 541 | 70 |
| 158 | Q | NE2 | 107 | 105 | 552 | 67 |
| 158 | Q | C | 106 | 127 | 576 | 71 |
| 158 | Q | O | 95 | 130 | 571 | 71 |
| 159 | E | N | 108 | 119 | 586 | 73 |
| 159 | E | CA | 97 | 110 | 590 | 75 |
| 159 | E | CB | 101 | 96 | 591 | 75 |
| 159 | E | CG | 110 | 92 | 603 | 76 |
| 159 | E | CD | 112 | 78 | 604 | 79 |
| 159 | E | OE1 | 123 | 73 | 607 | 81 |
| 159 | E | OE2 | 102 | 70 | 603 | 79 |
| 159 | E | C | 88 | 114 | 602 | 76 |
| 159 | E | O | 77 | 109 | 604 | 76 |
| 160 | S | N | 93 | 124 | 610 | 77 |
| 160 | S | CA | 85 | 132 | 620 | 78 |
| 160 | S | CB | 92 | 132 | 633 | 78 |
| 160 | S | OG | 105 | 135 | 632 | 78 |
| 160 | S | C | 81 | 146 | 616 | 78 |
| 160 | S | O | 76 | 154 | 623 | 79 |
| 160 | S | OXT | 83 | 151 | 605 | 77 |
| 7 | H | N | 176 | 473 | 515 | 80 |
| 7 | H | CA | 182 | 461 | 509 | 80 |
| 7 | H | CB | 175 | 448 | 514 | 80 |
| 7 | H | CG | 173 | 447 | 529 | 80 |
| 7 | H | ND1 | 184 | 450 | 538 | 79 |
| 7 | H | CE1 | 179 | 448 | 550 | 78 |
| 7 | H | NE2 | 166 | 445 | 550 | 78 |
| 7 | H | CD2 | 162 | 445 | 536 | 78 |
| 7 | H | C | 183 | 461 | 494 | 80 |
| 7 | H | O | 189 | 452 | 488 | 80 |
| 8 | A | N | 176 | 471 | 488 | 80 |
| 8 | A | CA | 177 | 473 | 473 | 79 |
| 8 | A | CB | 165 | 481 | 468 | 79 |
| 8 | A | C | 190 | 480 | 470 | 77 |
| 8 | A | O | 198 | 475 | 462 | 78 |
| 9 | A | N | 192 | 493 | 475 | 76 |
| 9 | A | CA | 204 | 500 | 471 | 74 |
| 9 | A | CB | 200 | 513 | 464 | 74 |
| 9 | A | C | 214 | 504 | 483 | 72 |
| 9 | A | O | 224 | 510 | 481 | 72 |
| 10 | G | N | 210 | 500 | 495 | 70 |
| 10 | G | CA | 219 | 499 | 507 | 66 |
| 10 | G | C | 228 | 488 | 505 | 62 |
| 10 | G | O | 240 | 488 | 509 | 62 |
| 11 | A | N | 223 | 478 | 499 | 60 |
| 11 | A | CA | 231 | 466 | 494 | 58 |
| 11 | A | CB | 222 | 457 | 487 | 57 |
| 11 | A | C | 243 | 471 | 485 | 56 |
| 11 | A | O | 254 | 466 | 487 | 56 |
| 12 | R | N | 240 | 481 | 476 | 53 |
| 12 | R | CA | 250 | 485 | 467 | 51 |
| 12 | R | CB | 243 | 495 | 456 | 53 |
| 12 | R | CG | 237 | 487 | 444 | 57 |
| 12 | R | CD | 239 | 494 | 431 | 63 |
| 12 | R | NE | 245 | 486 | 420 | 68 |
| 12 | R | CZ | 253 | 490 | 410 | 70 |
| 12 | R | NH1 | 256 | 503 | 409 | 70 |
| 12 | R | NH2 | 258 | 481 | 402 | 71 |
| 12 | R | C | 262 | 492 | 472 | 49 |
| 12 | R | O | 273 | 488 | 468 | 47 |
| 13 | A | N | 260 | 501 | 482 | 45 |
| 13 | A | CA | 272 | 508 | 487 | 43 |
| 13 | A | CB | 268 | 520 | 497 | 44 |
| 13 | A | C | 280 | 498 | 495 | 41 |
| 13 | A | O | 292 | 499 | 496 | 40 |
| 14 | T | N | 273 | 488 | 501 | 40 |
| 14 | T | CA | 280 | 478 | 510 | 40 |
| 14 | T | CB | 270 | 468 | 516 | 40 |
| 14 | T | OG1 | 260 | 476 | 523 | 42 |

| | | | | | | | | | | | | |
|---|---|---|---|---|---|---|---|---|---|---|---|---|
| 14 | T | CG2 | 277 | 459 | 527 | 39 | 24 | I | CA | 454 | 407 | 474 | 38 |
| 14 | T | C | 290 | 469 | 501 | 40 | 24 | I | CB | 462 | 398 | 483 | 38 |
| 14 | T | O | 301 | 467 | 505 | 38 | 24 | I | CG1 | 454 | 390 | 492 | 38 |
| 15 | L | N | 284 | 464 | 490 | 42 | 24 | I | CD1 | 462 | 379 | 500 | 43 |
| 15 | L | CA | 291 | 457 | 480 | 44 | 24 | I | CG2 | 474 | 406 | 490 | 37 |
| 15 | L | CB | 282 | 452 | 469 | 45 | 24 | I | C | 444 | 399 | 466 | 39 |
| 15 | L | CG | 272 | 442 | 474 | 49 | 24 | I | O | 432 | 399 | 468 | 38 |
| 15 | L | CD1 | 262 | 439 | 464 | 49 | 25 | S | N | 450 | 391 | 457 | 37 |
| 15 | L | CD2 | 280 | 429 | 477 | 55 | 25 | S | CA | 443 | 383 | 448 | 37 |
| 15 | L | C | 303 | 464 | 474 | 44 | 25 | S | CB | 450 | 381 | 435 | 36 |
| 15 | L | O | 314 | 459 | 473 | 43 | 25 | S | OG | 441 | 374 | 426 | 34 |
| 16 | M | N | 301 | 477 | 472 | 43 | 25 | S | C | 439 | 370 | 454 | 38 |
| 16 | M | CA | 312 | 485 | 467 | 41 | 25 | S | O | 447 | 362 | 459 | 39 |
| 16 | M | CB | 307 | 500 | 464 | 42 | 26 | L | N | 426 | 366 | 452 | 38 |
| 16 | M | CG | 319 | 510 | 462 | 46 | 26 | L | CA | 421 | 353 | 454 | 40 |
| 16 | M | SD | 314 | 526 | 452 | 54 | 26 | L | CB | 408 | 353 | 447 | 42 |
| 16 | M | CE | 303 | 519 | 440 | 53 | 26 | L | CG | 398 | 342 | 450 | 49 |
| 16 | M | C | 323 | 486 | 477 | 41 | 26 | L | CD1 | 388 | 347 | 459 | 54 |
| 16 | M | O | 335 | 487 | 474 | 38 | 26 | L | CD2 | 392 | 338 | 436 | 53 |
| 17 | L | N | 320 | 488 | 490 | 39 | 26 | L | C | 430 | 342 | 447 | 39 |
| 17 | L | CA | 331 | 489 | 500 | 40 | 26 | L | O | 432 | 331 | 453 | 37 |
| 17 | L | CB | 326 | 494 | 514 | 40 | 27 | F | N | 434 | 345 | 435 | 38 |
| 17 | L | CG | 320 | 508 | 513 | 41 | 27 | F | CA | 443 | 337 | 427 | 39 |
| 17 | L | CD1 | 309 | 510 | 525 | 41 | 27 | F | CB | 443 | 342 | 412 | 37 |
| 17 | L | CD2 | 330 | 519 | 514 | 37 | 27 | F | CG | 430 | 339 | 405 | 35 |
| 17 | L | C | 338 | 477 | 502 | 37 | 27 | F | CD1 | 427 | 326 | 400 | 37 |
| 17 | L | O | 351 | 477 | 504 | 38 | 27 | F | CE1 | 415 | 323 | 394 | 37 |
| 18 | L | N | 331 | 466 | 501 | 36 | 27 | F | CZ | 406 | 334 | 393 | 35 |
| 18 | L | CA | 337 | 452 | 502 | 36 | 27 | F | CE2 | 409 | 347 | 398 | 31 |
| 18 | L | CB | 326 | 442 | 502 | 36 | 27 | F | CD2 | 420 | 349 | 404 | 30 |
| 18 | L | CG | 320 | 437 | 516 | 38 | 27 | F | C | 457 | 335 | 433 | 40 |
| 18 | L | CD1 | 308 | 429 | 513 | 37 | 27 | F | O | 464 | 326 | 429 | 42 |
| 18 | L | CD2 | 332 | 429 | 524 | 37 | 28 | S | N | 460 | 344 | 442 | 40 |
| 18 | L | C | 346 | 450 | 491 | 36 | 28 | S | CA | 473 | 342 | 449 | 42 |
| 18 | L | O | 357 | 444 | 493 | 37 | 28 | S | CB | 479 | 355 | 454 | 42 |
| 19 | A | N | 342 | 454 | 479 | 35 | 28 | S | OG | 481 | 363 | 443 | 43 |
| 19 | A | CA | 351 | 453 | 467 | 36 | 28 | S | C | 470 | 333 | 462 | 42 |
| 19 | A | CB | 343 | 457 | 454 | 35 | 28 | S | O | 480 | 331 | 470 | 41 |
| 19 | A | C | 363 | 461 | 469 | 36 | 29 | C | N | 457 | 328 | 464 | 40 |
| 19 | A | O | 374 | 457 | 466 | 38 | 29 | C | CA | 453 | 322 | 477 | 41 |
| 20 | Q | N | 362 | 473 | 474 | 36 | 29 | C | CB | 444 | 331 | 484 | 41 |
| 20 | Q | CA | 373 | 482 | 476 | 36 | 29 | C | SG | 452 | 347 | 488 | 45 |
| 20 | Q | CB | 368 | 496 | 478 | 37 | 29 | C | C | 447 | 309 | 474 | 41 |
| 20 | Q | CG | 362 | 503 | 466 | 37 | 29 | C | O | 438 | 304 | 482 | 40 |
| 20 | Q | CD | 356 | 517 | 470 | 44 | 30 | L | N | 450 | 302 | 463 | 40 |
| 20 | Q | OE1 | 352 | 519 | 482 | 45 | 30 | L | CA | 443 | 290 | 459 | 41 |
| 20 | Q | NE2 | 355 | 526 | 461 | 41 | 30 | L | CB | 447 | 286 | 445 | 42 |
| 20 | Q | C | 382 | 478 | 487 | 38 | 30 | L | CG | 443 | 295 | 433 | 44 |
| 20 | Q | O | 393 | 483 | 488 | 39 | 30 | L | CD1 | 449 | 287 | 421 | 50 |
| 21 | M | N | 377 | 470 | 496 | 37 | 30 | L | CD2 | 429 | 296 | 432 | 46 |
| 21 | M | CA | 386 | 465 | 507 | 38 | 30 | L | C | 446 | 279 | 469 | 41 |
| 21 | M | CB | 377 | 459 | 519 | 37 | 30 | L | O | 437 | 271 | 471 | 40 |
| 21 | M | CG | 370 | 470 | 527 | 40 | 31 | K | N | 457 | 279 | 476 | 42 |
| 21 | M | SD | 356 | 462 | 537 | 46 | 31 | K | CA | 459 | 269 | 486 | 44 |
| 21 | M | CE | 365 | 451 | 545 | 42 | 31 | K | CB | 474 | 269 | 492 | 44 |
| 21 | M | C | 396 | 455 | 503 | 37 | 31 | K | CG | 476 | 282 | 500 | 46 |
| 21 | M | O | 406 | 453 | 510 | 38 | 31 | K | CD | 491 | 283 | 506 | 51 |
| 22 | R | N | 394 | 449 | 491 | 37 | 31 | K | CE | 492 | 294 | 517 | 52 |
| 22 | R | CA | 403 | 439 | 485 | 38 | 31 | K | NZ | 486 | 308 | 513 | 47 |
| 22 | R | CB | 398 | 435 | 472 | 39 | 31 | K | C | 449 | 270 | 498 | 43 |
| 22 | R | CG | 404 | 423 | 465 | 41 | 31 | K | O | 447 | 260 | 505 | 44 |
| 22 | R | CD | 416 | 426 | 456 | 36 | 32 | D | N | 443 | 282 | 499 | 41 |
| 22 | R | NE | 418 | 416 | 445 | 41 | 32 | D | CA | 433 | 285 | 510 | 41 |
| 22 | R | CZ | 427 | 418 | 436 | 36 | 32 | D | CB | 436 | 298 | 516 | 41 |
| 22 | R | NH1 | 435 | 429 | 436 | 34 | 32 | D | CG | 450 | 298 | 522 | 46 |
| 22 | R | NH2 | 429 | 409 | 427 | 36 | 32 | D | OD1 | 453 | 290 | 531 | 45 |
| 22 | R | C | 418 | 444 | 485 | 41 | 32 | D | OD2 | 459 | 306 | 517 | 50 |
| 22 | R | O | 421 | 455 | 480 | 39 | 32 | D | C | 419 | 284 | 506 | 40 |
| 23 | R | N | 427 | 436 | 491 | 40 | 32 | D | O | 410 | 288 | 513 | 37 |
| 23 | R | CA | 441 | 439 | 491 | 42 | 33 | R | N | 416 | 280 | 494 | 39 |
| 23 | R | CB | 446 | 438 | 506 | 43 | 33 | R | CA | 403 | 278 | 488 | 40 |
| 23 | R | CG | 440 | 448 | 515 | 50 | 33 | R | CB | 403 | 270 | 475 | 41 |
| 23 | R | CD | 444 | 447 | 529 | 58 | 33 | R | CG | 391 | 271 | 466 | 45 |
| 23 | R | NE | 456 | 456 | 532 | 65 | 33 | R | CD | 388 | 260 | 455 | 47 |
| 23 | R | CZ | 466 | 452 | 539 | 71 | 33 | R | NE | 383 | 248 | 461 | 54 |
| 23 | R | NH1 | 467 | 440 | 544 | 72 | 33 | R | CZ | 371 | 245 | 464 | 56 |
| 23 | R | NH2 | 477 | 461 | 540 | 73 | 33 | R | NH1 | 361 | 254 | 463 | 53 |
| 23 | R | C | 450 | 430 | 483 | 42 | 33 | R | NH2 | 368 | 234 | 470 | 56 |
| 23 | R | O | 460 | 434 | 477 | 43 | 33 | R | C | 394 | 270 | 497 | 39 |
| 24 | I | N | 446 | 417 | 482 | 40 | 33 | R | O | 398 | 260 | 502 | 37 |

| | | | | | | | | | | | | |
|---|---|---|---|---|---|---|---|---|---|---|---|---|
| 34 | H | N | 382 | 274 | 499 | 38 | 43 | F | CB | 181 | 346 | 505 | 54 |
| 34 | H | CA | 373 | 267 | 509 | 37 | 43 | F | CG | 189 | 347 | 518 | 51 |
| 34 | H | CB | 375 | 273 | 523 | 37 | 43 | F | CD1 | 199 | 337 | 521 | 51 |
| 34 | H | CG | 369 | 265 | 534 | 39 | 43 | F | CE1 | 206 | 338 | 533 | 51 |
| 34 | H | ND1 | 376 | 254 | 539 | 41 | 43 | F | CZ | 203 | 347 | 543 | 52 |
| 34 | H | CE1 | 368 | 248 | 548 | 41 | 43 | F | CE2 | 193 | 357 | 540 | 51 |
| 34 | H | NE2 | 356 | 253 | 547 | 39 | 43 | F | CD2 | 186 | 356 | 528 | 51 |
| 34 | H | CD2 | 357 | 264 | 538 | 34 | 43 | F | C | 162 | 339 | 491 | 60 |
| 34 | H | C | 359 | 268 | 504 | 37 | 43 | F | O | 163 | 349 | 484 | 59 |
| 34 | H | O | 355 | 279 | 500 | 37 | 44 | G | N | 156 | 328 | 487 | 63 |
| 35 | D | N | 351 | 258 | 504 | 38 | 44 | G | CA | 151 | 326 | 474 | 67 |
| 35 | D | CA | 337 | 259 | 502 | 38 | 44 | G | C | 135 | 325 | 473 | 69 |
| 35 | D | CB | 331 | 246 | 495 | 39 | 44 | G | O | 128 | 327 | 483 | 69 |
| 35 | D | CG | 337 | 244 | 482 | 47 | 45 | N | N | 130 | 322 | 461 | 73 |
| 35 | D | OD1 | 342 | 233 | 479 | 50 | 45 | N | CA | 116 | 323 | 459 | 75 |
| 35 | D | OD2 | 337 | 254 | 474 | 56 | 45 | N | CB | 113 | 325 | 444 | 76 |
| 35 | D | C | 329 | 259 | 516 | 36 | 45 | N | CG | 120 | 337 | 438 | 79 |
| 35 | D | O | 329 | 249 | 523 | 36 | 45 | N | OD1 | 120 | 348 | 443 | 81 |
| 36 | F | N | 322 | 270 | 518 | 35 | 45 | N | ND2 | 125 | 334 | 426 | 82 |
| 36 | F | CA | 316 | 272 | 531 | 34 | 45 | N | C | 107 | 312 | 465 | 76 |
| 36 | F | CB | 317 | 287 | 535 | 32 | 45 | N | O | 95 | 312 | 463 | 76 |
| 36 | F | CG | 331 | 292 | 538 | 33 | 46 | Q | N | 113 | 304 | 473 | 77 |
| 36 | F | CD1 | 338 | 299 | 529 | 30 | 46 | Q | CA | 105 | 293 | 480 | 78 |
| 36 | F | CE1 | 351 | 303 | 532 | 34 | 46 | Q | CB | 114 | 282 | 485 | 78 |
| 36 | F | CZ | 357 | 300 | 544 | 32 | 46 | Q | CG | 118 | 272 | 475 | 78 |
| 36 | F | CE2 | 350 | 293 | 553 | 31 | 46 | Q | CD | 127 | 261 | 481 | 76 |
| 36 | F | CD2 | 337 | 289 | 551 | 31 | 46 | Q | OE1 | 134 | 254 | 473 | 73 |
| 36 | F | C | 302 | 268 | 531 | 33 | 46 | Q | NE2 | 128 | 259 | 494 | 76 |
| 36 | F | O | 295 | 268 | 542 | 34 | 46 | Q | C | 98 | 300 | 491 | 80 |
| 37 | G | N | 296 | 265 | 520 | 32 | 46 | Q | O | 89 | 294 | 497 | 80 |
| 37 | G | CA | 282 | 260 | 519 | 32 | 47 | F | N | 102 | 312 | 495 | 81 |
| 37 | G | C | 272 | 270 | 524 | 34 | 47 | F | CA | 98 | 319 | 507 | 82 |
| 37 | G | O | 263 | 267 | 532 | 34 | 47 | F | CB | 109 | 321 | 517 | 82 |
| 38 | F | N | 272 | 282 | 518 | 34 | 47 | F | CG | 115 | 308 | 521 | 84 |
| 38 | F | CA | 262 | 292 | 521 | 36 | 47 | F | CD1 | 109 | 300 | 531 | 86 |
| 38 | F | CB | 265 | 305 | 513 | 35 | 47 | F | CE1 | 115 | 287 | 535 | 87 |
| 38 | F | CG | 255 | 316 | 516 | 38 | 47 | F | CZ | 127 | 283 | 529 | 87 |
| 38 | F | CD1 | 254 | 322 | 529 | 40 | 47 | F | CE2 | 133 | 291 | 519 | 86 |
| 38 | F | CE1 | 245 | 332 | 531 | 42 | 47 | F | CD2 | 127 | 303 | 515 | 84 |
| 38 | F | CZ | 238 | 337 | 520 | 42 | 47 | F | C | 91 | 333 | 504 | 83 |
| 38 | F | CE2 | 239 | 332 | 508 | | 47 | F | O | 96 | 340 | 495 | 82 |
| 38 | F | CD2 | 248 | 322 | 505 | 42 | 48 | G | N | 80 | 335 | 511 | 84 |
| 38 | F | C | 248 | 288 | 518 | 37 | 48 | G | CA | 73 | 348 | 511 | 85 |
| 38 | F | O | 245 | 284 | 507 | 38 | 48 | G | C | 79 | 361 | 505 | 86 |
| 39 | P | N | 239 | 289 | 528 | 39 | 48 | G | O | 76 | 366 | 495 | 86 |
| 39 | P | CA | 225 | 284 | 525 | 39 | 49 | A | N | 89 | 366 | 513 | 85 |
| 39 | P | CB | 219 | 282 | 539 | 40 | 49 | A | CA | 96 | 379 | 511 | 84 |
| 39 | P | CG | 227 | 292 | 548 | 38 | 49 | A | CB | 90 | 388 | 499 | 85 |
| 39 | P | CD | 241 | 292 | 542 | 37 | 49 | A | C | 95 | 387 | 524 | 84 |
| 39 | P | C | 217 | 294 | 517 | 38 | 49 | A | O | 103 | 396 | 527 | 84 |
| 39 | P | O | 208 | 300 | 522 | 40 | 50 | A | N | 85 | 384 | 532 | 83 |
| 40 | Q | N | 220 | 296 | 505 | 39 | 50 | A | CA | 84 | 388 | 546 | 82 |
| 40 | Q | CA | 214 | 306 | 496 | 42 | 50 | A | CB | 69 | 391 | 549 | 82 |
| 40 | Q | CB | 222 | 307 | 483 | 43 | 50 | A | C | 89 | 377 | 555 | 80 |
| 40 | Q | CG | 221 | 295 | 475 | 48 | 50 | A | O | 92 | 379 | 567 | 80 |
| 40 | Q | CD | 227 | 296 | 461 | 53 | 51 | E | N | 89 | 365 | 549 | 79 |
| 40 | Q | OE1 | 239 | 297 | 459 | 54 | 51 | E | CA | 95 | 353 | 556 | 78 |
| 40 | Q | NE2 | 218 | 298 | 451 | 55 | 51 | E | CB | 91 | 340 | 547 | 79 |
| 40 | Q | C | 199 | 303 | 494 | 44 | 51 | E | CG | 77 | 335 | 550 | 83 |
| 40 | Q | O | 191 | 313 | 491 | 44 | 51 | E | CD | 76 | 320 | 546 | 88 |
| 41 | E | N | 194 | 291 | 496 | 44 | 51 | E | OE1 | 74 | 312 | 556 | 89 |
| 41 | E | CA | 180 | 287 | 493 | 45 | 51 | E | OE2 | 77 | 317 | 534 | 88 |
| 41 | E | CB | 178 | 272 | 494 | 43 | 51 | E | C | 110 | 353 | 557 | 75 |
| 41 | E | CG | 181 | 266 | 507 | 44 | 51 | E | O | 116 | 348 | 566 | 74 |
| 41 | E | CD | 196 | 264 | 511 | 41 | 52 | T | N | 117 | 359 | 546 | 72 |
| 41 | E | OE1 | 205 | 268 | 503 | 39 | 52 | T | CA | 131 | 359 | 546 | 69 |
| 41 | E | OE2 | 199 | 258 | 521 | 39 | 52 | T | CB | 136 | 360 | 531 | 69 |
| 41 | E | C | 171 | 294 | 504 | 47 | 52 | T | OG1 | 131 | 372 | 525 | 71 |
| 41 | E | O | 159 | 295 | 502 | 47 | 52 | T | CG2 | 130 | 349 | 523 | 69 |
| 42 | E | N | 177 | 298 | 515 | 48 | 52 | T | C | 137 | 371 | 554 | 67 |
| 42 | E | CA | 170 | 305 | 525 | 50 | 52 | T | O | 148 | 369 | 559 | 66 |
| 42 | E | CB | 179 | 306 | 538 | 51 | 53 | I | N | 130 | 382 | 555 | 63 |
| 42 | E | CG | 175 | 298 | 550 | 52 | 53 | I | CA | 134 | 393 | 564 | 60 |
| 42 | E | CD | 175 | 283 | 548 | 53 | 53 | I | CB | 122 | 403 | 568 | 61 |
| 42 | E | OE1 | 185 | 279 | 542 | 57 | 53 | I | CG1 | 117 | 411 | 556 | 61 |
| 42 | E | OE2 | 166 | 276 | 552 | 55 | 53 | I | CD1 | 128 | 414 | 545 | 64 |
| 42 | E | C | 164 | 319 | 521 | 52 | 53 | I | CG2 | 125 | 412 | 580 | 61 |
| 42 | E | O | 156 | 325 | 528 | 54 | 53 | I | C | 142 | 389 | 577 | 57 |
| 43 | F | N | 170 | 325 | 510 | 54 | 53 | I | O | 153 | 394 | 578 | 58 |
| 43 | F | CA | 168 | 339 | 506 | 56 | 54 | P | N | 137 | 381 | 586 | 55 |

| | | | | | | |
|---|---|---|---|---|---|---|
| 54 | P | CA | 144 | 378 | 598 | 53 |
| 54 | P | CB | 135 | 368 | 605 | 53 |
| 54 | P | CG | 121 | 370 | 599 | 54 |
| 54 | P | CD | 123 | 375 | 585 | 54 |
| 54 | P | C | 158 | 370 | 596 | 52 |
| 54 | P | O | 167 | 370 | 605 | 49 |
| 55 | V | N | 159 | 363 | 585 | 49 |
| 55 | V | CA | 171 | 355 | 581 | 48 |
| 55 | V | CB | 168 | 343 | 572 | 48 |
| 55 | V | CG1 | 167 | 347 | 558 | 45 |
| 55 | V | CG2 | 178 | 332 | 574 | 50 |
| 55 | V | C | 181 | 365 | 575 | 47 |
| 55 | V | O | 193 | 365 | 578 | 46 |
| 56 | L | N | 176 | 374 | 567 | 47 |
| 56 | L | CA | 184 | 384 | 561 | 49 |
| 56 | L | CB | 175 | 392 | 551 | 49 |
| 56 | L | CG | 180 | 405 | 545 | 53 |
| 56 | L | CD1 | 194 | 403 | 538 | 58 |
| 56 | L | CD2 | 169 | 408 | 535 | 59 |
| 56 | L | C | 189 | 394 | 572 | 49 |
| 56 | L | O | 201 | 398 | 572 | 49 |
| 57 | H | N | 181 | 396 | 582 | 48 |
| 57 | H | CA | 185 | 403 | 594 | 48 |
| 57 | H | CB | 173 | 408 | 603 | 48 |
| 57 | H | CG | 166 | 420 | 596 | 52 |
| 57 | H | ND1 | 156 | 427 | 603 | 55 |
| 57 | H | CE1 | 151 | 436 | 595 | 54 |
| 57 | H | NE2 | 158 | 436 | 583 | 57 |
| 57 | H | CD2 | 167 | 426 | 584 | 55 |
| 57 | H | C | 196 | 396 | 603 | 47 |
| 57 | H | O | 204 | 403 | 608 | 45 |
| 58 | E | N | 195 | 383 | 605 | 44 |
| 58 | E | CA | 206 | 375 | 610 | 44 |
| 58 | E | CB | 203 | 360 | 610 | 44 |
| 58 | E | CG | 212 | 351 | 619 | 46 |
| 58 | E | CD | 212 | 356 | 634 | 53 |
| 58 | E | OE1 | 223 | 354 | 640 | 54 |
| 58 | E | OE2 | 202 | 362 | 639 | 47 |
| 58 | E | C | 220 | 377 | 602 | 42 |
| 58 | E | O | 230 | 379 | 608 | 41 |
| 59 | M | N | 219 | 377 | 589 | 42 |
| 59 | M | CA | 230 | 378 | 580 | 42 |
| 59 | M | CB | 224 | 378 | 566 | 42 |
| 59 | M | CG | 234 | 378 | 554 | 47 |
| 59 | M | SD | 243 | 362 | 552 | 53 |
| 59 | M | CE | 254 | 367 | 539 | 45 |
| 59 | M | C | 238 | 391 | 583 | 42 |
| 59 | M | O | 250 | 391 | 586 | 40 |
| 60 | I | N | 230 | 402 | 583 | 41 |
| 60 | I | CA | 236 | 415 | 586 | 42 |
| 60 | I | CB | 225 | 427 | 583 | 42 |
| 60 | I | CG1 | 223 | 427 | 568 | 45 |
| 60 | I | CD1 | 209 | 430 | 565 | 55 |
| 60 | I | CG2 | 231 | 440 | 588 | 42 |
| 60 | I | C | 242 | 415 | 600 | 41 |
| 60 | I | O | 253 | 420 | 601 | 42 |
| 61 | Q | N | 235 | 410 | 610 | 41 |
| 61 | Q | CA | 241 | 410 | 623 | 41 |
| 61 | Q | CB | 231 | 404 | 633 | 41 |
| 61 | Q | CG | 237 | 402 | 647 | 45 |
| 61 | Q | CD | 241 | 416 | 654 | 51 |
| 61 | Q | OE1 | 252 | 419 | 657 | 52 |
| 61 | Q | NE2 | 230 | 423 | 657 | 53 |
| 61 | Q | C | 254 | 402 | 623 | 40 |
| 61 | Q | O | 264 | 406 | 628 | 42 |
| 62 | Q | N | 254 | 390 | 617 | 38 |
| 62 | Q | CA | 266 | 381 | 616 | 37 |
| 62 | Q | CB | 263 | 368 | 609 | 37 |
| 62 | Q | CG | 253 | 359 | 617 | 37 |
| 62 | Q | CD | 259 | 355 | 631 | 44 |
| 62 | Q | OE1 | 271 | 353 | 632 | 45 |
| 62 | Q | NE2 | 250 | 355 | 641 | 40 |
| 62 | Q | C | 278 | 388 | 608 | 35 |
| 62 | Q | O | 289 | 387 | 612 | 36 |
| 63 | I | N | 275 | 395 | 597 | 36 |
| 63 | I | CA | 286 | 403 | 590 | 37 |
| 63 | I | CB | 280 | 409 | 577 | 37 |
| 63 | I | CG1 | 276 | 398 | 567 | 34 |
| 63 | I | CD1 | 268 | 403 | 555 | 34 |
| 63 | I | CG2 | 290 | 419 | 570 | 37 |
| 63 | I | C | 291 | 414 | 600 | 38 |
| 63 | I | O | 303 | 416 | 601 | 36 |
| 64 | F | N | 282 | 421 | 606 | 39 |
| 64 | F | CA | 286 | 430 | 617 | 39 |
| 64 | F | CB | 275 | 438 | 624 | 40 |
| 64 | F | CG | 280 | 445 | 636 | 46 |
| 64 | F | CD1 | 284 | 459 | 636 | 49 |
| 64 | F | CE1 | 289 | 465 | 647 | 48 |
| 64 | F | CZ | 292 | 458 | 659 | 42 |
| 64 | F | CE2 | 288 | 445 | 659 | 46 |
| 64 | F | CD2 | 283 | 439 | 648 | 44 |
| 64 | F | C | 296 | 423 | 626 | 38 |
| 64 | F | O | 307 | 428 | 629 | 40 |
| 65 | N | N | 292 | 412 | 631 | 38 |
| 65 | N | CA | 300 | 405 | 641 | 37 |
| 65 | N | CB | 294 | 392 | 647 | 37 |
| 65 | N | CG | 281 | 394 | 656 | 43 |
| 65 | N | OD1 | 274 | 385 | 660 | 47 |
| 65 | N | ND2 | 278 | 407 | 660 | 41 |
| 65 | N | C | 314 | 402 | 636 | 37 |
| 65 | N | O | 324 | 404 | 642 | 37 |
| 66 | L | N | 314 | 396 | 624 | 36 |
| 66 | L | CA | 326 | 391 | 617 | 34 |
| 66 | L | CB | 322 | 385 | 603 | 33 |
| 66 | L | CG | 333 | 380 | 594 | 35 |
| 66 | L | CD1 | 341 | 370 | 601 | 29 |
| 66 | L | CD2 | 327 | 374 | 581 | 31 |
| 66 | L | C | 336 | 402 | 615 | 33 |
| 66 | L | O | 347 | 400 | 617 | 34 |
| 67 | F | N | 331 | 414 | 610 | 35 |
| 67 | F | CA | 341 | 424 | 606 | 37 |
| 67 | F | CB | 336 | 432 | 594 | 34 |
| 67 | F | CG | 338 | 424 | 581 | 37 |
| 67 | F | CD1 | 327 | 416 | 577 | 36 |
| 67 | F | CE1 | 329 | 408 | 565 | 37 |
| 67 | F | CZ | 341 | 408 | 558 | 39 |
| 67 | F | CE2 | 351 | 416 | 563 | 41 |
| 67 | F | CD2 | 350 | 424 | 575 | 42 |
| 67 | F | C | 344 | 435 | 617 | 41 |
| 67 | F | O | 350 | 446 | 614 | 41 |
| 68 | S | N | 339 | 433 | 629 | 42 |
| 68 | S | CA | 340 | 442 | 640 | 44 |
| 68 | S | CB | 327 | 445 | 647 | 43 |
| 68 | S | OG | 322 | 434 | 654 | 47 |
| 68 | S | C | 350 | 438 | 651 | 45 |
| 68 | S | O | 350 | 444 | 661 | 48 |
| 69 | T | N | 357 | 427 | 648 | 47 |
| 69 | T | CA | 367 | 421 | 658 | 47 |
| 69 | T | CB | 370 | 407 | 655 | 46 |
| 69 | T | OG1 | 376 | 406 | 642 | 46 |
| 69 | T | CG2 | 358 | 398 | 654 | 45 |
| 69 | T | C | 380 | 429 | 656 | 47 |
| 69 | T | O | 383 | 436 | 646 | 46 |
| 70 | A | N | 389 | 426 | 666 | 48 |
| 70 | A | CA | 403 | 432 | 666 | 49 |
| 70 | A | CB | 410 | 429 | 679 | 51 |
| 70 | A | C | 410 | 426 | 653 | 49 |
| 70 | A | O | 418 | 433 | 647 | 49 |
| 71 | D | N | 407 | 414 | 650 | 49 |
| 71 | D | CA | 413 | 407 | 638 | 48 |
| 71 | D | CB | 409 | 392 | 638 | 48 |
| 71 | D | CG | 413 | 386 | 651 | 52 |
| 71 | D | OD1 | 425 | 382 | 653 | 52 |
| 71 | D | OD2 | 405 | 384 | 660 | 54 |
| 71 | D | C | 409 | 414 | 625 | 46 |
| 71 | D | O | 418 | 416 | 617 | 46 |
| 72 | S | N | 397 | 417 | 623 | 45 |
| 72 | S | CA | 392 | 424 | 612 | 45 |
| 72 | S | CB | 377 | 425 | 613 | 44 |
| 72 | S | OG | 372 | 434 | 603 | 46 |
| 72 | S | C | 398 | 438 | 611 | 46 |
| 72 | S | O | 403 | 443 | 600 | 46 |
| 73 | S | N | 398 | 446 | 622 | 47 |
| 73 | S | CA | 404 | 459 | 623 | 49 |
| 73 | S | CB | 402 | 464 | 637 | 50 |
| 73 | S | OG | 389 | 470 | 638 | 54 |
| 73 | S | C | 419 | 458 | 619 | 48 |
| 73 | S | O | 424 | 467 | 612 | 48 |
| 74 | A | N | 426 | 448 | 622 | 48 |
| 74 | A | CA | 440 | 446 | 617 | 48 |

| | | | | | |
|---|---|---|---|---|---|
| 74 | A | CB | 447 | 435 | 626 | 48 |
| 74 | A | C | 441 | 442 | 602 | 48 |
| 74 | A | O | 452 | 445 | 596 | 48 |
| 75 | A | N | 431 | 436 | 596 | 47 |
| 75 | A | CA | 432 | 431 | 583 | 45 |
| 75 | A | CB | 424 | 419 | 581 | 44 |
| 75 | A | C | 428 | 441 | 572 | 44 |
| 75 | A | O | 432 | 439 | 560 | 45 |
| 76 | W | N | 419 | 451 | 575 | 43 |
| 76 | W | CA | 413 | 460 | 565 | 43 |
| 76 | W | CB | 398 | 457 | 565 | 42 |
| 76 | W | CG | 394 | 443 | 563 | 42 |
| 76 | W | CD1 | 388 | 434 | 572 | 41 |
| 76 | W | NE1 | 387 | 421 | 567 | 39 |
| 76 | W | CE2 | 392 | 422 | 554 | 41 |
| 76 | W | CD2 | 397 | 435 | 552 | 41 |
| 76 | W | CE3 | 403 | 438 | 539 | 40 |
| 76 | W | CZ3 | 404 | 427 | 530 | 43 |
| 76 | W | CH2 | 400 | 414 | 533 | 44 |
| 76 | W | CZ2 | 394 | 411 | 545 | 39 |
| 76 | W | C | 415 | 474 | 568 | 45 |
| 76 | W | O | 417 | 479 | 579 | 45 |
| 77 | D | N | 414 | 482 | 557 | 45 |
| 77 | D | CA | 416 | 496 | 558 | 48 |
| 77 | D | CB | 415 | 503 | 544 | 47 |
| 77 | D | CG | 416 | 518 | 544 | 54 |
| 77 | D | OD1 | 406 | 525 | 539 | 56 |
| 77 | D | OD2 | 426 | 524 | 549 | 60 |
| 77 | D | C | 405 | 503 | 567 | 47 |
| 77 | D | O | 393 | 501 | 564 | 46 |
| 78 | E | N | 410 | 510 | 577 | 48 |
| 78 | E | CA | 401 | 516 | 587 | 49 |
| 78 | E | CB | 408 | 524 | 598 | 51 |
| 78 | E | CG | 398 | 530 | 609 | 57 |
| 78 | E | CD | 403 | 534 | 622 | 68 |
| 78 | E | OE1 | 394 | 536 | 631 | 72 |
| 78 | E | OE2 | 415 | 536 | 624 | 71 |
| 78 | E | C | 390 | 525 | 581 | 48 |
| 78 | E | O | 378 | 524 | 584 | 48 |
| 79 | T | N | 394 | 533 | 571 | 46 |
| 79 | T | CA | 384 | 542 | 564 | 47 |
| 79 | T | CB | 392 | 551 | 554 | 47 |
| 79 | T | OG1 | 402 | 558 | 561 | 50 |
| 79 | T | CG2 | 383 | 562 | 549 | 49 |
| 79 | T | C | 372 | 535 | 557 | 45 |
| 79 | T | O | 360 | 539 | 557 | 45 |
| 80 | L | N | 376 | 524 | 550 | 43 |
| 80 | L | CA | 366 | 516 | 543 | 41 |
| 80 | L | CB | 373 | 506 | 533 | 42 |
| 80 | L | CG | 379 | 512 | 520 | 46 |
| 80 | L | CD1 | 385 | 501 | 511 | 48 |
| 80 | L | CD2 | 369 | 520 | 512 | 45 |
| 80 | L | C | 357 | 509 | 553 | 39 |
| 80 | L | O | 345 | 508 | 551 | 38 |
| 81 | L | N | 363 | 503 | 563 | 37 |
| 81 | L | CA | 355 | 496 | 574 | 40 |
| 81 | L | CB | 364 | 490 | 585 | 39 |
| 81 | L | CG | 370 | 477 | 583 | 43 |
| 81 | L | CD1 | 379 | 474 | 596 | 44 |
| 81 | L | CD2 | 360 | 465 | 580 | 41 |
| 81 | L | C | 345 | 505 | 580 | 39 |
| 81 | L | O | 334 | 501 | 582 | 41 |
| 82 | D | N | 349 | 517 | 584 | 40 |
| 82 | D | CA | 340 | 527 | 590 | 41 |
| 82 | D | CB | 347 | 540 | 594 | 40 |
| 82 | D | CG | 356 | 538 | 606 | 45 |
| 82 | D | OD1 | 364 | 548 | 609 | 45 |
| 82 | D | OD2 | 355 | 528 | 613 | 48 |
| 82 | D | C | 328 | 530 | 582 | 40 |
| 82 | D | O | 317 | 529 | 586 | 41 |
| 83 | K | N | 331 | 532 | 569 | 40 |
| 83 | K | CA | 319 | 534 | 559 | 40 |
| 83 | K | CB | 325 | 538 | 545 | 41 |
| 83 | K | CG | 332 | 552 | 546 | 46 |
| 83 | K | CD | 343 | 554 | 534 | 56 |
| 83 | K | CE | 344 | 569 | 530 | 62 |
| 83 | K | NZ | 333 | 572 | 519 | 67 |
| 83 | K | C | 311 | 521 | 558 | 40 |
| 83 | K | O | 298 | 522 | 555 | 40 |
| 84 | F | N | 318 | 510 | 558 | 38 |
| 84 | F | CA | 311 | 497 | 557 | 38 |
| 84 | F | CB | 322 | 486 | 557 | 37 |
| 84 | F | CG | 316 | 472 | 557 | 39 |
| 84 | F | CD1 | 310 | 467 | 545 | 39 |
| 84 | F | CE1 | 306 | 454 | 544 | 39 |
| 84 | F | CZ | 308 | 445 | 555 | 36 |
| 84 | F | CE2 | 315 | 449 | 566 | 40 |
| 84 | F | CD2 | 319 | 463 | 567 | 37 |
| 84 | F | C | 301 | 495 | 569 | 38 |
| 84 | F | O | 289 | 492 | 567 | 39 |
| 85 | Y | N | 306 | 498 | 581 | 38 |
| 85 | Y | CA | 297 | 499 | 593 | 41 |
| 85 | Y | CB | 306 | 501 | 606 | 41 |
| 85 | Y | CG | 311 | 487 | 610 | 42 |
| 85 | Y | CD1 | 301 | 478 | 615 | 53 |
| 85 | Y | CE1 | 305 | 465 | 618 | 52 |
| 85 | Y | CZ | 318 | 461 | 616 | 55 |
| 85 | Y | OH | 321 | 448 | 619 | 61 |
| 85 | Y | CE2 | 328 | 470 | 610 | 49 |
| 85 | Y | CD2 | 324 | 483 | 607 | 49 |
| 85 | Y | C | 285 | 508 | 592 | 41 |
| 85 | Y | O | 274 | 504 | 596 | 41 |
| 86 | T | N | 287 | 520 | 587 | 42 |
| 86 | T | CA | 276 | 529 | 584 | 44 |
| 86 | T | CB | 282 | 542 | 578 | 44 |
| 86 | T | OG1 | 290 | 548 | 588 | 46 |
| 86 | T | CG2 | 271 | 552 | 577 | 48 |
| 86 | T | C | 266 | 523 | 576 | 45 |
| 86 | T | O | 254 | 524 | 578 | 45 |
| 87 | E | N | 270 | 515 | 565 | 43 |
| 87 | E | CA | 260 | 508 | 558 | 42 |
| 87 | E | CB | 265 | 502 | 544 | 43 |
| 87 | E | CG | 271 | 514 | 536 | 42 |
| 87 | E | CD | 261 | 524 | 531 | 46 |
| 87 | E | OE1 | 250 | 520 | 527 | 47 |
| 87 | E | OE2 | 265 | 536 | 531 | 46 |
| 87 | E | C | 253 | 496 | 566 | 43 |
| 87 | E | O | 241 | 494 | 564 | 44 |
| 88 | L | N | 260 | 589 | 574 | 42 |
| 88 | L | CA | 254 | 478 | 581 | 42 |
| 88 | L | CB | 264 | 470 | 588 | 41 |
| 88 | L | CG | 275 | 462 | 580 | 41 |
| 88 | L | CD1 | 284 | 454 | 589 | 37 |
| 88 | L | CD2 | 269 | 454 | 570 | 40 |
| 88 | L | C | 243 | 483 | 592 | 43 |
| 88 | L | O | 233 | 476 | 593 | 42 |
| 89 | Y | N | 245 | 494 | 599 | 43 |
| 89 | Y | CA | 235 | 500 | 608 | 45 |
| 89 | Y | CB | 241 | 513 | 614 | 43 |
| 89 | Y | CG | 254 | 511 | 622 | 42 |
| 89 | Y | CD1 | 255 | 499 | 629 | 43 |
| 89 | Y | CE1 | 267 | 497 | 636 | 44 |
| 89 | Y | CZ | 277 | 507 | 635 | 43 |
| 89 | Y | OH | 289 | 504 | 642 | 47 |
| 89 | Y | CE2 | 276 | 518 | 628 | 40 |
| 89 | Y | CD2 | 264 | 520 | 621 | 41 |
| 89 | Y | C | 222 | 503 | 601 | 47 |
| 89 | Y | O | 212 | 499 | 607 | 46 |
| 90 | Q | N | 222 | 509 | 590 | 50 |
| 90 | Q | CA | 210 | 512 | 582 | 54 |
| 90 | Q | CB | 214 | 520 | 569 | 54 |
| 90 | Q | CG | 220 | 534 | 572 | 61 |
| 90 | Q | CD | 224 | 541 | 559 | 69 |
| 90 | Q | OE1 | 220 | 537 | 548 | 72 |
| 90 | Q | NE2 | 231 | 552 | 560 | 71 |
| 90 | Q | C | 202 | 500 | 578 | 55 |
| 90 | Q | O | 190 | 500 | 577 | 54 |
| 91 | Q | N | 210 | 489 | 576 | 57 |
| 91 | Q | CA | 203 | 476 | 572 | 58 |
| 91 | Q | CB | 212 | 469 | 562 | 58 |
| 91 | Q | CG | 214 | 475 | 549 | 60 |
| 91 | Q | CD | 223 | 467 | 539 | 64 |
| 91 | Q | OE1 | 218 | 458 | 531 | 67 |
| 91 | Q | NE2 | 236 | 470 | 539 | 63 |
| 91 | Q | C | 199 | 467 | 584 | 58 |
| 91 | Q | O | 192 | 457 | 581 | 59 |
| 92 | L | N | 203 | 470 | 596 | 59 |
| 92 | L | CA | 201 | 460 | 607 | 60 |
| 92 | L | CB | 209 | 464 | 619 | 60 |
| 92 | L | CG | 223 | 459 | 622 | 63 |

| | | | | | | |
|---|---|---|---|---|---|---|
| 92 | L | CD1 | 229 | 467 | 637 | 66 |
| 92 | L | CD2 | 223 | 444 | 625 | 62 |
| 92 | L | C | 187 | 458 | 612 | 62 |
| 92 | L | O | 183 | 446 | 616 | 61 |
| 93 | N | N | 179 | 469 | 613 | 63 |
| 93 | N | CA | 166 | 468 | 620 | 65 |
| 93 | N | CB | 168 | 469 | 635 | 63 |
| 93 | N | CG | 155 | 468 | 643 | 64 |
| 93 | N | OD1 | 145 | 463 | 638 | 63 |
| 93 | N | ND2 | 156 | 471 | 656 | 62 |
| 93 | N | C | 157 | 480 | 614 | 67 |
| 93 | N | O | 153 | 489 | 621 | 67 |
| 94 | D | N | 154 | 479 | 601 | 69 |
| 94 | D | CA | 147 | 490 | 594 | 71 |
| 94 | D | CB | 153 | 492 | 580 | 71 |
| 94 | D | CG | 153 | 480 | 572 | 72 |
| 94 | D | OD1 | 150 | 481 | 560 | 74 |
| 94 | D | OD2 | 155 | 468 | 577 | 72 |
| 94 | D | C | 132 | 488 | 593 | 72 |
| 94 | D | O | 125 | 496 | 587 | 73 |
| 95 | L | N | 127 | 478 | 600 | 74 |
| 95 | L | CA | 112 | 476 | 602 | 76 |
| 95 | L | CB | 108 | 484 | 615 | 76 |
| 95 | L | CG | 116 | 483 | 627 | 75 |
| 95 | L | CD1 | 116 | 497 | 634 | 75 |
| 95 | L | CD2 | 112 | 472 | 637 | 74 |
| 95 | L | C | 103 | 480 | 590 | 77 |
| 95 | L | O | 98 | 491 | 589 | 77 |
| 96 | E | N | 103 | 470 | 580 | 78 |
| 96 | E | CA | 95 | 472 | 568 | 79 |
| 96 | E | CB | 102 | 464 | 556 | 79 |
| 96 | E | CG | 107 | 451 | 560 | 81 |
| 96 | E | CD | 122 | 451 | 565 | 83 |
| 96 | E | OE1 | 130 | 446 | 558 | 84 |
| 96 | E | OE2 | 124 | 455 | 577 | 82 |
| 96 | E | C | 81 | 466 | 569 | 79 |
| 96 | E | O | 78 | 458 | 578 | 79 |
| 112 | A | N | 109 | 307 | 618 | 61 |
| 112 | A | CA | 120 | 305 | 609 | 60 |
| 112 | A | CB | 122 | 318 | 600 | 60 |
| 112 | A | C | 133 | 301 | 617 | 59 |
| 112 | A | O | 144 | 304 | 612 | 59 |
| 113 | A | N | 132 | 295 | 629 | 57 |
| 113 | A | CA | 144 | 292 | 637 | 56 |
| 113 | A | CB | 140 | 287 | 650 | 56 |
| 113 | A | C | 155 | 283 | 631 | 55 |
| 113 | A | O | 167 | 285 | 634 | 54 |
| 114 | D | N | 151 | 273 | 623 | 54 |
| 114 | D | CA | 161 | 264 | 617 | 52 |
| 114 | D | CB | 154 | 252 | 611 | 53 |
| 114 | D | CG | 150 | 241 | 621 | 59 |
| 114 | D | OD1 | 140 | 234 | 619 | 66 |
| 114 | D | OD2 | 156 | 239 | 632 | 66 |
| 114 | D | C | 169 | 272 | 606 | 49 |
| 114 | D | O | 180 | 269 | 605 | 48 |
| 115 | S | N | 162 | 281 | 599 | 49 |
| 115 | S | CA | 168 | 289 | 589 | 50 |
| 115 | S | CB | 157 | 296 | 582 | 50 |
| 115 | S | OG | 153 | 290 | 570 | 57 |
| 115 | S | C | 178 | 299 | 595 | 49 |
| 115 | S | O | 189 | 301 | 589 | 49 |
| 116 | I | N | 174 | 306 | 605 | 46 |
| 116 | I | CA | 183 | 315 | 613 | 45 |
| 116 | I | CB | 176 | 321 | 625 | 46 |
| 116 | I | CG1 | 169 | 333 | 619 | 46 |
| 116 | I | CD1 | 158 | 339 | 630 | 55 |
| 116 | I | CG2 | 186 | 326 | 636 | 44 |
| 116 | I | C | 195 | 307 | 617 | 44 |
| 116 | I | O | 207 | 312 | 616 | 43 |
| 117 | L | N | 193 | 295 | 623 | 42 |
| 117 | L | CA | 204 | 287 | 627 | 41 |
| 117 | L | CB | 199 | 275 | 635 | 42 |
| 117 | L | CG | 210 | 264 | 639 | 45 |
| 117 | L | CD1 | 221 | 268 | 650 | 50 |
| 117 | L | CD2 | 203 | 250 | 642 | 50 |
| 117 | L | C | 214 | 282 | 616 | 40 |
| 117 | L | O | 226 | 281 | 617 | 40 |
| 118 | A | N | 208 | 280 | 604 | 39 |
| 118 | A | CA | 216 | 277 | 592 | 38 |
| 118 | A | CB | 206 | 275 | 579 | 36 |
| 118 | A | C | 225 | 288 | 589 | 37 |
| 118 | A | O | 237 | 286 | 586 | 38 |
| 119 | V | N | 220 | 300 | 590 | 38 |
| 119 | V | CA | 229 | 312 | 588 | 38 |
| 119 | V | CB | 220 | 325 | 587 | 40 |
| 119 | V | CG1 | 229 | 337 | 585 | 36 |
| 119 | V | CG2 | 211 | 325 | 575 | 38 |
| 119 | V | C | 240 | 313 | 598 | 37 |
| 119 | V | O | 251 | 315 | 595 | 37 |
| 120 | R | N | 237 | 311 | 611 | 37 |
| 120 | R | CA | 247 | 312 | 621 | 38 |
| 120 | R | CB | 240 | 310 | 635 | 39 |
| 120 | R | CG | 232 | 321 | 640 | 43 |
| 120 | R | CD | 226 | 320 | 654 | 46 |
| 120 | R | NE | 218 | 332 | 656 | 51 |
| 120 | R | CZ | 208 | 333 | 665 | 53 |
| 120 | R | NH1 | 204 | 322 | 672 | 52 |
| 120 | R | NH2 | 201 | 344 | 666 | 52 |
| 120 | R | C | 258 | 301 | 620 | 38 |
| 120 | R | O | 269 | 304 | 622 | 38 |
| 121 | K | N | 253 | 289 | 616 | 36 |
| 121 | K | CA | 263 | 278 | 614 | 36 |
| 121 | K | CB | 255 | 265 | 611 | 36 |
| 121 | K | CG | 250 | 259 | 623 | 39 |
| 121 | K | CD | 243 | 245 | 620 | 46 |
| 121 | K | CE | 238 | 238 | 633 | 51 |
| 121 | K | NZ | 230 | 225 | 632 | 62 |
| 121 | K | C | 272 | 282 | 602 | 34 |
| 121 | K | O | 283 | 278 | 603 | 34 |
| 122 | Y | N | 267 | 288 | 592 | 33 |
| 122 | Y | CA | 276 | 292 | 581 | 32 |
| 122 | Y | CB | 267 | 299 | 571 | 31 |
| 122 | Y | CG | 274 | 307 | 560 | 34 |
| 122 | Y | CD1 | 282 | 301 | 550 | 33 |
| 122 | Y | CE1 | 288 | 309 | 541 | 33 |
| 122 | Y | CZ | 287 | 323 | 541 | 37 |
| 122 | Y | OH | 293 | 331 | 532 | 35 |
| 122 | Y | CE2 | 279 | 329 | 551 | 40 |
| 122 | Y | CD2 | 273 | 321 | 560 | 33 |
| 122 | Y | C | 287 | 302 | 586 | 32 |
| 122 | Y | O | 299 | 301 | 583 | 30 |
| 123 | F | N | 283 | 311 | 594 | 31 |
| 123 | F | CA | 293 | 320 | 600 | 32 |
| 123 | F | CB | 287 | 333 | 606 | 31 |
| 123 | F | CG | 283 | 343 | 595 | 32 |
| 123 | F | CD1 | 292 | 352 | 591 | 33 |
| 123 | F | CE1 | 289 | 361 | 581 | 33 |
| 123 | F | CZ | 276 | 360 | 575 | 33 |
| 123 | F | CE2 | 267 | 351 | 579 | 29 |
| 123 | F | CD2 | 270 | 342 | 589 | 30 |
| 123 | F | C | 302 | 314 | 610 | 31 |
| 123 | F | O | 314 | 318 | 612 | 32 |
| 124 | Q | N | 297 | 304 | 617 | 32 |
| 124 | Q | CA | 306 | 296 | 625 | 33 |
| 124 | Q | CB | 298 | 285 | 633 | 34 |
| 124 | Q | CG | 291 | 291 | 644 | 38 |
| 124 | Q | CD | 280 | 281 | 650 | 47 |
| 124 | Q | OE1 | 279 | 270 | 646 | 45 |
| 124 | Q | NE2 | 273 | 286 | 660 | 49 |
| 124 | Q | C | 317 | 289 | 617 | 32 |
| 124 | Q | O | 329 | 288 | 622 | 32 |
| 125 | R | N | 313 | 284 | 606 | 31 |
| 125 | R | CA | 324 | 278 | 597 | 31 |
| 125 | R | CB | 317 | 270 | 585 | 30 |
| 125 | R | CG | 308 | 259 | 589 | 34 |
| 125 | R | CD | 303 | 250 | 578 | 33 |
| 125 | R | NE | 294 | 257 | 569 | 34 |
| 125 | R | CZ | 281 | 258 | 570 | 33 |
| 125 | R | NH1 | 275 | 253 | 581 | 31 |
| 125 | R | NH2 | 274 | 263 | 560 | 30 |
| 125 | R | C | 334 | 288 | 593 | 29 |
| 125 | R | O | 345 | 285 | 592 | 30 |
| 126 | I | N | 329 | 300 | 589 | 29 |
| 126 | I | CA | 338 | 311 | 585 | 30 |
| 126 | I | CB | 330 | 323 | 580 | 30 |
| 126 | I | CG1 | 325 | 321 | 566 | 32 |
| 126 | I | CD1 | 315 | 332 | 561 | 34 |
| 126 | I | CG2 | 340 | 336 | 579 | 27 |
| 126 | I | C | 348 | 315 | 596 | 32 |
| 126 | I | O | 360 | 316 | 594 | 32 |

| | | | | | | | | | | | | |
|---|---|---|---|---|---|---|---|---|---|---|---|---|
| 127 | T | N | 342 | 317 | 609 | 32 | 135 | Y | CD2 | 413 | 360 | 622 | 44 |
| 127 | T | CA | 350 | 320 | 620 | 36 | 135 | Y | C | 450 | 356 | 592 | 39 |
| 127 | T | CB | 340 | 322 | 632 | 36 | 135 | Y | O | 453 | 368 | 592 | 39 |
| 127 | T | OG1 | 332 | 333 | 628 | 43 | 136 | S | N | 454 | 347 | 584 | 38 |
| 127 | T | CG2 | 347 | 328 | 643 | 44 | 136 | S | CA | 464 | 351 | 574 | 40 |
| 127 | T | C | 361 | 309 | 623 | 35 | 136 | S | CB | 469 | 339 | 567 | 41 |
| 127 | T | O | 372 | 313 | 626 | 35 | 136 | S | OG | 459 | 332 | 559 | 42 |
| 128 | L | N | 357 | 297 | 623 | 35 | 136 | S | C | 457 | 361 | 564 | 41 |
| 128 | L | CA | 366 | 286 | 626 | 36 | 136 | S | O | 445 | 361 | 562 | 40 |
| 128 | L | CB | 358 | 272 | 626 | 37 | 137 | P | N | 466 | 369 | 556 | 41 |
| 128 | L | CG | 367 | 261 | 629 | 41 | 137 | P | CA | 460 | 377 | 545 | 41 |
| 128 | L | CD1 | 372 | 262 | 645 | 43 | 137 | P | CB | 473 | 383 | 539 | 41 |
| 128 | L | CD2 | 361 | 247 | 627 | 45 | 137 | P | CG | 482 | 385 | 552 | 43 |
| 128 | L | C | 377 | 285 | 615 | 37 | 137 | P | CD | 480 | 371 | 559 | 41 |
| 128 | L | O | 388 | 283 | 619 | 36 | 137 | P | C | 452 | 369 | 535 | 39 |
| 129 | Y | N | 373 | 287 | 603 | 34 | 137 | P | O | 442 | 374 | 531 | 38 |
| 129 | Y | CA | 383 | 288 | 592 | 33 | 138 | C | N | 457 | 357 | 532 | 38 |
| 129 | Y | CB | 376 | 290 | 578 | 33 | 138 | C | CA | 450 | 348 | 522 | 39 |
| 129 | Y | CG | 385 | 294 | 567 | 30 | 138 | C | CB | 459 | 337 | 519 | 38 |
| 129 | Y | CD1 | 390 | 284 | 558 | 30 | 138 | C | SG | 470 | 341 | 506 | 46 |
| 129 | Y | CE1 | 398 | 287 | 547 | 32 | 138 | C | C | 436 | 344 | 527 | 38 |
| 129 | Y | CZ | 401 | 301 | 544 | 34 | 138 | C | O | 427 | 342 | 520 | 37 |
| 129 | Y | OH | 409 | 304 | 534 | 33 | 139 | A | N | 436 | 340 | 540 | 35 |
| 129 | Y | CE2 | 395 | 311 | 553 | 32 | 139 | A | CA | 423 | 335 | 546 | 34 |
| 129 | Y | CD2 | 387 | 307 | 564 | 31 | 139 | A | CB | 426 | 329 | 560 | 32 |
| 129 | Y | C | 393 | 299 | 594 | 31 | 139 | A | C | 413 | 347 | 546 | 33 |
| 129 | Y | O | 405 | 296 | 593 | 33 | 139 | A | O | 402 | 344 | 543 | 33 |
| 130 | L | N | 389 | 311 | 597 | 33 | 140 | W | N | 418 | 359 | 549 | 32 |
| 130 | L | CA | 399 | 322 | 600 | 35 | 140 | W | CA | 409 | 370 | 550 | 34 |
| 130 | L | CB | 392 | 335 | 603 | 33 | 140 | W | CB | 415 | 382 | 555 | 34 |
| 130 | L | CG | 387 | 341 | 590 | 38 | 140 | W | CG | 413 | 384 | 570 | 38 |
| 130 | L | CD1 | 377 | 352 | 595 | 33 | 140 | W | CD1 | 422 | 384 | 581 | 40 |
| 130 | L | CD2 | 398 | 347 | 581 | 33 | 140 | W | NE1 | 415 | 386 | 593 | 37 |
| 130 | L | C | 409 | 318 | 612 | 36 | 140 | W | CE2 | 402 | 387 | 591 | 37 |
| 130 | L | O | 421 | 321 | 612 | 35 | 140 | W | CD2 | 400 | 386 | 576 | 36 |
| 131 | K | N | 403 | 312 | 622 | 39 | 140 | W | CE3 | 387 | 387 | 571 | 34 |
| 131 | K | CA | 410 | 309 | 634 | 41 | 140 | W | CZ3 | 376 | 390 | 580 | 34 |
| 131 | K | CB | 401 | 304 | 645 | 42 | 140 | W | CH2 | 378 | 391 | 594 | 34 |
| 131 | K | CG | 408 | 299 | 658 | 49 | 140 | W | CZ2 | 391 | 389 | 600 | 38 |
| 131 | K | CD | 399 | 294 | 669 | 55 | 140 | W | C | 404 | 374 | 536 | 33 |
| 131 | K | NE | 407 | 294 | 682 | 61 | 140 | W | O | 392 | 378 | 534 | 32 |
| 131 | K | CZ | 398 | 293 | 694 | 66 | 141 | E | N | 412 | 372 | 526 | 33 |
| 131 | K | C | 420 | 298 | 631 | 41 | 141 | E | CA | 408 | 374 | 512 | 32 |
| 131 | K | O | 432 | 300 | 633 | 41 | 141 | E | CB | 420 | 374 | 502 | 33 |
| 132 | E | N | 416 | 287 | 624 | 42 | 141 | E | CG | 415 | 374 | 487 | 31 |
| 132 | E | CA | 426 | 277 | 620 | 43 | 141 | E | CD | 405 | 386 | 484 | 33 |
| 132 | E | CB | 419 | 265 | 615 | 44 | 141 | E | OE1 | 405 | 397 | 491 | 33 |
| 132 | E | CG | 410 | 259 | 626 | 52 | 141 | E | OE2 | 399 | 385 | 474 | 34 |
| 132 | E | CD | 403 | 246 | 623 | 62 | 141 | E | C | 398 | 364 | 507 | 33 |
| 132 | E | OE1 | 398 | 243 | 612 | 63 | 141 | E | O | 388 | 367 | 501 | 33 |
| 132 | E | OE2 | 403 | 237 | 633 | 67 | 142 | V | N | 401 | 351 | 511 | 32 |
| 132 | E | C | 436 | 282 | 610 | 43 | 142 | V | CA | 390 | 341 | 508 | 31 |
| 132 | E | O | 448 | 277 | 610 | 43 | 142 | V | CB | 394 | 327 | 513 | 30 |
| 133 | K | N | 433 | 292 | 602 | 41 | 142 | V | CG1 | 383 | 317 | 513 | 30 |
| 133 | K | CA | 443 | 297 | 592 | 42 | 142 | V | CG2 | 406 | 322 | 503 | 31 |
| 133 | K | CB | 436 | 303 | 580 | 41 | 142 | V | C | 377 | 345 | 514 | 31 |
| 133 | K | CG | 429 | 293 | 571 | 41 | 142 | V | O | 366 | 343 | 508 | 32 |
| 133 | K | CD | 439 | 285 | 563 | 42 | 143 | V | N | 377 | 350 | 526 | 30 |
| 133 | K | NE | 432 | 276 | 554 | 41 | 143 | V | CA | 365 | 352 | 534 | 29 |
| 133 | K | CZ | 442 | 271 | 545 | 42 | 143 | V | CB | 367 | 354 | 549 | 30 |
| 133 | K | C | 451 | 309 | 598 | 42 | 143 | V | CG1 | 355 | 361 | 556 | 27 |
| 133 | K | O | 460 | 315 | 591 | 41 | 143 | V | CG2 | 370 | 339 | 555 | 27 |
| 134 | K | N | 449 | 312 | 611 | 42 | 143 | V | C | 358 | 365 | 528 | 30 |
| 134 | K | CA | 456 | 322 | 619 | 44 | 143 | V | O | 346 | 365 | 526 | 31 |
| 134 | K | CB | 470 | 317 | 622 | 44 | 144 | R | N | 366 | 375 | 525 | 30 |
| 134 | K | CG | 471 | 303 | 627 | 49 | 144 | R | CA | 361 | 388 | 519 | 30 |
| 134 | K | CD | 484 | 300 | 635 | 59 | 144 | R | CB | 372 | 398 | 517 | 29 |
| 134 | K | NE | 486 | 285 | 637 | 63 | 144 | R | CG | 367 | 413 | 512 | 31 |
| 134 | K | CZ | 499 | 280 | 642 | 68 | 144 | R | CD | 378 | 420 | 503 | 33 |
| 134 | K | C | 455 | 336 | 613 | 44 | 144 | R | NE | 381 | 412 | 492 | 31 |
| 134 | K | O | 464 | 344 | 614 | 44 | 144 | R | CZ | 374 | 411 | 481 | 36 |
| 135 | Y | N | 443 | 339 | 608 | 42 | 144 | R | NH1 | 363 | 419 | 479 | 35 |
| 135 | Y | CA | 439 | 351 | 603 | 41 | 144 | R | NH2 | 378 | 402 | 471 | 38 |
| 135 | Y | CB | 437 | 362 | 613 | 41 | 144 | R | C | 353 | 384 | 506 | 31 |
| 135 | Y | CG | 427 | 357 | 624 | 43 | 144 | R | O | 341 | 388 | 504 | 31 |
| 135 | Y | CD1 | 431 | 350 | 635 | 45 | 145 | A | N | 359 | 376 | 497 | 34 |
| 135 | Y | CE1 | 422 | 345 | 644 | 48 | 145 | A | CA | 353 | 373 | 484 | 35 |
| 135 | Y | CZ | 408 | 348 | 642 | 46 | 145 | A | CB | 363 | 365 | 475 | 35 |
| 135 | Y | OH | 399 | 344 | 651 | 45 | 145 | A | C | 341 | 365 | 487 | 34 |
| 135 | Y | CE2 | 404 | 356 | 631 | 45 | 145 | A | O | 330 | 367 | 480 | 36 |

| | | | | | | | | | | | |
|---|---|---|---|---|---|---|---|---|---|---|---|
| 146 | E | N | 341 | 356 | 496 | 34 | 155 | T | CA | 202 | 407 | 487 | 69 |
| 146 | E | CA | 330 | 348 | 500 | 33 | 155 | T | CB | 214 | 416 | 488 | 69 |
| 146 | E | CB | 334 | 337 | 511 | 33 | 155 | T | OG1 | 215 | 422 | 501 | 69 |
| 146 | E | CG | 323 | 331 | 518 | 33 | 155 | T | CG2 | 213 | 428 | 478 | 70 |
| 146 | E | CD | 316 | 321 | 509 | 40 | 155 | T | C | 194 | 406 | 474 | 71 |
| 146 | E | OE1 | 304 | 318 | 512 | 35 | 155 | T | O | 182 | 407 | 474 | 72 |
| 146 | E | OE2 | 322 | 316 | 500 | 39 | 156 | N | N | 201 | 405 | 463 | 73 |
| 146 | E | C | 318 | 356 | 505 | 33 | 156 | N | CA | 195 | 405 | 449 | 74 |
| 146 | E | O | 306 | 354 | 501 | 32 | 156 | N | CB | 205 | 403 | 438 | 75 |
| 147 | I | N | 321 | 366 | 514 | 33 | 156 | N | CG | 217 | 413 | 439 | 78 |
| 147 | I | CA | 310 | 374 | 520 | 34 | 156 | N | OD1 | 226 | 412 | 430 | 81 |
| 147 | I | CB | 315 | 383 | 532 | 33 | 156 | N | ND2 | 218 | 422 | 448 | 78 |
| 147 | I | CG1 | 319 | 373 | 543 | 35 | 156 | N | C | 183 | 395 | 448 | 75 |
| 147 | I | CD1 | 308 | 364 | 548 | 38 | 156 | N | O | 184 | 383 | 451 | 75 |
| 147 | I | CG2 | 305 | 393 | 536 | 33 | 1 | X | ZN | −21 | −79 | 311 | 39 |
| 147 | I | C | 305 | 383 | 508 | 35 | 2 | X | ZN | 186 | 256 | 536 | 50 |
| 147 | I | O | 293 | 385 | 507 | 36 | 3 | X | ZN | 374 | 545 | 626 | 66 |
| 148 | M | N | 314 | 389 | 500 | 37 | 4 | X | ZN | 153 | 448 | 566 | 66 |
| 148 | M | CA | 309 | 397 | 489 | 40 | 1 | X | O | −22 | −96 | 310 | 59 |
| 148 | M | CB | 321 | 402 | 481 | 39 | 2 | X | O | −33 | 69 | 334 | 42 |
| 148 | M | CG | 319 | 416 | 478 | 47 | 3 | X | O | 267 | 131 | 442 | 33 |
| 148 | M | SD | 329 | 419 | 464 | 55 | 4 | X | O | 423 | 411 | 502 | 33 |
| 148 | M | CE | 317 | 430 | 456 | 54 | 5 | X | O | −22 | −37 | 332 | 32 |
| 148 | M | C | 298 | 389 | 480 | 41 | 6 | X | O | 56 | 73 | 351 | 35 |
| 148 | M | O | 287 | 394 | 478 | 41 | 7 | X | O | 407 | 389 | 448 | 31 |
| 149 | R | N | 302 | 377 | 477 | 41 | 8 | X | O | 148 | 118 | 391 | 33 |
| 149 | R | CA | 293 | 367 | 470 | 43 | 9 | X | O | 415 | 471 | 529 | 38 |
| 149 | R | CB | 300 | 354 | 467 | 44 | 10 | X | O | 129 | 82 | 215 | 36 |
| 149 | R | CG | 309 | 354 | 455 | 45 | 11 | X | O | 221 | 127 | 389 | 36 |
| 149 | R | CG | 294 | 345 | 457 | 47 | 12 | X | O | 177 | 70 | 390 | 27 |
| 149 | R | CD | 315 | 340 | 453 | 48 | 13 | X | O | 369 | 36 | 556 | 38 |
| 149 | R | CD | 297 | 329 | 458 | 51 | 14 | X | O | 227 | 249 | 517 | 36 |
| 149 | R | NE | 329 | 340 | 452 | 49 | 15 | X | O | 227 | 116 | 304 | 35 |
| 149 | R | NE | 297 | 326 | 472 | 56 | 16 | X | O | 330 | 92 | 437 | 37 |
| 149 | R | CZ | 338 | 335 | 461 | 50 | 17 | X | O | 99 | 16 | 222 | 30 |
| 149 | R | CZ | 289 | 317 | 478 | 57 | 18 | X | O | 160 | 190 | 390 | 37 |
| 149 | R | NH1 | 334 | 329 | 471 | 50 | 19 | X | O | 478 | 390 | 450 | 36 |
| 149 | R | NH1 | 280 | 310 | 472 | 56 | 20 | X | O | 332 | 131 | 584 | 38 |
| 149 | R | NH2 | 351 | 336 | 458 | 52 | 21 | X | O | 147 | 150 | 438 | 37 |
| 149 | R | NH2 | 290 | 316 | 491 | 56 | 22 | X | O | 240 | 231 | 504 | 33 |
| 149 | R | C | 280 | 364 | 478 | 43 | 23 | X | O | 362 | 330 | 484 | 39 |
| 149 | R | O | 270 | 365 | 472 | 44 | 24 | X | O | 346 | −14 | 519 | 49 |
| 150 | S | N | 281 | 360 | 490 | 42 | 25 | X | O | 159 | 149 | 314 | 31 |
| 150 | S | CA | 269 | 355 | 496 | 43 | 26 | X | O | 168 | 135 | 337 | 33 |
| 150 | S | CB | 272 | 346 | 508 | 44 | 27 | X | O | 234 | −18 | 396 | 37 |
| 150 | S | OG | 279 | 354 | 518 | 48 | 28 | X | O | 245 | 249 | 537 | 34 |
| 150 | S | C | 260 | 367 | 501 | 44 | 29 | X | O | 169 | 144 | 291 | 41 |
| 150 | S | O | 248 | 366 | 503 | 44 | 30 | X | O | 331 | 221 | 520 | 41 |
| 151 | F | N | 266 | 379 | 503 | 44 | 31 | X | O | 112 | 206 | 308 | 43 |
| 151 | F | CA | 258 | 391 | 506 | 46 | 32 | X | O | 65 | 28 | 201 | 41 |
| 151 | F | CB | 267 | 402 | 512 | 45 | 33 | X | O | 246 | 265 | 573 | 35 |
| 151 | F | CG | 260 | 414 | 515 | 47 | 34 | X | O | 328 | 237 | 612 | 35 |
| 151 | F | CD1 | 252 | 416 | 526 | 48 | 35 | X | O | 80 | 85 | 360 | 33 |
| 151 | F | CE1 | 244 | 427 | 529 | 49 | 36 | X | O | −16 | 23 | 377 | 29 |
| 151 | F | CZ | 244 | 438 | 520 | 51 | 37 | X | O | −13 | −65 | 383 | 42 |
| 151 | F | CE2 | 252 | 437 | 508 | 52 | 38 | X | O | 227 | 251 | 558 | 40 |
| 151 | F | CD2 | 259 | 425 | 506 | 47 | 39 | X | O | 285 | 240 | 605 | 33 |
| 151 | F | C | 250 | 396 | 494 | 49 | 40 | X | O | −39 | −21 | 344 | 32 |
| 151 | F | O | 237 | 397 | 495 | 47 | 41 | X | O | 335 | 245 | 562 | 44 |
| 152 | S | N | 256 | 397 | 482 | 51 | 42 | X | O | 350 | 151 | 594 | 43 |
| 152 | S | CA | 249 | 399 | 469 | 54 | 43 | X | O | 291 | 88 | 608 | 36 |
| 152 | S | CB | 257 | 396 | 457 | 55 | 44 | X | O | 382 | 37 | 513 | 42 |
| 152 | S | OG | 268 | 405 | 456 | 58 | 45 | X | O | 21 | 19 | 356 | 40 |
| 152 | S | C | 237 | 389 | 469 | 55 | 46 | X | O | 202 | 265 | 465 | 40 |
| 152 | S | O | 226 | 393 | 466 | 56 | 47 | X | O | 62 | 207 | 374 | 46 |
| 153 | L | N | 240 | 376 | 471 | 58 | 48 | X | O | 58 | 3 | 206 | 39 |
| 153 | L | CA | 229 | 366 | 469 | 59 | 49 | X | O | 299 | 181 | 578 | 43 |
| 153 | L | CB | 235 | 352 | 470 | 59 | 50 | X | O | 481 | 294 | 470 | 50 |
| 153 | L | CG | 243 | 346 | 459 | 59 | 51 | X | O | 434 | 398 | 613 | 44 |
| 153 | L | CD1 | 251 | 333 | 464 | 58 | 52 | X | O | 360 | 422 | 447 | 40 |
| 153 | L | CD2 | 234 | 342 | 447 | 58 | 53 | X | O | 27 | 61 | 198 | 45 |
| 153 | L | C | 218 | 367 | 479 | 60 | 54 | X | O | 309 | 237 | 542 | 43 |
| 153 | L | O | 207 | 363 | 476 | 61 | 55 | X | O | 433 | 413 | 547 | 42 |
| 154 | S | N | 221 | 371 | 492 | 61 | 56 | X | O | 34 | 46 | 349 | 45 |
| 154 | S | CA | 210 | 372 | 502 | 62 | 57 | X | O | 75 | 193 | 297 | 47 |
| 154 | S | CB | 216 | 373 | 516 | 62 | 58 | X | O | −20 | 65 | 385 | 39 |
| 154 | S | OG | 225 | 384 | 517 | 62 | 59 | X | O | 257 | 91 | 384 | 45 |
| 154 | S | C | 202 | 385 | 498 | 64 | 60 | X | O | 15 | −126 | 370 | 49 |
| 154 | S | O | 190 | 386 | 503 | 62 | 61 | X | O | 387 | 46 | 535 | 37 |
| 155 | T | N | 207 | 393 | 490 | 66 | 62 | X | O | 277 | −19 | 289 | 46 |

-continued

| | | | | | | |
|---|---|---|---|---|---|---|
| 63 | X | O | 304 | 266 | 493 | 43 |
| 64 | X | O | -13 | 96 | 345 | 47 |
| 65 | X | O | 372 | 297 | 482 | 42 |
| 66 | X | O | 224 | 261 | 485 | 45 |
| 67 | X | O | -8 | -15 | 355 | 39 |
| 68 | X | O | 129 | 53 | 388 | 37 |
| 69 | X | O | 288 | 245 | 472 | 37 |
| 70 | X | O | 483 | 346 | 534 | 44 |
| 71 | X | O | 310 | 183 | 605 | 49 |
| 72 | X | O | 297 | 363 | 625 | 43 |
| 73 | X | O | 238 | 114 | 228 | 49 |
| 74 | X | O | 436 | 384 | 403 | 35 |
| 75 | X | O | 141 | 295 | 479 | 46 |
| 76 | X | O | 117 | 60 | 568 | 61 |
| 77 | X | O | -11 | -44 | 364 | 42 |
| 78 | X | O | 368 | 386 | 626 | 38 |
| 79 | X | O | 161 | 97 | 403 | 50 |
| 80 | X | O | 391 | 61 | 450 | 41 |
| 81 | X | O | 325 | 120 | 427 | 58 |
| 82 | X | O | 150 | 73 | 393 | 43 |
| 83 | X | O | 413 | 311 | 466 | 41 |
| 84 | X | O | -35 | 53 | 401 | 39 |
| 85 | X | O | 344 | 212 | 496 | 47 |
| 86 | X | O | 236 | 136 | 347 | 47 |
| 87 | X | O | 229 | 106 | 372 | 44 |
| 88 | X | O | 390 | 525 | 449 | 47 |
| 89 | X | O | 305 | 328 | 645 | 46 |
| 90 | X | O | 176 | 310 | 462 | 58 |
| 91 | X | O | 320 | 290 | 496 | 45 |
| 92 | X | O | 436 | 401 | 526 | 38 |
| 93 | X | O | 346 | -22 | 443 | 47 |
| 94 | X | O | 356 | 260 | 588 | 51 |
| 95 | X | O | 135 | 455 | 614 | 47 |
| 96 | X | O | 177 | 171 | 310 | 43 |
| 97 | X | O | 359 | 293 | 660 | 49 |
| 98 | X | O | 10 | 159 | 319 | 58 |
| 99 | X | O | 215 | 152 | 384 | 47 |
| 100 | X | O | 323 | 155 | 579 | 40 |
| 101 | X | O | 361 | 232 | 514 | 50 |
| 102 | X | O | 377 | 337 | 641 | 42 |
| 103 | X | O | -28 | 25 | 400 | 51 |
| 104 | X | O | 258 | 102 | 362 | 47 |
| 105 | X | O | 408 | 467 | 463 | 55 |
| 106 | X | O | 226 | -35 | 418 | 50 |
| 107 | X | O | 305 | 64 | 612 | 51 |
| 108 | X | O | 267 | 133 | 248 | 50 |
| 109 | X | O | 320 | 191 | 426 | 42 |
| 110 | X | O | 276 | 324 | 640 | 43 |
| 111 | X | O | 220 | 240 | 592 | 50 |
| 112 | X | O | 193 | 245 | 610 | 58 |
| 113 | X | O | 337 | 378 | 453 | 49 |
| 114 | X | O | 76 | 199 | 400 | 45 |
| 115 | X | O | 426 | 253 | 530 | 48 |
| 116 | X | O | 290 | 252 | 629 | 46 |
| 117 | X | O | 477 | 306 | 445 | 44 |
| 118 | X | O | 470 | 310 | 549 | 53 |
| 119 | X | O | 357 | 220 | 577 | 52 |
| 120 | X | O | 422 | 145 | 424 | 49 |
| 121 | X | O | 284 | 134 | 425 | 45 |
| 122 | X | O | 453 | 403 | 594 | 53 |
| 123 | X | O | -5 | 143 | 190 | 65 |
| 124 | X | O | 402 | 73 | 427 | 53 |
| 125 | X | O | 260 | 169 | 430 | 38 |
| 126 | X | O | 452 | 475 | 446 | 47 |
| 127 | X | O | 233 | 117 | 623 | 46 |
| 128 | X | O | 346 | 240 | 594 | 53 |
| 129 | X | O | 86 | 215 | 307 | 54 |
| 130 | X | O | 318 | 312 | 661 | 45 |
| 131 | X | O | 334 | 291 | 651 | 46 |
| 132 | X | O | 164 | 163 | 274 | 45 |
| 133 | X | O | 240 | 188 | 597 | 48 |
| 134 | X | O | 125 | 91 | 559 | 52 |
| 135 | X | O | 62 | 94 | 176 | 58 |
| 136 | X | O | 247 | 118 | 328 | 48 |
| 137 | X | O | 442 | 128 | 531 | 48 |
| 138 | X | O | 244 | 145 | 292 | 58 |
| 139 | X | O | 299 | 142 | 603 | 66 |
| 140 | X | O | 237 | 158 | 398 | 49 |
| 141 | X | O | 320 | 156 | 396 | 59 |
| 142 | X | O | 145 | 157 | 202 | 46 |
| 143 | X | O | 100 | 174 | 185 | 57 |
| 144 | X | O | 305 | 174 | 410 | 48 |
| 145 | X | O | 87 | 192 | 440 | 51 |
| 146 | X | O | 275 | 194 | 581 | 45 |
| 147 | X | O | 152 | -290 | 226 | 58 |
| 148 | X | O | 128 | 211 | 519 | 55 |
| 149 | X | O | 80 | 213 | 359 | 53 |
| 150 | X | O | 101 | 218 | 434 | 65 |
| 151 | X | O | 103 | 223 | 269 | 57 |
| 152 | X | O | 317 | 255 | 626 | 48 |
| 153 | X | O | 250 | 260 | 493 | 49 |
| 154 | X | O | 292 | 292 | 502 | 57 |
| 155 | X | O | 187 | -196 | 200 | 61 |
| 156 | X | O | 442 | 314 | 655 | 48 |
| 158 | X | O | 33 | -130 | 300 | 49 |
| 159 | X | O | 471 | 364 | 636 | 59 |
| 160 | X | O | 250 | 385 | 672 | 49 |
| 161 | X | O | 236 | -97 | 301 | 58 |
| 162 | X | O | 459 | 415 | 527 | 50 |
| 163 | X | O | 268 | -67 | 239 | 53 |
| 164 | X | O | 223 | -64 | 445 | 49 |
| 165 | X | O | 26 | -48 | 166 | 50 |
| 166 | X | O | 185 | 494 | 609 | 52 |
| 167 | X | O | 209 | -48 | 488 | 47 |
| 168 | X | O | 428 | 455 | 451 | 52 |
| 169 | X | O | 300 | -33 | 429 | 51 |
| 170 | X | O | -21 | -19 | 311 | 30 |
| 171 | X | O | 135 | 12 | 164 | 55 |
| 173 | X | O | 119 | 22 | 499 | 53 |
| 174 | X | O | 136 | 30 | 404 | 55 |
| 175 | X | O | 406 | 26 | 529 | 48 |
| 177 | X | O | 407 | 45 | 466 | 59 |
| 178 | X | O | 403 | 39 | 496 | 58 |
| 179 | X | O | -21 | 48 | 311 | 49 |
| 180 | X | O | 140 | 59 | 519 | 48 |
| 181 | X | O | 2 | 60 | 196 | 48 |
| 182 | X | O | 280 | 81 | 391 | 50 |
| 183 | X | O | 49 | -3 | 182 | 50 |
| 184 | X | O | 151 | 146 | 227 | 37 |
| 185 | X | O | 312 | 14 | 609 | 52 |
| 186 | X | O | -6 | 82 | 260 | 61 |

Example 12

Crystallographic Analysis of Flight Derived Crystal Experiments (Form 1)

Prior to data collection, crystals were washed with the reservoir solution of the crystallization setup and transferred into the same solution with 25% glycerol added. The crystals were then flash-cooled in a nitrogen stream at 95 K or in liquid nitrogen. X-ray diffraction was collected at CHESS equipped with an ADSC Quantum 210 detector. Data were integrated and scaled using the HKL package.

| Data collection statistics: | |
|---|---|
| Resolution | 20.0 – 3.90 Å |
| No. of collected reflections | 40838 |
| No. of unique reflections (F >= 0) | 11959 |
| R-sym | 12.4% |
| Percent of theoretical (I/s >= 1) | 94.1% |
| Unit Cell | a = 62.405 Å, b = 76.169 Å, c = 150.453 Å, α = 90° β = 91.67°, γ = 90° |
| Space Group | P2$_1$ (Number 4) |
| Asymmetric unit | 6 molecule |

Example 13

Structure Determination of Flight Derived Crystals (Form1)

The crystal structure was solved using molecular replacement using the search models 1 RH2 from the PDB. Refinement was done using the program CNX.

| | |
|---|---|
| Theoretical number of reflections | 11959 |
| Resolution Limits | 20.0 – 3.9 Å |
| Number of unobserved reflections | 749 (5.9%) |
| Number of reflections in working set | 11959 (94.1%) |
| Number of reflections in test set | 768 (6.0%) |
| Number of protein residues | 780 |
| Number of solvent atoms | 4 (ZN) |
| R-factor | 0.321 |
| R-free | 0.335 |

Example 14

Production of $Zn^{2+}$ Dimerized Preferentially PEGylated PEG-Interferon Alpha 2b In this example, zinc dimerized interferon alpha 2b is expressed first, then the dimers are PEGylated. The PEGylated dimers comprise no significant PEGylation on His 34; rather, the PEG moieties are distributed on residues on Lys 49, Lys 121, Lys 31, His 7 and Cys 1.

Zinc Dimerized Interferon Alpha 2b Expression and Purification.

The interferon-alpha 2 employed is recombinant interferon-alpha 2b expressed in *E. coil* as described in Weissmann, et al. Science, 209, 1342 (1980). The cells are cultured, harvested and extracted as previously described in U.S. Pat. No. 4,315,852. Bacteria altered by recombinant techniques also produce contaminants and structural isoforms of the protein intended to be produced. These contaminants and isoforms include oligermeric proteins and reduced protein isoforms (see U.S. Pat. No. 4,765,903 to D'Andrea et al.), cell debris and viruses (see U.S. Pat. No. 4,732,683 to Georgiadis et al.). The extracts can be purified by a combination of conventional purification steps including cation, anion exchange chromatography steps using chromatographic media such as S-sepharose and DEAE CL-6B sepharose from Amersham Biosciences, Piscataway, N.J., USA using a salt gradient 0-0.25M sodium chloride elution and a size exclusion chromatography step using chromatographic media such as a HPSEC Superdex 200 HR Hiload column 26×60 cm, 34 um particle size, Amersham Biosciences, Piscataway, N.J., USA) The resulting purified interferon-alpha 2b is dialyzed versus double glass distilled water and lyophilized to amorphous solid.

Preparation of SC PEG 5000-interferon-alpha 2b Conjugate.

Solid SC-PEG 5000 (Zalipsky et al., Biotechnol. Appl. Biochem 15, 100-114 (1992)) succinimidyl carbonyl methoxypolyethylene glycol 5000 is added 20 molar equivalents to 10 mg of solid interferon-alpha 2b dissolved in 10 ml of 30 mM sodium acetate, 50 mM sodium chloride, pH and temperature is maintained at 4° C. for 18 hours. The resulting SC-PEG5000-interferon-alpha 2b conjugate can be purified on a HPSEC Superdex 200 HR Hiload, 26×60 cm, 34 um particle size particle size; Amersham Biosciences, Piscataway, N.J., USA as described in Grace et al. (2005) J. Biol. Chem. 280 6327-6336.

* * *

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. A crystalline composition comprising a crystal of an interferon-alpha 2b-$Zn^{2+}$-interferon-alpha 2b complex in space group C2 comprising unit cell dimensions a=114.7 Å, b=98.4 Å, c=62.4 Å and α=90°, β=93.9°; γ=90°; wherein said interferon-alpha 2b of the complex comprises the amino acid sequence set forth in SEQ ID NO: 1.

2. The crystalline composition of claim 1 wherein the interferon-alpha 2b-$Zn^{2+}$-interferon-alpha 2b complex has a three dimensional structure having structural coordinates comprising a root mean square deviation of common residue backbone atoms or alpha carbon atoms of less than 1.5 Å when superimposed on backbone atoms or alpha carbon atoms of a three dimensional structure having the structural coordinates of Table 3 or 4.

3. The crystalline composition of claim 2 wherein the interferon-alpha 2b-$Zn^{2+}$-interferon-alpha 2b complex has a three dimensional structure having the structural coordinates of Table 3 or 4.

4. The crystalline composition of claim 1 wherein said crystalline composition diffracts X-rays to 1.95 Å resolution or a lower number.

5. The crystalline composition of claim 1 wherein said crystalline composition comprises a particle diameter of from 1 μm to 70 μm or from 0.5 μm to 7 μm.

6. The crystalline composition of claim 1, further comprising a pharmaceutically acceptable carrier.

7. An injectable device comprising the crystalline composition of claim 6.

8. The crystalline composition of claim 6 which is a sustained release formulation.

9. The crystalline composition of claim 6 which is suitable for pulmonary delivery.

10. A method for treating a host infected with hepatitis C virus, comprising administering to said host a therapeutically effective amount of the crystalline composition of claim 1.

11. The method of claim 10 wherein the crystalline composition is administered by inhalation.

12. The method of claim 10 wherein the crystalline composition is in a sustained-release formulation.

* * * * *